US009242933B2

(12) United States Patent
Geneste et al.

(10) Patent No.: US 9,242,933 B2
(45) Date of Patent: Jan. 26, 2016

(54) HETEROCYCLIC COMPOUNDS AS POSITIVE MODULATORS OF METABOTROPIC GLUTAMATE RECEPTOR 2 (MGLU2 RECEPTOR)

(75) Inventors: Herve Geneste, Ludwigshafen (DE); Daryl Sauer, Abbott Park, IL (US); Wilfried Braje, Ludwigshafen (DE); Wilhelm Amberg, Ludwigshafen (DE); Mario Mezler, Ludwigshafen (DE); Margaretha Henrica Maria Bakker, Ludwigshafen (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 567 days.

(21) Appl. No.: 12/126,174

(22) Filed: May 23, 2008

(65) Prior Publication Data
US 2008/0300260 A1  Dec. 4, 2008

Related U.S. Application Data

(60) Provisional application No. 60/931,869, filed on May 25, 2007.

(51) Int. Cl.
C07D 207/335 (2006.01)
C07D 409/06 (2006.01)
C07D 215/12 (2006.01)
C07D 231/12 (2006.01)
A61K 31/44 (2006.01)
C07D 209/14 (2006.01)
C07D 209/26 (2006.01)
C07D 213/36 (2006.01)
C07D 213/38 (2006.01)
C07D 233/58 (2006.01)
C07D 239/26 (2006.01)
C07D 261/08 (2006.01)
C07D 277/28 (2006.01)
C07D 307/14 (2006.01)
C07D 307/54 (2006.01)
C07D 333/20 (2006.01)
C07D 333/58 (2006.01)
C07D 407/04 (2006.01)
C07D 409/04 (2006.01)

(52) U.S. Cl.
CPC .......... C07D 209/14 (2013.01); C07D 207/335 (2013.01); C07D 209/26 (2013.01); C07D 213/36 (2013.01); C07D 213/38 (2013.01); C07D 215/12 (2013.01); C07D 231/12 (2013.01); C07D 233/58 (2013.01); C07D 239/26 (2013.01); C07D 261/08 (2013.01); C07D 277/28 (2013.01); C07D 307/14 (2013.01); C07D 307/54 (2013.01); C07D 333/20 (2013.01); C07D 333/58 (2013.01); C07D 407/04 (2013.01); C07D 409/04 (2013.01); C07D 409/06 (2013.01)

(58) Field of Classification Search
CPC ............. C07D 207/335; C07D 409/06; C07D 215/12; C07D 231/12; A61K 31/44
See application file for complete search history.

(56) References Cited

U.S. PATENT DOCUMENTS

| 5,990,139 | A | 11/1999 | Yano et al. |
| 6,040,327 | A | 3/2000 | De Nanteuil et al. |
| 7,179,823 | B1 | 2/2007 | Momose et al. |
| 7,253,196 | B2 | 8/2007 | Henriksson et al. |
| 2002/0143007 | A1 | 10/2002 | Garvey et al. |
| 2003/0207939 | A1 | 11/2003 | Ishibuchi et al. |
| 2004/0063744 | A1 | 4/2004 | Wang et al. |
| 2005/0033055 | A1 | 2/2005 | Bugianesi et al. |
| 2007/0185334 | A1 | 8/2007 | Uchida |
| 2008/0194640 | A1 | 8/2008 | Nakamura et al. |
| 2008/0269220 | A1 | 10/2008 | Yasuma et al. |
| 2009/0270460 | A1 | 10/2009 | Bell et al. |
| 2010/0041656 | A1 | 2/2010 | Nakamura et al. |
| 2010/0069367 | A1 | 3/2010 | Boren et al. |
| 2010/0075964 | A1 | 3/2010 | Busch et al. |
| 2010/0183513 | A1 | 7/2010 | Froestl et al. |

FOREIGN PATENT DOCUMENTS

| CA | 1331619 | 8/1994 |
| CA | 2046883 | 8/2000 |
| CA | 2396908 | 7/2001 |
| EA | 014419 A1 | 6/2007 |
| EP | 1228067 | 7/2004 |
| EP | 1726580 | 11/2006 |
| JP | 11-130753 | 5/1999 |
| JP | 2003104964 | 4/2003 |
| JP | 2004-123732 | 4/2004 |

(Continued)

OTHER PUBLICATIONS

Alzheimer's Disease Treatment Phases, http://www.alzheimerstreatment.org/treatment/disease-treatment.htm.*
Alzheimer's Drugs, Consumer Reports Best Buy Drugs (p. 1-5).*
Ghose et al., Am J Psychiatry, 166:7, 2009, 812-820.*
SchizophreniaCure, 2013, http://www.mayoclinic.com/health/schizophrenia/DS00196/DSECTION=treatments-and-drugs.*
SchizophreniaPrevention, 2013, http://www.mayoclinic.com/health/schizophrenia/DS00196/DSECTION=prevention.*
De Babot et al., caplus an 1965:454668.*
Ksida et al., caplus an 1991:23959.*

(Continued)

Primary Examiner — Sun Jae Yoo
(74) Attorney, Agent, or Firm — Lisa V. Mueller; Michael Best & Friedrich LLP

(57) ABSTRACT

The present invention relates to heterocyclic compounds which are positive modulators of metabotropic glutamate receptor. The present invention also relates to the use of these compounds for preparing a pharmaceutical composition and to a method of treating a medical disorder, selected from neurological and psychiatric disorders associated with glutamate dysfunction.

18 Claims, No Drawings

(56) References Cited

FOREIGN PATENT DOCUMENTS

| JP | 2006-117568 | 5/2006 |
|---|---|---|
| JP | 2007-119478 | 5/2007 |
| WO | 01/38325 | 5/2001 |
| WO | WO 01/56990 | 8/2001 |
| WO | 01/64651 | 9/2001 |
| WO | 03/062252 | 7/2003 |
| WO | 2004/043337 | 5/2004 |
| WO | 2004/082677 | 9/2004 |
| WO | 2004/098528 | 11/2004 |
| WO | 2005/060959 | 7/2005 |
| WO | 2005/061458 | 7/2005 |
| WO | 2005/105755 | 11/2005 |
| WO | 2005/116002 A2 | 12/2005 |
| WO | 2006/014185 | 2/2006 |
| WO | WO2006/014918 | 2/2006 |
| WO | WO2006/015158 | 2/2006 |
| WO | WO2006/020879 | 2/2006 |
| WO | WO2006/030032 | 3/2006 |
| WO | WO2006/047237 | 5/2006 |
| WO | WO2006/049969 | 5/2006 |
| WO | WO2006/057860 | 6/2006 |
| WO | WO2006/057869 | 6/2006 |
| WO | WO2006/057870 | 6/2006 |
| WO | WO2006/091496 | 8/2006 |
| WO | 2007/002559 | 1/2007 |
| WO | WO2007/021308 | 2/2007 |
| WO | WO2007/021309 | 2/2007 |
| WO | 2007/140183 | 12/2007 |
| WO | 2008/061795 A2 | 5/2008 |
| WO | 2008/073825 | 6/2008 |

OTHER PUBLICATIONS

El Kodadi et al., caplus an 2004:366235, 2004.*
Huck et al., caplus an 2004:430797.*
Monn et al., J. Med. Chem. 39(15), 2990-3000, 1996.
Trombley and Westbrook, J. Neurosci, 12(6), 2043-50, 1992.
D. A. Barda et al., Bioorganic and Medicinal Chemistry Letters, 14, 3099-3102, 2004.
Cartmell and Schoepp, J. Neurochem. 75(3), 889-907, 2000.
Brauner-Osborne et al., J. Med. Chem. 43 (14), 2609-2645, 2000.
Monn et al., J. Med. Chem. 40(4), 528-37, 1997.
Monn et al., J. Med. Chem. 42(6), 1027-40, 1999.
Nakazato et al., J. Med. Chem. 43(25), 4893-909, 2000.
Kingston et al., Neuropharmacology 37(1), 1-12, 1998.
Johnson et al., Neuropharmacology 38(10), 1519-29, 1999.
Johnson et al., J. Med. Chem. 46(15), 3189-92, 2003.
Schaffhauser et al., Mol. Pharmacol. 64(4), 798-810, 2003.
Galici et al., JPET 315(3), 1181-1187, 2005.
Johnson et al., Psychopharmacol, 179(1), 271-83, 2005.
Higgins et al., Neuropharmacol 46, 907-917, 2004.
Moghaddam and Adams, Science 281(5381), 1349-52, 1998.
International Search Report for PCT Application No. PCT/EP2008/056378, dated Oct. 9, 2008.
International Preliminary Report on Patentability for PCT Application No. PCT/EP2008/056378, dated Dec. 1, 2009.
Charles, E.S. et al., "Synthesis of 2,5-disubstituted benzimidazoles as potential antihookworm and antimicrobial agents," Eur. J. med. Chem. Chimica Therapeutica (1979) 14(5):435-438.
Fahmy, H.H. et al., "Synthesis of some new heterocyclic compounds containing benzimidazole moiety as potential antimicrobial agents," Egypt. J. Chem. (2003) 46(2):313-327.
Ghoneim, K.M. et al., "Synthesis and cyclocondensation reactions of 4(5)—imidazolylmethylaminochalcones," Egypt. J. Chem. (1989) 32(1):41-50.
Ito, I. et al., "Synthesis of pyrazolone derivatives. XXX. Synthesis of pyrazolo[3,4-b][1,4]oxazepines," Chem. Pharm. Bull. (1977) 25(6):1443-1446.
Mustafa, A. et al., "Reactions with 1(2H)-phthalazinones, 4,5-dihydro-3(2H)-pyridazinones and 3-pyrazolin-5-ones," Tetrahedron (1964) 20:531-544.
Walker, G.N. et al., "3-aminomethylindoles and 2-(3-indolyl)oxazolidines from indole-3-aldimines. Some observations on the acetylation of schiff bases," J. Org. Chem. (1961) 26:432-439.
Wrzeciono, U. et al., "Sulfonamide," Pharmazie (1975) 30(H.9):582-585.
Wrzeciono, U., "Sulfonamidderivate des 1-phenyl-3.5-dimethyl-4-formyl-und 1-phenyl-3.4.5-trimethylpyrazols," Pharmazie (1975) 30(H.3):157-160.

* cited by examiner

HETEROCYCLIC COMPOUNDS AS POSITIVE MODULATORS OF METABOTROPIC GLUTAMATE RECEPTOR 2 (MGLU2 RECEPTOR)

CROSS-REFERENCE TO RELATED APPLICATION

This application claims priority to US Provisional Application No. 60/931,869 filed Mar. 25, 2007, the entire disclosure of which is incorporated herein by reference.

The present invention relates to heterocyclic compounds which are positive modulators of metabotropic glutamate receptor. The present invention also relates to the use of these compounds for preparing a pharmaceutical composition and to a method of treating a medical disorder, selected from neurological and psychiatric disorders associated with glutamate dysfunction.

BACKGROUND OF THE INVENTION

Glutamate, the major excitatory neurotransmitter in the brain, elicits its effects by activating ligand-gated cation channels, termed ionotropic glutamate receptors (iGluRs), as well as metabotropic glutamate receptors (mGlu receptors). The latter belong to the G-Protein coupled receptor (GPCR) family 3 (Conn and Pin, Annu. Rev. Pharmacol. Toxicol. 37, 205-37, 1997) and are coupled through heterotrimeric G-proteins to intracellular effector systems. These receptor types exert multiple modulatory effects within the central nervous system (CNS). Eight mGlu receptor subtypes have been cloned from mammalian brain to date. Depending on their G-protein coupling profile, pharmacology and sequence identity, these receptors are classified into three groups (Conn and Pin, Annu. Rev. Pharmacol. Toxicol. 37, 205-37, 1997). Group I mGlu receptors primarily couple through Gq to increases in phosphoinositide hydrolysis and the cellular $Ca^{2+}$-system via phospholipase C (PLC), and include the mGlu1 receptor and mGlu5 receptor. Group II mGlu receptors, which include mGlu2 and mGlu3, inhibit adenylylcyclase (AC), just as group III mGlu receptors, which comprise mGlu4, mGlu6, mGlu7 and mGlu8. Thereby, in groups II and III, the pertussis-toxin sensitive G-protein Gi is involved in signal transduction. However, group II and group III mGlu receptors differ in their sequence identity and pharmacological profile.

Of the 8 mGlu receptor subtypes various splice variants exist. Within group I mGlu receptors the splicing variability is most pronounced. MGlu 1 exists in 6 different splicing forms. The receptors mGlu1a/a, 1b/b, 1c, 1d and 1f all differ in their C-terminal, intracellular domain (Prezeau et al., Mol. Pharmacol. 49, 422-429, 1996; Soloviev et al., Biochimica et Biophysica Acta 1446, 161-166, 1999), and mGlu1e is truncated N-terminally, lacking most of the protein coding region (Pin and Duvoisin, Neuropharmacol. 34, 1-26, 1995). So far of mGlu5 (group I), and the group III receptors mGlu4, mGlu7 and mGlu8 two splicing variants have been demonstrated. mGlu6, which is located solely in ON-bipolar cells of the retina (Nakanishi et al., Brain Res. Rev. 26, 230-235, 1998), only has one isoform. The same holds for mGlu2 and mGlu3 receptors (Fagni et al., TINS 23 (2), 80-88, 2000).

The synaptic localization of group I mGlu receptors and group II/III mGlu receptors differs. While group I receptors are located predominantly postsynaptically, group III mGlu receptors rather show a presynaptic localization (Shigemoto et al., J Neurosci. 17, 7503-7522, 1997; Cartmell & Schoepp, J. Neurochem. 75(3), 889-907, 2000). Group II receptors seem to be located pre- and postsynaptically, depending on brain region and synapse-type. A perisynaptic localization of mGlu2 has also been demonstrated. In this case the receptor might only be activated under high frequency stimulation, then preventing further transmitter release and thus reducing pathologically high levels of glutamate within the synaptic cleft. Autoreceptor function (medial perforant path, mossy fiber-CA3, spinal cord synapse, corticostriatal synapse) and heteroreceptor functions have been demonstrated for group II mGlu receptors at synapses in diverse brain regions. The pre- and perisynaptic localization of group II mGlu receptors, combined with their auto- and heteroreceptor function and their coupling to inhibitory intracellular signalling cascades implies an important role of this receptor type for the regulation of excitatory neurotransmission.

The first compounds which discriminated between the 3 different groups of mGlu receptors were low affinity agonists: 3,5-dihydroxyphenylglycine (3,4-DHPG), which selectively stimulates the group 1 mGlu receptors; (2R,4R)-4-aminopyrrolidine-carboxylic acid (2R,4R-APDC) activating group II mGlu receptors (Monn et al., J. Med. Chem. 39(15), 2990-3000, 1996) and L-Amino-4-phosphonobutyrate (L-AP4, Trombley and Westbrook, J. Neurosci. 12(6), 2043-50, 1992) for the activation of group III mGlu receptors. All these compounds have been valuable tools for the investigation of the various functions of mGlu receptors by in vitro studies, but none of these compounds has been shown to exert potent central effects after systemic administration. Other early compounds, which have mainly been used for in vitro studies, turned out to activate ionotropic glutamate receptors as well. For the widely used group II mGlu receptor agonist (2S,1'R, 2'R,3'R)-2-(2',3'-dicarboxypropyl)glycine also activates NMDA receptors.

For studying the in vivo effects and therapeutic applications of group II agonists, the breakthrough came from the discovery of LY354740 and LY379268 (Formulae given e.g. in D. A. Barda et al, Bioorganic and Medicinal Chemistry Letters, 14, 3099-3102, 2004). These two compounds are highly specific group II receptor agonists with only very low affinity to other mGlu receptors or ionotropic glutamate receptors. They have $EC_{50}$ values of 10 and 20 nM (LY354740) and 3 and 5 nM (LY379268), for mGlu2 and 3 respectively. While a differentiation between the two group II receptors is not possible, a specificity of >1:30.000 towards group I receptors and between 1:100 (mGlu6) to >1:30.000 (mGlu7) to group III receptors offers a high discrimination potential to these receptor types (Cartmell and Schoepp, J. Neurochem. 75(3), 889-907, 2000; Bräuner-Osborne et al., J. Med. Chem. 43 (14), 2609-2645, 2000). Both compounds were designed as conformationally constrained analogues of glutamate (Monn et al., J. Med. Chem. 40(4), 528-37, 1997; J. Med. Chem. 42(6), 1027-40, 1999), and represent competitive agonists at the glutamate binding site. Furthermore these two compounds are systemically active.

Derivatives of these compounds, MGS 0008 and MGS 0028 (Nakazato et al., J. Med. Chem. 43(25), 4893-909, 2000) and have a higher oral availability. They also show increased antagonistic effects on PCP-induced head-weaving and hyperactivity in rats. Recently also a highly selective antagonist for group II mGlu receptors has been identified (Kingston et al., Neuropharmacology 37(1), 1-12, 1998; Johnson et al., Neuropharmacology 38(10), 1519-29, 1999). No appreciable specific binding of the radio-ligand [3H]-LY341495 (formula given in D. A. Barda et al. 2004) was found in membranes of cells expressing human mGlu1a, mGlu5a, mGlu4a, mGlu6, or mGlu7a receptors. Many effects induced by group II receptor agonists could be reversed by this compound. Thus LY341495 also represents a highly selective tool compound.

Positive modulators activate the mGlu2 receptor dependent on the presence of glutamate (potentiators). Thus, the compound "sensitizes" the receptor to react already at lower concentrations of the ligand. Positive modulators can also activate the mGlu2 receptor directly. The mGlu receptors consist of a large extracellular N-terminal domain, which binds the natural ligand, glutamate, which is homologous to the periplasmatic amino acid binding proteins from bacteria. This domain is linked to a 7-transmembrane domain. This canonical domain, common to all G-protein coupled receptors, contains the canonical ligand binding site for GPCRs (compare rhodopsin in retinal). In the mGluRs this site is free and may play a role as modulatory site for positive and negative allosteric compounds.

A hint for the exact amino acid sites responsible for ligand binding of a model potentiator (LY487379, see Johnson et al., J. Med. Chem. 46(15), 3189-92, 2003) come from the amino acid comparison between mGlu2 receptor and mGluR3 in this region. As the potentiator is specific for mGlu2 receptor, the binding should not take place at mGluR3 and the responsible amino acids should be exactly the ones which differ between the two receptors. Recently the binding site of a model potentiator (LY487379) has been mapped by site directed mutagenesis. The binding site seems to be within the transmembrane domain of mGlu2 receptor (Schaffhauser et al., Mol. Pharmacol. 64(4), 798-810, 2003). In particular the amino acids 688, 689 and 735 are indicated for binding.

MGlu2 receptor is expressed in both separate and overlapping circuits of relevance for neuropsychiatric and neurological disorders. This includes expression in neocortex, thalamus, striatum, amygdala and hippocampus. Within these circuits mGlu2 receptor is mainly expressed presynaptically. As a consequence of this expression pattern it has been shown that excitatory transmitter release is regulated by group II agonists in diverse brain regions. For, it has been demonstrated that group II agonists normalize PCP-induced increase of glutamate in the prefrontal cortex (PFC) and that dopamine is regulated by group II agonists in a region-specific manner. As one function group II agonists increase dopamine and metabolites in the PFC. Also serotonin and metabolites are regulated in the PFC. This has further been demonstrated by a functional antagonism of 5-HT2A receptors in this brain region.

These data indicate that the mGlu2 receptor approach may normalize a number of de-regulated transmitters in schizophrenia. The mGlu2 receptor agonist/potentiator concept will likely give rise to the opportunity to normalize positive symptoms, due to regulation of glutamate, negative symptoms, due to regulation of dopamine and serotonin, and cognitive symptoms, due to regulation of acetylcholine in the PFC.

Besides schizophrenia, drug abuse may be an interesting disease indication, as group II agonists block of expression of locomotor sensitization by amphetamine, among a multitude of other described effects. The usefulness of such compounds is not limited to the disease states described above.

The potentiator concept for mGlu2 receptor is relatively new (Barda et al., 2004), but necessary to evaluate the relevance of mGlu2 receptor versus mGluR3. This is of note, as the group II agonists described above do cross react with both receptor types. Within the last year, reports directly demonstrate the relevance of mGlu2 receptor in psychosis models in rodents by describing function of mGlu2 receptor potentiators in models of PCP-induced hyperlocomotion, amphetamine-induced hyperlocomotion, and reversal of amphetamine-induced disruption of PPI in mice (Galici et al., JPET 315(3), 1181-1187, 2005).

Beyond these data, indicating a relevance of mGlu2 receptor potentiators in schizophrenia, new reports furthermore demonstrate efficacy of mGlu2 receptor potentiators in anxiety, as potentiators have been shown to be efficacious in rat fear-potentiated startle and stress-induced hyperthermia in mice (Johnson et al. Psychopharmacol, 179(1), 271-83, 2005).

A pure NMDA activation approach (the "glutamatergic hypothesis of schizophrenia") may result in side effect liabilities. In particular excitotoxicity is a relevant side effect which needs to be considered early within a potential screening cascade of such projects. This side effect liability may limit the usefulness of such approaches.

As described above, the mGlu2 receptor positive modulator approach does not purely rely on the glutamatergic hypothesis, but likely is involved in the normalization of release of a number of excitatory neurotransmitters. Consequently, to date there is no evidence for excitotoxic liability of group II agonists or mGlu2 receptor positive modulators. Group II agonists even show the opposite effects. They are neuroprotective in the MPTP model of Parkinson's disease, they reduce low $Mg^{2+}$-induced epileptiform discharges in slice preparations and they have anticonvulsant action in acute seizure models.

As a relevant side effect, a negative influence on cognition was described for group II agonists (Higgins et al., Neuropharmacol 46, 907-917, 2004). However, to date this finding is controversial in the literature. While one group finds a reversal of cognitive deficits induced by PCP (Moghaddam and Adams, Science 281(5381), 1349-52, 1998), a second group finds a reduction of DNMTP performance with the mGlu2 receptor agonist LY354740, which is not present in mGlu2 receptor knockout mice (Higgins et al., Neuropharmacol. 46, 907-917, 2004). This finding contrasts to the data from Moghaddam and Adams and would also contradict the normalization of ACh release in the PFC by this compound (see above).

WO 2001/56990 describes N-substituted N-(phenyl)aminomethylpyridine compounds, which are potentiators of the glutamate receptors.

WO 2006/014918 describes heterocyclic compounds carrying a 4-acylphenyl moiety. The compounds are potentiators of metabotropic glutamate receptors, including the mGlu2 receptor, and thus are useful in the treatment or prevention of neurological and psychiatric disorders associated with glutamate dysfunction and diseases in which metabotropic glutamate receptors are involved.

WO 2006/015158 and WO 2006/047237 describe heterocyclic compounds carrying an indanone moiety, the compounds being potentiators of metabotropic glutamate receptors, including the mGlu2 receptor.

WO 2006/0030032 describes pyridinone compounds which are potentiators of metabotropic glutamate receptors, including the mGlu2 receptor.

WO 2006/049969 describes N-(phenyl)aminoalkyl substituted pyrimidine compounds, which are potentiators of metabotropic glutamate receptors, including the mGlu2 receptor.

WO 2006/057860, WO 2006/057869 and WO 2006/057870 describe compounds carrying a 4-acyl-3-hydroxyphenyl moiety. The compounds are suggested to be potentiators of metabotropic glutamate receptors, including the mGlu2 receptor.

WO 2006/091496 describes compounds carrying an benzazole moiety, the compounds being suggested as potentiators of metabotropic glutamate receptors, including the mGlu2 receptor.

WO 2006/020879, WO2007/021308 and WO 2007/021309 disclose isoindolone compounds, which are suggested as potentiators of metabotropic glutamate receptors, including the mGlu2 receptor.

Although the compounds of prior art have a high affinity with regard to the mGlu2 receptor, their receptor binding profile and/or their pharmacological profile is not always satisfactory. In particular, the compounds often have poor selectivity with regard to mGlu2 receptor in comparison with mGlu3 or group III mGlu receptors or are glutamate agonists. Moreover the metabolic stability or metabolic behavior and or the bioavailability is not satisfactory.

It is an object of the present invention to provide further compounds which are positive modulators of metabotropic glutamate receptors, in particular of the mGlu2 receptor, and which thus are useful in the treatment or prevention of neurological and psychiatric disorders associated with glutamate dysfunction and diseases in which metabotropic glutamate receptors are involved. The compounds should be positive modulators of the mGlu2 receptor having no or reduced agonist activity in order to reduce or avoid side effects associated with an agonistic activity. The compounds should preferably also have a favourable metabolic behaviour such as a decreased inhibition of the mitochondrial respiration and decreased interaction with cytochrome P450 isoenzymes. The compounds should also have a good bioavailability.

These and further objects are solved by the compounds of the general formula I, as described herein, as well as by the tautomers thereof, and by their pharmaceutically acceptable salts.

SUMMARY OF INVENTION

The present invention thus provides compounds of formula I

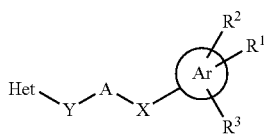

(I)

wherein

X is O, S, S(O), S(O)$_2$, NH, NHC(O), NR$^x$ or a chemical bond;

R$^x$ is C$_1$-C$_6$-alkyl, which is unsubstituted or carries one radical selected from OH, C$_1$-C$_4$-alkoxy, C$_3$-C$_8$-cycloalkyl and phenyl wherein the phenyl ring itself is unsubstituted or carries 1, 2, 3, 4 or 5 identical or different radicals R$^{xa}$, C$_1$-C$_6$-haloalkyl, C$_3$-C$_8$-cycloalkyl, C$_1$-C$_6$-alkoxy, C$_1$-C$_6$-haloalkoxy, phenyl, 5- or 6-membered hetaryl having 1, 2 or 3 heteroatoms as ring members, the heteroatoms being selected from O, S and N, wherein hetaryl and phenyl are unsubstituted or carry 1, 2, 3, 4 or 5 identical or different radicals R$^{xb}$, C(=O)—R$^{x1}$, C(=O)—OR$^{x2}$, C(=O)NR$^{x3}$R$^{x4}$ S(O)$_2$R$^{x5}$ or S(O)$_2$NR$^{x3}$R$^{x4}$, wherein R$^{x1}$ is selected from hydrogen, C$_1$-C$_8$-alkyl, which is unsubstituted or carries one radical selected from OH, C$_1$-C$_4$-alkoxy, C$_3$-C$_8$-cycloalkyl and phenyl wherein the phenyl ring itself is unsubstituted or carries 1, 2, 3, 4 or 5 identical or different radicals R$^{xa}$, C$_1$-C$_6$-haloalkyl, C$_3$-C$_8$-cycloalkyl, which is unsubstituted or carries 1, 2, 3 or 4 radicals selected from halogen, C$_1$-C$_4$-alkyl and C$_1$-C$_4$-alkoxy, phenyl and 5- or 6-membered hetaryl having 1, 2 or 3 heteroatoms as ring members, the heteroatoms being selected from O, S and N, wherein phenyl and hetaryl are unsubstituted or may carry a fused benzene ring and/or may carry 1, 2, 3, 4 or 5 identical or different radicals R$^{xb}$;

R$^{xa}$ is selected from the group consisting of halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy;

R$^{xb}$ is selected from the group consisting of halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy;

R$^{X2}$ is selected from C$_1$-C$_8$-alkyl, which is unsubstituted or carries one radical selected from OH, C$_1$-C$_4$-alkoxy, C$_3$-C$_8$-cycloalkyl, and phenyl wherein the phenyl ring itself is unsubstituted or carries 1, 2, 3, 4 or 5 identical or different radicals R$^{xa}$, C$_1$-C$_8$-haloalkyl, and C$_3$-C$_8$-cycloalkyl, which is unsubstituted or carries 1, 2, 3 or 4 radicals selected from halogen, C$_1$-C$_4$-alkyl and C$_1$-C$_4$-alkoxy;

R$^{x3}$ is selected from hydrogen, C$_1$-C$_8$-alkyl, which is unsubstituted or carries one radical selected from OH, C$_1$-C$_4$-alkoxy, C$_3$-C$_8$-cycloalkyl and phenyl wherein the phenyl ring itself is unsubstituted or carries 1, 2, 3, 4 or 5 identical or different radicals R$^{xa}$, C$_1$-C$_6$-haloalkyl, C$_1$-C$_8$-alkoxy and C$_1$-C$_8$-haloalkoxy, C$_3$-C$_8$-cycloalkyl, which is unsubstituted or carries 1, 2, 3 or 4 radicals selected from halogen, C$_1$-C$_4$-alkyl and C$_1$-C$_4$-alkoxy;

R$^{x4}$ is selected from hydrogen and C$_1$-C$_8$-alkyl, or

R$^{x3}$ and R$^{x4}$ together with the nitrogen atom, to which they are bound, form a heterocyclic radical, selected from pyrrolidinyl, piperidinyl, piperazinyl, N-alkylpiperazinyl, N-phenylpiperazinyl and morpholinyl; and R$^{x5}$ has one of the meanings given for R$^{x1}$;

Y is O, S, S(O), S(O)$_2$, NH, NR$^x$, O-phenylene, S-phenylene, NH-phenylene, or a chemical bond, wherein the heteroatom in O-phenylene, S-phenylene and NH-phenylene is attached to Het and wherein the phenylene moiety is unsubstituted or carries 1, 2, 3 or 4 radicals selected from halogen, C$_1$-C$_4$-alkyl and C$_1$-C$_4$-haloalkyl;

provided that at least one of X and Y is different from a chemical bond;

A is C$_1$-C$_5$-alkylene, which may carry 1, 2, 3 or 4 radicals selected from halogen, OH, C$_1$-C$_4$-alkyl, C$_1$-C$_4$-haloalkyl, C$_1$-C$_4$-alkoxy and C$_1$-C$_4$-haloalkoxy;

Ar is phenyl or a is a 5- or 6-membered hetaryl having 1, 2 or 3 heteroatoms as ring members, the heteroatoms being selected from O, S and N;

R$^1$ is C$_1$-C$_8$-alkyl, which is unsubstituted or carries one radical selected from OH, C$_1$-C$_4$-alkoxy and C$_3$-C$_8$-cycloalkyl, C$_1$-C$_8$-alkoxy, which is unsubstituted or carries one radical selected from OH, C$_1$-C$_4$-alkoxy and C$_3$-C$_8$-cycloalkyl, C$_1$-C$_8$-haloalkyl, C$_1$-C$_8$-haloalkoxy, $C_3$-$C_8$-cycloalkyl, $C_3$-$C_8$-cycloalkyloxy, wherein the last two mentioned radicals are unsubstituted or carry 1, 2, 3 or 4 radicals selected from halogen, $C_1$-$C_4$-alkyl and $C_1$-$C_4$-alkoxy;

C(=O)—$R^4$, C(=O)—$OR^5$, $NR^6R^7$, C(=O)$NR^6R^7$, $SO_2NR^6R^7$, $NR^8C$(=O)$R^9$, $SO_2R^9$, $NR^8SO_2R^9$, phenyl, O-phenyl, $CH_2$-phenyl, CH($CH_3$)-phenyl, CH(OH)phenyl, S-phenyl, and O—$CH_2$-phenyl, wherein the phenyl ring in the last seven mentioned radicals may be unsubstituted or may carry 1, 2, 3, 4 or 5 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, or a radical Het', O-Het', $CH_2$-Het', CH($CH_3$)-Het', CH(OH)-Het', S-Het', $OCH_2$-Het, wherein Het' is a 5- or 6-membered saturated, unsaturated or aromatic heterocycle, having 1, 2 or 3 heteroatoms as ring members, the heteroatoms being selected from O, S and N, the heterocycle may be unsubstituted or may carry 1, 2, 3 or 4 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy;

$R^2$ is hydrogen, CN, OH, halogen, $C_1$-$C_8$-alkyl, which is unsubstituted or carries one radical selected from OH, $C_3$-$C_6$-cycloalkyl and $C_1$-$C_4$-alkoxy, $C_3$-$C_6$-cycloalkyl, $C_1$-$C_8$-haloalkyl, $C_1$-$C_8$-alkoxy and $C_1$-$C_8$-haloalkoxy, or $R^1$ and $R^2$, if bound to adjacent carbon atoms, may together form a 5- or 6-membered heterocyclic ring fused to the benzene ring and having 1, 2 or 3 nitrogen atoms as ring members or 1 oxygen atom and optionally a further heteroatom selected from O, S and N as ring members, and wherein the fused heterocyclic ring may be unsubstituted or may carry 1, 2, 3, 4 or 5 substituents selected from halogen, OH, CN, $NH_2$, $C_1$-$C_4$-alkyl, $C_3$-$C_6$-cycloalkyl, $C_1$-$C_4$-alkoxy, $C_1$-$C_4$-alkylamino, di-($C_1$-$C_4$-alkyl)amino, $C_1$-$C_4$-haloalkyl, $C_1$-$C_4$-haloalkoxy, $C_1$-$C_4$-alkylsulfonyl, $C_1$-$C_4$-haloalkylsulfonyl and phenylsulfonyl, wherein the phenyl ring may be unsubstituted or may carry 1, 2, 3 or 4 substituents selected from halogen, CN, $C_1$-$C_4$-alkyl, $C_1$-$C_4$-haloalkyl, $C_1$-$C_4$-alkoxy and $C_1$-$C_4$-haloalkoxy;

$R^3$ is hydrogen, halogen, $C_1$-$C_4$-alkyl, which is unsubstituted or carries one radical selected from OH and $C_1$-$C_4$-alkoxy, $C_1$-$C_4$-haloalkyl, $C_1$-$C_4$-alkoxy and $C_1$-$C_4$-haloalkoxy, $C_3$-$C_8$-cycloalkyl, which is unsubstituted or carries 1, 2, 3 or 4 radicals selected from halogen, $C_1$-$C_4$-alkyl and $C_1$-$C_4$-alkoxy;

$R^4$ is selected from hydrogen, $C_1$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals $R^{4a}$, $C_1$-$C_8$-haloalkyl, $C_2$-$C_8$-alkenyl, $C_2$-$C_8$-alkynyl, $C_3$-$C_8$-cycloalkyl, which is unsubstituted or carries 1, 2, 3 or 4 radicals selected from halogen, $C_1$-$C_4$-alkyl and $C_1$-$C_4$-alkoxy, and phenyl, which is unsubstituted or carries 1, 2, 3, 4 or 5 identical or different radicals $R^{4b}$, 5- or 6-membered hetaryl having 1, 2 or 3 heteroatoms as ring members, the heteroatoms being selected from O, S and N, wherein hetaryl is unsubstituted or carries 1, 2, 3 or 4 identical or different radicals $R^{4b}$, or $R^4$ together with $R^2$ forms a $C_1$-$C_5$-alkylene or $C_2$-$C_5$-alkenylene moiety, wherein one $CH_2$-moiety may be replaced by oxygen, sulphur or a N—$R^{4c}$-moiety and wherein $C_1$-$C_5$-alkylene and $C_2$-$C_5$-alkenylene may be unsubstituted or carry 1, 2, 3, or 4 radicals selected from halogen, CN, OH, $NH_2$, $C_1$-$C_4$-alkyl, $C_3$-$C_6$-cycloalkyl, $C_1$-$C_4$-haloalkyl, $C_1$-$C_4$-alkylamino, di-($C_1$-$C_4$-alkyl)amino, $C_1$-$C_4$-alkoxy and $C_1$-$C_4$-haloalkoxy;

$R^{4a}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy;

$R^{4b}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy;

$R^{4c}$ is selected from the group consisting of hydrogen, CN, OH, $C_1$-$C_8$-alkyl, in particular $C_1$-$C_4$-alkyl, which is unsubstituted or carries a radical selected from $C_1$-$C_4$-alkoxy, $C_1$-$C_4$-alkylthio, $C_1$-$C_4$-haloalkoxy, $C_1$-$C_4$-haloalkylthio, $C_3$-$C_6$-cycloalkyl, which is unsubstituted or carries 1, 2, 3, 4 or 5 identical or different radicals selected from halogen and $C_1$-$C_4$-alkyl, and phenyl or benzyl, wherein the phenyl ring in the last two radicals itself is unsubstituted or carries 1, 2, 3, 4 or 5 identical or different radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, $C_3$-$C_6$-cycloalkyl, $C_1$-$C_4$-haloalkyl, $C_1$-$C_4$-alkoxy and $C_1$-$C_4$-haloalkoxy;

$R^5$ is selected from $C_1$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals $R^{5a}$, $C_1$-$C_8$-haloalkyl, and $C_3$-$C_8$-cycloalkyl, which is unsubstituted or carries 1, 2, 3 or 4 radicals selected from halogen, $C_1$-$C_4$-alkyl and $C_1$-$C_4$-alkoxy;

$R^{5a}$ has one of the meanings given for $R^{4a}$;

$R^6$ is selected from hydrogen, $C_1$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals $R^{6a}$, and $C_3$-$C_8$-cycloalkyl, which is unsubstituted or carries 1, 2, 3 or 4 radicals selected from halogen, $C_1$-$C_4$-alkyl and $C_1$-$C_4$-alkoxy;

$R^{6a}$ has one of the meanings given for $R^{4a}$;

$R^7$ is selected from hydrogen and $C_1$-$C_8$-alkyl, or $R^6$ and $R^7$ together with the nitrogen atom, to which they are bound, form a heterocyclic radical, selected from pyrrolidinyl, piperidinyl, piperazinyl, N-alkylpiperazinyl, N-phenylpiperazinyl and morpholinyl;

$R^8$ is selected from hydrogen, $C_1$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals $R^{6a}$, and C$_3$-C$_8$-cycloalkyl, which is unsubstituted or carries 1, 2, 3 or 4 radicals selected from halogen, C$_1$-C$_4$-alkyl and C$_1$-C$_4$-alkoxy;

R$^{6a}$ has one of the meanings given for R$^{4a}$;

R$^9$ has one of the meanings given for R$^4$;

Het is a 5- or 6-membered saturated, unsaturated or aromatic heterocycle, having 1, 2 or 3 heteroatoms as ring members, the heteroatoms being selected from O, S and N, wherein Het is unsubstituted or may carry a first substituent R$^{10}$ and additionally may carry 1 or 2 further substituents R$^{11}$, R$^{12}$, and wherein Het may also carry a fused benzene, pyridine, pyrimidine or pyridazine ring;

R$^{10}$ is selected from halogen, cyano,
- C$_1$-C$_8$-alkyl, which is unsubstituted or carries one radical selected from OH,
- C$_1$-C$_4$-alkoxy and phenyl wherein the phenyl ring itself is unsubstituted or carries 1, 2, 3, 4 or 5 identical or different radicals R$^{4a}$,
- C$_1$-C$_8$-alkoxy, which is unsubstituted or carries one radical selected from OH, C$_1$-C$_4$-alkoxy and phenyl wherein the phenyl ring itself is unsubstituted or carries 1, 2, 3, 4 or 5 identical or different radicals R$^{4a}$,
- C$_1$-C$_8$-haloalkyl,
- C$_1$-C$_8$-haloalkoxy,
- C$_2$-C$_8$-alkenyl,
- C$_2$-C$_8$-alkynyl,
- C$_3$-C$_8$-cycloalkyl, which is unsubstituted or carries 1, 2, 3 or 4 radicals selected from halogen, C$_1$-C$_4$-alkyl and C$_1$-C$_4$-alkoxy,
- C$_3$-C$_8$-cycloalkoxy, which is unsubstituted or carries 1, 2, 3 or 4 radicals selected from halogen, C$_1$-C$_4$-alkyl and C$_1$-C$_4$-alkoxy,
- C(=O)—R$^{13}$, C(=O)—OR$^{14}$, NR$^{15}$R$^{16}$, C(=O)NR$^{15}$R$^{16}$, SO$_2$R$^{17}$,
- phenyl, O-phenyl, CH$_2$-phenyl, CH(CH$_3$)-phenyl, CH(OH)phenyl, S-phenyl, and O—CH$_2$-phenyl, wherein the phenyl ring in the last seven mentioned radicals may be unsubstituted or may carry 1, 2, 3, 4 or 5 substituents selected from halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy,
- 5- or 6-membered heteroaryl, having 1, 2 or 3 heteroatoms as ring members, the heteroatoms being selected from O, S and N, which is unsubstituted or may carry 1, 2, 3, 4 or 5 substituents selected from halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy;

R$^{11}$ is CN, OH, halogen, C$_1$-C$_8$-alkyl, which is unsubstituted or carries one radical selected from OH and C$_1$-C$_4$-alkoxy, C$_1$-C$_8$-haloalkyl, C$_1$-C$_8$-alkoxy, C$_1$-C$_8$-haloalkoxy, or phenyl, which may be unsubstituted or may carry 1, 2, 3, 4 or 5 substituents selected from halogen, CN, C$_1$-C$_4$-alkyl, C$_1$-C$_4$-haloalkyl, C$_1$-C$_4$-alkoxy and C$_1$-C$_4$-haloalkoxy;

R$^{12}$ is CN, OH, halogen, C$_1$-C$_8$-alkyl, which is unsubstituted or carries one radical selected from OH and C$_1$-C$_4$-alkoxy, C$_1$-C$_8$-haloalkyl, C$_1$-C$_8$-alkoxy and C$_1$-C$_8$-haloalkoxy, or R$^{11}$ and R$^{12}$ together with the carbon atom, to which they are bound, form a carbonyl group;

R$^{13}$ is selected from hydrogen,
- C$_1$-C$_8$-alkyl, which is unsubstituted or carries one radical selected from OH,
- C$_1$-C$_4$-alkoxy and phenyl wherein the phenyl ring itself is unsubstituted or carries 1, 2, 3, 4 or 5 identical or different radicals R$^{13a}$,
- C$_1$-C$_8$-haloalkyl,
- C$_3$-C$_8$-cycloalkyl, which is unsubstituted or carries 1, 2, 3 or 4 radicals selected from halogen, C$_1$-C$_4$-alkyl and C$_1$-C$_4$-alkoxy,
- phenyl and 5- or 6-membered hetaryl having 1, 2 or 3 heteroatoms as ring members, the heteroatoms being selected from O, S and N, wherein phenyl and hetaryl are unsubstituted or carry 1, 2, 3, 4 or 5 identical or different radicals R$^{13b}$;

R$^{13a}$ is selected from the group consisting of halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy;

R$^{13b}$ is selected from the group consisting of halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy;

R$^{14}$ is selected from
- C$_1$-C$_8$-alkyl, which is unsubstituted or carries one radical selected from OH,
- C$_1$-C$_4$-alkoxy and phenyl wherein the phenyl ring itself is unsubstituted or carries 1, 2, 3, 4 or 5 identical or different radicals R$^{13a}$,
- C$_1$-C$_8$-haloalkyl, and
- C$_3$-C$_8$-cycloalkyl, which is unsubstituted or carries 1, 2, 3 or 4 radicals selected from halogen, C$_1$-C$_4$-alkyl and C$_1$-C$_4$-alkoxy;

R$^{15}$ is selected from hydrogen,
- C$_1$-C$_8$-alkyl, which is unsubstituted or carries one radical selected from OH,
- C$_1$-C$_4$-alkoxy and phenyl wherein the phenyl ring itself is unsubstituted or carries 1, 2, 3, 4 or 5 identical or different radicals R$^{13a}$, and
- C$_3$-C$_8$-cycloalkyl, which is unsubstituted or carries 1, 2, 3 or 4 radicals selected from halogen, C$_1$-C$_4$-alkyl and C$_1$-C$_4$-alkoxy;

R$^{16}$ is selected from hydrogen and C$_1$-C$_8$-alkyl, or

R$^{15}$ and R$^{16}$ together with the nitrogen atom, to which they are bound, form a heterocyclic radical, selected from pyrrolidinyl, piperidinyl, piperazinyl, N-alkylpiperazinyl, N-phenylpiperazinyl and morpholinyl;

R$^{17}$C$_1$-C$_8$-alkyl, which is unsubstituted or carries one radical selected from OH,
- C$_1$-C$_4$-alkoxy and phenyl wherein the phenyl ring itself is unsubstituted or carries 1, 2, 3, 4 or 5 identical or different radicals R$^{17a}$,
- C$_1$-C$_8$-haloalkyl,
- C$_3$-C$_8$-cycloalkyl, which is unsubstituted or carries 1, 2, 3 or 4 radicals selected from halogen, C$_1$-C$_4$-alkyl and C$_1$-C$_4$-alkoxy,
- phenyl and 5- or 6-membered hetaryl having 1, 2 or 3 heteroatoms as ring members, the heteroatoms being selected from O, S and N, wherein phenyl and hetaryl are unsubstituted or carry 1, 2, 3, 4 or 5 identical or different radicals R$^{17b}$, wherein R$^{17a}$ is as defined for R$^{13a}$ and R$^{17b}$ is as defined for R$^{13b}$.

provided that Het is a heterocyclic radical selected from furyl, pyrrolyl, thienyl, pyrazolyl, thiazolyl, benzothiazolyl, oxazolyl, isoxazolyl, isothiazolyl, pyrazinyl, pyridazinyl, triazolyl, thiadiazolyl, imidazolonyl, oxazolonyl, thiazolonyl, tetrahydrotriazolopyridyl, tetrahydrotriazolopyrimidinyl, isoindolyl, pyridonyl, phatalazinyl, naphtyridinyl, quinoxalinyl, quinazolyl, oxazolopyridyl, thiazolopyridyl, imidazopyridazinyl, oxazolopyridazinyl, thiazolopyridazinyl, cinnolinyl, pteridinyl, furazanyl, benzotriazolyl, pyrazolopyridinyl and naphtyridinyl, if X is O, NHC(O), S(O)$_2$ or a bond, wherein the aforementioned heterocyclic radicals may carry a first substituent R$^{10}$ and additionally may carry 1 or 2 further substituents R$^{11}$, R$^{12}$, further provided that at least one of the provisos (1) or (2) are met, if Het is a 6-membered heterocycle or a 6-membered heterocycle fused to a benzene, pyridine, pyrimidine or pyridazine ring, wherein the 6-membered heterocycle and the 6-membered heterocycle fused to a benzene, pyridine, pyrimidine or pyridazine ring may carry a first substituent R$^{10}$ and additionally may carry 1 or 2 further substituents R$^{11}$, R$^{12}$;

(1) R$^1$ is a radical selected from
the group consisting of C(=O)—R$^4$, C(=O)—OR$^5$, NR$^6$R$^7$, C(=O)NR$^6$R$^7$, SO$_2$NR$^6$R$^7$, NR$^8$C(=O)R$^9$, SO$_2$R$^9$ and NR$^8$SO$_2$R$^9$, or from the group consisting of Het', O-Het', CH$_2$-Het', CH(CH$_3$)-Het', CH(OH)-Het', S-Het', OCH$_2$-Het, wherein Het' is a 5- or 6-membered saturated, unsaturated or aromatic heterocycle, having 1, 2 or 3 heteroatoms as ring members, the heteroatoms being selected from O, S and N, the heterocycle may be unsubstituted or may carry 1, 2, 3 or 4 substituents selected from halogen, CN, C$_1$-C$_4$-alkyl, C$_1$-C$_4$-haloalkyl, C$_1$-C$_4$-alkoxy and C$_1$-C$_4$-haloalkoxy;

(2) Het carries a first substituent R$^{10}$ and additionally may carry 1 or 2 further substituents R$^{11}$, R$^{12}$ and R$^{10}$ is selected from C$_2$-C$_8$-alkenyl, C$_2$-C$_8$-alkynyl, C$_3$-C$_8$-cycloalkyl, which is unsubstituted or carries 1, 2, 3 or 4 radicals selected from halogen, C$_1$-C$_4$-alkyl and C$_1$-C$_4$-alkoxy,
C(=O)—R$^{13}$, C(=O)—OR$^{14}$, NR$^{15}$R$^{16}$, C(=O)NR$^{15}$R$^{16}$, SO$_2$R$^{17}$, and 5- or 6-membered heteroaryl, having 1, 2 or 3 heteroatoms as ring members, the heteroatoms being selected from O, S and N, which is unsubstituted or may carry 1, 2, 3, 4 or 5 substituents selected from halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy;

and the pharmaceutically acceptable salts and the tautomers thereof.

The compounds of the present invention are positive modulators of metabotropic glutamate (mGlu) receptor function, in particular they are positive modulators of mGlu2 receptors. That is, the compounds of the present invention do not appear to bind at the glutamate recognition site on the mGlu receptor, but in the presence of glutamate or a glutamate agonist, the compounds of the present invention increase mGlu receptor response. The present positive modulators are expected to have their effect at mGlu receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGlu2 receptor. Thus, the compounds of the present invention are expected to be useful in the treatment of various neurological and psychiatric disorders associated with glutamate dysfunction described to be treated herein and others that can be treated by such positive modulators as are appreciated by those skilled in the art.

The present invention also relates to pharmaceutical compositions comprising at least one compound of the formula I, a tautomer thereof and/or a pharmaceutically acceptable salt thereof, optionally together with at least one physiologically acceptable carrier or auxiliary substance.

The present invention also relates to a method for treating a medical disorder, selected from neurological and psychiatric disorders associated with glutamate dysfunction, said method comprising administering an effective amount of at least one compound of the formula I, a tautomer thereof and/or a pharmaceutically acceptable salt thereof to a subject in need thereof.

The present invention also relates to a method for potentiation of metabotropic glutamate receptor activity in a mammal which comprises administering an effective amount of at least one compound of the formula I, a tautomer thereof and/or a pharmaceutically acceptable salt thereof.

The compounds of the formula I, their tautomers and their pharmaceutically acceptable salt are particularly useful for preparing a medicament for treating, controlling, ameliorating or reducing the risk of anxiety in a mammalian;

a medicament for preparing a medicament for treating, controlling, ameliorating or reducing the risk of depression in a mammalian; a medicament for treating, controlling, ameliorating or reducing the risk of migraine in a mammalian;

a medicament for treating, controlling, ameliorating or reducing the risk of schizophrenia in a mammalian;

a medicament for treating, controlling, ameliorating or reducing the risk of epilepsy in a mammalian;

a medicament for treating or ameliorating the symptoms associated with substance-related disorders in a mammalian.

The present invention also relates to
a method for treating, controlling, ameliorating or reducing the risk of anxiety in a mammalian;
a method for treating, controlling, ameliorating or reducing the risk of depression in a mammalian;
a method for treating, controlling, ameliorating or reducing the risk of schizophrenia in a mammalian;
a method for treating, controlling, ameliorating or reducing the risk of epilepsy in a mammalian;
a method for treating, controlling, ameliorating or reducing the risk of migraine in a mammalian;
a method for treating or ameliorating the symptoms associated with substance-related disorders in a mammalian;
which methods comprising administering an effective amount of at least one compound of the formula I, a tautomer thereof and/or a pharmaceutically acceptable salt thereof to a mammal in need thereof.

DETAILED DESCRIPTION OF THE INVENTION

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the conversion of the enantiomeric mixture of compounds compounds I into a diastereomeric mixture, e.g. by reaction with a chiral auxiliary such as a chiral acid or base, followed by separation of the individual diastereomers by standard methods, such as fractional crystallization or chromatography. The enantiomeric mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I is acidic, salts may be prepared from pharmaceutically acceptable non-toxic bases, including inorganic and organic bases. Salts derived from inorganic bases include salts, wherein the counter ion is aluminum, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylamino-ethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkoxyalkyl, alkylamino, dialkylamino and alkylsulfonyl denotes in each case a straight-chain or branched alkyl group having usually from 1 to 8 carbon atoms, frequently from 1 to 6 carbon atoms, preferably 1 to 4 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylpentyl, n-oxtyl, 1-methyloctyl, 2-methylheptyl, 1-ethylhexyl, 2-ethylhexyl, 1,2-dimethylhexyl, 1-propylpentyl and 2-propylpentyl.

The term "haloalkyl" as used herein and in the haloalkyl moieties of haloalkylsulfonyl, denotes in each case a straight-chain or branched alkyl group having usually from 1 to 8 carbon atoms, frequently from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl or $C_1$-$C_4$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2,2-trifluoro-1-methylethyl, 2,2,2-trifluoro-1-trifluormethylethyl, 3,3,3-trifluoropropyl, 4,4,4-trifluorobutyl and the like.

The term "alkylene" as used herein denotes a straight-chain or branched saturated bivalent alkandiyl group having usually from 1 to 5 carbon atoms, examples including methylene, 1,1-ethylene (1,1-ethandiyl), 1,2-ethylene (1,2-ethandiyl), 1,1-propandiyl, 1,2-propandiyl, 2,2-propandiyl, 1,3-propandiyl, 1,1-butandiyl, 1,2-butandiyl, 1,3-butandiyl, 1,4-butandiyl, 2,3-butandiyl, 2,2-butanediyl. The term "$C_1$-$C_5$-alkylene" as used herein denotes preferably a straight-chain bivalent alkandiyl group having from 1 to 5 carbon atoms, examples including methylene, 1,2-ethylene, 1,3-propandiyl, 1,4-butandiyl or 1,5-pentandiyl.

The term "alkenylene" as used herein denotes a straight-chain or branched bivalent alkandiyl group having usually from 2 to 5 carbon atoms, and comprising a ethylenically unsaturated double bond, examples including 1,2-ethendiyl, 1,3-propendiyl, 1-buten-1,4-diyl, 2-buten-1,4-diyl, 1-penten-1,5-diyl, 2-penten-1,5 diyl etc.

The term "alkoxy" as used herein denotes in each case a straight-chain or branched alkyl group which is bound via an oxygen atom and has usually from 1 to 8 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert-butyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy n-heptyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 3-ethylpentyloxy, 1-propylpentyloxy, n-oxtyloxy, 1-methyloctyloxy, 2-methylheptyloxy, 1-ethylhexyloxy, 2-ethylhexyloxy, 1,2-dimethylhexyloxy, 1-propylpentoxy and 2-propylpentyloxy.

The term "haloalkoxy" as used herein denotes in each case a straight-chain or branched alkoxy group having from 1 to 8 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and the like.

The term "cycloalkyl" as used herein and in the cycloalkyl moieties of $C_3$-$C_6$-cycloalkyl-methyl denotes in each case a mono- or bicyclic cycloaliphatic radical having usually from 3 to 8 C atoms or 3 to 6 C atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1] heptyl, and bicyclo[2.2.2]octyl.

The term "alkenyl" as used herein denotes in each case a singly unsaturated hydrocarbon radical having usually 2, 3, 4, 5, 6, 7 or 8 C-atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkynyl" as used herein denotes in each case a singly unsaturated hydrocarbon radical having usually 2, 3, 4, 5, 6, 7 or 8 C-atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "5- or 6-membered heterocyclic radicals comprising as ring members 1, 2 or 3 heteroatoms selected from N, O and S" include saturated, unsaturated and aromatic radicals (=hetaryl).

The term "hetaryl" as used herein denotes in each case a heterocyclic radical selected from the group consisting of monocyclic 5- or 6-membered heteroaromatic radicals comprising as ring members 1, 2 or 3 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

Saturated or unsaturated 5 or 6 membered heterocyclic rings comprise saturated or unsaturated, non-aromatic heterocyclic rings. Examples therefore include di- and tetrahydrofuranyl, pyrrolinyl, pyrrolidinyl, oxopyrrolidinyl, pyrazolinyl, pyrazolidinyl, imidazolinyl, imidazolidinyl, oxazolinyl, oxazolidinyl, oxo-oxazolidinyl, isoxazolinyl, isoxazolidinyl, piperidinyl, piperazinyl, morpholinyl, thiomorpholinyl, oxothiomorpholinyl, dioxothiomorpholinyl and the like.

The term "chemical bond" as used in the definition of X and Y has to be understood as a covalent bond (single bond).

A preferred embodiment of the present invention relates to compounds of the formula I, wherein Ar is a phenyl ring, and to their pharmaceutically acceptable salts and the tautomers. In other embodiments of the invention, Ar is a 5- or 6-membered aromatic heterocycle as defined above.

A preferred embodiment of the present invention relates to compounds of the formula I, wherein X is O, S, S(O)$_2$, NH or NR$^X$, in particular O, NH or NR$^X$, and to their pharmaceutically acceptable salts and the tautomers.

Amongst those compounds, wherein X is NR$^X$ the radical R$^x$ is preferably selected from the group consisting of $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl, benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, and a radical SO$_2$—R$^{x5}$, wherein R$^{x5}$ is as defined above. R$^{x5}$ is preferably selected from $C_1$-$C_4$-alkyl, $C_1$-$C_4$-fluoroalkyl, in particular CH$_2$CF$_3$, 5- or 6-membered hetaryl which may contain a fused benzene ring, in particular pyridyl, pyrimidinyl and quinolinyl, and phenyl, which is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. Amongst these, preference is given to compound of the formula I, wherein the radical R$^x$ a radical SO$_2$—R$^{x5}$, wherein R$^{x5}$ is as defined above. Likewise preferred are compounds of the formula I, wherein the radical R$^x$ is $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl or benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy.

In the embodiment, wherein X is NHC(O), the nitrogen atom can be either attached to A or to Ar.

Preferably, Y is selected from O, S, S(O)$_2$, NH or a chemical bond. A preferred embodiment of the present invention relates to compounds of the formula I, wherein Y is a chemical bond, and to their pharmaceutically acceptable salts and the tautomers. In another embodiment, Y is selected from the group consisting of O, S, S(O)$_2$ and NH. In this other embodiment, i.e. Y being O, S, S(O)$_2$ or NH, X is preferably a covalent bond.

A preferred embodiment of the present invention relates to compounds of the formula I, wherein A is CR$^a$R$^b$, wherein R$^a$ and R$^b$ are, independently of each other, selected from hydrogen, halogen, $C_1$-$C_4$-alkyl, $C_1$-$C_4$-haloalkyl, $C_1$-$C_4$-alkoxy and $C_1$-$C_4$-haloalkoxy, R$^b$ may also be OH, if R$^a$ is hydrogen, $C_1$-$C_4$-alkyl or $C_1$-$C_4$-haloalkyl. Preferably R$^a$ and R$^b$ are selected, independently of each other, from the group consisting of hydrogen, fluorine, methyl, ethyl and methoxy. In particular, R$^a$ and R$^b$ are hydrogen, i.e. A is CH$_2$.

A preferred embodiment of the present invention relates to compounds of the formula I, wherein Het is a 5-membered heteroaromatic ring having 1, 2 or 3 heteroatoms as ring members, the heteroatoms being selected from O, S and N, wherein the 5-membered heteroaromatic ring may carry a first substituent R$^{10}$ and additionally may carry 1 or 2 further substituents R$^{11}$, R$^{12}$. Het is in particular a heterocyclic radical selected from furyl, pyrrolyl, thienyl, pyrazolyl, thiazolyl, benzothiazolyl, oxazolyl, isoxazolyl, isothiazolyl, pyrazolyl, triazolyl and imidazolyl, wherein the heterocyclic radicals may carry a first substituent $R^{10}$ and additionally may carry 1 or 2 further substituents $R^{11}$, $R^{12}$, provided that X is NH or $NR^x$ if Het is imidazolyl or benzimidazolyl which may carry a first substituent $R^{10}$ and additionally may carry 1 or 2 further substituents $R^{11}$, $R^{12}$. In a very preferred embodiment of the invention, Het in formula I is pyrazolyl, in particular 4-pyrazolyl, which may carry a first substituent $R^{10}$ and additionally may carry a further substituent $R^{11}$.

In a very preferred embodiment of the invention Het is a radical of the following formulae Het-1 to Het-7, in particular of the following formulae Het-1 to Het-4:

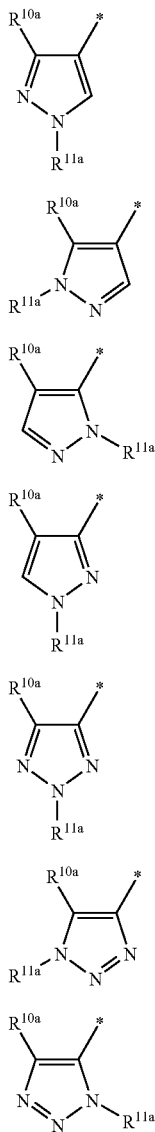

wherein $R^{10a}$ is hydrogen or has one of the meanings given for $R^{10}$, $R^{11a}$ is hydrogen or has one of the meanings given for $R^{11}$ and wherein * denotes the point of attachment to the moiety Y. In particular $R^{11a}$ is hydrogen. In particular $R^{10a}$ is different from hydrogen. Preferably $R^{10a}$ has one of the meanings given below as preferred meanings for $R^{10}$. More preferably $R^{10a}$ is $C_1$-$C_8$-haloalkyl, in particular $C_1$-$C_2$-fluoroalkyl, $C_3$-$C_8$-cycloalkyl, which is unsubstituted or carries 1, 2, 3 or 4 radicals selected from halogen, $C_1$-$C_4$-alkyl and $C_1$-$C_4$-alkoxy, $C_1$-$C_8$-alkyl, which is unsubstituted or carries one radical selected from OH, $C_1$-$C_4$-alkoxy and phenyl wherein the phenyl ring itself is unsubstituted or carries 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy, and most preferably phenyl, which is unsubstituted or may carry 1, 2, 3, 4 or 5 substituents as mentioned above, which are preferably selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy.

In a first particular embodiment of the present invention, $R^1$ is selected from the group of C(=O)—$R^4$, C(=O)—$OR^5$, $NR^6R^7$, C(=O)$NR^6R^7$, $SO_2NR^6R^7$, $NR^8C$(=O)$R^9$, $SO_2R^9$ and $NR^8SO_2R^9$, wherein $R^4$, $R^5$, $R^6$, $R^7$, $R^8$ and $R^9$ are as defined herein. In the first particular embodiment, Ar is preferably a benzene ring. In this first particular embodiment $R^1$ is preferably located in the 3- or 4-position of the benzene ring.

Amongst the compounds of the first particular embodiment, preference is given to those, wherein Ar is a benzene ring and $R^1$ is C(=O)—$R^4$, which is located in the 3- or 4-position of the benzene ring.

Amongst the compounds I, wherein $R^1$ is C(=O)—$R^4$, a particular embodiment relates to those compounds, wherein $R^4$ is selected from $C_3$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, in particular $C_3$-$C_8$-alkyl, $C_1$-$C_3$-alkyl which is substituted with a radical selected from $C_1$-$C_4$-alkoxy or phenyl which is unsubstituted or substituted as given above, $C_1$-$C_8$-haloalkyl, in particular $C_1$-$C_2$-fluoroalkyl, $C_3$-$C_8$-cycloalkyl, which is unsubstituted or carries 1, 2, 3 or 4 radicals selected from halogen, $C_1$-$C_4$-alkyl and $C_1$-$C_4$-alkoxy, phenyl, which is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, 5- or 6-membered hetaryl, having 1, 2 or 3 heteroatoms as ring members, the heteroatoms being selected from O, S and N, in particular furyl, thienyl, oxazolyl, thiazolyl, isoxazolyl, isothiazolyl, 1,2,4-triazolyl, 1,2,3-triazolyl, pyridyl, pyrimidinyl or pyrazinyl, wherein hetaryl is unsubstituted or carries 1, 2, 3 or 4 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy.

Amongst the compounds I, wherein $R^1$ is C(=O)—$R^4$, another particular embodiment relates to those compounds, wherein $R^4$ together with $R^2$ forms a $C_1$-$C_5$-alkylene or $C_2$-$C_5$-alkenylene moiety, in particular a ethan-1,2-diyl moiety or propan-1,3-diyl moiety, wherein one $CH_2$-moiety may be replaced by oxygen, sulphur or a N—$R^{4c}$-moiety, and wherein $C_1$-$C_5$-alkylene and $C_2$-$C_5$-alkenylene (and likewise the ethan-1,2-diyl moiety and the propan-1,3-diyl moiety) may be unsubstituted or carry 1, 2, 3, or 4 radicals, in particular 0, 1 or 2 radicals, selected from halogen, CN, OH, $NH_2$, $C_1$-$C_4$-alkyl, in particular methyl, $C_3$-$C_6$-cycloalkyl, in particular cyclopropyl, cyclobutyl or cyclopentyl, $C_1$-$C_4$-haloalkyl, in particular difluoromethyl or trifluoromethyl, $C_1$-$C_4$-alkylamino, such as methylamino, ethylamino, di-($C_1$-$C_4$-alkyl)amino, such as dimethylamino, diethylamino, $C_1$-$C_4$-alkoxy such as methoxy or ethoxy, and $C_1$-$C_4$-haloalkoxy, such as difluoromethyloxy or trifluoromethoxy, and wherein $R^{4c}$ is as defined herein. In one embodiment $R^{4c}$ is selected from hydrogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. Preferably, $R^{4c}$ is selected from hydrogen, $C_1$-$C_4$-alkyl, $C_3$-$C_6$-cycloalkyl, $C_1$-$C_4$-haloalkyl, $C_3$-$C_6$-cycloalkylmethyl and benzyl, wherein the phenyl ring is unsubstituted or may carry a substituent selected from halogen, difluoromethyl, trifluoromethyl, difluoromethoxy and trifluoromethoxy. In particular, $R^{4c}$ is selected from hydrogen, methyl, ethyl, 2-bromoethyl, 2,2-difluoroethyl, 2,2,2-trifluoroethyl, n-propyl, 3,3,3-trifluoropropyl, n-butyl, 4,4,4-trifluorobutyl, 3-methylbutyl, 2-trifluoromethoxyethyl, 2-methylpropyl, cyclopentylmethyl, cyclohexylmethyl, benzyl, 4-trifluoromethoxybenzyl and phenyl.

Amongst the compounds of the first particular embodiment, preference is also given to those, wherein Ar is a benzene ring and $R^1$ is C(=O)—$OR^5$, which is located in the 3- or 4-position of the benzene ring. $R^5$ is preferably $C_1$-$C_4$-alkyl, $C_3$-$C_6$-cycloalkyl, $C_3$-$C_6$-cycloalkylmethyl or benzyl.

Amongst the compounds of the first particular embodiment, preference is also given to those, wherein Ar is a benzene ring and $R^1$ is $NR^6R^7$, which is located in the 3- or 4-position of the benzene ring. In the radical $NR^6R^7$, $R^6$ is preferably hydrogen, $C_1$-$C_4$-alkyl, $C_1$-$C_4$-alkoxy, CHO or C(O)—$C_1$-$C_4$-alkyl such as acetyl or propionyl. $R^7$ is preferably hydrogen or $C_1$-$C_4$-alkyl. Preference is also given to compounds, wherein the moiety $NR^6R^7$ forms piperidin-1-yl, pyrrolidin-1-yl, morpholin-4-yl, piperazin-1-yl or 4-methylpiperazin-1-yl radical.

Amongst the compounds of the first particular embodiment, preference is also given to those, wherein Ar is a benzene ring and $R^1$ is C(=O)$NR^6R^7$, which is located in the 3- or 4-position of the benzene ring. In the radical C(=O)$NR^6R^7$, $R^6$ is preferably hydrogen, $C_1$-$C_4$-alkyl or $C_1$-$C_4$-alkoxy. $R^7$ is preferably hydrogen or $C_1$-$C_4$-alkyl. Preference is also given to compounds, wherein the moiety $NR^6R^7$ forms piperidin-1-yl, pyrrolidin-1-yl, morpholin-4-yl, piperazin-1-yl or 4-methylpiperazin-1-yl radical.

Amongst the compounds of the first particular embodiment, preference is also given to those, wherein Ar is a benzene ring and $R^1$ is $SO_2NR^6R^7$, which is located in the 3- or 4-position of the benzene ring. In the radical $SO_2NR^6R^7$, $R^6$ is preferably hydrogen, $C_1$-$C_4$-alkyl or $C_1$-$C_4$-alkoxy. $R^7$ is preferably hydrogen or $C_1$-$C_4$-alkyl. Preference is also given to compounds, wherein the moiety $NR^6R^7$ forms piperidin-1-yl, pyrrolidin-1-yl, morpholin-4-yl, piperazin-1-yl or 4-methylpiperazin-1-yl radical.

Amongst the compounds of the first particular embodiment, preference is also given to those, wherein Ar is a benzene ring and $R^1$ is $NR^8C(=O)R^9$, which is located in the 3- or 4-position of the benzene ring. In the radical $NR^8C(=O)R^9$, $R^8$ is preferably hydrogen. $R^9$ is preferably selected from the group consisting of hydrogen,
$C_1$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, in particular $C_1$-$C_4$-alkyl, $C_1$-$C_4$-alkyl which is substituted with a radical selected from $C_1$-$C_4$-alkoxy or phenyl which is unsubstituted or substituted as given above,
$C_1$-$C_8$-haloalkyl, in particular $C_1$-$C_2$-fluoroalkyl,
$C_3$-$C_8$-cycloalkyl, which is unsubstituted or carries 1, 2, 3 or 4 radicals selected from halogen, $C_1$-$C_4$-alkyl and $C_1$-$C_4$-alkoxy,
phenyl, which is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy,
5- or 6-membered hetaryl, having 1, 2 or 3 heteroatoms as ring members, the heteroatoms being selected from O, S and N, in particular furyl, thienyl, oxazolyl, thiazolyl, isoxazolyl, isothiazolyl, 1,2,4-triazolyl, 1,2,3-triazolyl, pyridyl, pyrimidinyl or pyrazinyl, wherein hetaryl is unsubstituted or carries 1, 2, 3 or 4 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy.

Amongst the compounds of the first particular embodiment, preference is also given to those, wherein Ar is a benzene ring and $R^1$ is $NR^8SO_2R^9$, which is located in the 3- or 4-position of the benzene ring. In the radical $NR^8SO_2R^9$, $R^8$ is preferably hydrogen. $R^9$ is preferably selected from the group consisting of $C_1$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, in particular $C_1$-$C_4$-alkyl, $C_1$-$C_4$-alkyl which is substituted with a radical selected from $C_1$-$C_4$-alkoxy or phenyl which is unsubstituted or substituted as given above,
$C_1$-$C_8$-haloalkyl, in particular $C_1$-$C_2$-fluoroalkyl,
$C_3$-$C_8$-cycloalkyl, which is unsubstituted or carries 1, 2, 3 or 4 radicals selected from halogen, $C_1$-$C_4$-alkyl and $C_1$-$C_4$-alkoxy,
phenyl, which is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy,
5- or 6-membered hetaryl, having 1, 2 or 3 heteroatoms as ring members, the heteroatoms being selected from O, S and N, in particular furyl, thienyl, oxazolyl, thiazolyl, isoxazolyl, isothiazolyl, 1,2,4-triazolyl, 1,2,3-triazolyl, pyridyl, pyrimidinyl or pyrazinyl, wherein hetaryl is unsubstituted or carries 1, 2, 3 or 4 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy.

Amongst the compounds of the first particular embodiment, preference is also given to those, wherein Ar is a benzene ring and $R^1$ is $SO_2R^9$, which is located in the 3- or 4-position of the benzene ring. In the radical $SO_2R^9$, $R^9$ is preferably selected from the group consisting of

- $C_1$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, in particular $C_1$-$C_4$-alkyl, $C_1$-$C_4$-alkyl which is substituted with a radical selected from $C_1$-$C_4$-alkoxy or phenyl which is unsubstituted or substituted as given above,
- $C_1$-$C_8$-haloalkyl, in particular $C_1$-$C_2$-fluoroalkyl,
- $C_3$-$C_8$-cycloalkyl, which is unsubstituted or carries 1, 2, 3 or 4 radicals selected from halogen, $C_1$-$C_4$-alkyl and $C_1$-$C_4$-alkoxy,
- phenyl, which is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy,
- 5- or 6-membered hetaryl, having 1, 2 or 3 heteroatoms as ring members, the heteroatoms being selected from O, S and N, in particular furyl, thienyl, oxazolyl, thiazolyl, isoxazolyl, isothiazolyl, 1,2,4-triazolyl, 1,2,3-triazolyl, pyridyl, pyrimidinyl or pyrazinyl, wherein hetaryl is unsubstituted or carries 1, 2, 3 or 4 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy.

In a second particular embodiment of the present invention, $R^1$ is selected from the group of Het', O-Het', $CH_2$-Het', $CH(CH_3)$-Het', CH(OH)-Het', S-Het', $OCH_2$-Het, wherein Het' is a 5- or 6-membered saturated, unsaturated or aromatic heterocycle, having 1, 2 or 3 heteroatoms as ring members, the heteroatoms being selected from O, S and N, the heterocycle may be unsubstituted or may carry 1, 2, 3 or 4 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. In the second particular embodiment Ar is preferably a benzene ring and $R^1$ is preferably located in the 3- or 4-position of the benzene ring. In the second particular embodiment is given to those compounds, wherein $R^1$ is Het'. Het' is preferably furyl, thienyl, oxazolyl, thiazolyl, isoxazolyl, isothiazolyl, 1,2,4-triazolyl, 1,2,3-triazolyl, pyridyl, pyrimidinyl or pyrazinyl.

In a third particular embodiment of the present invention, $R^1$ is selected from the group consisting of

- $C_1$-$C_8$-alkoxy, which is unsubstituted or carries one radical selected from OH, $C_1$-$C_4$-alkoxy and $C_3$-$C_8$-cycloalkyl,
- $C_1$-$C_8$-haloalkoxy,
- $C_3$-$C_8$-cycloalkyloxy, wherein the last two mentioned radicals are unsubstituted or carry 1, 2, 3 or 4 radicals selected from halogen, $C_1$-$C_4$-alkyl and $C_1$-$C_4$-alkoxy,
- O-phenyl, $CH_2$-phenyl, $CH(CH_3)$-phenyl, CH(OH)phenyl, S-phenyl, and O—$CH_2$-phenyl, wherein the phenyl ring in the last six mentioned radicals may be unsubstituted or may carry 1, 2, 3, 4 or 5 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy.

In the third particular embodiment Ar is preferably a benzene ring and $R^1$ is preferably located in the 3- or 4-position of the benzene ring.

In a fourth particular embodiment of the present invention, $R^1$ and $R^2$ are bound to adjacent carbon atoms and together the atoms, to which they are attached, form a 5- or 6-membered heterocyclic ring fused to Ar and having 1, 2 or 3 nitrogen atoms as ring members or 1 oxygen atom and optionally a further heteroatom selected from O, S and N as ring members, and wherein the fused heterocyclic ring may be unsubstituted or may carry 1, 2, 3, 4 or 5 substituents selected from halogen, OH, CN, $NH_2$, $C_1$-$C_4$-alkyl, $C_3$-$C_6$-cycloalkyl, $C_1$-$C_4$-alkoxy, $C_1$-$C_4$-alkylamino, di-($C_1$-$C_4$-alkyl)amino, $C_1$-$C_4$-haloalkyl, $C_1$-$C_4$-haloalkoxy, $C_1$-$C_4$-alkylsulfonyl, $C_1$-$C_4$-haloalkylsulfonyl and phenylsulfonyl, wherein the phenyl ring may be unsubstituted or may carry 1, 2, 3 or 4 substituents selected from halogen, CN, $C_1$-$C_4$-alkyl, $C_1$-$C_4$-haloalkyl, $C_1$-$C_4$-alkoxy and $C_1$-$C_4$-haloalkoxy.

In the fourth particular embodiment Ar is preferably a benzene ring and $R^1$ and $R^2$ are preferably located in the 3- and 4-position of the benzene ring. In particular, $R^1$ and $R^2$ together with the benzene ring form a bicyclic ring which is attached to the remainder of the molecule via the benzene ring, the bicyclic ring being selected from indolyl, benzopyrazolyl, benzimidazolyl, benzoxazolyl and benzotriazolyl, wherein the bicyclic ring is unsubstituted or substituted as given above.

$R^2$ is preferably selected from hydrogen, halogen, in particular fluorine or chlorine, $C_1$-$C_4$-alkyl, in particular methyl or ethyl, $C_1$-$C_4$-haloalkyl, in particular trifluoromethyl, $C_1$-$C_4$-alkoxy, in particular methoxy or ethoxy, and $C_1$-$C_4$-haloalkoxy, in particular difluoromethoxy or trifluoromethoxy.

$R^3$ is preferably selected from hydrogen, halogen, in particular fluorine or chlorine, $C_1$-$C_4$-alkyl, in particular methyl or ethyl, $C_1$-$C_4$-haloalkyl, in particular trifluoromethyl, $C_1$-$C_4$-alkoxy, in particular methoxy or ethoxy, and $C_1$-$C_4$-haloalkoxy, in particular difluoromethoxy or trifluoromethoxy. In particular, $R^3$ is hydrogen.

Apart from that, $R^{10}$ is preferably selected from
- halogen,
- cyano
- $C_1$-$C_8$-alkyl, which is unsubstituted or carries one radical selected from OH, $C_1$-$C_4$-alkoxy and phenyl wherein the phenyl ring itself is unsubstituted or carries 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy,
- $C_1$-$C_8$-alkoxy,
- $C_1$-$C_8$-haloalkyl,
- $C_1$-$C_8$-haloalkoxy,
- $C_3$-$C_8$-cycloalkyl, which is unsubstituted or carries 1, 2, 3 or 4 radicals selected from halogen, $C_1$-$C_4$-alkyl and $C_1$-$C_4$-alkoxy,
- $C_3$-$C_8$-cycloalkoxy, which is unsubstituted or carries 1, 2, 3 or 4 radicals selected from halogen, $C_1$-$C_4$-alkyl and $C_1$-$C_4$-alkoxy,
- $C(=O)—R^{13}$,
- $C(=O)—OR^{14}$,
- $NR^{15}R^{16}$,
- $C(=O)NR^{15}R^{16}$,
- $SO_2R^{17}$,
- phenyl, which is unsubstituted or may carry 1, 2, 3, 4 or 5 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy,
- 5- or 6-membered heteroaryl, in particular oxazolyl, thiazolyl, isoxazolyl, isothiazolyl, pyrazolyl, imidazolyl, pyridyl, pyrimidinyl or pyrazinyl, having 1, 2 or 3 heteroatoms as ring members, the heteroatoms being selected from O, S and N, which is unsubstituted or may carry 1, 2 or 3 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1 or 2 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy.

$R^{11}$ is preferably selected from halogen, in particular fluorine or chlorine, $C_1$-$C_4$-alkyl, in particular methyl or ethyl, $C_1$-$C_4$-haloalkyl, in particular trifluoromethyl, $C_1$-$C_4$-alkoxy, in particular methoxy or ethoxy, and $C_1$-$C_4$-haloalkoxy, in particular difluoromethoxy or trifluoromethoxy.

$R^{12}$ is preferably selected from hydrogen, halogen, in particular fluorine or chlorine, $C_1$-$C_4$-alkyl, in particular methyl or ethyl, $C_1$-$C_4$-haloalkyl, in particular trifluoromethyl, $C_1$-$C_4$-alkoxy, in particular methoxy or ethoxy, and $C_1$-$C_4$-haloalkoxy, in particular difluoromethoxy or trifluoromethoxy. In particular, $R^{12}$ is not present.

In the radical $C(O)R^{13}$, $R^{13}$ is preferably selected from:
$C_1$-$C_4$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, in particular $C_1$-$C_4$-alkyl, $C_1$-$C_4$-alkyl which is substituted with a radical selected from $C_1$-$C_4$-alkoxy or phenyl which is unsubstituted or substituted as given above, $C_1$-$C_8$-haloalkyl, in particular $C_1$-$C_2$-fluoroalkyl, $C_3$-$C_8$-cycloalkyl, which is unsubstituted or carries 1, 2, 3 or 4 radicals selected from halogen, $C_1$-$C_4$-alkyl and $C_1$-$C_4$-alkoxy, phenyl, which is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, 5- or 6-membered hetaryl, having 1, 2 or 3 heteroatoms as ring members, the heteroatoms being selected from O, S and N, in particular furyl, thienyl, oxazolyl, thiazolyl, isoxazolyl, isothiazolyl, 1,2,4-triazolyl, 1,2,3-triazolyl, pyridyl, pyrimidinyl or pyrazinyl, wherein hetaryl is unsubstituted or carries 1, 2, 3 or 4 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy.

In the radical $C(=O)$—$OR^{14}$, $R^{14}$ is preferably $C_1$-$C_4$-alkyl, $C_3$-$C_6$-cycloalkyl, $C_3$-$C_6$-cycloalkylmethyl or benzyl.

In the radical $NR^{15}R^{16}$, $R^{15}$ is preferably hydrogen, $C_1$-$C_4$-alkyl, $C_1$-$C_4$-alkoxy, CHO or $C(O)$—$C_1$-$C_4$-alkyl such as acetyl or propionyl. $R^{16}$ is preferably hydrogen or $C_1$-$C_4$-alkyl. Preference is also given to compounds, wherein the moiety $NR^{15}R^{16}$ forms piperidin-1-yl, pyrrolidin-1-yl, morpholin-4-yl, piperazin-1-yl or 4-methylpiperazin-1-yl radical.

In the radical $C(=O)NR^{15}R^{16}$, $R^{15}$ is preferably hydrogen, $C_1$-$C_4$-alkyl or $C_1$-$C_4$-alkoxy. $R^{16}$ is preferably hydrogen or $C_1$-$C_4$-alkyl. Preference is also given to compounds, where in the radical $C(=O)NR^{15}R^{16}$, the moiety $NR^{15}R^{16}$ forms piperidin-1-yl, pyrrolidin-1-yl, morpholin-4-yl, piperazin-1-yl or 4-methylpiperazin-1-yl radical.

In the radical $SO_2R^{17}$, $R^{17}$ is preferably selected from:
$C_1$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, in particular $C_1$-$C_4$-alkyl, $C_1$-$C_4$-alkyl which is substituted with a radical selected from $C_1$-$C_4$-alkoxy or phenyl which is unsubstituted or substituted as given above, $C_1$-$C_8$-haloalkyl, in particular $C_1$-$C_2$-fluoroalkyl, phenyl, which is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, A preferred embodiment of the invention relates to compounds of the formula I, and to their tautomers and pharmaceutically acceptable salts, wherein
Ar is a benzene ring,
A is $CR^aR^b$, wherein $R^a$ and $R^b$ are, independently of each other, selected from hydrogen, halogen, $C_1$-$C_4$-alkyl, $C_1$-$C_4$-haloalkyl, $C_1$-$C_4$-alkoxy and $C_1$-$C_4$-haloalkoxy, $R^b$ may also be OH, if $R^a$ is hydrogen, $C_1$-$C_4$-alkyl or $C_1$-$C_4$-haloalkyl,
X is NH or N—$R^x$, and
Y is a chemical bond.

Another preferred embodiment of the invention relates to compounds of the formula I, and to their tautomers and pharmaceutically acceptable salts, wherein
Ar is a benzene ring,
A is $CR^aR^b$, wherein $R^a$ and $R^b$ are, independently of each other, selected from hydrogen, halogen, $C_1$-$C_4$-alkyl, $C_1$-$C_4$-haloalkyl, $C_1$-$C_4$-alkoxy and $C_1$-$C_4$-haloalkoxy, $R^b$ may also be OH, if $R^a$ is hydrogen, $C_1$-$C_4$-alkyl or $C_1$-$C_4$-haloalkyl,
X is O, and
Y is a chemical bond,
provided that Het is selected from furyl, pyrrolyl, thienyl, pyrazolyl, thiazolyl, benzothiazolyl, oxazolyl, isoxazolyl, isothiazolyl, pyrazinyl, pyridazinyl, triazolyl, thiadiazolyl, imidazolonyl, oxazolonyl, thiazolonyl, tetrahydrotriazolopyridyl, tetrahydrotriazolopyrimidinyl, isoindolyl, pyridonyl, phatalazinyl, naphtyridinyl, quinoxalinyl, quinazolyl, oxazolopyridyl, thiazolopyridyl, imidazopyridazinyl, oxazolopyridazinyl, thiazolopyridazinyl, cinnolinyl, pteridinyl, furazanyl, benzotriazolyl, pyrazolopyridinyl and naphtyridinyl, wherein the aforementioned heterocyclic radicals may carry a first substituent $R^{10}$ and additionally may carry 1 or 2 further substituents $R^{11}$, $R^{12}$.

A particular preferred embodiment relates to compounds of the formula I, wherein the moiety

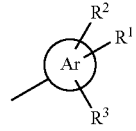

is of the formula

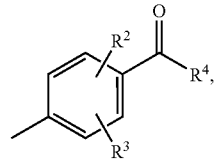

wherein $R^2$, $R^3$ and $R^4$ are as defined above. Amongst these compounds particular preference is given to compounds, wherein $R^2$ and $R^3$ are hydrogen and $R^4$ is as defined above and preferably selected from $C_3$-$C_8$-alkyl, $C_1$-$C_4$-haloalkyl, in particular $C_1$-$C_4$-fluoroalkyl, $C_3$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy. In particular $R^4$ is $C_3$-$C_8$-alkyl, $C_1$-$C_3$-alkyl which is substituted with a radical selected from $C_1$-$C_4$-alkoxy and $C_3$-$C_6$-cycloalkyl, or $C_1$-$C_4$-haloalkyl, in particular $C_1$-$C_4$-fluoroalkyl.

Likewise preference is given to compounds of this particularly preferred embodiment, wherein $R^3$ is hydrogen and $R^4$ together with $R^2$ forms a $C_1$-$C_5$-alkylene or $C_2$-$C_5$-alkenylene moiety, in particular a ethan-1,2-diyl moiety, ethen-1,2-diyl moiety, 1,3-propendiyl moiety or propan-1,3-diyl moiety, wherein one $CH_2$-moiety may be replaced by oxygen, sulphur or a N—$R^{4c}$ moiety, and wherein $C_1$-$C_5$-alkylene and $C_2$-$C_5$-alkenylene (and likewise the ethan-1,2-diyl moiety, ethen-1, 2-diyl moiety, 1,3-propendiyl moiety and the propan-1,3-diyl moiety) may be unsubstituted or carry 1, 2, 3, or 4 radicals, in particular 0, 1 or 2 radicals, selected from halogen, CN, OH, $NH_2$, $C_1$-$C_4$-alkyl, in particular methyl, $C_3$-$C_6$-cycloalkyl, in particular cyclopropyl, cyclobutyl or cyclopentyl, $C_1$-$C_4$-haloalkyl, in particular difluoromethyl or trifluoromethyl, $C_1$-$C_4$-alkylamino, such as methylamino, ethylamino, di-($C_1$-$C_4$-alkyl)amino, such as dimethylamino, diethylamino, $C_1$-$C_4$-alkoxy such as methoxy or ethoxy, and $C_1$-$C_4$-haloalkoxy, such as difluoromethyloxy or trifluoromethoxy, and wherein $R^{4c}$ is as defined herein. Preferably, $R^{4c}$ is selected from $C_1$-$C_6$-alkyl, which is unsubstituted or carries an alkoxy or haloalkoxy radical, in particular $C_1$-$C_4$-alkyl, $C_3$-$C_6$-cycloalkyl, $C_1$-$C_4$-haloalkyl, $C_3$-$C_6$-cycloalkylmethyl and benzyl, wherein the phenyl ring is unsubstituted or may carry a substituent selected from halogen, difluoromethyl, trifluoromethyl, difluoromethoxy and trifluoromethoxy. In particular, $R^{4c}$ is selected from methyl, ethyl, 2-bromoethyl, 2,2-difluoroethyl, 2,2,2-trifluoroethyl, n-propyl, 3,3,3-trifluoropropyl, n-butyl, 4,4,4-trifluorobutyl, 3-methylbutyl, 2-trifluoromethoxyethyl, 2-methylpropyl, cyclopentylmethyl, cyclohexylmethyl, benzyl and 4-trifluoromethoxybenzyl.

More preference is given to compounds of this particularly preferred embodiment, wherein the moiety

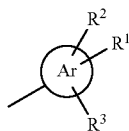

is of the formula

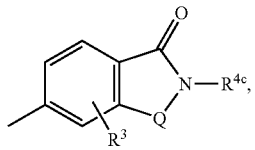

wherein $R^3$ and $R^{4c}$ are as defined above and wherein -Q- is —$C(R^{Q1}R^{Q2})$—, —$C(R^{Q1}R^{Q2})$—$C(R^{Q3}R^{Q4})$— or —$C(R^{Q1})$=$C(R^{Q2})$—, wherein $R^{Q1}$, $R^{Q2}$, $R^{Q3}$, $R^{Q4}$ are each independently of each other selected from hydrogen, halogen, CN, OH, $NH_2$, $C_1$-$C_4$-alkyl, $C_3$-$C_6$-cycloalkyl, $C_1$-$C_4$-haloalkyl, $C_1$-$C_4$-alkylamino, di-($C_1$-$C_4$-alkyl)amino, $C_1$-$C_4$-alkoxy and $C_1$-$C_4$-haloalkoxy. Preferably, -Q- is —$C(R^{Q1}R^{Q2})$—. Preferably, $R^{Q1}$, $R^{Q2}$, $R^{Q3}$, $R^{Q4}$ are each independently of each other selected from hydrogen, halogen, $C_1$-$C_4$-alkyl, $C_3$-$C_6$-cycloalkyl and $C_1$-$C_4$-haloalkyl. In particular Q is $CH_2$, $CH_2CH_2$ or CH=CH, more preferably $CH_2$. More preferably $R^3$ is hydrogen.

In these preferred embodiments, Het, $R^x$, $R^1$, $R^2$ and $R^3$ are as defined above and have preferably one of the meanings given as preferred meanings.

In these preferred embodiments, Het is particularly preferable a 5-membered heteroaromatic ring having 1, 2 or 3 heteroatoms as ring members, wherein the 5-membered heteroaromatic ring may carry a first substituent $R^{10}$ and additionally may carry 1 or 2 further substituents $R^{11}$, $R^{12}$, wherein $R^{10}$, $R^{11}$ and $R^{12}$ are as defined above and have preferably one of the meanings given as preferred meanings.

Thus, a particular preferred embodiment of the present invention relates to compounds of the formula Ia and to the pharmaceutically acceptable salts and the tautomers thereof.

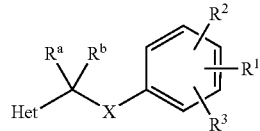

(Ia)

In formula Ia, X, $R^a$, $R^b$, Het, $R^x$, $R^1$, $R^2$ and $R^3$ are as defined herein and have preferably one of the meanings given as preferred meanings. Preferably X in formula Ia is NH or N—$R^x$. In formula Ia, X may also preferably be O, if Het is selected from furyl, pyrrolyl, thienyl, pyrazolyl, thiazolyl, benzothiazolyl, oxazolyl, isoxazolyl, isothiazolyl, pyrazinyl, pyridazinyl, triazolyl, thiadiazolyl, imidazolonyl, oxazolonyl, thiazolonyl, tetrahydrotriazolopyridyl, tetrahydrotriazolopyrimidinyl, isoindolyl, pyridonyl, phatalazinyl, naphtyridinyl, quinoxalinyl, quinazolyl, oxazolopyridyl, thiazolopyridyl, imidazopyridazinyl, oxazolopyridazinyl, thiazolopyridazinyl, cinnolinyl, pteridinyl, furazanyl, benzotriazolyl, pyrazolopyridinyl and naphtyridinyl, wherein the aforementioned heterocyclic radicals may carry a first substituent $R^{10}$ and additionally may carry 1 or 2 further substituents $R^{11}$, $R^{12}$.

Preferably $R^a$ and $R^b$ are selected, independently of each other, from the group consisting of hydrogen, fluorine, methyl, ethyl and methoxy. In particular, $R^a$ and $R^b$ are hydrogen.

Amongst those compounds Ia, wherein X is $NR^X$ the radical $R^x$ is preferably selected from the group consisting of $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl, benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, and a radical $SO_2$—$R^{X5}$, wherein $R^{x5}$ is as defined above. $R^{x5}$ is preferably selected from $C_1$-$C_4$-alkyl, $C_1$-$C_4$-fluoroalkyl, in particular $CH_2CF_3$, 5- or 6-membered hetaryl which may contain a fused benzene ring, in particular pyridyl, pyrimidinyl and quinolinyl, and phenyl, which is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. Amongst these, preference is given to compound of the formula Ia, wherein the radical $R^x$ a radical SO₂—R^{x5}, wherein R^{x5} is as defined above. Likewise preferred are compounds of the formula Ia, wherein the radical R^x is $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl or benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy.

A preferred embodiment of the present invention relates to compounds of the formula Ia, wherein Het is a 5-membered heteroaromatic ring having 1, 2 or 3 heteroatoms as ring members, wherein the 5-membered heteroaromatic ring may carry a first substituent $R^{10}$ and additionally may carry 1 or 2 further substituents $R^{11}$, $R^{12}$. Het is in particular a heterocyclic radical selected from furyl, pyrrolyl, thienyl, pyrazolyl, thiazolyl, benzothiazolyl, oxazolyl, isoxazolyl, isothiazolyl, pyrazolyl, triazolyl and imidazolyl, wherein the heterocyclic radicals may carry a first substituent $R^{10}$ and additionally may carry 1 or 2 further substituents $R^{11}$, $R^{12}$, provided that X is NH or NR^X if Het is imidazolyl or benzimidazolyl which may carry a first substituent $R^{10}$ and additionally may carry 1 or 2 further substituents $R^{11}$, $R^{12}$. In a more preferred embodiment of the compounds of formula Ia, Het is a radical of the formulae Het-1 to Het-7, in particular of the formulae Het-1, Het-2, Het-3 and Het-4, as defined above, wherein $R^{10a}$ and $R^{11a}$ have the meanings given above, in particular the preferred meanings. In a very preferred embodiment of the invention, Het in formula Ia is pyrazolyl, in particular 4-pyrazolyl, which may carry a first substituent $R^{10}$ and additionally may carry a further substituent $R^{11}$. Most preferably, Het is a radical of the formulae Het-1 to Het-4 as defined above, wherein $R^{10a}$ and $R^{11a}$ have the meanings given above, in particular the preferred meanings.

Amongst the compounds of the formula Ia, particular preference is given to those, wherein the moiety

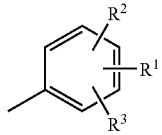

is of the formula

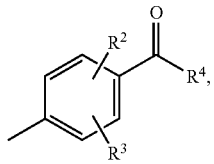

wherein $R^2$, $R^3$ and $R^4$ are as defined above. Amongst these compounds particular preference is given to compounds, wherein $R^2$ and $R^3$ are hydrogen and $R^4$ is as defined above and preferably selected from $C_3$-$C_8$-alkyl, $C_1$-$C_4$-haloalkyl, in particular $C_1$-$C_4$-fluoroalkyl, $C_3$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy. In particular $R^4$ is $C_3$-$C_8$-alkyl, $C_1$-$C_3$-alkyl which is substituted with a radical selected from $C_1$-$C_4$-alkoxy and $C_3$-$C_6$-cycloalkyl, or $C_1$-$C_4$-haloalkyl, in particular $C_1$-$C_4$-fluoroalkyl.

Likewise preference is given to compounds of the formula Ia, wherein $R^3$ is hydrogen and $R^4$ together with $R^2$ forms a $C_1$-$C_5$-alkylene or $C_2$-$C_5$-alkenylene moiety, in particular a ethan-1,2-diyl moiety, ethen-1,2-diyl moiety, 1,3-propendiyl moiety or propan-1,3-diyl moiety, wherein one $CH_2$-moiety may be replaced by oxygen, sulphur or a N—$R^{4c}$-moiety, and wherein $C_1$-$C_5$-alkylene and $C_2$-$C_5$-alkenylene (and likewise the ethan-1,2-diyl moiety, ethen-1,2-diyl moiety, 1,3-propendiyl moiety and the propan-1,3-diyl moiety) may be unsubstituted or carry 1, 2, 3, or 4 radicals, in particular 0, 1 or 2 radicals, selected from halogen, CN, OH, $NH_2$, $C_1$-$C_4$-alkyl, in particular methyl, $C_3$-$C_6$-cycloalkyl, in particular cyclopropyl, cyclobutyl or cyclopentyl, $C_1$-$C_4$-haloalkyl, in particular difluoromethyl or trifluoromethyl, $C_1$-$C_4$-alkylamino, such as methylamino, ethylamino, di-($C_1$-$C_4$-alkyl)amino, such as dimethylamino, diethylamino, $C_1$-$C_4$-alkoxy such as methoxy or ethoxy, and $C_1$-$C_4$-haloalkoxy, such as difluoromethyloxy or trifluoromethoxy, and wherein $R^{4c}$ is as defined herein. Preferably, $R^{4c}$ is selected from $C_1$-$C_6$-alkyl, which is unsubstituted or carries an alkoxy or haloalkoxy radical, in particular $C_1$-$C_4$-alkyl, $C_3$-$C_6$-cycloalkyl, $C_1$-$C_4$-haloalkyl, $C_3$-$C_6$-cycloalkylmethyl and benzyl, wherein the phenyl ring is unsubstituted or may carry a substituent selected from halogen, difluoromethyl, trifluoromethyl, difluoromethoxy and trifluoromethoxy. In particular, $R^{4c}$ is selected from methyl, ethyl, 2-bromoethyl, 2,2-difluoroethyl, 2,2,2-trifluoroethyl, n-propyl, 3,3,3-trifluoropropyl, n-butyl, 4,4,4-trifluorobutyl, 3-methylbutyl, 2-trifluoromethoxyethyl, 2-methylpropyl, cyclopentylmethyl, cyclohexylmethyl, benzyl and 4-trifluoromethoxybenzyl.

More preference is given to compounds of the formula Ia, wherein the moiety

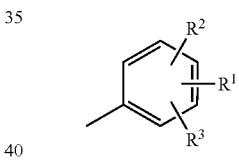

is of the formula

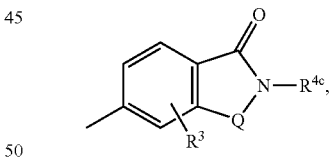

wherein $R^3$ and $R^{4c}$ are as defined above and wherein -Q- is —$C(R^{Q1}R^{Q2})$—, —$C(R^{Q1}R^{Q2})$—$C(R^{Q3}R^{Q4})$— or —$C(R^{Q1})$=$C(R^{Q2})$—, wherein $R^{Q1}$, $R^{Q2}$, $R^{Q3}$, $R^{Q4}$ are each independently of each other selected from hydrogen, halogen, CN, OH, $NH_2$, $C_1$-$C_4$-alkyl, $C_3$-$C_6$-cycloalkyl, $C_1$-$C_4$-haloalkyl, $C_1$-$C_4$-alkylamino, di-($C_1$-$C_4$-alkyl)amino, $C_1$-$C_4$-alkoxy and $C_1$-$C_4$-haloalkoxy. Preferably, -Q- is —$C(R^{Q1}R^{Q2})$—. Preferably, $R^{Q1}$, $R^{Q2}$, $R^{Q3}$, $R^{Q4}$ are each independently of each other selected from hydrogen, halogen, $C_1$-$C_4$-alkyl, $C_3$-$C_6$-cycloalkyl and $C_1$-$C_4$-haloalkyl. In particular Q is $CH_2$, $CH_2CH_2$ or CH=CH, more preferably $CH_2$. More preferably $R^3$ is hydrogen.

A particular preferred embodiment of the present invention relates to compounds of the formula I.1, to their isomers of the formulae I.2, I.3 and I.4 and to the pharmaceutically acceptable salts thereof:

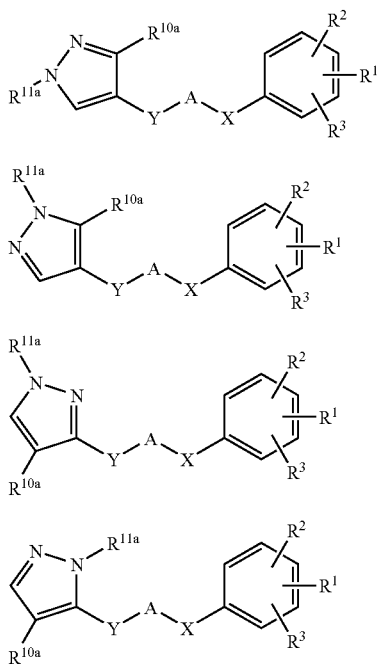

In formulae I.1, I.2, I.3 and I.4, X, A, Y, $R^1$, $R^2$ and $R^3$ are as defined herein and have preferably one of the meanings given as preferred meanings. $R^{10a}$ is hydrogen or has one of the meanings given for $R^{10}$, $R^{11a}$ is hydrogen or has one of the meanings given for $R^{11}$.

In particular, $R^{10a}$ is selected from
hydrogen
halogen,
cyano
$C_1$-$C_8$-alkyl, which is unsubstituted or carries one radical selected from OH, $C_1$-$C_4$-alkoxy and phenyl wherein the phenyl ring itself is unsubstituted or carries 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy,
$C_1$-$C_8$-alkoxy,
$C_1$-$C_8$-haloalkyl,
$C_1$-$C_8$-haloalkoxy,
$C_3$-$C_8$-cycloalkyl, which is unsubstituted or carries 1, 2, 3 or 4 radicals selected from halogen, $C_1$-$C_4$-alkyl and $C_1$-$C_4$-alkoxy,
$C_3$-$C_8$-cycloalkoxy, which is unsubstituted or carries 1, 2, 3 or 4 radicals selected from halogen, $C_1$-$C_4$-alkyl and $C_1$-$C_4$-alkoxy,
$C(=O)$—$R^{13}$,
$C(=O)$—$OR^{14}$,
$NR^{15}R^{16}$,
$C(=O)NR^{15}R^{16}$,
$SO_2R^{17}$,
phenyl, which is unsubstituted or may carry 1, 2, 3, 4 or 5 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy,
5- or 6-membered heteroaryl, in particular furyl, thienyl, oxazolyl, thiazolyl, isoxazolyl, isothiazolyl, pyrazolyl, imidazolyl, pyridyl, pyrimidinyl or pyrazinyl, having 1, 2 or 3 heteroatoms as ring members, the heteroatoms being selected from O, S and N, which is unsubstituted or may carry 1, 2 or 3 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1 or 2 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy. More preferably $R^{10a}$ is
$C_1$-$C_8$-haloalkyl, in particular $C_1$-$C_2$-fluoroalkyl,
$C_3$-$C_8$-cycloalkyl, which is unsubstituted or carries 1, 2, 3 or 4 radicals selected from halogen, $C_1$-$C_4$-alkyl and $C_1$-$C_4$-alkoxy,
$C_1$-$C_8$-alkyl, which is unsubstituted or carries one radical selected from OH, $C_1$-$C_4$-alkoxy and phenyl wherein the phenyl ring itself is unsubstituted or carries 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy, and
most preferably
phenyl, which is unsubstituted or may carry 1, 2, 3, 4 or 5 substituents as mentioned above, which are preferably selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy.

In particular $R^{11a}$ is a hydrogen or a C-bound radical which is preferably selected from CN, $C_1$-$C_4$-alkyl, $C_1$-$C_4$-haloalkyl and phenyl, which is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. More preferably $R^{11a}$ is hydrogen.

$R^{10a}$ and $R^{11a}$, together with the atoms to which they are attached, may also form a fused pyridine or pyrimidine ring, which are unsubstituted or may carry 1, 2 or 3 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1 or 2 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy.

A particular preferred embodiment of the present invention relates to compounds of the formulae I.1, I.2, I.3 and I.4, wherein X is NH or $NR^X$, and to their pharmaceutically acceptable salts.

Another particular preferred embodiment of the present invention relates to compounds of the formulae I.1, I.2, I.3 and I.4, wherein X is O, and to their pharmaceutically acceptable salts.

Amongst those compounds of the formulae I.1, I.2, I.3 and I.4, wherein X is $NR^x$ the radical $R^x$ is preferably selected from the group consisting of $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl, benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, and a radical $SO_2$—$R^{x5}$, wherein $R^{x5}$ is as defined above. $R^{x5}$ is preferably selected from $C_1$-$C_4$-alkyl, $C_1$-$C_4$-fluoroalkyl, in particular $CH_2CF_3$, 5- or 6-membered hetaryl which may contain a fused benzene ring, in particular pyridyl, pyrimidinyl and quinolinyl, and phenyl, which is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. Amongst these, preference is given to compound of the formulae I' and I", wherein the radical $R^x$ a radical $SO_2$—$R^{x5}$, wherein $R^{x5}$ is as defined above. Likewise preferred are compounds of the formulae I' and I", wherein the radical $R^x$ is $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl or benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy.

A preferred embodiment of the present invention relates to compounds of the formulae I.1, I.2, I.3 and I.4, wherein Y is a chemical bond, and to their pharmaceutically acceptable salts.

A preferred embodiment of the present invention relates to compounds of the formulae I.1, I.2, I.3 and I.4, wherein A is $CR^aR^b$, wherein $R^a$ and $R^b$ are, independently of each other, selected from hydrogen, halogen, $C_1$-$C_4$-alkyl, $C_1$-$C_4$-haloalkyl, $C_1$-$C_4$-alkoxy and $C_1$-$C_4$-haloalkoxy, $R^b$ may also be OH, if $R^a$ is hydrogen, $C_1$-$C_4$-alkyl or $C_1$-$C_4$-haloalkyl. Preferably $R^a$ and $R^b$ are selected, independently of each other, from the group consisting of hydrogen, fluorine, methyl, ethyl and methoxy. In particular, $R^a$ and $R^b$ are hydrogen, i.e. A is $CH_2$.

Thus, a particular preferred embodiment of the present invention relates to compounds of the formula Ia.1, to their isomers Ia.2, Ia.3 and Ia.4, and to the pharmaceutically acceptable salts thereof.

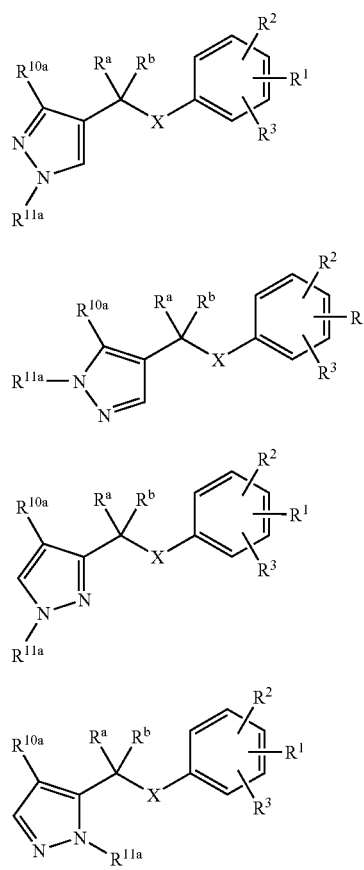

In formulae Ia.1, Ia.2, Ia.3 and Ia.4, $R^a$ and $R^b$ are as defined for formula Ia, and have preferably one of the meanings given as preferred meanings. X is as defined herein and preferably O, NH or N—$R^x$, in particular O or NH. $R^x$, $R^1$, $R^2$ and $R^3$ are as defined herein and have preferably one of the meanings given as preferred meanings. $R^{10a}$ and $R^{11}$ are as defined for formulae I.1, I.2, I.3 and I.4. In particular $R^{10a}$ and $R^{11a}$, independently of each other, have one of the meanings, given for formulae I' and I" as preferred meanings.

Preferably, $R^a$ and $R^b$ in formulae Ia.1, Ia.2, Ia.3 and Ia.4 are selected, independently of each other, from the group consisting of hydrogen, fluorine, methyl, ethyl and methoxy. In particular, $R^a$ and $R^b$ are hydrogen.

Amongst those compounds of formulae Ia.1, Ia.2, Ia.3 and Ia.4, wherein X is $NR^X$ the radical $R^x$ is preferably selected from the group consisting of $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl, benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, and a radical $SO_2$—$R^{x5}$, wherein $R^{x5}$ is as defined above. $R^{x5}$ is preferably selected from $C_1$-$C_4$-alkyl, $C_1$-$C_4$-fluoroalkyl, in particular $CH_2CF_3$, 5- or 6-membered hetaryl which may contain a fused benzene ring, in particular pyridyl, pyrimidinyl and quinolinyl, and phenyl, which is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. Amongst these, preference is given to compound of the formulae Ia.1, Ia.2, Ia.3 or Ia.4, wherein the radical $R^x$ a radical $SO_2$—$R^{x5}$, wherein $R^{x5}$ is as defined above. Likewise preferred are compounds of the formulae Ia' or Ia", wherein the radical $R^x$ is $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl or benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy.

An especially preferred embodiment of the invention relates to compounds of the formula I.1, I.2, I.3, I.4, Ia.1, Ia.2, Ia.3 and Ia.4 and to the pharmaceutically acceptable salts and the tautomers thereof, wherein $R^1$ is a radical $C(O)R^4$, which is located in the 3- or in particular in the 4-position of the benzene ring.

Thus, an especially preferred embodiment of the present invention relates to compounds of the formula I.1.a, I.2.a, I.3.a and I.4.a

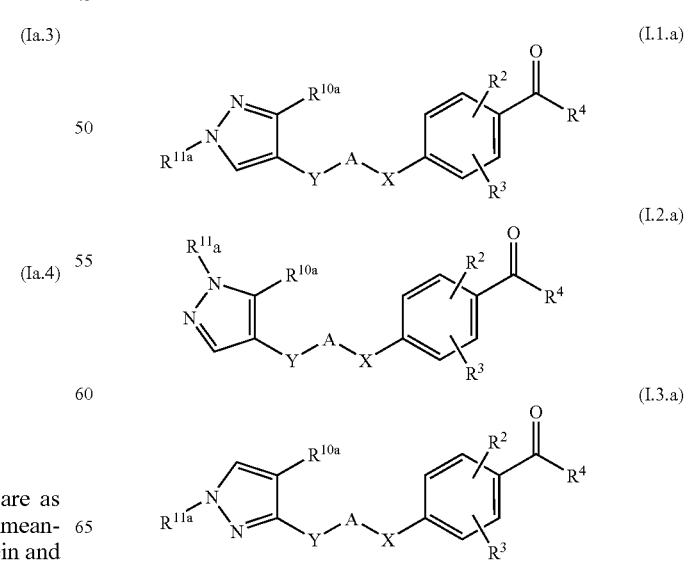

-continued

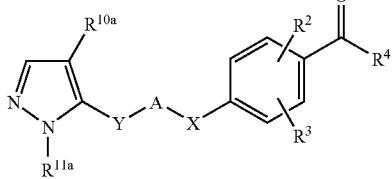
(I.4.a)

and in particular to compounds of the formulae Ia.1.a, Ia.2.a, Ia.3.a and Ia.4.a

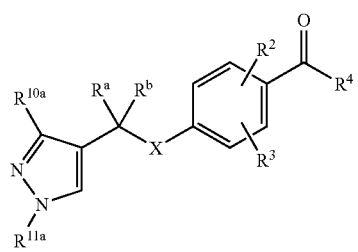
(Ia.1.a)

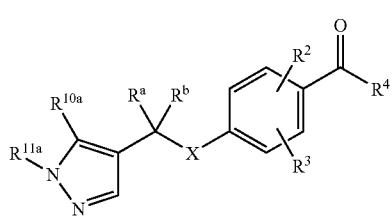
(Ia.2.a)

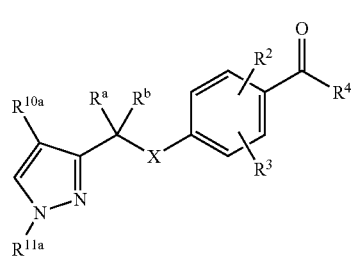
(Ia.3.a)

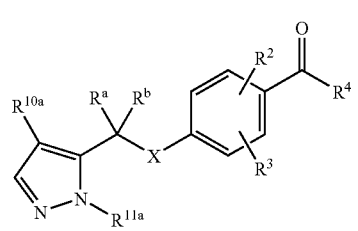
(Ia.4.a)

and to the pharmaceutically acceptable salts thereof.

In formulae I.1.a, I.2.a, I.3.a and I.4.a, the variables X, A, Y, $R^2$, $R^3$ and $R^4$ are as defined herein and have preferably one of the meanings given as preferred meanings. $R^{10a}$ and $R^{11a}$ are as defined for Het-1 to Het-7, and for formulae I.1, I.2, I.3 and I.4. In particular $R^{10a}$ and $R^{11a}$, independently of each other, have one of the meanings, given for formulae I.1, I.2, I.3 or I.4 as preferred meanings.

In formulae Ia.1.a, Ia.2.a, Ia.3.a or Ia.4.a, the variables X, $R^a$, $R^b$, $R^2$, $R^3$ and $R^4$ are as defined herein and have preferably one of the meanings given as preferred meanings. $R^{10a}$ and $R^{11a}$ are as defined for Het-1 to Het-7, and for formulae I.1, I.2, I.3 and I.4. In particular $R^{10a}$ and $R^{11a}$, independently of each other, have one of the meanings, given for formulae I.1, I.2, I.3 or I.4 as preferred meanings.

A particular preferred embodiment of the present invention relates to compounds of the formulae I.1.a, I.2.a, I.3.a or I.4.a, wherein X is O, NH or $NR^x$, in particular O or NH, and to their pharmaceutically acceptable salts.

A preferred embodiment of the present invention relates to compounds of the formulae I.1.a, I.2.a, I.3.a or I.4.a, wherein Y is a chemical bond, and to their pharmaceutically acceptable salts.

A preferred embodiment of the present invention relates to compounds of the formulae I.1.a, I.2.a, I.3. or I.4.a, wherein A is $CR^aR^b$, wherein $R^a$ and $R^b$ are, independently of each other, selected from hydrogen, halogen, $C_1$-$C_4$-alkyl, $C_1$-$C_4$-haloalkyl, $C_1$-$C_4$-alkoxy and $C_1$-$C_4$-haloalkoxy, $R^b$ may also be OH, if $R^a$ is hydrogen, $C_1$-$C_4$-alkyl or $C_1$-$C_4$-haloalkyl. Preferably $R^a$ and $R^b$ are selected, independently of each other, from the group consisting of hydrogen, fluorine, methyl, ethyl and methoxy. In particular, $R^a$ and $R^b$ are hydrogen, i.e. A is $CH_2$.

In formulae Ia.1.a, Ia.2.a, Ia.3.a or Ia.4.a, $R^a$ and $R^b$ are as defined for formula Ia, and have preferably one of the meanings given as preferred meanings. In particular $R^a$ and $R^b$ are hydrogen. X is preferably O, NH or N—$R^x$, and $R^{10a}$, $R^{11a}$, $R^2$, $R^3$ and $R^4$ are as defined herein and have preferably one of the meanings given as preferred meanings.

Preferably, $R^a$ and $R^b$ in formulae Ia.1.a, Ia.2.a, Ia.3.a or Ia.4.a, are selected, independently of each other, from the group consisting of hydrogen, fluorine, methyl, ethyl and methoxy. In particular, $R^a$ and $R^b$ are hydrogen.

Amongst those compounds of the formulae I.1.a, I.2.a, I.3.a, I.4.a, Ia.1.a, Ia.2.a, Ia.3.a or Ia.4.a, wherein X is $NR^x$ the radical $R^x$ is preferably selected from the group consisting of $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl, benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, and a radical $SO_2$—$R^{x5}$, wherein $R^{x5}$ is as defined above. $R^{x5}$ is preferably selected from $C_1$-$C_4$-alkyl, $C_1$-$C_4$-fluoroalkyl, in particular $CH_2CF_3$, 5- or 6-membered hetaryl which may contain a fused benzene ring, in particular pyridyl, pyrimidinyl and quinolinyl, and phenyl, which is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. Amongst these, preference is given to compound of the formulae I.1.a, I.2.a, I.3.a, I.4.a, Ia.1.a, Ia.2.a, Ia.3.a or Ia.4.a, wherein the radical $R^x$ a radical $SO_2$—$R^{x5}$, wherein $R^{x5}$ is as defined above. Likewise preferred are compounds of the formulae I.1.a, I.2.a, I.3.a, I.4.a, Ia.1.a, Ia.2.a, Ia.3.a or Ia.4.a, wherein the radical $R^x$ is $C_1$-$C_6$-alkyl, $C_1$-$C_4$-haloalkyl, $C_1$-$C_4$-alkoxy-$C_1$-$C_4$-alkyl, $C_3$-$C_6$-cycloalkyl, $C_3$-$C_6$-cycloalkylmethyl or benzyl, wherein the phenyl ring is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy.

In a particular preferred embodiment of the compounds formulae Ia.1.a, Ia.2.a, Ia.3.a or Ia.4.a, $R^a$ and $R^b$ are hydrogen.

In the formulae I.1, I.2, I.3, I.4, I.1.a, I.2.a, I.3.a, I.4.a, Ia.1.a, Ia.2.a, Ia.3.a or Ia.4.a, $R^{10a}$ is preferably selected from
  hydrogen
  halogen,
  cyano
  $C_1$-$C_8$-alkyl, which is unsubstituted or carries one radical selected from OH, $C_1$-$C_4$-alkoxy and phenyl wherein the phenyl ring itself is unsubstituted or carries 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy, $C_1$-$C_8$-alkoxy, $C_1$-$C_8$-haloalkyl, $C_1$-$C_8$-haloalkoxy, $C_3$-$C_8$-cycloalkyl, which is unsubstituted or carries 1, 2, 3 or 4 radicals selected from halogen, $C_1$-$C_4$-alkyl and $C_1$-$C_4$-alkoxy, $C_3$-$C_8$-cycloalkoxy, which is unsubstituted or carries 1, 2, 3 or 4 radicals selected from halogen, $C_1$-$C_4$-alkyl and $C_1$-$C_4$-alkoxy, $C(=O)$—$R^{13}$, $C(=O)$—$OR^{14}$, $NR^{15}R^{16}$, $C(=O)NR^{15}R^{16}$, $SO_2R^{17}$, phenyl, which is unsubstituted or may carry 1, 2, 3, 4 or 5 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy, 5- or 6-membered heteroaryl, in particular furyl, thienyl, oxazolyl, thiazolyl, isoxazolyl, isothiazolyl, pyrazolyl, imidazolyl, pyridyl, pyrimidinyl or pyrazinyl, having 1, 2 or 3 heteroatoms as ring members, the heteroatoms being selected from O, S and N, which is unsubstituted or may carry 1, 2 or 3 substituents selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1 or 2 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy.

In the formulae I.1, I.2, I.3, I.4, I.1.a, I.2.a, I.3.a, I.4.a, Ia.1.a, Ia.2.a, Ia.3.a or Ia.4.a, $R^{10a}$ is more preferably $C_1$-$C_8$-haloalkyl, in particular $C_1$-$C_2$-fluoroalkyl, $C_3$-$C_8$-cycloalkyl, which is unsubstituted or carries 1, 2, 3 or 4 radicals selected from halogen, $C_1$-$C_4$-alkyl and $C_1$-$C_4$-alkoxy, $C_1$-$C_8$-alkyl, which is unsubstituted or carries one radical selected from OH, $C_1$-$C_4$-alkoxy and phenyl wherein the phenyl ring itself is unsubstituted or carries 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy, and most preferably phenyl, which is unsubstituted or may carry 1, 2, 3, 4 or 5 substituents as mentioned above, which are preferably selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy, in particular 1, 2, 3 or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy and trifluoromethoxy.

In particular $R^{11a}$ in the formulae I.1, I.2, I.3, I.4, I.1.a, I.2.a, I.3.a, I.4.a, Ia.1.a, Ia.2.a, Ia.3.a or Ia.4.a is hydrogen or a C-bound radical which is preferably selected from CN, $C_1$-$C_4$-alkyl, $C_1$-$C_4$-haloalkyl and phenyl, which is unsubstituted or carries 1, 2 or 3 radicals selected from halogen, CN, OH, $C_1$-$C_4$-alkyl, $C_3$-$C_6$-cycloalkyl, $C_1$-$C_4$-haloalkyl, $C_1$-$C_4$-alkoxy and $C_1$-$C_4$-haloalkoxy. More preferably $R^1$ in the formulae I.1, I.2, I.3, I.4, I.1.a, I.2.a, I.3.a, I.4.a, Ia.1.a, Ia.2.a, Ia.3.a or Ia.4.a is hydrogen.

A particular preferred embodiment relates to compounds the formulae I.1, I.2, I.3, I.4, I.1.a, I.2.a, I.3.a, I.4.a, Ia.1.a, Ia.2.a, Ia.3.a or Ia.4.a, wherein $R^4$ is preferably selected from $C_3$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, in particular $C_3$-$C_8$-alkyl, $C_1$-$C_3$-alkyl which is substituted with a radical selected from $C_1$-$C_4$-alkoxy or phenyl which is unsubstituted or substituted as given above, $C_1$-$C_8$-haloalkyl, in particular $C_1$-$C_2$-fluoroalkyl, $C_3$-$C_8$-cycloalkyl, which is unsubstituted or carries 1, 2, 3 or 4 radicals selected from halogen, $C_1$-$C_4$-alkyl and $C_1$-$C_4$-alkoxy, phenyl, which is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, 5- or 6-membered hetaryl, having 1, 2 or 3 heteroatoms as ring members, the heteroatoms being selected from O, S and N, in particular furyl, thienyl, oxazolyl, thiazolyl, isoxazolyl, isothiazolyl, 1,2,4-triazolyl, 1,2,3-triazolyl, pyridyl, pyrimidinyl or pyrazinyl, wherein hetaryl is unsubstituted or carries 1, 2, 3 or 4 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy; and More preferably $R^4$ in formulae I.1, I.2, I.3, I.4, I.1.a, I.2.a, I.3.a, I.4.a, Ia.1.a, Ia.2.a, Ia.3.a or Ia.4.a is selected from $C_3$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy, in particular $C_3$-$C_8$-alkyl, $C_1$-$C_3$-alkyl which is substituted with a radical selected from $C_1$-$C_4$-alkoxy or phenyl which is unsubstituted or substituted as given above. $C_1$-$C_4$-haloalkyl, in particular $C_1$-$C_4$-fluoroalkyl, $C_3$-$C_8$-alkyl, which is unsubstituted or carries one radical selected from OH, $C_1$-$C_4$-alkoxy, $C_3$-$C_8$-cycloalkyl and phenyl wherein the phenyl ring itself is unsubstituted or carries 1, 2, 3, 4 or 5 identical or different radicals selected from fluorine, chlorine, CN, $C_1$-$C_2$-alkyl, $C_1$-$C_2$-alkoxy, difluoromethyl, trifluoromethyl, difluoromethoxy and trifluoromethoxy. In particular $R^4$ in formulae I.1, I.2, I.3, I.4, I.1.a, I.2.a, I.3.a, I.4.a, Ia.1.a, Ia.2.a, Ia.3.a or Ia.4.a is $C_3$-$C_8$-alkyl, $C_1$-$C_3$-alkyl which is substituted with a radical selected from $C_1$-$C_4$-alkoxy and $C_3$-$C_6$-cycloalkyl, or $C_1$-$C_4$-haloalkyl, in particular $C_1$-$C_4$-fluoroalkyl. More preferably, $R^2$ and $R^3$ in formulae I.1, I.2, I.3, I.4, I.1.a, I.2.a, I.3.a, I.4.a, Ia.1.a, Ia.2.a, Ia.3.a or Ia.4.a are hydrogen.

A further embodiment relates to compounds of the formulae I.1, I.2, I.3, I.4, I.1.a, I.2.a, I.3.a, I.4.a, Ia.1.a, Ia.2.a, Ia.3.a or Ia.4.a, wherein $R^4$ together with $R^2$ forms a $C_1$-$C_5$-alkylene or $C_2$-$C_5$-alkenylene moiety, in particular a ethan-1,2-diyl moiety or propan-1,3-diyl moiety, wherein one $CH_2$-moiety may be replaced by oxygen, sulphur or a N—$R^{4c}$-moiety, and wherein $C_1$-$C_5$-alkylene and $C_2$-$C_5$-alkenylene (and likewise the ethan-1,2-diyl moiety and the propan-1,3-diyl moiety)

may be unsubstituted or carry 1, 2, 3, or 4 radicals, in particular 0, 1 or 2 radicals, selected from halogen, CN, OH, NH$_2$, C$_1$-C$_4$-alkyl, in particular methyl, C$_3$-C$_6$-cycloalkyl, in particular cyclopropyl, cyclobutyl or cyclopentyl, C$_1$-C$_4$-haloalkyl, in particular difluoromethyl or trifluoromethyl, C$_1$-C$_4$-alkylamino, such as methylamino, ethylamino, di-(C$_1$-C$_4$-alkyl)amino, such as dimethylamino, diethylamino, C$_1$-C$_4$-alkoxy such as methoxy or ethoxy, and C$_1$-C$_4$-haloalkoxy, such as difluoromethyloxy or trifluoromethoxy, and wherein R$^{4c}$ is as defined herein. Preferably, R$^{4c}$ is selected from C$_1$-C$_6$-alkyl, which is unsubstituted or carries an alkoxy or haloalkoxy radical, in particular C$_1$-C$_4$-alkyl, C$_3$-C$_6$-cycloalkyl, C$_1$-C$_4$-haloalkyl, C$_3$-C$_6$-cycloalkylmethyl and benzyl, wherein the phenyl ring is unsubstituted or may carry a substituent selected from halogen, difluoromethyl, trifluoromethyl, difluoromethoxy and trifluoromethoxy. In particular, R$^{4c}$ is selected from methyl, ethyl, 2-bromoethyl, 2,2-difluoroethyl, 2,2,2-trifluoroethyl, n-propyl, 3,3,3-trifluoropropyl, n-butyl, 4,4,4-trifluorobutyl, 3-methylbutyl, 2-trifluoromethoxyethyl, 2-methylpropyl, cyclopentylmethyl, cyclohexylmethyl, benzyl and 4-trifluoromethoxybenzyl.

A very preferred embodiment of the invention relates to compounds of the formulae Ia.1.a', Ia.2.a'. Ia.3.a' or Ia.4.a' and to their pharmaceutically acceptable salts

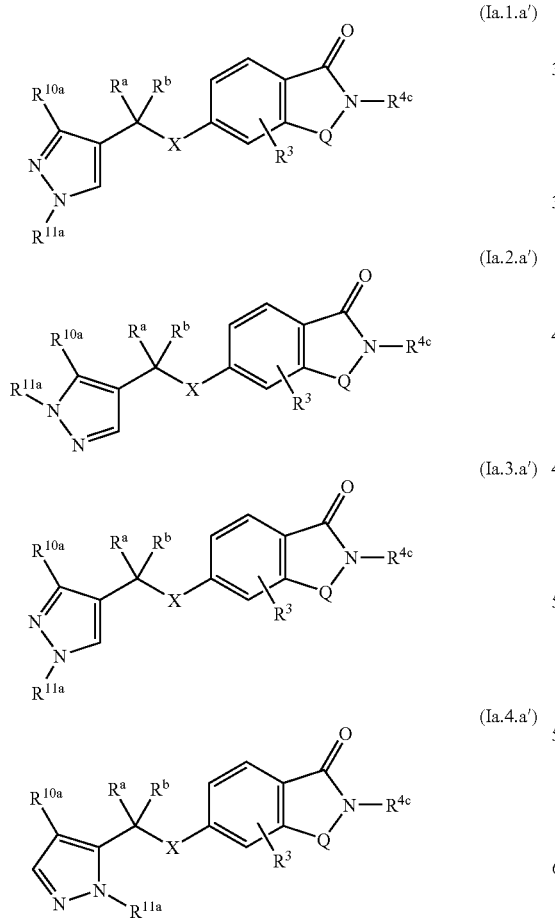

(Ia.1.a')
(Ia.2.a')
(Ia.3.a')
(Ia.4.a')

wherein Q, X R$^3$, R$^{4c}$, R$^{11a}$, R$^{11a}$, R$^a$ and R$^b$ are as defined herein.

Preferably, -Q- is —C(R$^{Q1}$R$^{Q2}$)—. Preferably, R$^{Q1}$. R$^{Q2}$, R$^{Q3}$, R$^{Q4}$ are each independently of each other selected from hydrogen, halogen, C$_1$-C$_4$-alkyl, C$_3$-C$_6$-cycloalkyl and C$_1$-C$_4$-haloalkyl. In particular Q is CH$_2$, CH$_2$CH$_2$ or CH=CH, more preferably CH$_2$.

X is preferably O, NH or N—R$^x$.

R$^3$ is in particular hydrogen.

R$^{4c}$ is preferably selected from C$_1$-C$_6$-alkyl, which is unsubstituted or carries an alkoxy or haloalkoxy radical, in particular C$_1$-C$_4$-alkyl, C$_3$-C$_6$-cycloalkyl, C$_1$-C$_4$-haloalkyl, C$_3$-C$_6$-cycloalkylmethyl and benzyl, wherein the phenyl ring is unsubstituted or may carry a substituent selected from halogen, difluoromethyl, trifluoromethyl, difluoromethoxy and trifluoromethoxy. In particular, R$^{4c}$ is selected from methyl, ethyl, 2-bromoethyl, 2,2-difluoroethyl, 2,2,2-trifluoroethyl, n-propyl, 3,3,3-trifluoropropyl, n-butyl, 4,4,4-trifluorobutyl, 3-methylbutyl, 2-trifluoromethoxyethyl, 2-methylpropyl, cyclopentylmethyl, cyclohexylmethyl, benzyl and 4-trifluoro-methoxybenzyl.

R$^a$ and R$^b$ are more preferably hydrogen.

In the formulae Ia.1.a', Ia.2.a'. Ia.3.a' or Ia.4.a' R$^{10a}$ is preferably selected from
hydrogen
halogen,
cyano
C$_1$-C$_8$-alkyl, which is unsubstituted or carries one radical selected from OH, C$_1$-C$_4$-alkoxy and phenyl wherein the phenyl ring itself is unsubstituted or carries 1, 2, 3 or 4 identical or different radicals selected from the group consisting of fluorine, chlorine, CN, C$_1$-C$_2$-alkyl, C$_1$-C$_2$-alkoxy, difluoromethyl, trifluoromethyl, difluoromethoxy and trifluoromethoxy,
C$_1$-C$_8$-alkoxy,
C$_1$-C$_8$-haloalkyl,
C$_1$-C$_8$-haloalkoxy,
C$_3$-C$_8$-cycloalkyl, which is unsubstituted or carries 1, 2, 3 or 4 radicals selected from halogen, C$_1$-C$_4$-alkyl and C$_1$-C$_4$-alkoxy,
C$_3$-C$_8$-cycloalkoxy, which is unsubstituted or carries 1, 2, 3 or 4 radicals selected from halogen, C$_1$-C$_4$-alkyl and C$_1$-C$_4$-alkoxy,
C(=O)—R$^{13}$,
C(=O)—OR$^{14}$,
C(=O)NR$^{15}$R$^{16}$,
SO$_2$R$^{17}$,
phenyl, which is unsubstituted or may carry 1, 2, 3, 4 or 5 substituents selected from halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy, in particular 1, 2, 3 or 4 identical or different radicals selected from the group consisting of fluorine, chlorine, CN, C$_1$-C$_2$-alkyl, C$_1$-C$_2$-alkoxy, difluoromethyl, trifluoromethyl, difluoromethoxy and trifluoromethoxy,
5- or 6-membered heteroaryl, in particular furyl, thienyl, oxazolyl, thiazolyl, isoxazolyl, isothiazolyl, pyrazolyl, imidazolyl, pyridyl, pyrimidinyl or pyrazinyl, having 1, 2 or 3 heteroatoms as ring members, the heteroatoms being selected from O, S and N, which is unsubstituted or may carry 1, 2 or 3 substituents selected from halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy, in particular 1 or 2 identical or different radicals selected from the group consisting of fluorine, chlorine, CN, C$_1$-C$_2$-alkyl, C$_1$-C$_2$-alkoxy, difluoromethyl, trifluoromethyl, difluoromethoxy and trifluoromethoxy. In the formulae I Ia.1.a', Ia.2.a'. Ia.3.a' or Ia.4.a' R$^{10a}$ is more preferably
C$_1$-C$_8$-haloalkyl, in particular C$_1$-C$_2$-fluoroalkyl,
C$_3$-C$_8$-cycloalkyl, which is unsubstituted or carries 1, 2, 3 or 4 radicals selected from halogen, C$_1$-C$_4$-alkyl and C$_1$-C$_4$-alkoxy, C$_1$-C$_8$-alkyl, which is unsubstituted or carries one radical selected from OH, C$_1$-C$_4$-alkoxy and phenyl wherein the phenyl ring itself is unsubstituted or carries 1, 2, 3 or 4 identical or different radicals selected from the group consisting of fluorine, chlorine, CN, C$_1$-C$_2$-alkyl, C$_1$-C$_2$-alkoxy, difluoromethyl, trifluoromethyl, difluoromethoxy and trifluoromethoxy, and most preferably phenyl, which is unsubstituted or may carry 1, 2, 3, 4 or 5 substituents as mentioned above, which are preferably selected from halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy, in particular 1, 2, 3 or 4 identical or different radicals selected from the group consisting of fluorine, chlorine, CN, C$_1$-C$_2$-alkyl, C$_1$-C$_2$-alkoxy, difluoromethyl, trifluoromethyl, difluoromethoxy and trifluoromethoxy.

In the formulae Ia.1.a', Ia.2.a'. Ia.3.a' or Ia.4.a' R$^{11a}$ is preferably selected from hydrogen and a C-bound radical which is preferably selected from CN, C$_1$-C$_4$-alkyl, C$_1$-C$_4$-haloalkyl and phenyl, which is unsubstituted or carries 1, 2 or 3 radicals selected from halogen, CN, OH, C$_1$-C$_4$-alkyl, C$_3$-C$_6$-cycloalkyl, C$_1$-C$_4$-haloalkyl, C$_1$-C$_4$-alkoxy and C$_1$-C$_4$-haloalkoxy. More preferably R$^{11a}$ in the formulae Ia.1.a', Ia.2.a'. Ia.3.a' or Ia.4.a' is hydrogen.

Examples of compounds according to the present invention include, but are not limited to:

1-{4-[(Thiophen-3-ylmethyl)amino]phenyl}-butan-1-one,
1-(4-{[5-(2-Chlorophenyl)-furan-2-ylmethyl]amino}phenyl)butan-1-one,
1-(4-{[5-(3-Chlorophenyl)furan-2-ylmethyl]amino}phenyl)-butan-1-one,
1-(4-{[5-(4-Chlorophenyl)furan-2-ylmethyl]amino}phenyl)butan-1-one,
1-{4-[(5-Chlorothiophen-2-ylmethyl)amino]phenyl}butan-1-one,
1-(4{-[5-(2-(Trifluoromethylphenyl)furan-2-ylmethyl]amino}phenyl)butan-1-one,
1-(4-{[5-(3-Trifluoromethylphenyl)furan-2-ylmethyl]amino}phenyl)butan-1-one,
1-{4-[(3H-Imidazol-4-ylmethyl)amino]phenyl}butan-1-one,
1-{4-[(5-Ethylthiophen-2-ylmethyl)amino]phenyl}butan-1-one,
1-{4-[(Benzo[b]thiophen-3-ylmethyl)amino]phenyl}butan-1-one,
(R)-1-{4-[(Tetrahydrofuran-2-ylmethyl)amino]phenyl}butan-1-one,
1-{4-[(1-Methyl-1H-indol-2-ylmethyl)amino]phenyl}butan-1-one,
1-{4-[(Furan-2-ylmethyl)amino]phenyl}butan-1-one,
1-{4-[(Pyridin-2-ylmethyl)amino]phenyl}butan-1-one,
1-{4-[(Pyridin-4-ylmethyl)amino]phenyl}butan-1-one,
1-{4-[(Pyridin-3-ylmethyl)amino]phenyl}butan-1-one,
1-{4-[(1-Methyl-1H-imidazol-2-ylmethyl)amino]phenyl}butan-1-one,
1-{4-[(5-Methylthiophen-2-ylmethyl)amino]phenyl}butan-1-one,
1-{4-[(3-Methylthiophen-2-ylmethyl)amino]phenyl}butan-1-one,
1-{4-[(5-(Hydroxymethylfuran-2-ylmethyl)amino]phenyl}butan-1-one,
1-{4-[(5-Methylfuran-2-ylmethyl)amino]phenyl}butan-1-one,
1-{4-[(3-Methylbenzo[b]thiophen-2-ylmethyl)amino]phenyl}butan-1-one,
Acetic acid 5-[(4-butyrylphenylamino)methyl]furan-2-ylmethyl ester,
1-{4-[(1-Acetyl-1H-indol-3-ylmethyl)amino]phenyl}butan-1-one,
1-{4-[(Quinolin-6-ylmethyl)amino]phenyl}butan-1-one,
1-{4-[(Thiazol-2-ylmethyl)amino]phenyl}butan-1-one,
1-(4-{[1-(toluene-4-sulfonyl)-1H-pyrrol-2-ylmethyl]amino}phenyl)butan-1-one,
1-{4-[(1-Methyl-1H-pyrazol-4-ylmethyl)amino]phenyl}butan-1-one,
1-(4-{[5-(Piperidin-1-yl)furan-2-ylmethyl]amino}phenyl)butan-1-one,
1-{4-[(4-Phenylthiazol-2-ylmethyl)amino]phenyl}butan-1-one,
1-{4-[(1H-Indol-2-ylmethyl)amino]phenyl}butan-1-one,
1-(4-{[1-(Toluene-4-sulfonyl)-1H-indol-3-ylmethyl]amino}phenyl)butan-1-one,
1-{4-[(5-Methyl-2H-pyrazol-3-ylmethyl)amino]phenyl}butan-1-one,
1-(4-{[4-Bromo-2-(4-chlorobenzyl)-2H-pyrazol-3-ylmethyl]amino}phenyl)butan-1-one,
4-{5-[(4-Butyrylphenylamino)methyl]furan-2-yl}benzenesulfonamide
1-(4-{[5-(2-(Trifluoromethoxyphenyl)furan-2-ylmethyl]amino}phenyl)butan-1-one,
1-(4-{[4-(3-Bromophenyl)pyridin-3-ylmethyl]amino}phenyl)butan-1-one,
1-(4-{[3-(4-Methoxyphenyl)-1-(thiophene-2-carbonyl)-1H-pyrazol-4-ylmethyl]amino}phenyl)butan-1-one,
1-(4-{[5-(3-(Trifluoromethoxyphenyl)furan-2-ylmethyl]amino}phenyl)butan-1-one,
1-(4-{[3-(Thiophen-2-yl)-1H-pyrazol-4-ylmethyl]amino}phenyl)butan-1-one,
1-{4-[(5-Chlorobenzo[b]thiophen-3-ylmethyl)amino]phenyl}butan-1-one,
1-(4-{[3-(4-(Trifluoromethylphenyl)-1H-pyrazol-4-ylmethyl]amino}phenyl)butan-1-one,
1-{4-[(5-Methyl-3-phenylisoxazol-4-ylmethyl)amino]phenyl}butan-1-one,
1-{4-[(2,5-Dimethyl-2H-pyrazol-3-ylmethyl)amino]phenyl}butan-1-one,
1-{4-[(5-Methyl-1-phenyl-1H-pyrazol-4-ylmethyl)amino]phenyl}butan-1-one,
1-{4-[(2-Phenylthiazol-4-ylmethyl)amino]phenyl}butan-1-one,
1-{4-[(4-Methyl-2-phenylpyrimidin-5-ylmethyl)amino]phenyl}butan-1-one,
1-(4-{[1-(Phenylsulfonyl)-1H-indol-3-ylmethyl]amino}phenyl)butan-1-one,
1-(4-{[5-(4-Chlorophenoxy)-1,3-dimethyl-1H-pyrazol-4-ylmethyl]amino}phenyl)butan-1-one,
1-(4-{[5-(3-Chlorophenoxy)-1,3-dimethyl-1H-pyrazol-4-ylmethyl]amino}phenyl)butan-1-one,
1-{4-[(5-Chloro-3-methyl-1-phenyl-1H-pyrazol-4-ylmethyl)amino]phenyl}butan-1-one,
1-(4-{[5-Chloro-1-methyl-3-(phenylthiomethyl)-1H-pyrazol-4-ylmethyl]amino}phenyl)butan-1-one,
1-(4-{[5-Chloro-1-methyl-3-(trifluoromethyl)-1H-pyrazol-4-yl]methylamino}phenyl)butan-1-one,
1-(4-{[4-(3-Chlorobenzoyl)-1-methyl-1H-pyrrol-2-ylmethyl]amino}phenyl)butan-1-one,
1-{4-[(1-Ethyl-5-methyl-1H-pyrazol-4-ylmethyl)amino]phenyl}butan-1-one,
1-{4-[(3,5-Dimethyl-1-phenyl-1H-pyrazol-4-ylmethyl)amino]phenyl}butan-1-one,
1-{4-[(2-Phenyl-2H-pyrazol-3-ylmethyl)amino]phenyl}butan-1-one, 1-{4-[(1-tert-Butyl-3,5-dimethyl-1H-pyrazol-4-ylmethyl) amino]phenyl)butan-1-one,
1-{4-[(5-Methyl-2H-pyrazol-3-ylmethyl)amino] phenyl}butan-1-one,
1-{4-[(1,5-Dimethyl-1H-pyrazol-4-ylmethyl)amino] phenyl}butan-1-one,
1-{4-[(1,3-Dimethyl-1H-pyrazol-4-ylmethyl)amino] phenyl}butan-1-one,
1-{4-[(1-Methyl-1H-pyrazol-4-ylmethyl)amino] phenyl}butan-1-one,
1-(4-{[3-(5-Methylfuran-2-yl)-1-phenyl-1H-pyrazol-4-ylmethyl]amino}phenyl)butan-1-one,
1-(4-{[1-Phenyl-3-(thiophen-2-yl)-1H-pyrazol-4-ylmethyl]amino}phenyl)butan-1-one,
1-{4-[(1-Ethyl-5-methyl-1H-pyrazol-4-ylmethyl)amino] phenyl}butan-1-one,
1-{4-[(1-Ethyl-3-methyl-1H-pyrazol-4-ylmethyl)amino] phenyl}butan-1-one,
1-{4-[(1-Ethyl-1H-pyrazol-4-ylmethyl)amino] phenyl}butan-1-one,
1-{4-[(1H-Pyrazol-4-ylmethyl)amino]phenyl}butan-1-one,
1-{4-[(2,5-Dimethyl-1H-pyrazol-3-ylmethyl)amino] phenyl}butan-1-one,
1-{4-[(3-Methyl-1-propyl-1H-pyrazol-4-ylmethyl)amino] phenyl}butan-1-one,
1-{4-[(5-Methyl-1-propyl-1H-pyrazol-4-ylmethyl)amino]) phenyl}butan-1-one,
1-{4-[(1-Methyl-1H-pyrazol-3-ylmethyl)amino] phenyl}butan-1-one,
1-{4-[(1-Methyl-5-phenyl-1H-pyrazol-4-ylmethyl)amino] phenyl})butan-1-one,
1-{4-[(1,5-Dimethyl-1H-pyrazol-3-ylmethyl)amino] phenyl}butan-1-one,
1-{4-[(1-Isopropyl-1H-pyrazol-4-ylmethyl)amino] phenyl}butan-1-one,
1-(4-{[3-(4-Hydroxyphenyl)-1H-pyrazol-4-ylmethyl] amino}phenyl)butan-1-one,
1-{4-[(3-tert-Butyl-1H-pyrazol-4-ylmethyl)amino] phenyl}butan-1-one,
N-Benzylthiazol-2-amine,
3-[(3-tert-Butyl-1H-pyrazol-4-ylmethyl)-amino]-phenol,
2,2,2-Trifluoroethanesulfonic acid (4-butyryl-phenyl)-[1-(2,2,2-trifluoro-ethanesulfonyl)-3-(4-trifluoromethylphenyl)-1H-pyrazol-4-ylmethyl]-amide,
5-{[3-(4-Trifluoromethylphenyl)-1H-pyrazol-4-ylmethyl]-amino}-indan-1-one,
6-{[3-(4-Trifluoromethylphenyl)-1H-pyrazol-4-ylmethyl]-amino}-3,4-dihydro-2H-naphthalen-1-one,
[4-(2-Methoxy-phenoxy)-phenyl]-[3-(4-trifluoromethylphenyl)-1H-pyrazol-4-ylmethyl]-amine,
N-Methoxy-N-methyl-4-{[3-(4-trifluoromethylphenyl)-1H-pyrazol-4-ylmethyl]-amino}-benzamide,
4-{[3-tert-Butyl-1-(2,2,2-trifluoroethanesulfonyl)-1H-pyrazol-4-ylmethyl]-amino}-N-methoxy-N-methyl-benzamide,
(3-tert-Butyl-1H-pyrazol-4-ylmethyl)-[3-(1-methyl-butoxy)-phenyl]-amine,
(3-tert-Butyl-1H-pyrazol-4-ylmethyl)-phenylamine,
(3-tert-Butyl-1H-pyrazol-4-ylmethyl)-o-tolylamine,
(3-tert-Butyl-1H-pyrazol-4-ylmethyl)-m-tolylamine,
(3-tert-Butyl-1H-pyrazol-4-ylmethyl)-p-tolylamine,
(3-tert-Butyl-1H-pyrazol-4-ylmethyl)-(2-methoxyphenyl)-amine,
(3-tert-Butyl-1H-pyrazol-4-ylmethyl)-(3-methoxyphenyl)-amine,
(3-tert-Butyl-1H-pyrazol-4-ylmethyl)-(4-methoxyphenyl)-amine,
(3-tert-Butyl-1H-pyrazol-4-ylmethyl)-(2-fluorophenyl)-amine,
(3-tert-Butyl-1H-pyrazol-4-ylmethyl)-(3-fluorophenyl)-amine,
(3-tert-Butyl-1H-pyrazol-4-ylmethyl)-(4-fluorophenyl)-amine,
(3-tert-Butyl-1H-pyrazol-4-ylmethyl)-(2-chlorophenyl)-amine,
(3-tert-Butyl-1H-pyrazol-4-ylmethyl)-(3-chlorophenyl)-amine,
(3-tert-Butyl-1H-pyrazol-4-ylmethyl)-(4-chlorophenyl)-amine,
(3-tert-Butyl-1H-pyrazol-4-ylmethyl)-(4-trifluoromethoxyphenyl)-amine,
(3-tert-Butyl-1H-pyrazol-4-ylmethyl)-(3-phenoxyphenyl)-amine,
N-(3-tert-Butyl-1H-pyrazol-4-ylmethyl)-N',N'-dimethyl-benzene-1,3-diamine,
(3-tert-Butyl-1H-pyrazol-4-ylmethyl)-(3-trifluoromethylphenyl)-amine,
(3-tert-Butyl-1H-pyrazol-4-ylmethyl)-(4-trifluoromethylphenyl)-amine,
(3-tert-Butyl-1H-pyrazol-4-ylmethyl)-(3-trifluoromethoxyphenyl)-amine,
(3-tert-Butyl-1H-pyrazol-4-ylmethyl)-(4-phenoxyphenyl)-amine,
(3-tert-Butyl-1H-pyrazol-4-ylmethyl)-(2,3-dimethylphenyl)-amine,
(3-tert-Butyl-1H-pyrazol-4-ylmethyl)-(2,4-dimethylphenyl)-amine,
(3-tert-Butyl-1H-pyrazol-4-ylmethyl)-(2,5-dimethylphenyl)-amine,
(3-tert-Butyl-1H-pyrazol-4-ylmethyl)-(3,4-dimethylphenyl)-amine,
(3-tert-Butyl-1H-pyrazol-4-ylmethyl)-(3,5-dimethylphenyl)-amine,
(3-tert-Butyl-1H-pyrazol-4-ylmethyl)-(2,3-dimethoxyphenyl)-amine,
(3-tert-Butyl-1H-pyrazol-4-ylmethyl)-(2,4-dimethoxyphenyl)-amine,
(3-tert-Butyl-1H-pyrazol-4-ylmethyl)-(2,5-dimethoxyphenyl)-amine,
(3-tert-Butyl-1H-pyrazol-4-ylmethyl)-(3,4-dimethoxyphenyl)-amine,
(3-tert-Butyl-1H-pyrazol-4-ylmethyl)-(3,5-dimethoxyphenyl)-amine,
Benzo[1,3]dioxol-5-yl-(3-tert-butyl-1H-pyrazol-4-ylmethyl)-amine,
(3-tert-Butyl-1H-pyrazol-4-ylmethyl)-(3,4,5-trimethoxyphenyl)-amine,
(3-tert-Butyl-1H-pyrazol-4-ylmethyl)-(2,3-dichlorophenyl)-amine,
(3-tert-Butyl-1H-pyrazol-4-ylmethyl)-(2,4-dichlorophenyl)-amine,
(3-tert-Butyl-1H-pyrazol-4-ylmethyl)-(2,5-dichlorophenyl)-amine,
(3-tert-Butyl-1H-pyrazol-4-ylmethyl)-(3,4-dichlorophenyl)-amine,
(3-tert-Butyl-1H-pyrazol-4-ylmethyl)-(3,5-dichlorophenyl)-amine,
(3-Thiophen-2-yl-1H-pyrazol-4-ylmethyl)-o-tolyl-amine,
(3-Thiophen-2-yl-1H-pyrazol-4-ylmethyl)-p-tolyl-amine,
(2-Methoxyphenyl)-(3-thiophen-2-yl-1H-pyrazol-4-ylmethyl)-amine,
(3-Methoxyphenyl)-(3-thiophen-2-yl-1H-pyrazol-4-ylmethyl)-amine, (4-Methoxyphenyl)-(3-thiophen-2-yl-1H-pyrazol-4-ylmethyl)-amine,
(2-Fluorophenyl)-(3-thiophen-2-yl-1H-pyrazol-4-ylmethyl)-amine,
(3-Fluorophenyl)-(3-thiophen-2-yl-1H-pyrazol-4-ylmethyl)-amine,
(2-Chlorophenyl)-(3-thiophen-2-yl-1H-pyrazol-4-ylmethyl)-amine,
(3-Chlorophenyl)-(3-thiophen-2-yl-1H-pyrazol-4-ylmethyl)-amine,
(4-Chlorophenyl)-(3-thiophen-2-yl-1H-pyrazol-4-ylmethyl)-amine,
(3-Thiophen-2-yl-1H-pyrazol-4-ylmethyl)-(4-trifluoromethoxyphenyl)-amine,
(3-Phenoxy-phenyl)-(3-thiophen-2-yl-1H-pyrazol-4-ylmethyl)-amine,
N,N-Dimethyl-N'-(3-thiophen-2-yl-1H-pyrazol-4-ylmethyl)-benzene-1,3-diamine,
N,N-Dimethyl-N'-(3-thiophen-2-yl-1H-pyrazol-4-ylmethyl)-benzene-1,4-diamine,
(3-Thiophen-2-yl-1H-pyrazol-4-ylmethyl)-(3-trifluoromethylphenyl)-amine,
(3-Thiophen-2-yl-1H-pyrazol-4-ylmethyl)-(4-trifluoromethylphenyl)-amine,
(3-Thiophen-2-yl-1H-pyrazol-4-ylmethyl)-(3-trifluoromethoxyphenyl)-amine,
(4-Phenoxyphenyl)-(3-thiophen-2-yl-1H-pyrazol-4-ylmethyl)-amine,
(2,3-Dimethylphenyl)-(3-thiophen-2-yl-1H-pyrazol-4-ylmethyl)-amine,
(2,4-Dimethylphenyl)-(3-thiophen-2-yl-1H-pyrazol-4-ylmethyl)-amine,
(2,5-Dimethylphenyl)-(3-thiophen-2-yl-1H-pyrazol-4-ylmethyl)-amine,
(3,5-Dimethylphenyl)-(3-thiophen-2-yl-1H-pyrazol-4-ylmethyl)-amine,
(2,3-Dimethoxyphenyl)-(3-thiophen-2-yl-1H-pyrazol-4-ylmethyl)-amine,
(2,4-Dimethoxyphenyl)-(3-thiophen-2-yl-1H-pyrazol-4-ylmethyl)-amine,
(2,5-Dimethoxyphenyl)-(3-thiophen-2-yl-1H-pyrazol-4-ylmethyl)-amine,
(3,4-Dimethoxyphenyl)-(3-thiophen-2-yl-1H-pyrazol-4-ylmethyl)-amine,
(3,5-Dimethoxyphenyl)-(3-thiophen-2-yl-1H-pyrazol-4-ylmethyl)-amine,
Benzo[1,3]dioxol-5-yl-(3-thiophen-2-yl-1H-pyrazol-4-ylmethyl)-amine,
(3-Thiophen-2-yl-1H-pyrazol-4-ylmethyl)-(3,4,5-trimethoxy-phenyl)-amine,
(2,3-Dichlorophenyl)-(3-thiophen-2-yl-1H-pyrazol-4-ylmethyl)-amine,
(2,4-Dichlorophenyl)-(3-thiophen-2-yl-1H-pyrazol-4-ylmethyl)-amine,
(2,5-Dichlorophenyl)-(3-thiophen-2-yl-1H-pyrazol-4-ylmethyl)-amine,
(3,4-Dichlorophenyl)-(3-thiophen-2-yl-1H-pyrazol-4-ylmethyl)-amine,
(3,5-Dichlorophenyl)-(3-thiophen-2-yl-1H-pyrazol-4-ylmethyl)-amine,
2,2,2-Trifluoroethanesulfonic acid [3-tert-butyl-1-(2,2,2-trifluoroethanesulfonyl)-1H-pyrazol-4-ylmethyl]-[3-(1-methyl-butoxy)-phenyl]-amide,
2-Fluoro-4-{[3-(4-trifluoromethyl-phenyl)-1H-pyrazol-4-ylmethyl]-amino}-benzonitrile,
(3-tert-Butyl-1H-pyrazol-4-ylmethyl)-[4-(1,1-dioxo-1$\lambda^6$-thiomorpholin-4-yl)-phenyl]-amine,
(3-tert-Butyl-1H-pyrazol-4-ylmethyl)-(4-oxazol-5-yl-phenyl)-amine,
(3-tert-Butyl-1H-pyrazol-4-ylmethyl)-(4-pyridin-4-yl-phenyl)-amine,
(3-tert-Butyl-1H-pyrazol-4-ylmethyl)-(4-pyridin-2-yl-phenyl)-amine,
(3-tert-Butyl-1H-pyrazol-4-ylmethyl)-(4-thiophen-3-yl-phenyl)-amine,
3-Fluoro-4-{[3-(4-trifluoromethyl-phenyl)-1H-pyrazol-4-ylmethyl]-amino}-benzonitrile,
2-Chloro-4-{[3-(4-trifluoromethyl-phenyl)-1H-pyrazol-4-ylmethyl]-amino}-benzonitrile,
(3-Methoxy-phenyl)-[3-(4-trifluoromethyl-phenyl)-1H-pyrazol-4-ylmethyl]-amine,
(4-Ethanesulfonyl-phenyl)-[3-(4-trifluoromethyl-phenyl)-1H-pyrazol-4-ylmethyl]-amine,
N,N-Dimethyl-4-{[3-(4-trifluoromethyl-phenyl)-1H-pyrazol-4-ylmethyl]-amino}-benzenesulfonamide,
(3-Benzyl-phenyl)-[3-(4-trifluoromethyl-phenyl)-1H-pyrazol-4-ylmethyl]-amine,
(3-tert-Butyl-1H-pyrazol-4-ylmethyl)-(4-thiophen-2-yl-phenyl)-amine,
(3-tert-Butyl-1H-pyrazol-4-ylmethyl)-[4-(4-methyl-piperazin-1-yl)-phenyl]-amine,
(3-tert-Butyl-1H-pyrazol-4-ylmethyl)-[4-(4,5-dimethyl-oxazol-2-yl)-phenyl]-amine,
o-Tolyl-[3-(4-trifluoromethyl-phenyl)-1H-pyrazol-4-ylmethyl]-amine,
m-Tolyl-[3-(4-trifluoromethyl-phenyl)-1H-pyrazol-4-ylmethyl]-amine,
p-Tolyl-[3-(4-trifluoromethyl-phenyl)-1H-pyrazol-4-ylmethyl]-amine,
(2-Methoxy-phenyl)-[3-(4-trifluoromethyl-phenyl)-1H-pyrazol-4-ylmethyl]-amine,
(3-Methoxy-phenyl)-[3-(4-trifluoromethyl-phenyl)-1H-pyrazol-4-ylmethyl]-amine,
(4-Methoxy-phenyl)-[3-(4-trifluoromethyl-phenyl)-1H-pyrazol-4-ylmethyl]-amine,
(2-Fluoro-phenyl)-[3-(4-trifluoromethyl-phenyl)-1H-pyrazol-4-ylmethyl]-amine,
(3-Fluoro-phenyl)-[3-(4-trifluoromethyl-phenyl)-1H-pyrazol-4-ylmethyl]-amine,
(4-Fluoro-phenyl)-[3-(4-trifluoromethyl-phenyl)-1H-pyrazol-4-ylmethyl]-amine,
(2-Chloro-phenyl)-[3-(4-trifluoromethyl-phenyl)-1H-pyrazol-4-ylmethyl]-amine,
(3-Chloro-phenyl)-[3-(4-trifluoromethyl-phenyl)-1H-pyrazol-4-ylmethyl]-amine,
(4-Chloro-phenyl)-[3-(4-trifluoromethyl-phenyl)-1H-pyrazol-4-ylmethyl]-amine,
(4-Trifluoromethoxy-phenyl)-[3-(4-trifluoromethyl-phenyl)-1H-pyrazol-4-ylmethyl]-amine;
(3-Phenoxy-phenyl)-[3-(4-trifluoromethyl-phenyl)-1H-pyrazol-4-ylmethyl]-amine,
(3-Dimethylaminomethyl-phenyl)-[5-(4-trifluoromethyl-phenyl)-1H-pyrazol-4-ylmethyl]-amine,
(3-Trifluoromethyl-phenyl)-[3-(4-trifluoromethyl-phenyl)-1H-pyrazol-4-ylmethyl]-amine,
(4-Trifluoromethyl-phenyl)-[3-(4-trifluoromethyl-phenyl)-1H-pyrazol-4-ylmethyl]-amine,
(3-Trifluoromethoxy-phenyl)-[3-(4-trifluoromethyl-phenyl)-1H-pyrazol-4-ylmethyl]-amine,
(4-Phenoxy-phenyl)-[3-(4-trifluoromethyl-phenyl)-1H-pyrazol-4-ylmethyl]-amine,
(2,3-Dimethyl-phenyl)-[3-(4-trifluoromethyl-phenyl)-1H-pyrazol-4-ylmethyl]-amine, (2,4-Dimethyl-phenyl)-[3-(4-trifluoromethyl-phenyl)-1H-pyrazol-4-ylmethyl]-amine,
(2,5-Dimethyl-phenyl)-[3-(4-trifluoromethyl-phenyl)-1H-pyrazol-4-ylmethyl]-amine,
(3,4-Dimethyl-phenyl)-[3-(4-trifluoromethyl-phenyl)-1H-pyrazol-4-ylmethyl]-amine,
(3,5-Dimethyl-phenyl)-[3-(4-trifluoromethyl-phenyl)-1H-pyrazol-4-ylmethyl]-amine,
(2,3-Dimethoxy-phenyl)-[3-(4-trifluoromethyl-phenyl)-1H-pyrazol-4-ylmethyl]-amine,
(2,4-Dimethoxy-phenyl)-[3-(4-trifluoromethyl-phenyl)-1H-pyrazol-4-ylmethyl]-amine,
(2,5-Dimethoxy-phenyl)-[3-(4-trifluoromethyl-phenyl)-1H-pyrazol-4-ylmethyl]-amine,
(3,4-Dimethoxy-phenyl)-[3-(4-trifluoromethyl-phenyl)-1H-pyrazol-4-ylmethyl]-amine,
(3,5-Dimethoxy-phenyl)-[3-(4-trifluoromethyl-phenyl)-1H-pyrazol-4-ylmethyl]-amine,
[3-(4-Trifluoromethyl-phenyl)-1H-pyrazol-4-ylmethyl]-(3,4,5-trimethoxy-phenyl)-amine,
(2,3-Dichloro-phenyl)-[3-(4-trifluoromethyl-phenyl)-1H-pyrazol-4-ylmethyl]-amine,
(2,4-Dichloro-phenyl)-[3-(4-trifluoromethyl-phenyl)-1H-pyrazol-4-ylmethyl]-amine,
(2,5-Dichloro-phenyl)-[3-(4-trifluoromethyl-phenyl)-1H-pyrazol-4-ylmethyl]-amine,
(3,4-Dichloro-phenyl)-[3-(4-trifluoromethyl-phenyl)-1H-pyrazol-4-ylmethyl]-amine,
(3,5-Dichloro-phenyl)-[3-(4-trifluoromethyl-phenyl)-1H-pyrazol-4-ylmethyl]-amine,
Ethanesulfonic acid (4-butyryl-phenyl)-[3-(4-trifluoromethyl-phenyl)-1H-pyrazol-4-ylmethyl]-amide,
2,2,2-Trifluoro-ethanesulfonic acid (4-butyryl-phenyl)-[3-(4-trifluoromethyl-phenyl)-1H-pyrazol-4-ylmethyl]-amide,
2,2,2-Trifluoro-ethanesulfonic acid (3-butyryl-phenyl)-[3-(4-trifluoromethyl-phenyl)-1H-pyrazol-4-ylmethyl]-amide,
Ethanesulfonic acid (3-butyryl-phenyl)-[3-(4-trifluoromethyl-phenyl)-1H-pyrazol-4-ylmethyl]-amide,
Ethanesulfonic acid [3-(1-methyl-butoxy)-phenyl]-[3-(4-trifluoromethyl-phenyl)-1H-pyrazol-4-ylmethyl]-amide,
2,2,2-Trifluoro-ethanesulfonic acid [3-(1-methyl-butoxy)-phenyl]-[3-(4-trifluoromethyl-phenyl)-1H-pyrazol-4-ylmethyl]-amide,
2,2,2-Trifluoro-ethanesulfonic acid [3-(1-ethyl-propoxy)-phenyl]-[3-(4-trifluoromethyl-phenyl)-1H-pyrazol-4-ylmethyl]-amide,
Ethanesulfonic acid [3-(1-ethyl-propoxy)-phenyl]-[3-(4-trifluoromethyl-phenyl)-1H-pyrazol-4-ylmethyl]-amide,
Ethanesulfonic acid [3-(2-methyl-butoxy)-phenyl]-[3-(4-trifluoromethyl-phenyl)-1H-pyrazol-4-ylmethyl]-amide,
2,2,2-Trifluoro-ethanesulfonic acid [3-(2-methyl-butoxy)-phenyl]-[3-(4-trifluoromethyl-phenyl)-1H-pyrazol-4-ylmethyl]-amide,
2,2,2-Trifluoro-ethanesulfonic acid (3-sec-butoxy-phenyl)-[3-(4-trifluoromethyl-phenyl)-1H-pyrazol-4-ylmethyl]-amide,
Ethanesulfonic acid (3-sec-butoxy-phenyl)-[3-(4-trifluoromethyl-phenyl)-1H-pyrazol-4-ylmethyl]-amide,
Ethanesulfonic acid (3-sec-butoxy-phenyl)-(3-thiophen-2-yl-1H-pyrazol-4-ylmethyl)-amide,
2,2,2-Trifluoro-ethanesulfonic acid (3-sec-butoxy-phenyl)-(3-thiophen-2-yl-1H-pyrazol-4-ylmethyl)-amide,
2,2,2-Trifluoro-ethanesulfonic acid [3-(2-methyl-butoxy)-phenyl]-(3-thiophen-2-yl-1H-pyrazol-4-ylmethyl)-amide,
Ethanesulfonic acid [3-(2-methyl-butoxy)-phenyl]-(3-thiophen-2-yl-1H-pyrazol-4-ylmethyl)-amide,
Ethanesulfonic acid [3-(1-ethyl-propoxy)-phenyl]-(3-thiophen-2-yl-1H-pyrazol-4-ylmethyl)-amide,
2,2,2-Trifluoro-ethanesulfonic acid [3-(1-ethyl-propoxy)-phenyl]-(3-thiophen-2-yl-1H-pyrazol-4-ylmethyl)-amide,
2,2,2-Trifluoro-ethanesulfonic acid [3-(1-methyl-butoxy)-phenyl]-(3-thiophen-2-yl-1H-pyrazol-4-ylmethyl)-amide,
Ethanesulfonic acid [3-(1-methyl-butoxy)-phenyl]-(3-thiophen-2-yl-1H-pyrazol-4-ylmethyl)-amide,
Ethanesulfonic acid (3-butyryl-phenyl)-(3-thiophen-2-yl-1H-pyrazol-4-ylmethyl)-amide,
2,2,2-Trifluoro-ethanesulfonic acid (3-butyryl-phenyl)-(3-thiophen-2-yl-1H-pyrazol-4-ylmethyl)-amide,
2,2,2-Trifluoro-ethanesulfonic acid (4-butyryl-phenyl)-(3-thiophen-2-yl-1H-pyrazol-4-ylmethyl)-amide,
Ethanesulfonic acid (4-butyryl-phenyl)-(3-thiophen-2-yl-1H-pyrazol-4-ylmethyl)-amide,
Ethanesulfonic acid (3-tert-butyl-1H-pyrazol-4-ylmethyl)-(4-butyryl-phenyl)-amide,
2,2,2-Trifluoro-ethanesulfonic acid (3-tert-butyl-1H-pyrazol-4-ylmethyl)-(4-butyryl-phenyl)-amide,
2,2,2-Trifluoro-ethanesulfonic acid (3-tert-butyl-1H-pyrazol-4-ylmethyl)-(3-butyryl-phenyl)-amide,
Ethanesulfonic acid (3-tert-butyl-1H-pyrazol-4-ylmethyl)-(3-butyryl-phenyl)-amide,
Ethanesulfonic acid (3-tert-butyl-1H-pyrazol-4-ylmethyl)-[3-(1-methyl-butoxy)-phenyl]-amide,
2,2,2-Trifluoro-ethanesulfonic acid (3-tert-butyl-1H-pyrazol-4-ylmethyl)-[3-(1-methyl-butoxy)-phenyl]-amide,
2,2,2-Trifluoro-ethanesulfonic acid (3-tert-butyl-1H-pyrazol-4-ylmethyl)-[3-(1-ethyl-propoxy)-phenyl]-amide,
Ethanesulfonic acid (3-tert-butyl-1H-pyrazol-4-ylmethyl)-[3-(1-ethyl-propoxy)-phenyl]-amide,
Ethanesulfonic acid (3-tert-butyl-1H-pyrazol-4-ylmethyl)-[3-(2-methyl-butoxy)-phenyl]-amide,
2,2,2-Trifluoro-ethanesulfonic acid (3-tert-butyl-1H-pyrazol-4-ylmethyl)-[3-(2-methyl-butoxy)-phenyl]-amide,
2,2,2-Trifluoro-ethanesulfonic acid (3-sec-butoxy-phenyl)-(3-tert-butyl-1H-pyrazol-4-ylmethyl)-amide,
Ethanesulfonic acid (3-sec-butoxy-phenyl)-(3-tert-butyl-1H-pyrazol-4-ylmethyl)-amide
1-(4-{[3-(4-Methoxy-phenyl)-1H-pyrazol-4-ylmethyl]-amino}-phenyl)-butan-1-one,
1-{4-[(3-Phenyl-1H-pyrazol-4-ylmethyl)-amino]-phenyl}-butan-1-one,
1-{4-[(1,3,5-Trimethyl-1H-pyrazol-4-ylmethyl)-amino]-phenyl}-butan-1-one,
1-{4-[(3-p-Tolyl-1H-pyrazol-4-ylmethyl)-amino]-phenyl}-butan-1-one,
1-(4-{[3-(3,5-Difluoro-phenyl)-1H-pyrazol-4-ylmethyl]-amino}-phenyl)-butan-1-one,
1-{4-[(1-Phenyl-3-pyridin-4-yl-1H-pyrazol-4-ylmethyl)-amino]-phenyl}-butan-1-one,
1-{4-[(1H-Indazol-3-ylmethyl)-amino]-phenyl}-butan-1-one,
1-{4-[(2-Methyl-2H-pyrazol-3-ylmethyl)-amino]-phenyl}-butan-1-one,
1-(4-{[3-(4-Chloro-phenyl)-1H-pyrazol-4-ylmethyl]-amino}-phenyl)-butan-1-one,
1-(4-{[3-(3,4-Dimethoxy-phenyl)-1H-pyrazol-4-ylmethyl]-amino}-phenyl)-butan-1-one,
1-{4-[(1-Methyl-1H-indazol-3-ylmethyl)-amino]-phenyl}-butan-1-one,
1-{4-[(1-Benzyl-1H-pyrazol-4-ylmethyl)-amino]-phenyl}-butan-1-one, 1-(4-{[3-(4-Fluoro-phenyl)-1-phenyl-1H-pyrazol-4-ylmethyl]-amino}-phenyl)-butan-1-one,
1-{4-[(1-Phenyl-3-pyridin-3-yl-1H-pyrazol-4-ylmethyl)-amino]-phenyl}-butan-1-one,
1-{4-[(5-Methoxy-1H-indazol-3-ylmethyl)-amino]-phenyl}-butan-1-one,
1-{4-[(3,5-Dimethyl-1H-pyrazol-4-ylmethyl)-amino]-phenyl}-butan-1-one,
1-(4-{[4-(4-Methoxy-phenyl)-thiazol-2-ylmethyl]-amino}-phenyl)-butan-1-one,
1-{4-[(1-Methyl-1H-benzoimidazol-2-ylmethyl)-amino]-phenyl}-butan-1-one,
1-{4-[(3,5-Dimethyl-isoxazol-4-ylmethyl)-amino]-phenyl}-butan-1-one,
1-{4-[(1-Methyl-1H-imidazol-4-ylmethyl)-amino]-phenyl}-butan-1-one,
1-{4-[(5-Thiophen-2-yl-isoxazol-3-ylmethyl)-amino]-phenyl}-butan-1-one,
1-{4-[(2,3-Dimethyl-3H-imidazol-4-ylmethyl)-amino]-phenyl}-butan-1-one,
1-{4-[(5-Methyl-2-phenyl-oxazol-4-ylmethyl)-amino]-phenyl}-butan-1-one,
1-{4-[(5-Furan-2-yl-isoxazol-3-ylmethyl)-amino]-phenyl}-butan-1-one,
1-{4-[(2-Methyl-4-phenyl-thiazol-5-ylmethyl)-amino]-phenyl}-butan-1-one,
1-(4-{[2-(4-Trifluoromethyl-phenyl)-thiazol-4-ylmethyl]-amino}-phenyl)-butan-1-one,
1-(4-{[2-(3-Chloro-phenyl)-thiazol-4-ylmethyl]-amino}-phenyl)-butan-1-one,
1-{4-[(5-Methyl-3H-imidazol-4-ylmethyl)-amino]-phenyl}-butan-1-one,
1-{4-[(4-Methyl-thiazol-5-ylmethyl)-amino]-phenyl}-butan-1-one,
1-(4-{[5-(4-Fluoro-phenyl)-isoxazol-3-ylmethyl]-amino}-phenyl)-butan-1-one,
1-{4-[(5-Methyl-isoxazol-3-ylmethyl)-amino]-phenyl}-butan-1-one,
1-{4-[(2,4-Dimethyl-thiazol-5-ylmethyl)-amino]-phenyl}-butan-1-one,
1-{4-[(4-Methyl-thiazol-2-ylmethyl)-amino]-phenyl}-butan-1-one,
1-(4-{[2-(2-Methoxy-phenyl)-thiazol-5-ylmethyl]-amino}-phenyl)-butan-1-one,
1-(4-{[2-(3-Methoxy-phenyl)-thiazol-5-ylmethyl]-amino}-phenyl)-butan-1-one,
1-(4-{[4-(4-Fluoro-phenyl)-thiazol-2-ylmethyl]-amino}-phenyl)-butan-1-one,
1-{4-[(5-Methyl-2-thiophen-2-yl-oxazol-4-ylmethyl)-amino]-phenyl}-butan-1-one,
1-{4-[(2-Phenyl-thiazol-5-ylmethyl)-amino]-phenyl}-butan-1-one,
1-{4-[(3-Methyl-3H-imidazol-4-ylmethyl)-amino]-phenyl}-butan-1-one,
1-{4-[(Thiazol-4-ylmethyl)-amino]-phenyl}-butan-1-one,
1-{4-[(Thiazol-5-ylmethyl)-amino]-phenyl}-butan-1-one,
1-{4-[(2,4-Dichloro-thiazol-5-ylmethyl)-amino]-phenyl}-butan-1-one,
1-{4-[(4,5-Dimethyl-1H-imidazol-2-ylmethyl)-amino]-phenyl}-butan-1-one,
1-{4-[(Oxazol-5-ylmethyl)-amino]-phenyl}-butan-1-one;
1-{4-[(Oxazol-2-ylmethyl)-amino]-phenyl}-butan-1-one;
1-(4-{[3-(3-Fluoro-phenyl)-isoxazol-5-ylmethyl]-amino}-phenyl)-butan-1-one;
1-(4-{[3-(2-Fluoro-phenyl)-isoxazol-5-ylmethyl]-amino}-phenyl)-butan-1-one;
1-(4-{[2-(4-Chloro-phenyl)-thiazol-4-ylmethyl]-amino}-phenyl)-butan-1-one;
1-{4-[(2-Chloro-thiazol-5-ylmethyl)-amino]-phenyl}-butan-1-one;
1-{4-[(5-Chloro-2-phenyl-3H-imidazol-4-ylmethyl)-amino]-phenyl}-butan-1-one;
1-(4-{[2-(Toluene-4-sulfonyl)-thiazol-5-ylmethyl]-amino}-phenyl)-butan-1-one;
1-(4-{[2-(4-Methoxy-phenoxy)-thiazol-5-ylmethyl]-amino}-phenyl)-butan-1-one;
1-{4-[(1-Propyl-1H-imidazol-2-ylmethyl)-amino]-phenyl}-butan-1-one;
1-{4-[(Imidazo[1,2-a]pyridin-2-ylmethyl)-amino]-phenyl}-butan-1-one;
1-{4-[(2-Methyl-thiazol-4-ylmethyl)-amino]-phenyl}-butan-1-one;
1-{4-[(2-Methyl-1H-imidazol-4-ylmethyl)-amino]-phenyl}-butan-1-one;
1-(4-{[2-(4-Methoxy-phenyl)-thiazol-5-ylmethyl]-amino}-phenyl)-butan-1-one;
1-(4-{[2-(3-Fluoro-phenyl)-thiazol-5-ylmethyl]-amino}-phenyl)-butan-1-one;
1-(4-{[2-(4-Trifluoromethyl-phenyl)-thiazol-5-ylmethyl]-amino}-phenyl)-butan-1-one;
1-{4-[(2-Isopropyl-thiazol-4-ylmethyl)-amino]-phenyl}-butan-1-one;
2-{4-[(3-tert-Butyl-1H-pyrazol-4-ylmethyl)-amino]-phenoxy}-benzonitrile;
(4-Butoxy-phenyl)-(3-tert-butyl-1H-pyrazol-4-ylmethyl)-amine;
(3-tert-Butyl-1H-pyrazol-4-ylmethyl)-[3-(1,1,2,2-tetrafluoro-ethoxy)-phenyl]-amine;
(3-tert-Butyl-1H-pyrazol-4-ylmethyl)-(4-difluoromethoxy-phenyl)-amine;
(3-tert-Butyl-1H-pyrazol-4-ylmethyl)-(4-propoxy-phenyl)-amine;
(3-tert-Butyl-1H-pyrazol-4-ylmethyl)-(3-difluoromethoxy-phenyl)-amine;
(3-tert-Butyl-1H-pyrazol-4-ylmethyl)-(4-ethoxy-phenyl)-amine;
(3-tert-Butyl-1H-pyrazol-4-ylmethyl)-[4-(2-chloro-phenoxy)-phenyl]-amine;
(3-tert-Butyl-1H-pyrazol-4-ylmethyl)-(4-o-tolyloxy-phenyl)-amine;
(3-tert-Butyl-1H-pyrazol-4-ylmethyl)-[4-(3,4-dichloro-phenoxy)-phenyl]-amine;
(4-Benzyloxy-phenyl)-(3-tert-butyl-1H-pyrazol-4-ylmethyl)-amine;
(3-tert-Butyl-1H-pyrazol-4-ylmethyl)-[4-(3-chloro-5-trifluoromethyl-pyridin-2-yloxy)-phenyl]-amine;
(3-tert-Butyl-1H-pyrazol-4-ylmethyl)-[4-(chloro-difluoro-methoxy)-phenyl]-amine;
[4-(3,5-Bis-trifluoromethyl-phenoxy)-phenyl]-(3-tert-butyl-1H-pyrazol-4-ylmethyl)-amine;
(3-tert-Butyl-1H-pyrazol-4-ylmethyl)-[4-(2-fluoro-phenoxy)-phenyl]-amine;
(3-tert-Butyl-1H-pyrazol-4-ylmethyl)-[4-(1-methyl-piperidin-4-yloxy)-phenyl]-amine;
(3-tert-Butyl-1H-pyrazol-4-ylmethyl)-[4-(pyridin-2-ylmethoxy)-phenyl]-amine;
(3-tert-Butyl-1H-pyrazol-4-ylmethyl)-(4-isobutoxy-phenyl)-amine;
(3-tert-Butyl-1H-pyrazol-4-ylmethyl)-[4-(2,3-dimethyl-phenoxy)-phenyl]-amine;
(3-tert-Butyl-1H-pyrazol-4-ylmethyl)-[4-(pyrimidin-2-yloxy)-phenyl]-amine;

(3-tert-Butyl-1H-pyrazol-4-ylmethyl)-[4-(1,1,2,2-tetrafluoro-ethoxy)-phenyl]-amine;
(3-tert-Butyl-1H-pyrazol-4-ylmethyl)-[4-(2-chloro-benzyloxy)-phenyl]-amine;
(3-tert-Butyl-1H-pyrazol-4-ylmethyl)-[4-(pyridin-3-yloxy)-phenyl]-amine;
(3-tert-Butyl-1H-pyrazol-4-ylmethyl)-[4-(4-fluoro-benzyloxy)-phenyl]-amine;
(3-tert-Butyl-1H-pyrazol-4-ylmethyl)-[4-(5-trifluoromethyl-pyridin-2-yloxy)-phenyl]-amine;
(3-tert-Butyl-1H-pyrazol-4-ylmethyl)-[4-(3-trifluoromethyl-phenoxy)-phenyl]-amine;
(3-tert-Butyl-1H-pyrazol-4-ylmethyl)-(4-m-tolyloxy-phenyl)-amine;
(3-tert-Butyl-1H-pyrazol-4-ylmethyl)-[4-(4-fluoro-phenoxy)-phenyl]-amine;
(3-tert-Butyl-1H-pyrazol-4-ylmethyl)-[4-(4-chloro-phenoxy)-phenyl]-amine;
(3-tert-Butyl-1H-pyrazol-4-ylmethyl)-[4-(3-methyl-butoxy)-phenyl]-amine;
(3-tert-Butyl-1H-pyrazol-4-ylmethyl)-[4-(2,4-dichloro-phenoxy)-phenyl]-amine;
(3-tert-Butyl-1H-pyrazol-4-ylmethyl)-(4-p-tolyloxy-phenyl)-amine;
(3-tert-Butyl-1H-pyrazol-4-ylmethyl)-(4-isopropoxy-phenyl)-amine;
1-{4-[(6-Dimethylamino-pyridin-3-ylmethyl)-amino]-phenyl}-butan-1-one;
1-{4-[(6-Morpholin-4-yl-pyridin-3-ylmethyl)-amino]-phenyl}-butan-1-one;
1-{4-[(6-Methoxy-pyridin-3-ylmethyl)-amino]-phenyl}-butan-1-one;
1-{4-[(6-Chloro-pyridin-3-ylmethyl)-amino]-phenyl}-butan-1-one;
1-{4-[(2-Methoxy-pyridin-3-ylmethyl)-amino]-phenyl}-butan-1-one;
1-{4-[(2,6-Dichloro-pyridin-3-ylmethyl)-amino]-phenyl}-butan-1-one;
1-{4-[(2-Fluoro-pyridin-3-ylmethyl)-amino]-phenyl}-butan-1-one;
1-{4-[(5-Methoxy-pyridin-3-ylmethyl)-amino]-phenyl}-butan-1-one;
1-{4-[(2-Isopropoxy-pyridin-3-ylmethyl)-amino]-phenyl}-butan-1-one;
1-{4-[(2-Propoxy-pyridin-3-ylmethyl)-amino]-phenyl}-butan-1-one;
1-{4-[(3,4,5,6-Tetrahydro-2H-[1,2']bipyridinyl-5'-ylmethyl)-amino]-phenyl}-butan-1-one;
1-{4-[(6-Cyclopentyloxy-pyridin-3-ylmethyl)-amino]-phenyl}-butan-1-one;
1-{4-[(2-Morpholin-4-yl-pyridin-3-ylmethyl)-amino]-phenyl}-butan-1-one;
1-{4-[(5-Fluoro-2-methoxy-pyridin-3-ylmethyl)-amino]-phenyl}-butan-1-one;
1-{4-[(5-Methyl-pyridin-3-ylmethyl)-amino]-phenyl}-butan-1-one;
1-{4-[(2,6-Dimethoxy-pyridin-3-ylmethyl)-amino]-phenyl}-butan-1-one;
1-{4-[(6-Fluoro-pyridin-3-ylmethyl)-amino]-phenyl}-butan-1-one;
1-{4-[(5-Fluoro-pyridin-3-ylmethyl)-amino]-phenyl}-butan-1-one;
1-{4-[(2,5-Dichloro-pyridin-3-ylmethyl)-amino]-phenyl}-butan-1-one;
1-{4-[(2-Thiophen-3-yl-pyridin-3-ylmethyl)-amino]-phenyl}-butan-1-one;
1-{4-[(2-Dimethylamino-pyridin-3-ylmethyl)-amino]-phenyl}-butan-1-one;
1-{4-[(6-Trifluoromethyl-pyridin-3-ylmethyl)-amino]-phenyl}-butan-1-one;
1-{4-[(6-Thiophen-2-yl-pyridin-3-ylmethyl)-amino]-phenyl}-butan-1-one;
1-{4-[(6-Furan-2-yl-pyridin-3-ylmethyl)-amino]-phenyl}-butan-1-one;
1-{4-[(4-Methyl-pyridin-3-ylmethyl)-amino]-phenyl}-butan-1-one;
[4-(Furan-2-ylmethoxy)-phenyl]-[3-(4-trifluoromethyl-phenyl)-1H-pyrazol-4-ylmethyl]-amine;
[4-(Thiophen-2-ylmethoxy)-phenyl]-[3-(4-trifluoromethyl-phenyl)-1H-pyrazol-4-ylmethyl]-amine;
(3-Isopropoxy-phenyl)-[3-(4-trifluoromethyl-phenyl)-1H-pyrazol-4-ylmethyl]-amine;
[3-(Pyridin-2-yloxy)-phenyl]-[3-(4-trifluoromethyl-phenyl)-1H-pyrazol-4-ylmethyl]-amine;
(4-Cyclopentyloxy-phenyl)-[3-(4-trifluoromethyl-phenyl)-1H-pyrazol-4-ylmethyl]-amine;
(2-Chloro-5-methyl-pyridin-3-yl)-[3-(4-trifluoromethyl-phenyl)-1H-pyrazol-4-ylmethyl]-amine;
(6-Chloro-4-methyl-pyridin-3-yl)-[3-(4-trifluoromethyl-phenyl)-1H-pyrazol-4-ylmethyl]-amine;
(4-Methyl-pyridin-2-yl)-[3-(4-trifluoromethyl-phenyl)-1H-pyrazol-4-ylmethyl]-amine;
(6-Chloro-pyridin-3-yl)-[3-(4-trifluoromethyl-phenyl)-1H-pyrazol-4-ylmethyl]-amine;
Phenyl-(3-{[3-(4-trifluoromethyl-phenyl)-1H-pyrazol-4-ylmethyl]-amino}-phenyl)-methanone;
(5-Fluoro-pyridin-2-yl)-[3-(4-trifluoromethyl-phenyl)-1H-pyrazol-4-ylmethyl]-amine;
(2-Methyl-pyridin-3-yl)-[3-(4-trifluoromethyl-phenyl)-1H-pyrazol-4-ylmethyl]-amine;
(6-Methyl-pyridin-3-yl)-[3-(4-trifluoromethyl-phenyl)-1H-pyrazol-4-ylmethyl]-amine;
(5-Chloro-pyridin-2-yl)-[3-(4-trifluoromethyl-phenyl)-1H-pyrazol-4-ylmethyl]-amine;
(4,6-Dimethyl-pyridin-2-yl)-[3-(4-trifluoromethyl-phenyl)-1H-pyrazol-4-ylmethyl]-amine;
(6-Methoxy-pyridin-3-yl)-[3-(4-trifluoromethyl-phenyl)-1H-pyrazol-4-ylmethyl]-amine;
(5-Methyl-pyridin-2-yl)-[3-(4-trifluoromethyl-phenyl)-1H-pyrazol-4-ylmethyl]-amine;
(6-Methyl-pyridin-2-yl)-[3-(4-trifluoromethyl-phenyl)-1H-pyrazol-4-ylmethyl]-amine;
Pyridin-2-yl-[3-(4-trifluoromethyl-phenyl)-1H-pyrazol-4-ylmethyl]-amine;
Pyridin-3-yl-[3-(4-trifluoromethyl-phenyl)-1H-pyrazol-4-ylmethyl]-amine;
(3,5-Difluoro-pyridin-2-yl)-[3-(4-trifluoromethyl-phenyl)-1H-pyrazol-4-ylmethyl]-amine;
(4-Methyl-pyridin-3-yl)-[3-(4-trifluoromethyl-phenyl)-1H-pyrazol-4-ylmethyl]-amine;
(6-Chloro-pyridin-2-yl)-[3-(4-trifluoromethyl-phenyl)-1H-pyrazol-4-ylmethyl]-amine;
(2,6-Dimethyl-pyridin-3-yl)-[3-(4-trifluoromethyl-phenyl)-1H-pyrazol-4-ylmethyl]-amine;
(2,6-Dimethoxy-pyridin-3-yl)-[3-(4-trifluoromethyl-phenyl)-1H-pyrazol-4-ylmethyl]-amine;
(4,6-Dimethyl-pyridin-3-yl)-[3-(4-trifluoromethyl-phenyl)-1H-pyrazol-4-ylmethyl]-amine;
Pyridin-4-yl-(4-{[3-(4-trifluoromethyl-phenyl)-1H-pyrazol-4-ylmethyl]-amino}-phenyl)-methanone;
(5-Chloro-pyridin-3-yl)-[3-(4-trifluoromethyl-phenyl)-1H-pyrazol-4-ylmethyl]-amine;

1-(3-{[3-(4-Trifluoromethyl-phenyl)-1H-pyrazol-4-ylmethyl]-amino}-thiophen-2-yl)-ethanone;
(6-Fluoro-pyridin-3-yl)-[3-(4-trifluoromethyl-phenyl)-1H-pyrazol-4-ylmethyl]-amine;
(2-Methoxy-pyridin-3-yl)-[3-(4-trifluoromethyl-phenyl)-1H-pyrazol-4-ylmethyl]-amine;
(2-Fluoro-pyridin-3-yl)-[3-(4-trifluoromethyl-phenyl)-1H-pyrazol-4-ylmethyl]-amine;
(6-Fluoro-pyridin-2-yl)-[3-(4-trifluoromethyl-phenyl)-1H-pyrazol-4-ylmethyl]-amine;
(5-Methoxy-pyridin-2-yl)-[3-(4-trifluoromethyl-phenyl)-1H-pyrazol-4-ylmethyl]-amine;
(5-Fluoro-pyridin-3-yl)-[3-(4-trifluoromethyl-phenyl)-1H-pyrazol-4-ylmethyl]-amine;
(3-Chloro-5-methyl-pyridin-2-yl)-[3-(4-trifluoromethyl-phenyl)-1H-pyrazol-4-ylmethyl]-amine;
(5,6-Dimethyl-pyridin-2-yl)-[3-(4-trifluoromethyl-phenyl)-1H-pyrazol-4-ylmethyl]-amine;
(2-Chloro-6-methyl-pyridin-3-yl)-[3-(4-chloro-phenyl)-1H-pyrazol-4-ylmethyl]-amine;
[3-(4-Chloro-phenyl)-1H-pyrazol-4-ylmethyl]-(6-fluoro-5-methyl-pyridin-3-yl)-amine;
[3-(4-Chloro-phenyl)-1H-pyrazol-4-ylmethyl]-(5-fluoro-4-methyl-pyridin-2-yl)-amine;
[3-(4-Chloro-phenyl)-1H-pyrazol-4-ylmethyl]-(6-methoxy-4-methyl-pyridin-3-yl)-amine;
[3-(4-Chloro-phenyl)-1H-pyrazol-4-ylmethyl]-(2-methoxy-4-methyl-pyridin-3-yl)-amine;
N3-[3-(4-Chloro-phenyl)-1H-pyrazol-4-ylmethyl]-N2,N2-dimethyl-5-trifluoromethyl-pyridine-2,3-diamine;
[3-(4-Chloro-phenyl)-1H-pyrazol-4-ylmethyl]-(4-methoxy-pyridin-3-yl)-amine;
N5-[3-(4-Chloro-phenyl)-1H-pyrazol-4-ylmethyl]-N2,N2-dimethyl-pyridine-2,5-diamine;
[3-(4-Chloro-phenyl)-1H-pyrazol-4-ylmethyl]-(4-methoxy-pyridin-2-yl)-amine;
3-Methyl-4-{[3-(4-trifluoromethyl-phenyl)-1H-pyrazol-4-ylmethyl]-amino}-benzonitrile;
1-(4-{[1-Methyl-3-(4-trifluoromethyl-phenyl)-1H-pyrazol-4-ylmethyl]-amino}-phenyl)-butan-1-one;
1-(4-{[1-Methyl-5-(4-trifluoromethyl-phenyl)-1H-pyrazol-4-ylmethyl]-amino}-phenyl)-butan-1-one;
[3-(2-Methyl-butoxy)-phenyl]-[3-(4-trifluoromethyl-phenyl)-1H-pyrazol-4-ylmethyl]-amine;
1-(4-{[3-(4-Chloro-phenyl)-1H-pyrazol-4-ylmethyl]-amino}-phenyl)-butan-1-one;
(3-sec-Butoxy-phenyl)-[3-(4-trifluoromethyl-phenyl)-1H-pyrazol-4-ylmethyl]-amine;
[3-(1-Methyl-butoxy)-phenyl]-[3-(4-trifluoromethyl-phenyl)-1H-pyrazol-4-ylmethyl]-amine;
[3-(1-Ethyl-propoxy)-phenyl]-[3-(4-trifluoromethyl-phenyl)-1H-pyrazol-4-ylmethyl]-amine;
(3-tert-Butyl-1H-pyrazol-4-ylmethyl)-(4-piperidin-4-yl-phenyl)-amine;
(3-tert-Butyl-1H-pyrazol-4-ylmethyl)-(4-piperazin-1-yl-phenyl)-amine;
2,2,2-Trifluoro-ethanesulfonic acid (4-butyryl-phenyl)-pyridin-3-ylmethyl-amide;
N N-Dimethyl-N'-pyridin-3-ylmethyl-benzene-1,4-diamine;
2,2,2-Trifluoro-ethanesulfonic acid (4-dimethylamino-phenyl)-pyridin-3-ylmethyl-amide;
1-{3-[(Pyridin-3-ylmethyl)-amino]-phenyl}-butan-1-one;
1-{4-[(6-Dimethylamino-pyridin-3-ylmethyl)-amino]-phenyl}-butan-1-one;
N,N-Dimethyl-N'-pyridin-3-ylmethyl-benzene-1,3-diamine;
2,2,2-Trifluoro-ethanesulfonic acid (3-dimethylamino-phenyl)-pyridin-3-ylmethyl-amide;
2,2,2-Trifluoro-ethanesulfonic acid (3-butyryl-phenyl)-pyridin-3-ylmethyl-amide;
2,2,2-Trifluoro-ethanesulfonic acid (4-butyryl-phenyl)-(6-dimethylamino-pyridin-3-ylmethyl)-amide;
1-(3-{Methyl-[3-(4-trifluoromethyl-phenyl)-1H-pyrazol-4-ylmethyl]-amino}-phenyl)-butan-1-one;
2,2,2-Trifluoro-ethanesulfonic acid (5-oxo-5,6,7,8-tetrahydro-naphthalen-2-yl)-[3-(4-trifluoromethyl-phenyl)-1H-pyrazol-4-ylmethyl]-amide;
2,2,2-Trifluoro-ethanesulfonic acid [4-(2-methoxy-phenoxy)-phenyl]-[3-(4-trifluoromethyl-phenyl)-1H-pyrazol-4-ylmethyl]-amide;
N,N-Dimethyl-4-{(2,2,2-trifluoro-ethanesulfonyl)-[3-(4-trifluoromethyl-phenyl)-1H-pyrazol-4-ylmethyl]-amino}-benzenesulfonamide;
[3-(2-Trifluoromethyl-benzyl)-phenyl]-[3-(4-trifluoromethyl-phenyl)-1H-pyrazol-4-ylmethyl]-amine;
[3-(2-Methoxy-phenoxy)-phenyl]-[3-(4-trifluoromethyl-phenyl)-1H-pyrazol-4-ylmethyl]-amine;
1-(3-Chloro-4-{[3-(4-trifluoromethyl-phenyl)-1H-pyrazol-4-ylmethyl]-amino}-phenyl)-ethanone;
(4-Methanesulfonyl-phenyl)-[3-(4-trifluoromethyl-phenyl)-1H-pyrazol-4-ylmethyl]-amine;
2-Methyl-7-{[3-(4-trifluoromethyl-phenyl)-1H-pyrazol-4-ylmethyl]-amino}-chromen-4-one;
1-(2-Fluoro-4-{[3-(4-trifluoromethyl-phenyl)-1H-pyrazol-4-ylmethyl]-amino}-phenyl)-ethanone;
2,2,2-Trifluoro-ethanesulfonic acid (3-tert-butyl-1H-pyrazol-4-ylmethyl)-[4-(4,5-dimethyl-oxazol-2-yl)-phenyl]-amide,
2,2,2-Trifluoro-ethanesulfonic acid (3-tert-butyl-1H-pyrazol-4-ylmethyl)-(4-oxazol-5-yl-phenyl)-amide;
2,2,2-Trifluoro-ethanesulfonic acid (3-tert-butyl-1H-pyrazol-4-ylmethyl)-(4-pyridin-2-yl-phenyl)-amide;
2,2,2-Trifluoro-ethanesulfonic acid (3-tert-butyl-1H-pyrazol-4-ylmethyl)-(4-pyridin-4-yl-phenyl)-amide;
[3-(1-Ethyl-propoxy)-phenyl]-methyl-[3-(4-trifluoromethyl-phenyl)-1H-pyrazol-4-ylmethyl]-amine;
Ethanesulfonic acid [3-(1-ethyl-propoxy)-phenyl]-[3-(4-trifluoromethyl-phenyl)-1H-pyrazol-4-ylmethyl]-amide;
N-[3-(1-Ethyl-propoxy)-phenyl]-N-[3-(4-trifluoromethyl-phenyl)-1H-pyrazol-4-ylmethyl]-methanesulfonamide;
1-(4-{Methyl-[3-(4-trifluoromethyl-phenyl)-1H-pyrazol-4-ylmethyl]-amino}-phenyl)-butan-1-one;
1-[4-(Methyl-pyridin-3-ylmethyl-amino)-phenyl]-butan-1-one;
2,2,2-Trifluoro-ethanesulfonic acid (4-butyryl-phenyl)-[1-methyl-5-(4-trifluoromethyl-phenyl)-1H-pyrazol-4-ylmethyl]-amide;
2,2,2-Trifluoro-ethanesulfonic acid (4-butyryl-phenyl)-[1-methyl-3-(4-trifluoromethyl-phenyl)-1H-pyrazol-4-ylmethyl]-amide;
(4-Butyl-phenyl)-[3-(4-trifluoromethyl-phenyl)-1H-pyrazol-4-ylmethyl]-amine;
2,2,2-Trifluoro-ethanesulfonic acid (4-butyryl-phenyl)-[3-(4-trifluoromethyl-phenyl)-1H-pyrazol-4-ylmethyl]-amide;
3-{[3-(4-Chloro-phenyl)-1H-pyrazol-4-ylmethyl]-amino}-N,N-dimethyl-benzamide;
1-(4-{[3-(3-Trifluoromethyl-phenyl)-1H-pyrazol-4-ylmethyl]-amino}-phenyl)-butan-1-one;
N-(4-Butyryl-phenyl)-N-pyridin-3-ylmethyl-benzenesulfonamide;
N-[3-(1-Ethyl-propoxy)-phenyl]-N-[3-(4-trifluoromethyl-phenyl)-1H-pyrazol-4-ylmethyl]-benzenesulfonamide;
1-[3-(Methyl-pyridin-3-ylmethyl-amino)-phenyl]-butan-1-one;

N-(3-Butyryl-phenyl)-N-pyridin-3-ylmethyl-benzene-sulfonamide;
N-(3-Butyryl-phenyl)-N-pyridin-3-ylmethyl-methane-sulfonamide;
N-(3-Butyryl-phenyl)-C-phenyl-N-pyridin-3-ylmethyl-methanesulfonamide;
1-{4-[4-(Pyridin-3-yloxy)-butoxy]-phenyl}-butan-1-one;
2,2,2-Trifluoro-ethanesulfonic acid (6-dimethylamino-pyridin-3-ylmethyl)-[3-(1-ethyl-propoxy)-phenyl]-amide;
[3-(4-Chloro-phenyl)-1H-pyrazol-4-ylmethyl]-(1,1-dioxo-2,3-dihydro-1H-benzo[b]thiophen-5-yl)-amine;
7-{[3-(4-Chloro-phenyl)-1H-pyrazol-4-ylmethyl]-amino}-3,4-dihydro-2H-naphthalen-1-one;
6-{[3-(4-Chloro-phenyl)-1H-pyrazol-4-ylmethyl]-amino}-indan-1-one;
4-{[3-(4-Chloro-phenyl)-1H-pyrazol-4-ylmethyl]-amino}-N-methyl-benzenesulfonamide;
[3-(4-Chloro-phenyl)-1H-pyrazol-4-ylmethyl]-[4-(pyrrolidine-1-sulfonyl)-phenyl]-amine;
3-{[3-(4-Chloro-phenyl)-1H-pyrazol-4-ylmethyl]-amino}-N,N-dimethyl-benzenesulfonamide;
[3-(4-Chloro-phenyl)-1H-pyrazol-4-ylmethyl]-(1,1-dioxo-1H-benzo[b]thiophen-5-yl)-amine;
4-{[3-(4-Chloro-phenyl)-1H-pyrazol-4-ylmethyl]-amino}-N,N-diethyl-benzenesulfonamide;
N,N-Dimethyl-4-{[3-(3-trifluoromethyl-phenyl)-1H-pyrazol-4-ylmethyl]-amino}-benzamide;
1-(2-Methoxy-4-{[3-(3-trifluoromethyl-phenyl)-1H-pyrazol-4-ylmethyl]-amino}-phenyl)-butan-1-one;
1-(2-Hydroxy-4-{[3-(3-trifluoromethyl-phenyl)-1H-pyrazol-4-ylmethyl]-amino}-phenyl)-butan-1-one;
1-(2-Hydroxy-3-propyl-4-{[3-(3-trifluoromethyl-phenyl)-1H-pyrazol-4-ylmethyl]-amino}-phenyl)-ethanone;
1-[4-{[3-(4-Chloro-phenyl)-1H-pyrazol-4-ylmethyl]-amino}-2-(1-ethyl-propoxy)-phenyl]-butan-1-one;
1-(4-{[3-(4-Chloro-phenyl)-1H-pyrazol-4-ylmethyl]-amino}-2-methoxy-3-methyl-phenyl)-ethanone;
1-(4-{[3-(4-Chloro-phenyl)-1H-pyrazol-4-ylmethyl]-amino}-2-methoxy-3-propyl-phenyl)-ethanone;
1-(4-{[3-(4-Chloro-phenyl)-1H-pyrazol-4-ylmethyl]-amino}-2-hydroxy-3-methyl-phenyl)-ethanone;
2-Phenyl-1-{4-[3-(3-trifluoromethyl-phenyl)-1H-pyrazol-4-ylmethoxy]-phenyl}-ethanone;
Cyclopentyl-{4-[3-(3-trifluoromethyl-phenyl)-1H-pyrazol-4-ylmethoxy]-phenyl}-methanone;
4-{[3-(4-Chloro-phenyl)-1H-pyrazol-4-ylmethyl]-amino}-benzoic acid methyl ester;
(4-{[3-(4-Chloro-phenyl)-1H-pyrazol-4-ylmethyl]-amino}-phenyl)-(4-methyl-piperazin-1-yl)-methanone;
(4-{[3-(4-Chloro-phenyl)-1H-pyrazol-4-ylmethyl]-amino}-phenyl)-[4-(1-methyl-piperidin-4-yl)-piperazin-1-yl]-methanone;
(4-{[3-(4-Chloro-phenyl)-1H-pyrazol-4-ylmethyl]-amino}-phenyl)-morpholin-4-yl-methanone;
4-{[3-(4-Chloro-phenyl)-1H-pyrazol-4-ylmethyl]-amino}-N-methyl-N-propyl-benzamide;
4-{[3-(4-Chloro-phenyl)-1H-pyrazol-4-ylmethyl]-amino}-N-propyl-benzamide;
1-[3-(Benzyl-pyridin-3-ylmethyl-amino)-phenyl]-butan-1-one;
(3-tert-Butyl-1H-pyrazol-4-ylmethyl)-[4-(1-methyl-piperidin-4-yl)-phenyl]-amine;
(3-tert-Butyl-1H-pyrazol-4-ylmethyl)-[4-(4-methyl-4H-[1,2,4]triazol-3-yl)-phenyl]-amine;
(3-tert-Butyl-1H-pyrazol-4-ylmethyl)-[4-(5-methyl-furan-2-yl)-phenyl]-amine;
(3-tert-Butyl-1H-pyrazol-4-ylmethyl)-(3-cyclopentyloxy-phenyl)-amine;
2,2,2-Trifluoro-ethanesulfonic acid [3-(1-ethyl-propoxy)-phenyl]-[3-(4-trifluoromethyl-phenyl)-1H-pyrazol-4-ylmethyl]-amide;
2,2,2-Trifluoro-ethanesulfonic acid [3-(1-methyl-butoxy)-phenyl]-[3-(4-trifluoromethyl-phenyl)-1H-pyrazol-4-ylmethyl]-amide;
2,2,2-Trifluoro-ethanesulfonic acid (3-sec-butoxy-phenyl)-[3-(4-trifluoromethyl-phenyl)-1H-pyrazol-4-ylmethyl]-amide;
2,2,2-Trifluoro-ethanesulfonic acid [3-(2-methyl-butoxy)-phenyl]-[3-(4-trifluoromethyl-phenyl)-1H-pyrazol-4-ylmethyl]-amide;
2,2,2-Trifluoro-ethanesulfonic acid (3-tert-butyl-1H-pyrazol-4-ylmethyl)-(3-cyclopentyloxy-phenyl)-amide;
(3-tert-Butyl-1H-pyrazol-4-ylmethyl)-(3-thiophen-2-yl-phenyl)-amine;
(3-tert-Butyl-1H-pyrazol-4-ylmethyl)-(3-furan-2-yl-phenyl)-amine;
(3-tert-Butyl-1H-pyrazol-4-ylmethyl)-[3-(4-methyl-thiazol-2-yl)-phenyl]-amine;
(3-tert-Butyl-1H-pyrazol-4-ylmethyl)-[3-(4,5-dimethyl-thiazol-2-yl)-phenyl]-amine;
(3-tert-Butyl-1H-pyrazol-4-ylmethyl)-(3-oxazol-5-yl-phenyl)-amine;
(3-tert-Butyl-1H-pyrazol-4-ylmethyl)-(3-thiophen-3-yl-phenyl)-amine;
(3-tert-Butyl-1H-pyrazol-4-ylmethyl)-[3-(4,5-dimethyl-oxazol-2-yl)-phenyl]-amine;
(3-tert-Butyl-1H-pyrazol-4-ylmethyl)-[3-(4-methyl-piperazin-1-yl)-phenyl]-amine;
(3-tert-Butyl-1H-pyrazol-4-ylmethyl)-(3-piperazin-1-yl-phenyl)-amine;
(3-tert-Butyl-1H-pyrazol-4-ylmethyl)-[3-(1,1-dioxo-1 lambda%6&-isothiazolidin-2-yl)-phenyl]-amine;
(3-tert-Butyl-1H-pyrazol-4-ylmethyl)-[3-(2-methyl-thiazol-4-yl)-phenyl]-amine;
(3-tert-Butyl-1H-pyrazol-4-ylmethyl)-(3-pyridin-2-yl-phenyl)-amine;
[4-(1-Ethyl-propoxy)-phenyl]-[3-(4-trifluoromethyl-phenyl)-1H-pyrazol-4-ylmethyl]-amine;
(2-Dimethylaminomethyl-phenyl)-[3-(4-trifluoromethyl-phenyl)-1H-pyrazol-4-ylmethyl]-amine;
(3-Dimethylaminomethyl-phenyl)-[3-(4-trifluoromethyl-phenyl)-1H-pyrazol-4-ylmethyl]-amine;
2,2,2-Trifluoro-ethanesulfonic acid [4-(1-ethyl-propoxy)-phenyl]-[3-(4-trifluoromethyl-phenyl)-1H-pyrazol-4-ylmethyl]-amide;
1-{4-[(3-Methyl-1H-pyrazol-4-ylmethyl)-amino]-phenyl}-butan-1-one;
1-{4-[(3-Propyl-1H-pyrazol-4-ylmethyl)-amino]-phenyl}-butan-1-one;
1-{4-[(3-Isopropyl-1H-pyrazol-4-ylmethyl)-amino]-phenyl}-butan-1-one;
1-{4-[(3-Ethyl-1H-pyrazol-4-ylmethyl)-amino]-phenyl}-butan-1-one;
(4-{[3-(4-Chloro-phenyl)-1H-pyrazol-4-ylmethyl]-amino}-phenyl)-morpholin-4-yl-methanone;
4-{[3-(4-Chloro-phenyl)-1H-pyrazol-4-ylmethyl]-amino}-N-methyl-N-propyl-benzamide;
4-{[3-(4-Chloro-phenyl)-1H-pyrazol-4-ylmethyl]-amino}-N-propyl-benzamide;
1-[3-(Benzyl-pyridin-3-ylmethylamino)-phenyl]-butan-1-one;
1-{4-[3-(4-Trifluoromethyl-phenyl)-1H-pyrazol-4-ylmethoxy]-phenyl}-ethanone;

1-{3-Chloro-4-[3-(4-trifluoromethyl-phenyl)-1H-pyrazol-4-ylmethoxy]-phenyl}-ethanone,
1-{2-Fluoro-4-[3-(4-trifluoromethyl-phenyl)-1H-pyrazol-4-ylmethoxy]-phenyl}-ethanone,
1-{3-Fluoro-4-[3-(4-trifluoromethyl-phenyl)-1H-pyrazol-4-ylmethoxy]-phenyl}-ethanone,
1-{2-Methyl-4-[3-(4-trifluoromethyl-phenyl)-1H-pyrazol-4-ylmethoxy]-phenyl}-ethanone,
1-{3-Methyl-4-[3-(4-trifluoromethyl-phenyl)-1H-pyrazol-4-ylmethoxy]-phenyl}-ethanone,
1-{4-[3-(4-Trifluoromethyl-phenyl)-1H-pyrazol-4-ylmethoxy]-phenyl}-propan-1-one,
1-{4-[3-(4-Trifluoromethyl-phenyl)-1H-pyrazol-4-ylmethoxy]-phenyl}-pentan-1-one,
1-{4-[3-(4-Trifluoromethyl-phenyl)-1H-pyrazol-4-ylmethoxy]-phenyl}-hexan-1-one,
1-{4-[3-(4-Trifluoromethyl-phenyl)-1H-pyrazol-4-ylmethylsulfanyl]-phenyl}-butan-1-one,
1-{4-[3-(4-Trifluoromethyl-phenyl)-1H-pyrazol-4-ylmethanesulfonyl]-phenyl}-butan-1-one,
1-{4-[3-(4-Trifluoromethyl-phenyl)-1H-pyrazol-4-ylmethoxy]-phenyl}-butan-1-one,
1-{4-[3-(4-Fluoro-phenyl)-1H-pyrazol-4-ylmethoxy]-phenyl}-butan-1-one,
1-{4-[3-(4-Chloro-phenyl)-1H-pyrazol-4-ylmethoxy]-phenyl}-butan-1-one,
1-{4-[3-(3-Fluoro-phenyl)-1H-pyrazol-4-ylmethoxy]-phenyl}-butan-1-one,
1-{4-[3-(3-Trifluoromethyl-phenyl)-1H-pyrazol-4-ylmethoxy]-phenyl}-butan-1-one,
1-[4-(3-Phenyl-1H-pyrazol-4-ylmethoxy)-phenyl]-butan-1-one, trifluoroacetic acid,
1-{4-[1-(3-Phenyl-1H-pyrazol-4-yl)-ethoxy]-phenyl}-butan-1-one,
1-(4-{[3-(4-Trifluoromethyl-phenyl)-1H-pyrazol-4-ylmethyl]-amino}-phenyl)-ethanone,
1-(3-Nitro-4-{[3-(4-trifluoromethyl-phenyl)-1H-pyrazol-4-ylmethyl]-amino}-phenyl)-ethanone,
1-(3-{[3-(4-Trifluoromethyl-phenyl)-1H-pyrazol-4-ylmethyl]-amino}-phenyl)-ethanone,
1-(3-{[3-(4-Trifluoromethyl-phenyl)-1H-pyrazol-4-ylmethyl]-amino}-phenyl)-butan-1-one,
Phenyl-(4-{[3-(4-trifluoromethyl-phenyl)-1H-pyrazol-4-ylmethyl]-amino}-phenyl)-methanone,
2,2-Dimethyl-1-(4-{[3-(4-trifluoromethyl-phenyl)-1H-pyrazol-4-ylmethyl]-amino}-phenyl)-propan-1-one,
2,2,2-Trifluoro-1-(4-{[3-(4-trifluoromethyl-phenyl)-1H-pyrazol-4-ylmethyl]-amino}-phenyl)-ethanone,
1-{1-[3-(4-Trifluoromethyl-phenyl)-1H-pyrazol-4-ylmethyl]2,3-dihydro1H-indol-5-yl}-ethanone,
1-(4-{[3-(4-Fluoro-phenyl)-1H-pyrazol-4-ylmethyl]-amino}-phenyl)-butan-1-one,
1-(4-{[3-(3-Chloro-phenyl)-1H-pyrazol-4-ylmethyl]-amino}-phenyl)-butan-1-one,
1-(4-{[3-(2-Chloro-phenyl)-1H-pyrazol-4-ylmethyl]-amino}-phenyl)-butan-1-one,
1-(4-{[3-(3-Fluoro-phenyl)-1H-pyrazol-4-ylmethyl]-amino}-phenyl)-butan-1-one,
1-{4-[(3-Pyridin-3-yl-1H-pyrazol-4-ylmethyl)-amino]-phenyl}-butan-1-one,
1-(4-{[4-(4-Methoxy-phenyl)-1H-pyrazol-3-ylmethyl]-amino}-phenyl)-butan-1-one,
1-(3-{[4-(4-Methoxy-phenyl)-1H-pyrazol-3-ylmethyl]-amino}-phenyl)-butan-1-one,
1-(3-{[4-(4-Ethyl-phenyl)-1H-pyrazol-3-ylmethyl]-amino}-phenyl)-butan-1-one,
1-(4-{[4-(4-Ethyl-phenyl)-1H-pyrazol-3-ylmethyl]-amino}-phenyl)-butan-1-one,
1-(4-{[4-(4-Trifluoromethyl-phenyl)-1H-pyrazol-3-ylmethyl]-amino}-phenyl)-butan-1-one,
1-(4-{[4-(4-Chloro-phenyl)-1H-pyrazol-3-ylmethyl]-amino}-phenyl)-butan-1-one,
1-{4-[(5-Phenyl-2H-[1,2,3]triazol-4-ylmethyl)-amino]-phenyl}-butan-1-one,
1-{4-[4-(4-Methoxy-phenyl)-1H-pyrazol-3-ylmethoxy]-phenyl}-butan-1-one,
1-{4-[4-(4-Ethyl-phenyl)-1H-pyrazol-3-ylmethoxy]-phenyl}-butan-1-one,
1-[4-(4-Bromo-1H-pyrazol-3-ylmethoxy)-phenyl]-butan-1-one,
1-{4-[(4-Phenyl-1H-pyrrol-3-ylmethyl)-amino]-phenyl}-butan-1-one,
1-{4-[(3-Phenyl-pyridin-4-ylmethyl)-amino]-phenyl}-butan-1-one,
1-{4-[(4-Phenyl-pyridin-3-ylmethyl)-amino]-phenyl}-butan-1-one,
1-{4-[(2-Phenyl-pyridin-3-ylmethyl)-amino]-phenyl}-butan-1-one,
1-{4-[(6-Phenyl-pyridin-3-ylmethyl)-amino]-phenyl}-butan-1-one,
1-(4-{[6-(4-Fluoro-phenyl)-pyridin-2-ylmethyl]-amino}-phenyl)-butan-1-one,
1-{4-[(Pyrazolo[1,5-a]pyridin-3-ylmethyl)-amino]-phenyl}-butan-1-one,
1-{4-[(3-Methyl-5-phenyl-isoxazol-4-ylmethyl)-amino]-phenyl}-butan-1-one,
2-Propyl-5-[3-(4-trifluoromethyl-phenyl)-1H-pyrazol-4-ylmethoxy]-2,3-dihydro-isoindol-1-one,
2-Propyl-5-[3-(3-trifluoromethyl-phenyl)-1H-pyrazol-4-ylmethoxy]-2,3-dihydro-isoindol-1-one,
5-[3-(4-Fluoro-phenyl)-1H-pyrazol-4-ylmethoxy]-2-propyl-2,3-dihydro-isoindol-1-one,
5-[3-(4-Chloro-phenyl)-1H-pyrazol-4-ylmethoxy]-2-propyl-2,3-dihydro-isoindol-1-one,
5-[3-(3-Chloro-phenyl)-1H-pyrazol-4-ylmethoxy]-2-propyl-2,3-dihydro-isoindol-1-one,
5-[3-(3-Fluoro-phenyl)-1H-pyrazol-4-ylmethoxy]-2-propyl-2,3-dihydro-isoindol-1-one,
5-(3-Phenyl-1H-pyrazol-4-ylmethoxy)-2-propyl-2,3-dihydro-isoindol-1-one,
5-[3-(3-Trifluoromethyl-phenyl)-1H-pyrazol-4-ylmethoxy]-2-(3,3,3-trifluoro-propyl)-2,3-dihydro-isoindol-1-one,
5-[3-(4-Chloro-phenyl)-1H-pyrazol-4-ylmethoxy]-2-(3,3,3-trifluoro-propyl)-2,3-dihydro-isoindol-1-one,
5-[3-(4-Fluoro-phenyl)-1H-pyrazol-4-ylmethoxy]-2-(3,3,3-trifluoro-propyl)-2,3-dihydro-isoindol-1-one,
5-[3-(3-Fluoro-phenyl)-1H-pyrazol-4-ylmethoxy]-2-(3,3,3-trifluoro-propyl)-2,3-dihydro-isoindol-1-one,
5-[3-(4-Trifluoromethyl-phenyl)-1H-pyrazol-4-ylmethoxy]-2-(3,3,3-trifluoro-propyl)-2,3-dihydro-isoindol-1-one,
5-(3-Phenyl-1H-pyrazol-4-ylmethoxy)-2-(3,3,3-trifluoropropyl)-2,3-dihydro-isoindol-1-one,
2-Butyl-5-[3-(4-trifluoromethyl-phenyl)-1H-pyrazol-4-ylmethoxy]-2,3-dihydro-isoindol-1-one,
2-Butyl-5-[3-(3-trifluoromethyl-phenyl)-1H-pyrazol-4-ylmethoxy]-2,3-dihydro-isoindol-1-one,
2-Butyl-5-[3-(4-chloro-phenyl)-1H-pyrazol-4-ylmethoxy]-2,3-dihydro-isoindol-1-one,
2-Butyl-5-[3-(3,4-dichloro-phenyl)-1H-pyrazol-4-ylmethoxy]-2,3-dihydro-isoindol-1-one,
2-Butyl-5-[3-(4-fluoro-phenyl)-1H-pyrazol-4-ylmethoxy]-2,3-dihydro-isoindol-1-one, 2-Butyl-5-[3-(3-chloro-phenyl)-1H-pyrazol-4-ylmethoxy]-2,3-dihydro-isoindol-1-one,
2-Butyl-5-[3-(3-fluoro-phenyl)-1H-pyrazol-4-ylmethoxy]-2,3-dihydro-isoindol-1-one,
2-Butyl-5-(3-phenyl-1H-pyrazol-4-ylmethoxy)-2,3-dihydro-isoindol-1-one, trifluoroacetic acid,
2-(4,4,4-Trifluoro-butyl)-5-[3-(4-trifluoromethyl-phenyl)-1H-pyrazol-4-ylmethoxy]-2,3-dihydro-isoindol-1-one,
5-(3-Phenyl-1H-pyrazol-4-ylmethoxy)-2-(4,4,4-trifluoro-butyl)-2,3-dihydro-isoindol-1-one,
5-[3-(3,4-dichloro-phenyl)-1H-pyrazol-4-ylmethoxy]-2-(4,4,4-trifluoro-butyl)-2,3-dihydro-isoindol-1-one,
2-(3-Methyl-butyl)-5-[3-(4-trifluoromethyl-phenyl)-1H-pyrazol-4-ylmethoxy]-2,3-dihydro-isoindol-1-one,
2-(3-Methyl-butyl)-5-(3-phenyl-1H-pyrazol-4-ylmethoxy)-2,3-dihydro-isoindol-1-one,
5-(3-Phenyl-1H-pyrazol-4-ylmethoxy)-2-(2-trifluoromethoxy-ethyl)-2,3-dihydro-isoindol-1-one,
2-Ethyl-5-[3-(3-trifluoromethyl-phenyl)-1H-pyrazol-4-ylmethoxy]-2,3-dihydro-isoindol-1-one,
2-Ethyl-5-[3-(4-fluoro-phenyl)-1H-pyrazol-4-ylmethoxy]-2,3-dihydro-isoindol-1-one,
2-Ethyl-5-[3-(3-fluoro-phenyl)-1H-pyrazol-4-ylmethoxy]-2,3-dihydro-isoindol-1-one,
5-[3-(3-Chloro-phenyl)-1H-pyrazol-4-ylmethoxy]-2-ethyl-2,3-dihydro-isoindol-1-one,
5-[3-(4-Chloro-phenyl)-1H-pyrazol-4-ylmethoxy]-2-ethyl-2,3-dihydro-isoindol-1-one,
2-Ethyl-5-(3-phenyl-1H-pyrazol-4-ylmethoxy)-2,3-dihydro-isoindol-1-one,
2-(2-Bromo-ethyl)-5-[3-(4-trifluoromethyl-phenyl)-1H-pyrazol-4-ylmethoxy]-2,3-dihydro-isoindol-1-one,
2-(2-Bromo-ethyl)-5-[3-(3-trifluoromethyl-phenyl)-1H-pyrazol-4-ylmethoxy]-2,3-dihydro-isoindol-1-one,
2-(2,2-Difluoro-ethyl)-5-[3-(4-trifluoromethyl-phenyl)-1H-pyrazol-4-ylmethoxy]-2,3-dihydro-isoindol-1-one,
2-(2,2-Difluoroethyl)-5-(3-phenyl-1H-pyrazol-4-ylmethoxy)-2,3-dihydro-isoindol-1-one,
2-(2,2,2-Trifluoroethyl)-5-[3-(4-trifluoromethyl-phenyl)-1H-pyrazol-4-ylmethoxy]-2,3-dihydro-isoindol-1-one,
2-(2,2,2-Trifluoroethyl)-5-[3-(3-trifluoromethyl-phenyl)-1H-pyrazol-4-ylmethoxy]-2,3-dihydro-isoindol-1-one,
5-[3-(4-Fluorophenyl)-1H-pyrazol-4-ylmethoxy]-2-(2,2,2-trifluoro-ethyl)-2,3-dihydro-isoindol-1-one,
5-[3-(3-Fluorophenyl)-1H-pyrazol-4-ylmethoxy]-2-(2,2,2-trifluoro-ethyl)-2,3-dihydro-isoindol-1-one,
5-[3-(4-Trifluoromethylphenyl)-1H-pyrazol-4-ylmethoxy]-2,3-dihydro-isoindol-1-one,
2-Methyl-5-[3-(4-trifluoromethylphenyl)-1H-pyrazol-4-ylmethoxy]-2,3-dihydro-isoindol-1-one,
2-Propyl-6-[3-(4-trifluoromethylphenyl)-1H-pyrazol-4-ylmethoxy]-3,4-dihydro-2H-isoquinolin-1-one,
2-Propyl-5-{[3-(4-trifluoromethylphenyl)-1H-pyrazol-4-ylmethyl]-amino}-2,3-dihydro-isoindol-1-one,
5-{[3-(4-Chlorophenyl)-1H-pyrazol-4-ylmethyl]-amino}-2-propyl-2,3-dihydro-isoindol-1-one,
5-{[3-(3-Chlorophenyl)-1H-pyrazol-4-ylmethyl]-amino}-2-propyl-2,3-dihydro-isoindol-1-one,
2-Propyl-5-{[3-(3-trifluoromethyl-phenyl)-1H-pyrazol-4-ylmethyl]-amino}-2,3-dihydro-isoindol-1-one,
5-{[3-(4-Fluorophenyl)-1H-pyrazol-4-ylmethyl]-amino}-2-propyl-2,3-dihydro-isoindol-1-one,
5-{[3-(3-Fluorophenyl)-1H-pyrazol-4-ylmethyl]-amino}-2-propyl-2,3-dihydro-isoindol-1-one,
5-[(3-Phenyl-1H-pyrazol-4-ylmethyl)-amino]-2-propyl-2,3-dihydro-isoindol-1-one,
2-Propyl-5-{[4-3-trifluoromethyl-phenyl)-1H-pyrazol-3-ylmethyl]-amino}-2,3-dihydro-isoindol-1-one,
2-Propyl-5-{[3-(4-trifluoromethyl-phenyl)-1H-pyrazol-4-ylmethyl]-amino}-isoindole-1,3-dione,
2-Propyl-6-{[3-(4-trifluoromethyl-phenyl)-1H-pyrazol-4-ylmethyl]-amino}-2,3-dihydro-isoquinolin-1-one,
2-(4-Trifluoromethoxy-benzyl)-5-[3-(4-trifluoromethyl-phenyl)-1H-pyrazol-4-ylmethoxy]-2,3-dihydro-isoindol-1-one,
2-Cyclohexylmethyl-5-[3-(4-trifluoromethyl-phenyl)-1H-pyrazol-4-ylmethoxy]-2,3-dihydro-isoindol-1-one,
2-Isobutyl-5-[3-(4-trifluoromethyl-phenyl)-1H-pyrazol-4-ylmethoxy]-2,3-dihydro-isoindol-1-one,
2-Cyclopentyl-5-[3-(4-trifluoromethyl-phenyl)-1H-pyrazol-4-ylmethoxy]-2,3-dihydro-isoindol-1-one,
2-Phenyl-5-[3-(4-trifluoromethyl-phenyl)-1H-pyrazol-4-ylmethoxy]-2,3-dihydro-isoindol-1-one;
5-[(3-Methyl-5-phenyl-isoxazol-4-ylmethyl)-amino]-2-propyl-2,3-dihydro-isoindol-1-one
and the pharmaceutically acceptable salts thereof.

The compounds according to the present invention can be prepared by analogy to well established techniques in the art of organic synthesis.

Compounds of the formula I, wherein X is NH or $NR^x$ and A is a moiety $A'CR^{a'}H$, wherein A' is a chemical bond or optionally substituted $C_1$-$C_4$-alkylene and Ra' is hydrogen or $C_1$-$C_4$-alkyl, in particular hydrogen, can be prepared by the reaction sequence depicted in scheme 1, including reductive amination of an aminoaryl compound II with a hetaryl aldehyde III.

Scheme 1:

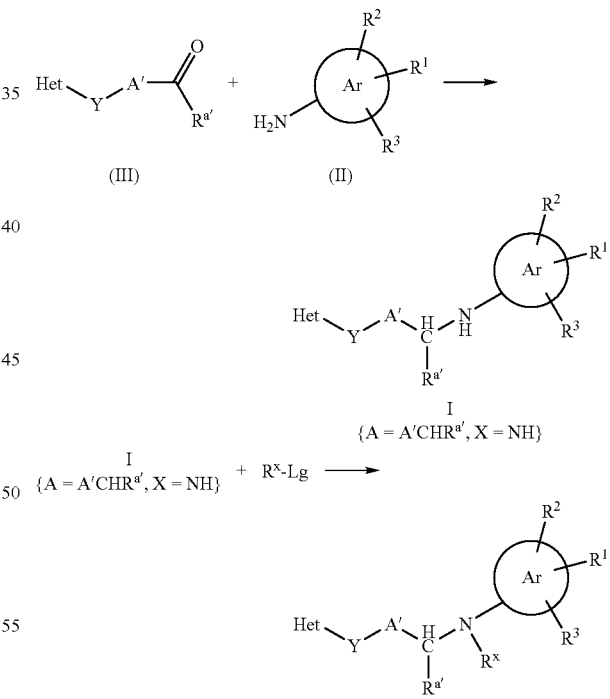

In scheme 1, the variables Het, Ar, X, Y, A', $R^{a'}$, $R^x$, $R^1$, $R^2$ and $R^3$ are as defined above. $R^x$ is in particular a radical $C(=O)$—$R^{x1}$, $C(=O)$—$OR^{x2}$, $C(=O)NR^{x3}R^{x4}$, $S(O)_2R^{x5}$ or $S(O)_2NR^{x3}R^{x4}$ or optionally substituted $C_1$-$C_6$-alkyl, $C_3$-$C_8$-cycloalkyl or $C_1$-$C_6$-haloalkyl. Lg is a nucleophilically replaceable group, including halogen, in particular chlorine or bromine, and O—$S(O)_2R$ with R being $C_1$-$C_6$-alkyl, $C_1$-$C_6$-haloalkyl or phenyl, which may be substituted by $C_1$-$C_6$-alkyl or halogen.

The reductive amination of III with II can be performed by standard procedures of reductive aminations that are known in the art. In particular, the compounds II and III are reacted with a reducing agent, in particular diborane, a borohydride, triacetoxyborohydride or cyanoborohydride such as an alkalimetal borohydride, an alkalimetal cyanoborohydride, an alkalimetal triacetoxyborohydride or polymer supported cyanoborohydride or polymer supported triacetoxyborohydride, e.g. macroporous cyanoborohydride.

Reaction of II and III is usually performed in an organic solvent, including aprotic organic solvents, e.g. substituted amides, lactames and ureas such as dimethylformamide, dimethylacetamide, N-methylpyrrolidone, tetramethyl urea, cyclic ethers such as dioxane, tetrahydrofurane, halogenated hydrocarbons such as dichloromethane, and mixtures thereof as well as mixtures thereof with $C_1$-$C_6$-alkanols and/or water.

The reaction of II and III will be usually performed at temperatures ranging from −10° C. to 100° C., depending on the reactivity of compounds II and III.

A compound I, wherein X is NH, e.g. the compound I obtained from the reaction of II and III, can be further subjected to an alkylation, acylation or sulfonylation reaction with a compound $R^x$-Lg in order to introduce the radical $R^x$. Compounds wherein $R^x$ is a radical C(=O)NH$R^{x3}$ may also be obtained by reacting the compound I {X=NH} with an isocyanate $R^{x3}$—NCO.

The reaction of the compound I with X being NH with the compound $R^x$-Lg can be performed by standard alkylation, acylation or sulfonylation techniques. Usually the reaction is performed in an inert solvent in the presence of a suitable base, including alkalimetal hydroxides, alkalimetal carbonates such as sodium carbonate or potassium carbonate, or a tertiary amine such as triethylamine or pyridine.

Suitable solvents include but are not limited to substituted amides, lactames and ureas such as dimethylformamide, dimethylacetamide, N-methylpyrrolidone, tetramethyl urea, cyclic ethers such as dioxane, tetrahydrofurane, halogenated hydrocarbons such as dichloromethane, as well as tertiary amines such as trialkylamines or pyridines, and mixtures thereof. The reaction of the compound I with X being NH with the compound $R^x$-Lg will be usually performed at temperatures ranging from 10° C. to 150° C., depending on the reactivity of the compound $R^x$-Lg.

Compounds of the formula I, wherein X is O or S, can be prepared by the reaction sequence depicted in scheme 2, including an alkylation reaction of an hydroxyaryl or mercaptoaryl compound IIa with the hetaryl compound IIIa.

Scheme 2:

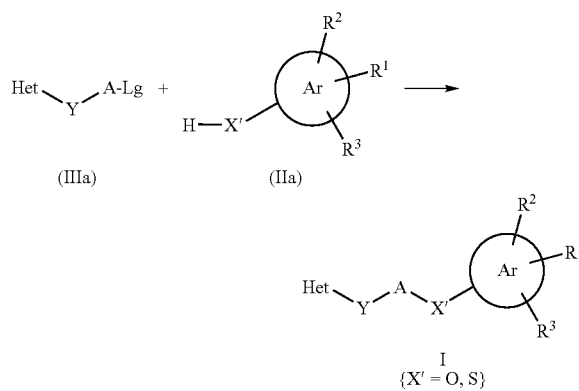

In scheme 2, the variables Het, Ar, X, A, $R^1$, $R^2$ and $R^3$ are as defined above. Lg is a nucleophilically replaceable group, including halogen, in particular bromine or iodine, and O—S(O)$_2$R with R being $C_1$-$C_6$-alkyl, $C_1$-$C_6$-haloalkyl or phenyl, which may be substituted by $C_1$-$C_6$-alkyl or halogen.

The reaction of the compound IIa with the compound IIIa can be performed by standard alkylation techniques. Usually the reaction is performed in an inert solvent in, optionally in the presence of a suitable base, including alkalimetal hydroxides, alkalimetal carbonates such as sodium carbonate or potassium carbonate, or a tertiary amine such as triethylamine or pyridine.

Suitable solvents include but are not limited to substituted amides, lactames and ureas such as dimethylformamide, dimethylacetamide, N-methylpyrrolidone, tetramethyl urea, cyclic ethers such as dioxane, tetrahydrofurane, halogenated hydrocarbons such as dichloromethane, as well as tertiary amines such as trialkylamines or pyridines, and mixtures thereof.

The reaction of the compound IIa with the compound IIIa will be usually performed at temperatures ranging from 10° C. to 150° C., depending on the reactivity of the leaving group Lg.

The reaction depicted in scheme 2 can also be applied to the preparation of compounds I, wherein X is NH, N$R^x$ or NH—C(O) by starting from compounds IIa, wherein HX' is NH$_2$, NH$R^x$ or H$_2$NC(O). The reaction is particularly suitable for the preparation of compounds I, wherein X is N$R^x$, wherein $R^x$ is in particular a radical C(=O)—$R^{x1}$, C(=O)—O$R^{x2}$, C(=O)N$R^{x3}R^{x4}$, S(O)$_2R^{x5}$ or S(O)$_2$N$R^{x3}R^{x4}$.

Compounds of the formula I, wherein X is O, can also be prepared by a condensation of the alcohols IIIb and aromatic alcohols IIb in the presence of azodicarboxylate esters such as Diethylazodicarboxylate (DEAD), Diisopropylazodicarboxylate (DIAD) or Di-t-butylazodicaroxylate and triarylphosphines such as triphenylphosphine as depicted in scheme 3 by analogy to Mitsunobu's reaction.

Scheme 3:

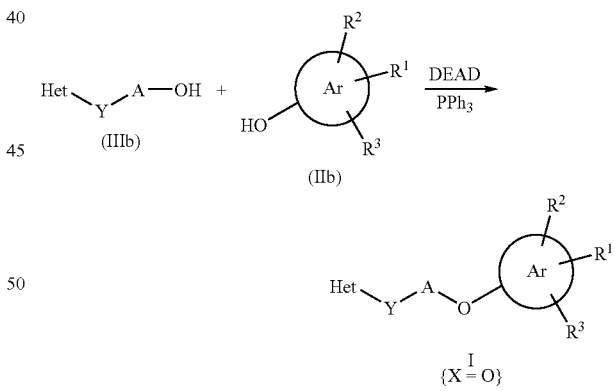

The compound I, obtained from the reactions described herein can be isolated and purified employing standard techniques such as solvent extraction, chromatography, crystallization, distillation and the like.

The utility of the compounds in accordance with the present invention as modulators of metabotropic glutamate receptor activity, in particular mGlu2 activity, may be demonstrated by methodology known in the art. The compounds of the present invention can be tested e.g. by evaluating intracellular $Ca^{2+}$ concentrations in cells permanently expressing human mGlu receptor, the rat glutamate transporter rGLAST and the Galpha16 subunit of the G-protein complex under standard conditions in a fluorometric imaging plate reader (FLIPR, Molecular Devices, Union City, Calif. 94587, USA) by measuring the response of the cells to a test compound in the absence of presence of glutamate. The FLIPR assay is a common functional assay to monitor native or recombinant Galphaq-coupled receptors, and native or recombinant receptors normally linked to other G-protein signalling cascades, which are coupled to calcium through co-expression of an alpha subunit of a promiscuous or chimeric G-protein. In the assay the increase of intracellular calcium is measured through a calcium-dependent fluorescent dye (e.g. Fluo-4 AM) in the FLIPR instrument.

For the purpose of the present study, a cell line permanently expressing a human mGlu receptor, such as the mGlu2 receptor, the rat glutamate transporter rGLAST and the GalphaG16 may be generated by transfection as described in the examples. For selection of a suitable cell clone and also the subsequent measurements, the selected clone the cells will be plated on suitable multiwell plates in a suitable medium (e.g. DMEM Glutamax (GIBCO #21885-025)/10% dialyzed FCS). Cells may be selected by gentamycin treatment as described in the examples. Cells will then be loaded with a suitable $Ca^{2+}$ sensitive fluorescence dye, e.g. with 2 µM Fluo-4 AM (Molecular Probes, F14201). Cells will then be washed with a suitable buffer (e.g. HEPES) and the thus treated plates will be measured in a fluorometric imaging plate reader (e.g. FLIPR, Molecular Devices, Union City, Calif. 94587, USA).

The compounds of the present invention were tested in the above-described FLIPR assay using the selected cell clone. Increased intracellular calcium levels were quantified following addition of test compound (agonism), as well as following addition of a submaximal concentration of glutamate (potentiation).

For the determination of the effect of the test compound by itself (agonism) or by increasing the response to a submaximal concentration (e.g. 1 µM) of glutamate (potentiation), the resulting signal is determined by subtraction of the background fluorescence from the maximal fluorescent peak height of the respective response. In the FLIPR instrument the compound is given to the cell and its fluorescence response quantified by the FLIPR instrument (agonism). The concentration at which the compound exerts half its maximal effect is named the 'effective concentration 50' or '$EC_{50}$'. The maximal effect induced by the test substance is normalized to the maximal effect exerted by 100 µM glutamate (set at 100%).

After addition of the test compound to the plate, a submaximal concentration of glutamate (e.g. 1 µM glutamate) will be added. A potentiator enhances the response of the receptor to glutamate. The response to glutamate in the presence of test compound is quantified. The concentration at which the test compound is able to exert half its maximal potentiation effect to glutamate is named the '$EC_{50}$'. The maximal response to the submaximal concentration of glutamate (e.g. 1 micromolar glutamate) in the presence of test compound is normalized to the maximal effect exerted by 100 micromolar glutamate (set at 100%). Least squares curve fitting with a four-parameter equation is then applied to the resulting dose-response curve to determine the resulting $EC_{50}$ values (Graph Pad Prism).

A control cell line, HEK293 cells expressing permanently rGLAST and Galpha16 was also plated to a multiwell plate for parallel testing to verify specificity of the test compound for mGlu2 receptor agonism or potentiation.

The compounds of the invention can be further characterized by measurement of their efficacy and potency to inhibit forskolin-induced cAMP levels in these cells on their own (agonism) or to potentiate the effect of glutamate (potentiation). Cyclic AMP levels were quantified using Alphascreen technology (PerkinElmer Life and Analytical Sciences, 710 Bridgeport Avenue, Shelton, Conn. USA) as described by the manufacturer for determining the effects of Galphai coupled receptors.

The concentration at which a compound exerts half its maximal effect is named the 'effective concentration 50' or '$EC_{50}$'. The maximal effect induced by the test substance is normalized to the maximal effect exerted by 100 µM glutamate (100%). Least squares curve fitting with a four-parameter equation is then applied to the resulting dose-response curve to determine the resulting $EC_{50}$ values (Graph Pad Prism).

In particular, the compounds of the following examples had activity in potentiating the mGlu2 receptor in the aforementioned assays, generally with an $EC_{50}$ of not more than about 10 µM. Preferred compounds within the present invention had activity in potentiating the mGlu2 receptor in the aforementioned assays with an $EC_{50}$ of less than 1 µM, in particular less than 0.5 µM, more preferably of at most 0.2 µM, of at most 0.1 µM. Such a result is indicative of the intrinsic activity of the compounds in use as positive modulators of mGlu2 receptor activity.

As stated above, the compounds of the present invention are positive modulators of metabotropic glutamate (mGluR) receptor function, in particular they are positive modulators of mGlu2 receptors. Thus, the compounds of the present invention can be used for treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, disorders associated with substance tolerance, disorders associated with substance withdrawal (including substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Of the disorders above, the treatment of schizophrenia, anxiety, depression, substance-related disorders, migraine, and epilepsy are of particular importance.

Therefore, the present invention relates to a method for treating a medical disorder, selected from neurological and psychiatric disorders associated with glutamate dysfunction, said method comprising administering an effective amount of at least one compound of the present invention to a subject in need thereof.

The compounds of the present invention frequently show an affinity towards the serotonin $5HT_{2A}$ receptor. In particular the compounds of the present invention are antagonist of the serotonin $5HT_{2A}$ receptor. Preferred compounds of the present invention have binding constants $Ki(5HT_{2A})$ below 1 µM, in particular of at most 0.5 µM, more preferably at most 250 nM or especially at most 100 nM. Thus the compounds of the present invention are particularly useful for treating the above mentioned disorders, in particular psychiatric disorders, such as schizophrenia, psychosis, cognitive disorders, drug abuse (i.e. disorders associated with substance tolerance, disorders associated with substance withdrawal (including substances such as opiates, nicotine, tobacco products, alcohol, benzodiazepines, cocaine, sedatives, hypnotics, etc.), anxiety (including generalized anxiety disorder, panic disorder, and obsessive compulsive disorder). The affinity towards the 5HT2A receptor as well as the antagonistic action can be determined by routine screening techniques, a skilled person is familiar with (for reviews see e.g. D. E. Nichols, Hallocinogens, in Pharmacology & Therapeutics 101 (2004) 131-181, J. A. Lieberman et al. Biol. Psychiatry 44 (1998) 1099-1117, S. Miyamoto et al., Mol. Psychiatry. 10 (2005), 79-104).

The subject treated in the present methods is generally a mammal, preferably a human being, male or female, in whom potentiation of metabotropic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of a compound of formula I, a tautomer and/or a pharmaceutically acceptable salt thereof. In another preferred embodiment the present invention provides a method for preventing or treating anxiety, comprising: administering to a patient in need thereof an effective amount of a compound of formula I, a tautomer and/or a pharmaceutically acceptable salt thereof. Particularly preferred anxiety disorders are generalized anxiety disorder, panic disorder, and obsessive compulsive disorder.

In another preferred embodiment the present invention provides a method for treating substance-related disorders, comprising: administering to a patient in need thereof an effective amount of a compound of formula I, a tautomer and/or a pharmaceutically acceptable salt thereof. In another preferred embodiment the present invention provides a method for treating migraine, comprising: administering to a patient in need thereof an effective amount of a compound of formula I, a tautomer and/or a pharmaceutically acceptable salt thereof. In yet another preferred embodiment the present invention provides a method for treating epilepsy, comprising: administering to a patient in need thereof an effective amount of a compound of formula I, a tautomer and/or a pharmaceutically acceptable salt thereof.

Of the neurological and psychiatric disorders associated with glutamate dysfunction which are treated according to the present invention, the treatment of schizophrenia, anxiety, depression, migraine, substance-related disorders, especially substance dependence, substance tolerance, substance withdrawal, and epilepsy are particularly preferred. Particularly preferred anxiety disorders are generalized anxiety disorder, panic disorder, and obsessive compulsive disorder.

Thus, in a preferred embodiment the present invention provides a method for treating schizophrenia, comprising: administering to a patient in need thereof an effective amount of a compound of formula I, a tautomer and/or a pharmaceutically acceptable salt thereof. At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment the present invention provides a method for treating anxiety, comprising: administering to a patient in need thereof an effective amount of a compound of formula I, a tautomer and/or a pharmaceutically acceptable salt thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment the present invention provides a method for treating depression, comprising: administering to a patient in need thereof an effective amount of a compound of formula I, a tautomer and/or a pharmaceutically acceptable salt thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment the present invention provides a method for treating substance-related disorders, especially substance dependence, substance abuse, substance tolerance, and substance withdrawal, comprising: administering to a patient in need thereof an effective amount of a compound of formula I, a tautomer and/or a pharmaceutically acceptable salt thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In another preferred embodiment the present invention provides a method for treating migraine, comprising: administering to a patient in need thereof an effective amount of a compound of formula I, a tautomer and/or a pharmaceutically acceptable salt thereof. In one of the available sources of diagnostic tools, Dorland's Medical Dictionary (23'rd Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another preferred embodiment the present invention provides a method for treating epilepsy, comprising: administering to a patient in need thereof an effective amount of a compound of formula I, a tautomer and/or a pharmaceutically acceptable salt thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams, hi the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds according to the present invention are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of formula I, a number of factors are considered by the attending diagnostician, including, but not limited to: the mGluR agonist selected to be administered, including its potency and selectivity; the compound of formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art. The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also includes therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered by conventional routes of administration, including parenteral (e.g., intramuscular, intrapentoneal, intravenous, ICV, intracisternal injection or infusion, subcutaneous injection, or implant), by inhalation spray, nasal, vaginal, rectal, sublingual, or topical routes of administration.

The compounds of the present invention may be formulated alone or together with further active compounds, in suitable dosage unit formulations containing conventional non-toxic pharmaceutically excipients. Excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], 4$^{th}$ edition, Aulendorf: ECV-Editio-Kantor-Verlag, 1996.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients.

The following examples are intended for further illustration of the present invention.

PREPARATION EXAMPLES

Abbreviations used in the Examples that follow are: DCM dichloromethane; DMA N,N-dimethylacetamide; DMSO dimethylsulfoxide; MeOH methanol; TFA trifluoroacetic acid; MP-CNBH$_3$ macroporous cyanoborohydride Example 1

1-{4-[(Thiophen-3-ylmethyl)amino]phenyl}-butan-1-one

In a 20 mL vial, to a solution of 1-(4-aminophenyl)-butan-1-one (19.64 mg, 0.1 mmol) in DCM/MeOH (0.7 mL) was added a solution of thiophene-3-carbaldehyde (22.4 mg, 0.2 mmol) in DMA (0.8 mL). A solution of acetic acid (18 mg, 0.3 mmol) in DCM/MeOH (0.7 mL) was added, followed by the addition of 160 mg of MP-CNBH$_3$ resin (3 eq.; subst. 2.25 mmoles/g). The vial was capped and was then heated with shaking overnight at 55° C. The progress of the reaction was monitored by LC/MS. After completion of the reaction, the reaction mixture was concentrated to dryness. The residue was dissolved in 1:1 DMSO/MeOH. Purification by reverse phase HPLC (TFA method) gave the title compound.

$^1$H-NMR (500 MHz, DMSO-d$_6$/D$_2$O) δ ppm 0.89 (t, 3H), 1.53-1.63 (m, 2H), 2.78 (t, 2H), 4.31-4.37 (m, 2H), 6.63-6.67 (m, 2H), 7.09 (dd, 1H), 7.31-7.37 (m, 1H), 7.45-7.49 (m, 1H), 7.69-7.75 (m, 2H);

MS (ESI) positive ion 260 (M+H)$^+$; negative ion 258 (M−H)$^−$.

Example 2

1-(4-{[5-(2-Chlorophenyl)-furan-2-ylmethyl]amino}phenyl)butan-1-one

Following a procedure analogous to Example 1, but using 5-(2-chlorophenyl)furan-2-carbaldehyde instead of thiophene-3-carbaldehyde the title compound was prepared.

$^1$H-NMR (500 MHz, DMSO-d$_6$/D$_2$O) δ ppm 0.90 (t, 3H), 1.55-1.64 (m, 2H), 2.81 (t, 2H), 4.43-4.46 (m, 2H), 6.51 (d, 1H), 6.72-6.78 (m, 2H), 7.07 (d, 1H), 7.29-7.36 (m, 1H), 7.41-7.45 (m, 1H), 7.54 (dd, 1H), 7.74-7.78 (m, 2H), 7.80 (dd, 1H);

MS (ESI) positive ion 354 (M+H)$^+$; negative ion 352 (M−H)$^−$.

Example 3

1-(4-{[5-(3-Chlorophenyl)furan-2-ylmethyl]amino}phenyl)-butan-1-one

Following a procedure analogous to Example 1, but using 5-(3-chlorophenyl)furan-2-carbaldehyde instead of thiophene-3-carbaldehyde the title compound was prepared.

$^1$H-NMR (500 MHz, DMSO-d$_6$/D$_2$O) δ ppm −0.00 (t, 3H), 0.61-0.77 (m, 2H), 1.92 (t, 2H), 3.52-3.57 (m, 2H), 5.58 (d, 1H), 5.85-5.89 (m, 2H), 6.07 (d, 1H), 6.41-6.47 (m, 1H), 6.56 (t, 1H), 6.71-6.74 (m, 1H), 6.79 (t, 1H), 6.85-6.92 (m, 2H);

MS (ESI) positive ion 354 (M+H)$^+$; negative ion 352 (M−H)$^−$.

Example 4

1-(4-{[5-(4-Chlorophenyl)furan-2-ylmethyl]amino}phenyl)butan-1-one

Following a procedure analogous to Example 1, but using 5-(4-chlorophenyl)furan-2-carbaldehyde instead of thiophene-3-carbaldehyde the title compound was prepared.

$^1$H-NMR (500 MHz, DMSO-d$_6$/D$_2$O) δ ppm 0.90 (t, 3H), 1.48-1.65 (m, 2H), 2.80 (t, 2H), 4.36-4.44 (m, 2H), 6.46 (d, 1H), 6.67-6.82 (m, 2H), 6.90 (d, 1H), 7.41-7.50 (m, 2H), 7.62-7.70 (m, 2H), 7.73-7.79 (m, 2H);

MS (ESI) positive ion 354 (M+H)$^+$; negative ion 352 (M−H)$^−$.

Example 5

1-{4-[(5-Chlorothiophen-2-ylmethyl)amino]phenyl}butan-1-one

Following a procedure analogous to Example 1, but using 5-chlorothiophene-2-carbaldehyde instead of thiophene-3-carbaldehyde the title compound was prepared.

$^1$H-NMR (500 MHz, DMSO-d$_6$/D$_2$O) δ ppm 0.89 (t, 3H), 1.48-1.64 (m, 2H), 2.79 (t, 2H), 4.41-4.53 (m, 2H), 6.60-6.75 (m, 2H), 6.88-6.99 (m, 2H), 7.69-7.76 (m, 2H);

MS (ESI) positive ion 394 (M+H)$^+$; negative ion 392 (M−H)$^−$.

Example 6

1-(4-{[5-(2-(Trifluoromethylphenyl)furan-2-ylmethyl]amino}phenyl)butan-1-one

Following a procedure analogous to Example 1, but using 5-[2-(trifluoromethyl)phenyl]furan-2-carbaldehyde instead of thiophene-3-carbaldehyde the title compound was prepared.

$^1$H-NMR (500 MHz, DMSO-d$_6$/D$_2$O) δ ppm 0.88 (t, 3H), 1.43-1.72 (m, 2H), 2.80 (t, 2H), 4.28-4.54 (m, 2H), 6.46-6.52 (m, 1H), 6.67-6.77 (m, 3H), 7.47-7.66 (m, 1H), 7.69-7.80 (m, 4H), 7.84 (d, 1H);

MS (ESI) positive ion 388 (M+H)⁺; negative ion 386 (M−H)⁻.

Example 7

1-(4-{[5-(3-Trifluoromethylphenyl)furan-2-ylmethyl]amino}phenyl)butan-1-one

Following a procedure analogous to Example 1, but using 5-[3-(trifluoromethyl)phenyl]furan-2-carbaldehyde instead of thiophene-3-carbaldehyde the title compound was prepared.

$^1$H-NMR (500 MHz, DMSO-$d_6$/$D_2O$) δ ppm 0.90 (t, 3H), 1.54-1.64 (m, 2H), 2.80 (t, 2H), 4.42-4.47 (m, 2H), 6.49 (d, 1H), 6.72-6.78 (m, 2H), 7.06 (d, 1H), 7.59-7.70 (m, 2H), 7.74-7.79 (m, 2H), 7.88-7.93 (m, 1H), 7.95 (d, 1H);

MS (ESI) positive ion 388 (M+H)⁺; negative ion 386 (M−H)⁻.

Example 8

1-{4-[(3H-Imidazol-4-ylmethyl)amino]phenyl}butan-1-one

Following a procedure analogous to Example 1, but using 3H-imidazole-4-carbaldehyde instead of thiophene-3-carbaldehyde the title compound was prepared.

$^1$H-NMR (500 MHz, DMSO-$d_6$/$D_2O$) δ ppm 0.90 (t, 3H), 1.53-1.66 (m, 2H), 2.81 (t, 2H), 4.43-4.48 (m, 2H), 6.66-6.72 (m, 2H), 7.51-7.55 (m, 1H), 7.74-7.80 (m, 2H), 8.95 (d, 1H);

MS (ESI) positive ion 244 (M+H)⁺; negative ion 242 (M−H)⁻.

Example 9

1-{4-[(5-Ethylthiophen-2-ylmethyl)amino]phenyl}butan-1-one

Following a procedure analogous to Example 1, but using 5-ethylthiophene-2-carbaldehyde instead of thiophene-3-carbaldehyde the title compound was prepared.

$^1$H-NMR (500 MHz, DMSO-$d_6$/$D_2O$) δ ppm 0.88 (t, 3H), 1.19 (t, 3H), 1.51-1.65 (m, 2H), 2.72 (q, 2H), 2.81 (t, 2H), 4.38-4.50 (m, 2H), 6.60-6.73 (m, 3H), 6.86 (d, 1H), 7.66-7.79 (m, 2H);

MS (ESI) positive ion 288 (M+H)⁺; negative ion 286 (M−H)⁻.

Example 10

1-{4-[(Benzo[b]thiophen-3-ylmethyl)amino]phenyl}butan-1-one

Following a procedure analogous to Example 1, but using benzo[b]thiophene-3-carbaldehyde instead of thiophene-3-carbaldehyde the title compound was prepared.

$^1$H-NMR (500 MHz, DMSO-$d_6$/$D_2O$) δ ppm 0.89 (t, 3H), 1.51-1.65 (m, 2H), 2.78 (t, 2H), 4.57-4.63 (m, 2H), 6.67-6.75 (m, 2H), 7.35-7.49 (m, 2H), 7.54-7.61 (m, 1H), 7.67-7.77 (m, 2H), 7.90-8.02 (m, 2H);

MS (ESI) positive ion 310 (M+H)⁺; negative ion 308 (M−H)⁻.

Example 11

(R)-1-{4-[(Tetrahydrofuran-2-ylmethyl)amino]phenyl}butan-1-one

Following a procedure analogous to Example 1, but using (R)-tetrahydrofuran-2-carbaldehyde instead of thiophene-3-carbaldehyde the title compound was prepared.

$^1$H-NMR (500 MHz, DMSO-$d_6$/$D_2O$) δ ppm 0.88 (t, 3H), 1.51-1.67 (m, 3H), 1.94-2.06 (m, 1H), 2.43-2.52 (m, 1H), 2.80 (t, 2H), 3.02-3.13 (m, 2H), 3.38-3.52 (m, 1H), 3.59-3.67 (m, 1H), 3.75-3.80 (m, 2H), 6.38-6.85 (m, 2H), 7.66-7.80 (m, 2H);

MS (ESI) positive ion 248 (M+H)⁺; negative ion 246 (M−H)⁻.

Example 12

1-{4-[(1-Methyl-1H-indol-2-ylmethyl)amino]phenyl}butan-1-one

Following a procedure analogous to Example 1, but using 1-methyl-1H-indole-2-carbaldehyde instead of thiophene-3-carbaldehyde the title compound was prepared.

$^1$H-NMR (500 MHz, DMSO-$d_6$/$D_2O$) δ ppm 0.88 (t, 3H), 1.50-1.64 (m, 2H), 2.78 (t, 2H), 3.73-3.74 (m, 3H), 4.50-4.61 (m, 2H), 6.32-6.43 (m, 1H), 6.70-6.77 (m, 2H), 6.95-7.05 (m, 1H), 7.09-7.17 (m, 1H), 7.41 (d, 1H), 7.48 (d, 1H), 7.70-7.79 (m, 2H);

MS (ESI) positive ion 307 (M+H)⁺; negative ion 305 (M−H)⁻.

Example 13

1-{4-[(Furan-2-ylmethyl)amino]phenyl}butan-1-one

Following a procedure analogous to Example 1, but using furan-2-carbaldehyde instead of thiophene-3-carbaldehyde the title compound was prepared.

$^1$H-NMR (500 MHz, DMSO-$d_6$/$D_2O$) δ ppm 0.90 (t, 3H), 1.51-1.68 (m, 2H), 2.79 (t, 2H), 4.30-4.38 (m, 2H), 6.30-6.35 (m, 1H), 6.38-6.46 (m, 1H), 6.63-6.78 (m, 2H), 7.53-7.57 (m, 1H), 7.68-7.77 (m, 2H);

MS (ESI) positive ion 244 (M+H)⁺; negative ion 242 (M−H)⁻.

Example 14

1-{4-[(Pyridin-2-ylmethyl)amino]phenyl}butan-1-one

Following a procedure analogous to Example 1, but using picolinaldehyde instead of thiophene-3-carbaldehyde the title compound was prepared.

$^1$H-NMR (500 MHz, DMSO-$d_6$/$D_2O$) δ ppm 0.89 (t, 3H), 1.47-1.65 (m, 2H), 2.79 (t, 2H), 4.57-4.65 (m, 2H), 6.62-6.69 (m, 2H), 7.56-7.65 (m, 2H), 7.71-7.78 (m, 2H), 8.08-8.16 (m, 1H), 8.60-8.68 (m, 1H);

MS (ESI) positive ion 255 (M+H)⁺; negative ion 253 (M−H)⁻.

Example 15

1-{4-[(Pyridin-4-ylmethyl)amino]phenyl}butan-1-one

Following a procedure analogous to Example 1, but using isonicotinaldehyde instead of thiophene-3-carbaldehyde the title compound was prepared.

$^1$H-NMR (500 MHz, DMSO-d$_6$/D$_2$O) δ ppm 0.90 (t, 3H), 1.48-1.65 (m, 2H), 2.78 (t, 2H), 4.60-4.69 (m, 2H), 6.57-6.66 (m, 2H), 7.69-7.77 (m, 2H), 7.80-7.88 (m, 2H), 8.69-8.76 (m, 2H);

MS (ESI) positive ion 255 (M+H)⁺; negative ion 253 (M−H)⁻.

Example 16

1-{4-[(Pyridin-3-ylmethyl)amino]phenyl}butan-1-one

Following a procedure analogous to Example 1, but using nicotinaldehyde instead of thiophene-3-carbaldehyde the title compound was prepared.

$^1$H-NMR (500 MHz, DMSO-d$_6$/D$_2$O) δ ppm 0.88 (t, 3H), 1.49-1.65 (m, 2H), 2.78 (t, 2H), 4.51-4.61 (m, 2H), 6.61-6.71 (m, 2H), 7.70-7.78 (m, 2H), 7.81-7.88 (m, 1H), 8.28 (d, 1H), 8.64-8.70 (m, 1H), 8.72-8.80 (m, 1H);

MS (ESI) positive ion 255 (M+H)⁺; negative ion 253 (M−H)⁻.

Example 17

1-{4-[(1-Methyl-1H-imidazol-2-ylmethyl)amino]phenyl}butan-1-one

Following a procedure analogous to Example 1, but using 1-methyl-1H-imidazole-2-carbaldehyde instead of thiophene-3-carbaldehyde the title compound was prepared.

$^1$H-NMR (500 MHz, DMSO-d$_6$/D$_2$O) δ ppm 0.91 (t, 3H), 1.52-1.68 (m, 2H), 2.84 (t, 2H), 3.81-3.87 (m, 3H), 4.64-4.80 (m, 2H), 6.65-6.75 (m, 2H), 7.46-7.55 (m, 1H), 7.57-7.62 (m, 1H), 7.75-7.84 (m, 2H);

MS (ESI) positive ion 258 (M+H)⁺; negative ion 256 (M−H)⁻.

Example 18

1-{4-[(5-Methylthiophen-2-ylmethyl)amino]phenyl}butan-1-one

Following a procedure analogous to Example 1, but using 5-methylthiophene-2-carbaldehyde instead of thiophene-3-carbaldehyde the title compound was prepared.

$^1$H-NMR (500 MHz, DMSO-d$_6$/D$_2$O) δ ppm 0.95 (t, 3H), 1.48-1.65 (m, 2H), 2.31-2.41 (m, 3H), 2.77 (t, 2H), 4.38-4.50 (m, 2H), 6.56-6.70 (m, 3H), 6.78-6.91 (m, 1H), 7.62-7.77 (m, 2H);

MS (ESI) positive ion 274 (M+H)⁺; negative ion 272 (M−H)⁻.

Example 19

1-{4-[(3-Methylthiophen-2-ylmethyl)amino]phenyl}butan-1-one

Following a procedure analogous to Example 1, but using 3-methylthiophene-2-carbaldehyde instead of thiophene-3-carbaldehyde the title compound was prepared.

$^1$H-NMR (500 MHz, DMSO-d$_6$/D$_2$O) δ ppm 0.90 (t, 3H), 1.48-1.64 (m, 2H), 2.18-2.23 (m, 3H), 2.81 (t, 2H), 4.35-4.43 (m, 2H), 6.57-6.67 (m, 2H), 6.82-6.89 (m, 1H), 7.27 (d, 1H), 7.67-7.78 (m, 2H);

MS (ESI) positive ion 274 (M+H)⁺; negative ion 272 (M−H)⁻.

Example 20

1-{4-[(5-(Hydroxymethylfuran-2-ylmethyl)amino]phenyl}butan-1-one

Following a procedure analogous to Example 1, but using 5-(hydroxymethyl)furan-2-carbaldehyde instead of thiophene-3-carbaldehyde the title compound was prepared.

$^1$H-NMR (500 MHz, DMSO-d$_6$/D$_2$O) δ ppm 0.91 (t, 3H), 1.52-1.65 (m, 2H), 2.80 (t, 2H), 4.28-4.33 (m, 2H), 4.32-4.37 (m, 2H), 6.11-6.34 (m, 2H), 6.55-6.87 (m, 2H), 7.66-7.78 (m, 2H);

MS (ESI) positive ion 274 (M+H)⁺; negative ion 272 (M−H)⁻.

Example 21

1-{4-[(5-Methylfuran-2-ylmethyl)amino]phenyl}butan-1-one

Following a procedure analogous to Example 1, but using 5-methylfuran-2-carbaldehyde instead of thiophene-3-carbaldehyde the title compound was prepared.

$^1$H-NMR (500 MHz, DMSO-d$_6$/D$_2$O) δ ppm 0.89 (t, 3H), 1.49-1.68 (m, 2H), 2.19-2.26 (m, 3H), 2.80 (t, 2H), 4.16-4.33 (m, 2H), 5.86-6.05 (m, 1H), 6.12-6.26 (m, 1H), 6.60-6.74 (m, 2H), 7.66-7.78 (m, 2H);

MS (ESI) positive ion 258 (M+H)⁺; negative ion 256 (M−H)⁻.

Example 22

1-{4-[(3-Methylbenzo[b]thiophen-2-ylmethyl)amino]phenyl}butan-1-one

Following a procedure analogous to Example 1, but using 3-methylbenzo[b]thiophene-2-carbaldehyde instead of thiophene-3-carbaldehyde the title compound was prepared.

$^1$H-NMR (500 MHz, DMSO-d$_6$/D$_2$O) δ ppm 0.88 (t, 3H), 1.50-1.63 (m, 2H), 2.40-2.45 (m, 3H), 2.78 (t, 2H), 4.59-4.63 (m, 2H), 6.60-6.71 (m, 2H), 7.29-7.36 (m, 1H), 7.37-7.42 (m, 1H), 7.69-7.76 (m, 3H), 7.82 (d, 1H);

MS (ESI) positive ion 324 (M+H)⁺.

Example 23

Acetic acid 5-[(4-butyrylphenylamino)methyl]furan-2-ylmethyl ester

Following a procedure analogous to Example 1, but using (5-formylfuran-2-yl)methyl acetate instead of thiophene-3-carbaldehyde the title compound was prepared.

$^1$H-NMR (500 MHz, DMSO-d$_6$/D$_2$O) δ ppm 0.91 (t, 3H), 1.52-1.65 (m, 2H), 1.99-2.06 (m, 3H), 2.79 (t, 2H), 4.29-4.41 (m, 2H), 4.93-5.02 (m, 2H), 6.28-6.36 (m, 1H), 6.40-6.49 (m, 1H), 6.61-6.72 (m, 2H), 7.66-7.78 (m, 2H);

MS (ESI) positive ion 316 (M+H)$^+$; negative ion 314 (M–H)$^-$.

Example 24

1-{4-[(1-Acetyl-1H-indol-3-ylmethyl)amino]phenyl}butan-1-one

Following a procedure analogous to Example 1, but using 1-acetyl-1H-indole-3-carbaldehyde instead of thiophene-3-carbaldehyde the title compound was prepared.

$^1$H-NMR (500 MHz, DMSO-d$_6$/D$_2$O) δ ppm 0.93 (t, 3H), 1.52-1.66 (m, 2H), 2.59-2.64 (m, 3H), 2.79 (t, 2H), 4.42-4.55 (m, 2H), 6.66-6.84 (m, 2H), 7.24-7.43 (m, 2H), 7.68-7.79 (m, 3H), 7.80-7.89 (m, 1H), 8.26-8.34 (m, 1H);

MS (ESI) positive ion 335 (M+H)$^+$; negative ion 333 (M–H)$^-$.

Example 25

1-{4-[(Quinolin-6-ylmethyl)amino]phenyl}butan-1-one

Following a procedure analogous to Example 1, but using quinoline-6-carbaldehyde instead of thiophene-3-carbaldehyde the title compound was prepared.

$^1$H-NMR (500 MHz, DMSO-d$_6$/D$_2$O) δ ppm 0.87 (t, 3H), 1.52-1.61 (m, 2H), 2.77 (t, 2H), 4.64-4.68 (m, 2H), 6.65-6.71 (m, 2H), 7.70-7.74 (m, 2H), 7.91-7.97 (m, 1H), 8.04-8.09 (m, 1H), 8.16-8.21 (m, 2H), 8.94 (d, 1H), 9.13 (dd, 1H);

MS (ESI) positive ion 305 (M+H)$^+$.

Example 26

1-{4-{(Thiazol-2-ylmethyl)amino]phenyl}butan-1-one

Following a procedure analogous to Example 1, but using thiazole-2-carbaldehyde instead of thiophene-3-carbaldehyde the title compound was prepared.

1H-NMR (500 MHz, DMSO-d$_6$/D$_2$O) δ ppm 0.90 (t, 3H), 1.50-1.65 (m, 2H), 2.80 (t, 2H), 4.64-4.71 (m, 2H), 6.63-6.73 (m, 2H), 7.57-7.63 (m, 1H), 7.72-7.79 (m, 3H); MS (ESI) positive ion 261 (M+H)$^+$; negative ion 259 (M–H)$^-$.

Example 27

1-(4-{[1-(touene-4-sulfonyl)-1H-pyrrol-2-ylmethyl]amino}phenyl)butan-1-one

Following a procedure analogous to Example 1, but using 1-(p-toluenesulfonyl)-1H-pyrrole-2-carbaldehyde instead of thiophene-3-carbaldehyde the title compound was prepared.

$^1$H-NMR (500 MHz, DMSO-d$_6$/D$_2$O) δ ppm 0.89 (t, 3H), 1.51-1.63 (m, 2H), 2.38-2.42 (m, 3H), 2.79 (t, 2H), 4.32-4.50 (m, 2H), 6.10-6.18 (m, 1H), 6.25-6.32 (m, 1H), 6.33-6.46 (m, 2H), 7.35-7.43 (m, 1H), 7.44-7.50 (m, 2H), 7.57-7.69 (m, 2H), 7.74-7.87 (m, 2H);

MS (ESI) positive ion 397 (M+H)$^+$; negative ion 395 (M–H)$^-$.

Example 28

1-{4-[(1-Methyl-1H-pyrazol-4-ylmethyl)amino]phenyl}butan-1-one

Following a procedure analogous to Example 1, but using 1-methyl-1H-pyrazole-4-carbaldehyde instead of thiophene-3-carbaldehyde the title compound was prepared.

$^1$H-NMR (500 MHz, DMSO-d$_6$/D$_2$O) δ ppm 0.90 (t, 3H), 1.52-1.69 (m, 2H), 2.79 (t, 2H), 3.77-3.80 (m, 3H), 4.12-4.23 (m, 2H), 6.60-6.68 (m, 2H), 7.34-7.44 (m, 1H), 7.58-7.64 (m, 1H), 7.69-7.76 (m, 2H);

MS (ESI) positive ion 258 (M+H)$^+$; negative ion 256 (M–H)$^-$.

Example 29

1-(4-{[5-(Piperidin-1-yl)furan-2-ylmethyl]amino}phenyl)butan-1-one

Following a procedure analogous to Example 1, but using 5-(piperidin-1-yl)furan-2-carbaldehyde instead of thiophene-3-carbaldehyde the title compound was prepared.

Example 30

1-{4-[(4-Phenylthiazol-2-ylmethyl)amino]phenyl}butan-1-one

Following a procedure analogous to Example 1, but using 4-phenylthiazole-2-carbaldehyde instead of thiophene-3-carbaldehyde the title compound was prepared.

$^1$H-NMR (500 MHz, DMSO-d$_6$/D$_2$O) δ ppm 0.88 (t, 3H), 1.45-1.71 (m, 2H), 2.82 (t, 2H), 4.71-4.79 (m, 2H), 6.67-6.74 (m, 2H), 7.34-7.40 (m, 1H), 7.42-7.52 (m, 2H), 7.71-7.80 (m, 2H), 7.90-7.98 (m, 3H);

MS (ESI) positive ion 337 (M+H)$^+$; negative ion 335 (M–H)$^-$.

Example 31

1-{4-[(1H-Indol-2-ylmethyl)amino]phenyl}butan-1-one

Following a procedure analogous to Example 1, but using 1H-indole-2-carbaldehyde instead of thiophene-3-carbaldehyde the title compound was prepared.

$^1$H-NMR (500 MHz, DMSO-d$_6$/D$_2$O) δ ppm 0.88 (t, 3H), 1.51-1.62 (m, 2H), 2.78 (t, 2H), 4.39-4.58 (m, 2H), 6.28-6.35 (m, 1H), 6.62-6.74 (m, 2H), 6.89-7.02 (m, 1H), 7.00-7.10 (m, 1H), 7.26-7.37 (m, 1H), 7.40-7.50 (m, 1H), 7.62-7.81 (m, 2H).

Example 32

1-(4-{[1-(Toluene-4-sulfonyl)-1H-indol-3-ylmethyl]amino}phenyl)butan-1-one

Following a procedure analogous to Example 1, but using 1-[(4-methylphenyl)sulfonyl]-1H-indole-3-carbaldehyde instead of thiophene-3-carbaldehyde the title compound was prepared.

¹H-NMR (500 MHz, DMSO-d₆/D₂O) δ ppm 0.94 (t, 3H), 1.58-1.69 (m, 2H), 2.28-2.38 (m, 3H), 2.84 (t, 2H), 4.48-4.55 (m, 2H), 6.62-6.81 (m, 2H), 7.24-7.43 (m, 4H), 7.67-7.84 (m, 6H), 7.94 (d, 1H);
MS (ESI) positive ion 447 (M+H)⁺; negative ion 445 (M−H)⁻.

Example 33

1-{4-[(5-Methyl-2H-pyrazol-3-ylmethyl)amino]phenyl}butan-1-one

Following a procedure analogous to Example 1, but using 3-methyl-1H-pyrazole-5-carbaldehyde instead of thiophene-3-carbaldehyde the title compound was prepared.
¹H-NMR (500 MHz, DMSO-d₆/D₂O) δ ppm 0.91 (t, 3H), 1.52-1.70 (m, 2H), 2.21-2.25 (m, 3H), 2.80 (t, 2H), 4.24-4.36 (m, 2H), 6.05-6.12 (m, 1H), 6.57-6.72 (m, 2H), 7.67-7.80 (m, 2H);
MS (ESI) positive ion 258 (M+H)⁺; negative ion 256 (M−H)⁻.

Example 34

1-(4-{[4-Bromo-2-(4-chlorobenzyl)-2H-pyrazol-3-ylmethyl]amino}phenyl)butan-1-one Following a procedure analogous to Example 1, but using 4-bromo-1-(4-chlorobenzyl)-1H-pyrazole-5-carbaldehyde instead of thiophene-3-carbaldehyde the title compound was prepared.
¹H-NMR (500 MHz, DMSO-d₆/D₂O) δ ppm 0.95 (t, 3H), 1.53-1.72 (m, 2H), 2.83 (t, 2H), 4.24-4.31 (m, 2H), 5.22-5.43 (m, 2H), 6.66-6.75 (m, 2H), 7.20-7.33 (m, 2H), 7.37-7.46 (m, 2H), 7.69-7.82 (m, 2H), 8.02-8.10 (m, 1H);
MS (ESI) positive ion 448 (M+H)⁺; negative ion 446 (M−H)⁻.

Example 35

4-{5-[(4-Butyrylphenylamino)methyl]furan-2-yl}benzenesulfonamide

Following a procedure analogous to Example 1, but using 4-(5-formylfuran-2-yl)benzenesulfonamide instead of thiophene-3-carbaldehyde the title compound was prepared.
¹H-NMR (500 MHz, DMSO-d₆/D₂O) δ ppm 0.91 (t, 3H), 1.53-1.68 (m, 2H), 2.77-2.87 (m, 2H), 4.38-4.51 (m, 2H), 6.52 (d, 1H), 6.71-6.81 (m, 2H), 7.06 (d, 1H), 7.66-7.74 (m, 1H), 7.74-7.81 (m, 2H), 7.81-7.89 (m, 3H);
MS (ESI) positive ion 399 (M+H)⁺; negative ion 397 (M−H)⁻.

Example 36

1-(4-{[5-(2-(Trifluoromethoxyphenyl)furan-2-ylmethyl]amino}phenyl)butan-1-one

Following a procedure analogous to Example 1, but using 5-(2-(trifluoromethoxy)phenyl)furan-2-carbaldehyde instead of thiophene-3-carbaldehyde the title compound was prepared.
¹H-NMR (500 MHz, DMSO-d₆/D₂O) δ ppm 0.91 (t, 3H), 1.51-1.66 (m, 2H), 2.81 (t, 2H), 4.42-4.50 (m, 2H), 6.53 (d, 1H), 6.70-6.78 (m, 2H), 6.82 (d, 1H), 7.39-7.55 (m, 3H), 7.72-7.81 (m, 2H), 7.84-7.90 (m, 1H);
MS (ESI) positive ion 404 (M+H)⁺; negative ion 402 (M−H)⁻.

Example 37

1-(4-{[4-(3-Bromophenyl)pyridin-3-ylmethyl]amino}phenyl)butan-1-one

Following a procedure analogous to Example 1, but using 4-(3-bromophenyl)nicotinaldehyde instead of thiophene-3-carbaldehyde the title compound was prepared.
¹H-NMR (500 MHz, DMSO-d₆/D₂O) δ ppm 0.87-0.93 (m, 3H), 1.51-1.65 (m, 2H), 2.81 (t, 2H), 4.31-4.51 (m, 2H), 6.41-6.60 (m, 2H), 7.51-7.86 (m, 7H), 8.69-8.83 (m, 2H);
MS (ESI) negative ion 407 (M−H)⁻.

Example 38

1-(4-{[3-(4-Methoxyphenyl)-1-(thiophene-2-carbonyl)-1H-pyrazol-4-ylmethyl]amino}phenyl)butan-1-one Following a procedure analogous to Example 1, but using 3-(4-methoxyphenyl)-1-(thiophene-2-carbonyl)-1H-pyrazole-4-carbaldehyde instead of thiophene-3-carbaldehyde the title compound was prepared.
¹H-NMR (500 MHz, DMSO-d₆/D₂O) δ ppm 0.95 (t, 3H), 1.60-1.70 (m, 2H), 2.87 (t, 2H), 3.87-3.89 (m, 3H), 4.48-4.52 (m, 2H), 6.72-6.77 (m, 2H), 7.14-7.19 (m, 2H), 7.36-7.41 (m, 1H), 7.80-7.84 (m, 2H), 7.87-7.91 (m, 2H), 8.24 (dd, 1H), 8.44 (dd, 1H), 8.50-8.52 (m, 1H);
MS (ESI) positive ion 460 (M+H)⁺; negative ion 458 (M−H)⁻.

Example 39

1-(4-{[5-(3-(Trifluoromethoxyphenyl)furan-2-ylmethyl]amino}phenyl)butan-1-one

Following a procedure analogous to Example 1, but using 5-[3-(trifluoromethoxy)phenyl]furan-2-carbaldehyde instead of thiophene-3-carbaldehyde the title compound was prepared.
¹H-NMR (500 MHz, DMSO-d₆/D₂O) δ ppm 0.87-0.96 (m, 3H), 1.55-1.65 (m, 2H), 2.76-2.85 (m, 2H), 4.40-4.47 (m, 2H), 6.45-6.52 (m, 1H), 6.72-6.81 (m, 2H), 7.00-7.04 (m, 1H), 7.23-7.29 (m, 1H), 7.52-7.59 (m, 2H), 7.66-7.72 (m, 1H), 7.75-7.80 (m, 2H);
MS (ESI) positive ion 404 (M+H)⁺; negative ion 402 (M−H)⁻.

Example 40

1-(4-{[3-(Thiophen-2-yl)-1H-pyrazol-4-ylmethyl]amino}phenyl)butan-1-one

Following a procedure analogous to Example 1, but using 3-(thiophen-2-yl)-1H-pyrazole-4-carbaldehyde instead of thiophene-3-carbaldehyde the title compound was prepared.
¹H-NMR (500 MHz, DMSO-d₆/D₂O) δ ppm 0.88-0.96 (m, 3H), 1.56-1.68 (m, 2H), 2.81 (t, 2H), 4.30-4.38 (m, 2H), 6.66-6.76 (m, 2H), 7.11-7.14 (m, 1H), 7.27-7.34 (m, 1H), 7.49-7.52 (m, 1H), 7.71-7.80 (m, 3H);
MS (ESI) positive ion 326 (M+H)⁺; negative ion 324 (M−H)⁻.

Example 41

1-{4-[(5-Chlorobenzo[b]thiophen-3-ylmethyl) amino]phenyl}butan-1-one

Following a procedure analogous to Example 1, but using 5-chlorobenzo[b]thiophene-3-carbaldehyde instead of thiophene-3-carbaldehyde the title compound was prepared.
$^1$H-NMR (500 MHz, DMSO-$d_6$/$D_2$O) δ ppm 0.93 (t, 3H), 1.54-1.68 (m, 2H), 2.84 (t, 2H), 4.61-4.66 (m, 2H), 6.69-6.81 (m, 2H), 7.42-7.52 (m, 1H), 7.72-7.85 (m, 3H), 7.98-8.13 (m, 2H);
MS (ESI) positive ion 344 (M+H)$^+$.

Example 42

1-(4-{[3-(4-(Trifluoromethylphenyl)-1H-pyrazol-4-ylmethyl]amino}phenyl)butan-1-one Following a procedure analogous to Example 1, but using 3-(4-(trifluoromethyl)phenyl)-1H-pyrazole-4-carbaldehyde instead of thiophene-3-carbaldehyde the title compound was prepared.
$^1$H-NMR (500 MHz, DMSO-$d_6$/$D_2$O) δ ppm 0.88-0.94 (m, 3H), 1.53-1.69 (m, 2H), 2.81 (t, 2H), 4.31-4.39 (m, 2H), 6.63-6.69 (m, 2H), 7.73-7.78 (m, 3H), 7.79-7.84 (m, 2H), 7.87-7.93 (m, 2H);

Example 43

1-{4-[(5-Methyl-3-phenylisoxazol-4-ylmethyl) amino]phenyl}butan-1-one

Following a procedure analogous to Example 1, but using 5-methyl-3-phenylisoxazole-4-carbaldehyde instead of thiophene-3-carbaldehyde the title compound was prepared.
$^1$H-NMR (500 MHz, DMSO-$d_6$/$D_2$O) δ ppm 0.80-0.90 (m, 3H), 1.44-1.61 (m, 2H), 2.39-2.45 (m, 3H), 2.72-2.79 (m, 2H), 4.06-4.13 (m, 2H), 6.52-6.61 (m, 2H), 7.43-7.49 (m, 3H), 7.57-7.64 (m, 2H), 7.67-7.73 (m, 2H);
MS (ESI) positive ion 335 (M+H)$^+$; negative ion 333 (M−H)$^-$.

Example 44

1-{4-[(2,5-Dimethyl-2H-pyrazol-3-ylmethyl)amino] phenyl}butan-1-one

Following a procedure analogous to Example 1, but using 1,3-dimethyl-1H-pyrazole-5-carbaldehyde instead of thiophene-3-carbaldehyde the title compound was prepared.
$^1$H-NMR (500 MHz, DMSO-$d_6$/$D_2$O) δ ppm 0.92 (t, 3H), 1.51-1.68 (m, 2H), 2.07-2.14 (m, 3H), 2.81 (t, 2H), 3.69-3.77 (m, 3H), 4.31-4.42 (m, 2H), 5.97-6.08 (m, 1H), 6.63-6.75 (m, 2H), 7.72-7.79 (m, 2H);
MS (ESI) positive ion 272 (M+H)$^+$; negative ion 270 (M−H)$^-$.

Example 45

1-{4-[(5-Methyl-1-phenyl-1H-pyrazol-4-ylmethyl) amino]phenyl}butan-1-one

Following a procedure analogous to Example 1, but using 5-methyl-1-phenyl-1H-pyrazole-4-carbaldehyde instead of thiophene-3-carbaldehyde the title compound was prepared.
$^1$H-NMR (500 MHz, DMSO-$d_6$/$D_2$O) δ ppm 0.92 (t, 3H), 1.55-1.69 (m, 2H), 2.30-2.36 (m, 3H), 2.82 (t, 2H), 4.17-4.25 (m, 2H), 6.69-6.78 (m, 2H), 7.43-7.59 (m, 5H), 7.62-7.66 (m, 1H), 7.74-7.81 (m, 2H);
MS (ESI) positive ion 334 (M+H)$^+$; negative ion 332 (M−H)$^-$.

Example 46

1-{4-[(2-Phenylthiazol-4-ylmethyl)amino] phenyl}butan-1-one

Following a procedure analogous to Example 1, but using 2-phenylthiazole-4-carbaldehyde instead of thiophene-3-carbaldehyde the title compound was prepared.
$^1$H-NMR (500 MHz, DMSO-$d_6$/$D_2$O) δ ppm 0.89-0.98 (m, 3H), 1.55-1.71 (m, 2H), 2.84 (t, 2H), 4.51-4.58 (m, 2H), 6.69-6.80 (m, 2H), 7.49-7.67 (m, 4H), 7.74-7.85 (m, 2H), 7.94-8.05 (m, 2H).

Example 47

1-{4-[(4-Methyl-2-phenylpyrimidin-5-ylmethyl) amino]phenyl}butan-1-one

Following a procedure analogous to Example 1, but using 4-methyl-2-phenylpyrimidine-5-carbaldehyde instead of thiophene-3-carbaldehyde the title compound was prepared.
$^1$H-NMR (500 MHz, DMSO-$d_6$/$D_2$O) δ ppm 0.91 (t, 3H), 1.57-1.72 (m, 2H), 2.61-2.69 (m, 3H), 2.85 (t, 2H), 4.41-4.51 (m, 2H), 6.62-6.77 (m, 2H), 7.50-7.62 (m, 3H), 7.74-7.84 (m, 2H), 8.28-8.46 (m, 2H), 8.60-8.68 (m, 1H);
MS (ESI) positive ion 346 (M+H)$^+$; negative ion 344 (M−H)$^-$.

Example 48

1-(4-{[1-(Phenylsulfonyl)-1H-indol-3-ylmethyl] amino}phenyl)butan-1-one

Following a procedure analogous to Example 1, but using 1-(phenylsulfonyl)-1H-indole-3-carbaldehyde instead of thiophene-3-carbaldehyde the title compound was prepared.
$^1$H-NMR (500 MHz, DMSO-$d_6$/$D_2$O) δ ppm 0.94 (t, 3H), 1.59-1.68 (m, 2H), 2.83 (t, 2H), 4.50-4.54 (m, 2H), 6.69-6.75 (m, 2H), 7.28-7.34 (m, 1H), 7.37-7.44 (m, 1H), 7.54-7.61 (m, 2H), 7.66-7.71 (m, 1H), 7.73-7.79 (m, 3H), 7.81-7.83 (m, 1H), 7.90-7.98 (m, 3H);
MS (ESI) positive ion 433 (M+H)$^+$; negative ion 431 (M−H)$^-$.

Example 49

1-(4-{[5-(4-Chlorophenoxy)-1,3-dimethyl-1H-pyrazol-4-ylmethyl]amino}phenyl)butan-1-one Following a procedure analogous to Example 1, but using 5-(4-chlorophenoxy)-1,3-dimethyl-1H-pyrazole-4-carbaldehyde instead of thiophene-3-carbaldehyde the title compound was prepared.
$^1$H-NMR (500 MHz, DMSO-$d_6$/$D_2$O) δ ppm 0.87-0.95 (m, 3H), 1.55-1.66 (m, 2H), 2.16-2.19 (m, 3H), 2.78 (t, 2H), 3.46-3.57 (m, 3H), 3.84-3.94 (m, 2H), 6.44-6.59 (m, 2H), 6.91-7.04 (m, 2H), 7.29-7.44 (m, 2H), 7.58-7.72 (m, 2H);
MS (ESI) positive ion 398 (M+H)$^+$; negative ion 396 (M−H)$^-$.

Example 50

1-(4-{[5-(3-Chlorophenoxy)-1,3-dimethyl-1H-pyrazol-4-ylmethyl]amino}phenyl)butan-1-one Following a procedure analogous to Example 1, but using 5-(3-chlorophenoxy)-1,3-dimethyl-1H-pyrazole-4-carbaldehyde instead of thiophene-3-carbaldehyde the title compound was prepared.

$^1$H-NMR (500 MHz, DMSO-$d_6$/$D_2$O) δ ppm 0.86-0.95 (m, 3H), 1.50-1.67 (m, 2H), 2.16-2.21 (m, 3H), 2.75-2.81 (m, 2H), 3.48-3.53 (m, 3H), 3.88-3.93 (m, 2H), 6.47-6.54 (m, 2H), 6.95 (dd, 1H), 6.98-7.02 (m, 1H), 7.13-7.20 (m, 1H), 7.37 (t, 1H), 7.61-7.72 (m, 2H);

MS (ESI) positive ion 398 (M+H)$^+$; negative ion 396 (M−H)$^−$.

Example 51

1-{4-[(5-Chloro-3-methyl-1-phenyl-1H-pyrazol-4-ylmethyl)amino]phenyl}butan-1-one Following a procedure analogous to Example 1, but using 5-chloro-3-methyl-1-phenyl-1H-pyrazole-4-carbaldehyde instead of thiophene-3-carbaldehyde the title compound was prepared.

$^1$H-NMR (500 MHz, DMSO-$d_6$/$D_2$O) δ ppm 0.94 (t, 3H), 1.54-1.71 (m, 2H), 2.26-2.34 (m, 3H), 2.85 (t, 2H), 4.18-4.27 (m, 2H), 6.65-6.80 (m, 2H), 7.48-7.65 (m, 5H), 7.74-7.87 (m, 2H);

MS (ESI) positive ion 368 (M+H)$^+$.

Example 52

1-(4-{[5-Chloro-1-methyl-3-(phenylthiomethyl)-1H-pyrazol-4-ylmethyl]amino}phenyl)butan-1-one Following a procedure analogous to Example 1, but using 5-chloro-1-methyl-3-(phenylthiomethyl)-1H-pyrazole-4-carbaldehyde instead of thiophene-3-carbaldehyde the title compound was prepared.

$^1$H-NMR (500 MHz, DMSO-$d_6$/$D_2$O) δ ppm 0.91 (t, 3H), 1.54-1.66 (m, 2H), 2.70-2.85 (m, 2H), 3.72-3.74 (m, 3H), 4.11-4.16 (m, 2H), 4.17-4.21 (m, 2H), 6.62-6.69 (m, 2H), 7.16-7.23 (m, 1H), 7.27-7.32 (m, 2H), 7.33-7.38 (m, 2H), 7.71-7.80 (m, 2H);

MS (ESI) positive ion 414 (M+H)$^+$; negative ion 412 (M−H)$^−$.

Example 53

1-(4-{[5-Chloro-1-methyl-3-(trifluoromethyl)-1H-pyrazol-4-yl]methylamino}phenyl)butan-1-one Following a procedure analogous to Example 1, but using 5-chloro-1-methyl-3-(trifluoromethyl)-1H-pyrazole-4-carbaldehyde instead of thiophene-3-carbaldehyde the title compound was prepared.

$^1$H-NMR (500 MHz, DMSO-$d_6$/$D_2$O) δ ppm 0.95 (t, 3H), 1.58-1.70 (m, 2H), 2.84 (t, 2H), 3.89-4.01 (m, 3H), 4.19-4.33 (m, 2H), 6.62-6.74 (m, 2H), 7.74-7.85 (m, 2H);

MS (ESI) positive ion 361 (M+H)$^+$.

Example 54

1-(4-{[4-(3-Chlorobenzoyl)-1-methyl-1H-pyrrol-2-ylmethyl]amino}phenyl)butan-1-one Following a procedure analogous to Example 1, but using 4-(3-chlorobenzoyl)-1-methyl-1H-pyrrole-2-carbaldehyde instead of thiophene-3-carbaldehyde the title compound was prepared.

$^1$H-NMR (500 MHz, DMSO-$d_6$/$D_2$O) δ ppm 0.82-0.99 (m, 3H), 1.53-1.66 (m, 2H), 2.78-2.85 (m, 2H), 3.68-3.70 (m, 3H), 4.33-4.40 (m, 2H), 6.51-6.55 (m, 1H), 6.60-6.66 (m, 1H), 6.71-6.77 (m, 2H), 7.41-7.47 (m, 1H), 7.64-7.80 (m, 5H);

MS (ESI) positive ion 395 (M+H)$^+$; negative ion 393 (M−H)$^−$.

Example 55

1-{4-[(1-Ethyl-5-methyl-1H-pyrazol-4-ylmethyl)amino]phenyl}butan-1-one

Following a procedure analogous to Example 1, but using 1-ethyl-5-methyl-1H-pyrazole-4-carbaldehyde instead of thiophene-3-carbaldehyde the title compound was prepared.

$^1$H-NMR (500 MHz, DMSO-$d_6$/$D_2$O) δ ppm 0.88-0.94 (m, 3H), 1.29 (t, 3H), 1.55-1.66 (m, 2H), 2.26-2.28 (m, 3H), 2.77-2.85 (m, 2H), 4.01-4.09 (m, 2H), 4.10-4.15 (m, 2H), 6.57-6.76 (m, 2H), 7.37-7.45 (m, 1H), 7.68-7.79 (m, 2H);

MS (ESI) positive ion 284 (M+H)$^+$; negative ion 286 (M−H)$^−$.

Example 56

1-{4-[(3,5-Dimethyl-1-phenyl-1H-pyrazol-4-ylmethyl)amino]phenyl}butan-1-one

In a 20 ml vial, to a solution of solution of 1-(4-aminophenyl)butan-1-one (46 mg, 0.28 mmol) dissolved in DCM/MeOH (0.6 mL) was added a solution of 3,5-dimethyl-1-phenyl-1H-pyrazole-4-carbaldehyde (112 mg, 0.56 mmol) in DMA (1.8 mL). A solution of acetic acid (50 mg, 0.84 mmol) in DCM/MeOH (0.6 mL) was then added, followed by the addition of 361 mg of MP-CNBH$_3$ resin (3 eq.; subst. 2.34 mmoles/g). The vial was capped and was then heated with shaking overnight at 55° C. The progress of the reaction was monitored by LC/MS. After completion of the reaction, the reaction mixture was concentrated to dryness. The resulting residue was dissolved in 1:1 DMSO/MeOH. Purification by reverse phase HPLC (TFA method) gave the title compound.

$^1$H-NMR (500 MHz, DMSO-$d_6$/$D_2$O) δ ppm 0.91 (t, 3H), 1.53-1.70 (m, 2H), 2.18-2.22 (m, 3H), 2.26-2.33 (m, 3H), 2.79 (t, 2H), 4.07-4.14 (m, 2H), 6.62-6.74 (m, 2H), 7.36-7.49 (m, 3H), 7.49-7.55 (m, 2H), 7.71-7.81 (m, 2H);

MS (ESI) positive ion 348 (M+H)$^+$; negative ion 346 (M−H)$^−$.

Example 57

1-{4-[(2-Phenyl-2H-pyrazol-3-ylmethyl)amino]phenyl}butan-1-one

Following a procedure analogous to Example 56, but using 1-phenyl-1H-pyrazole-5-carbaldehyde instead of 3,5-dimethyl-1-phenyl-1H-pyrazole-4-carbaldehyde the title compound was obtained.

¹H-NMR (500 MHz, DMSO-d₆/D₂O) δ ppm 0.89 (t, 3H), 1.53-1.64 (m, 2H), 2.79 (t, 2H), 4.37-4.47 (m, 2H), 6.36-6.41 (m, 1H), 6.53-6.61 (m, 2H), 7.41-7.51 (m, 1H), 7.51-7.59 (m, 4H), 7.61-7.66 (m, 1H), 7.66-7.76 (m, 2H);
MS (ESI) positive ion 32 0 (M+H)⁺; negative ion 318 (M−H)⁻.

Example 58

1-{4-[(1-tert-Butyl-3,5-dimethyl-1H-pyrazol-4-ylmethyl)amino]phenyl)butan-1-one

Following a procedure analogous to Example 56, but using 1-tert-butyl-3,5-dimethyl-1H-pyrazole-4-carbaldehyde instead of 3,5-dimethyl-1-phenyl-1H-pyrazole-4-carbaldehyde the title compound was obtained.
¹H-NMR (500 MHz, DMSO-d₆/D₂O) δ ppm 0.87-0.93 (m, 3H), 1.52-1.56 (m, 9H), 1.56-1.64 (m, 2H), 2.06-2.12 (m, 3H), 2.33-2.38 (m, 3H), 2.75-2.83 (m, 2H), 3.90-4.01 (m, 2H), 6.61-6.74 (m, 2H), 7.70-7.78 (m, 2H);
MS (ESI) positive ion 328 (M+H)⁺; negative ion 326 (M−H)⁻.

Example 59

1-{4-[(5-Methyl-2H-pyrazol-3-ylmethyl)amino]phenyl}butan-1-one

Following a procedure analogous to Example 56, but using 3-methyl-1H-pyrazole-5-carbaldehyde instead of 3,5-dimethyl-1-phenyl-1H-pyrazole-4-carbaldehyde, the title compound was obtained.
¹H-NMR (500 MHz, DMSO-d₆/D₂O) δ ppm 0.84-0.95 (m, 3H), 1.50-1.66 (m, 2H), 2.17-2.22 (m, 3H), 2.79 (t, 2H), 4.24-4.31 (m, 2H), 5.99-6.05 (m, 1H), 6.58-6.73 (m, 2H), 7.65-7.80 (m, 2H);
MS (ESI) positive ion 258 (M+H)⁺; negative ion 256 (M−H)⁻.

Example 60

1-{4-[(1,5-Dimethyl-1H-pyrazol-4-ylmethyl)amino]phenyl}butan-1-one

Following a procedure analogous to Example 56, but using 1,5-dimethyl-1H-pyrazole-4-carbaldehyde instead of 3,5-dimethyl-1-phenyl-1H-pyrazole-4-carbaldehyde the title compound was obtained.
¹H-NMR (500 MHz, DMSO-d₆/D₂O) δ ppm 0.90 (t, 3H), 1.54-1.65 (m, 2H), 2.22-2.25 (m, 3H), 2.75-2.82 (m, 2H), 3.65-3.72 (m, 3H), 4.01-4.15 (m, 2H), 6.60-6.66 (m, 2H), 7.26-7.36 (m, 1H), 7.63-7.84 (m, 2H);
MS (ESI) positive ion 272 (M+H)⁺.

Example 61

1-{4-[(1,3-Dimethyl-1H-pyrazol-4-ylmethyl)amino]phenyl}butan-1-one

Following a procedure analogous to Example 56, but using 1,3-dimethyl-1H-pyrazole-4-carbaldehyde instead of 3,5-dimethyl-1-phenyl-1H-pyrazole-4-carbaldehyde the title compound was obtained.
¹H-NMR (500 MHz, DMSO-d₆/D₂O) δ ppm 0.85-0.95 (m, 3H), 1.52-1.66 (m, 2H), 2.09-2.16 (m, 3H), 2.79 (t, 2H), 3.65-3.71 (m, 3H), 4.01-4.11 (m, 2H), 6.61-6.68 (m, 2H), 7.51-7.53 (m, 1H), 7.70-7.76 (m, 2H);
MS (ESI) positive ion 272 (M+H)⁺; negative ion 270 (M−H)⁻.

Example 62

1-{4-[(1-Methyl-1H-pyrazol-4-ylmethyl)amino]phenyl}butan-1-one

Following a procedure analogous to Example 56, but using 1-methyl-1H-pyrazole-4-carbaldehyde instead of 3,5-dimethyl-1-phenyl-1H-pyrazole-4-carbaldehyde the title compound was obtained.
¹H-NMR (500 MHz, DMSO-d₆/D₂O) δ ppm 0.89 (t, 3H), 1.49-1.68 (m, 2H), 2.79 (t, 2H), 3.77-3.80 (m, 3H), 4.10-4.20 (m, 2H), 6.57-6.71 (m, 2H), 7.34-7.43 (m, 1H), 7.58-7.64 (m, 1H), 7.66-7.79 (m, 2H);
MS (ESI) positive ion 258 (M+H)⁺; negative ion 256 (M−H)⁻.

Example 63

1-(4-{[3-(5-Methylfuran-2-yl)-1-phenyl-1H-pyrazol-4-ylmethyl]amino}phenyl)butan-1-one Following a procedure analogous to Example 56, but using 3-(5-methylfuran-2-yl)-1-phenyl-1H-pyrazole-4-carbaldehyde instead of 3,5-dimethyl-1-phenyl-1H-pyrazole-4-carbaldehyde, the title compound was obtained.
¹H-NMR (500 MHz, DMSO-d₆/D₂O) δ ppm 0.90 (t, 3H), 1.52-1.67 (m, 2H), 2.31-2.37 (m, 3H), 2.80 (t, 2H), 4.35-4.44 (m, 2H), 6.19-6.26 (m, 1H), 6.65 (d, 1H), 6.68-6.77 (m, 2H), 7.24-7.37 (m, 1H), 7.46-7.61 (m, 2H), 7.69-7.87 (m, 4H), 8.37-8.48 (m, 1H);
MS (ESI) negative ion 398 (M−H)⁻.

Example 64

1-(4-{[1-Phenyl-3-(thiophen-2-yl)-1H-pyrazol-4-ylmethyl]amino}phenyl)butan-1-one Following a procedure analogous to Example 56, but using 1-phenyl-3-(thiophen-2-yl)-1H-pyrazole-4-carbaldehyde instead of 3,5-dimethyl-1-phenyl-1H-pyrazole-4-carbaldehyde, the title compound was obtained.
¹H-NMR (500 MHz, DMSO-d₆/D₂O) δ ppm 0.91 (t, 3H), 1.53-1.66 (m, 2H), 2.81 (t, 2H), 4.37-4.43 (m, 2H), 6.70-6.76 (m, 2H), 7.14-7.19 (m, 1H), 7.32-7.37 (m, 1H), 7.41 (dd, 1H), 7.50-7.60 (m, 3H), 7.74-7.85 (m, 4H), 8.50-8.54 (m, 1H);
MS (ESI) positive ion 402 (M+H)⁺; negative ion 400 (M−H)⁻.

Example 65

1-{4-[(1-Ethyl-5-methyl-1H-pyrazol-4-ylmethyl)amino]phenyl}butan-1-one

Following a procedure analogous to Example 56, but using 1-ethyl-5-methyl-1H-pyrazole-4-carbaldehyde instead of 3,5-dimethyl-1-phenyl-1H-pyrazole-4-carbaldehyde, the title compound was obtained.
¹H-NMR (500 MHz, DMSO-d₆/D₂O) δ ppm 0.90 (t, 3H), 1.27 (t, 3H), 1.54-1.64 (m, 2H), 2.20-2.27 (m, 3H), 2.79 (t, 2H), 4.03 (q, 2H), 4.07-4.10 (m, 2H), 6.43-6.83 (m, 2H), 7.25-7.49 (m, 1H), 7.58-7.86 (m, 2H);
MS (ESI) positive ion 286 (M+H)⁺; negative ion 284 (M−H)⁻.

Example 66

1-{4-[(1-Ethyl-3-methyl-1H-pyrazol-4-ylmethyl)amino]phenyl}butan-1-one

Following a procedure analogous to Example 56, but using 1-ethyl-3-methyl-1H-pyrazole-4-carbaldehyde instead of 3,5-dimethyl-1-phenyl-1H-pyrazole-4-carbaldehyde the title compound was obtained.

$^1$H-NMR (500 MHz, DMSO-$d_6$/$D_2O$) δ ppm 0.89 (t, 3H), 1.32 (t, 3H), 1.52-1.65 (m, 2H), 2.11-2.17 (m, 3H), 2.79 (t, 2H), 3.98 (q, 2H), 4.06-4.12 (m, 2H), 6.57-6.71 (m, 2H), 7.52-7.61 (m, 1H), 7.69-7.77 (m, 2H);

MS (ESI) positive ion 286 (M+H)$^+$; negative ion 284 (M−H)$^-$.

Example 67

1-{4-[(1-Ethyl-1H-pyrazol-4-ylmethyl)amino]phenyl}butan-1-one

Following a procedure analogous to Example 56, but using 1-ethyl-1H-pyrazole-4-carbaldehyde instead of 3,5-dimethyl-1-phenyl-1H-pyrazole-4-carbaldehyde the title compound was obtained.

$^1$H-NMR (500 MHz, DMSO-$d_6$/$D_2O$) δ ppm 0.90 (t, 3H), 1.34 (t, 3H), 1.51-1.66 (m, 2H), 2.79 (t, 2H), 4.07 (q, 2H), 4.13-4.21 (m, 2H), 6.63-6.71 (m, 2H), 7.35-7.47 (m, 1H), 7.63-7.70 (m, 1H), 7.70-7.77 (m, 2H);

MS (ESI) positive ion 272 (M+H)$^+$; negative ion 270 (M−H)$^-$.

Example 68

1-{4-[(1H-Pyrazol-4-ylmethyl)amino]phenyl}butan-1-one

Following a procedure analogous to Example 56, but using 1H-pyrazole-4-carbaldehyde instead of 3,5-dimethyl-1-phenyl-1H-pyrazole-4-carbaldehyde the title compound was obtained.

$^1$H-NMR (500 MHz, DMSO-$d_6$/$D_2O$) δ ppm 0.89 (t, 3H), 1.50-1.67 (m, 2H), 2.79 (t, 2H), 4.14-4.27 (m, 2H), 6.55-6.72 (m, 2H), 7.53-7.59 (m, 2H), 7.66-7.78 (m, 2H);

MS (ESI) positive ion 244 (M+H)$^+$; negative ion 242 (M−H)$^-$.

Example 69

1-{4-[(2,5-Dimethyl-1H-pyrazol-3-ylmethyl)amino]phenyl}butan-1-one

Following a procedure analogous to Example 56, but using 2,5-dimethyl-2H-pyrazole-3-carbaldehyde instead of 3,5-dimethyl-1-phenyl-1H-pyrazole-4-carbaldehyde, the title compound was obtained.

$^1$H-NMR (500 MHz, DMSO-$d_6$/$D_2O$) δ ppm 0.90 (t, 3H), 1.49-1.65 (m, 2H), 2.04-2.10 (m, 3H), 2.80 (t, 2H), 3.63-3.72 (m, 3H), 4.26-4.38 (m, 2H), 5.94-6.00 (m, 1H), 6.60-6.75 (m, 2H), 7.65-7.79 (m, 2H);

MS (ESI) positive ion 272 (M+H)$^+$; negative ion 270 (M−H)$^-$.

Example 70

1-{4-[(3-Methyl-1-propyl-1H-pyrazol-4-ylmethyl)amino]phenyl}butan-1-one

Following a procedure analogous to Example 56, but using 3-methyl-1-propyl-1H-pyrazole-4-carbaldehyde instead of 3,5-dimethyl-1-phenyl-1H-pyrazole-4-carbaldehyde the title compound was obtained.

$^1$H-NMR (500 MHz, DMSO-$d_6$/$D_2O$) δ ppm 0.79 (t, 3H), 0.90 (t, 3H), 1.53-1.65 (m, 2H), 1.66-1.76 (m, 2H), 2.11-2.18 (m, 3H), 2.78 (t, 2H), 3.91 (t, 2H), 4.06-4.12 (m, 2H), 6.61-6.68 (m, 2H), 7.56-7.62 (m, 1H), 7.68-7.76 (m, 2H);

MS (ESI) positive ion 300 (M+H)$^+$; negative ion 298 (M−H)$^-$.

Example 71

1-{4-[(5-Methyl-1-propyl-1H-pyrazol-4-ylmethyl)amino])phenyl}butan-1-one

Following a procedure analogous to Example 56, but using 5-methyl-1-propyl-1H-pyrazole-4-carbaldehyde instead of 3,5-dimethyl-1-phenyl-1H-pyrazole-4-carbaldehyde the title compound was obtained.

$^1$H-NMR (500 MHz, DMSO-$d_6$/$D_2O$) δ ppm 0.82 (t, 3H), 0.90 (t, 3H), 1.53-1.63 (m, 2H), 1.65-1.77 (m, 2H), 2.18-2.28 (m, 3H), 2.78 (t, 2H), 3.95 (t, 2H), 4.06-4.12 (m, 2H), 6.61-6.67 (m, 2H), 7.32-7.39 (m, 1H), 7.67-7.77 (m, 2H);

MS (ESI) positive ion 300 (M+H)$^+$; negative ion 298 (M−H)$^-$.

Example 72

1-{4-[(1-Methyl-1H-pyrazol-3-ylmethyl)amino]phenyl}butan-1-one

Following a procedure analogous to Example 56, but using 1-methyl-1H-pyrazole-3-carbaldehyde instead of 3,5-dimethyl-1-phenyl-1H-pyrazole-4-carbaldehyde, the title compound was obtained.

$^1$H-NMR (500 MHz, DMSO-$d_6$/$D_2O$) δ ppm 0.90 (t, 3H), 1.53-1.66 (m, 2H), 2.79 (t, 2H), 3.78-3.80 (m, 3H), 4.24-4.27 (m, 2H), 6.15 (d, 1H), 6.63-6.69 (m, 2H), 7.57 (d, 1H), 7.69-7.76 (m, 2H);

MS (ESI) positive ion 258 (M+H)$^+$; negative ion 256 (M−H)$^-$.

Example 73

1-{4-[(1-Methyl-5-phenyl-1H-pyrazol-4-ylmethyl)amino]phenyl})butan-1-one

Following a procedure analogous to Example 56, but using 1-methyl-5-phenyl-1H-pyrazole-4-carbaldehyde instead of 3,5-dimethyl-1-phenyl-1H-pyrazole-4-carbaldehyde the title compound was obtained.

$^1$H-NMR (500 MHz, DMSO-$d_6$/$D_2O$) δ ppm 0.89 (t, 3H), 1.48-1.66 (m, 2H), 2.78 (t, 2H), 3.72-3.73 (m, 3H), 4.00-4.06 (m, 2H), 6.49-6.58 (m, 2H), 7.38-7.59 (m, 6H), 7.64-7.72 (m, 2H);

MS (ESI) positive ion 334 (M+H)$^+$; negative ion 332 (M−H)$^-$.

Example 74

1-{4-[(1,5-Dimethyl-1H-pyrazol-3-ylmethyl)amino]phenyl}butan-1-one

Following a procedure analogous to Example 56, but using 1,5-dimethyl-1H-pyrazole-3-carbaldehyde (instead of 3,5-dimethyl-1-phenyl-1H-pyrazole-4-carbaldehyde the title compound was obtained.

$^1$H-NMR (500 MHz, DMSO-d$_6$/D$_2$O) δ ppm 0.90 (t, 3H), 1.51-1.66 (m, 2H), 2.05-2.10 (m, 3H), 2.80 (t, 2H), 3.68-3.72 (m, 3H), 4.25-4.36 (m, 2H), 5.76-6.20 (m, 1H), 6.49-6.77 (m, 2H), 7.64-7.82 (m, 2H);
MS (ESI) positive ion 272 (M+H)$^+$; negative ion 270 (M−H)$^−$.

Example 75

1-{4-[(1-Isopropyl-1H-pyrazol-4-ylmethyl)amino]phenyl}butan-1-one

Following a procedure analogous to Example 56, but using 1-isopropyl-1H-pyrazole-4-carbaldehyde instead of 3,5-dimethyl-1-phenyl-1H-pyrazole-4-carbaldehyde the title compound was obtained.

$^1$H-NMR (500 MHz, DMSO-d$_6$/D$_2$O) δ ppm 0.88 (t, 3H), 1.37 (d, 6H), 1.52-1.68 (m, 2H), 2.80 (t, 2H), 4.12-4.20 (m, 2H), 4.37-4.49 (m, 1H), 6.63-6.69 (m, 2H), 7.37-7.44 (m, 1H), 7.66-7.78 (m, 3H);
MS (ESI) positive ion 286 (M+H)$^+$; negative ion 284 (M−H)$^−$.

Example 76

1-(4-{[3-(4-Hydroxyphenyl)-1H-pyrazol-4-ylmethyl]amino}phenyl)butan-1-one

Following a procedure analogous to Example 56, but using 3-(4-hydroxyphenyl)-1H-pyrazole-4-carbaldehyde instead of 3,5-dimethyl-1-phenyl-1H-pyrazole-4-carbaldehyde the title compound was obtained.

$^1$H-NMR (500 MHz, DMSO-d$_6$/D$_2$O) δ ppm 0.90 (t, 3H), 1.52-1.67 (m, 2H), 2.79 (t, 2H), 4.18-4.27 (m, 2H), 6.56-6.68 (m, 2H), 6.81-6.90 (m, 2H), 7.39-7.48 (m, 2H), 7.57-7.64 (m, 1H), 7.70-7.78 (m, 2H);
MS (ESI) positive ion 334 (M+H)$^+$.

Example 77

1-{4-[(3-tert-Butyl-1H-pyrazol-4-ylmethyl)amino]phenyl}butan-1-one

Following a procedure analogous to Example 56, but using 3-tert-butyl-1H-pyrazole-4-carbaldehyde instead of 3,5-dimethyl-1-phenyl-1H-pyrazole-4-carbaldehyde the title compound was obtained.

$^1$H-NMR (500 MHz, DMSO-d$_6$/D$_2$O) δ ppm 0.89 (t, 3H), 1.28-1.36 (m, 9H), 1.53-1.67 (m, 2H), 2.79 (t, 2H), 4.20-4.26 (m, 2H), 6.60-6.71 (m, 2H), 7.37-7.41 (m, 1H), 7.68-7.78 (m, 2H);
MS (ESI) positive ion 300 (M+H)$^+$; negative ion 298 (M−H)$^−$.

Example 78

N-Benzylthiazol-2-amine

In a 20 mL vial, to a solution of benzaldehyde (40 mg, 0.38 mmol) in DCM/MeOH (1.4 mL) was added a solution of thiazol-2-amine (47 mg, 0.47 mmol) in DMA (1.8 mL). A solution of acetic acid (66 mg, 1.1 mmol) in DCM/MeOH (1.4 mL) was then added, followed by the addition of 470 mg of MP-CNBH$_3$ resin (3 eq.; subst. 2.36 mmoles/g). The vial was capped and was then heated with shaking overnight at 65° C. The progress of the reaction was monitored by LC/MS. After completion of the reaction, the reaction mixture was concentrated to dryness. The residue was dissolved in 1:1 DMSO/MeOH. Purification by reverse phase HPLC (TFA method) gave the title compound.

$^1$H-NMR (500 MHz, DMSO-d$_6$/D$_2$O) δ ppm 4.47-4.67 (m, 2H), 6.83-6.93 (m, 1H), 7.19-7.30 (m, 1H), 7.30-7.46 (m, 5H);
MS (ESI) positive ion 191 (M+H)$^+$.

Following a procedure analogous to Example 1 or 56, the novel compounds of Examples 79 and 81 to 482 were prepared.

Example 79

3-[(3-tert-Butyl-1H-pyrazol-4-ylmethyl)-amino]-phenol

MS (ESI) 246.15 (M+H)$^+$.

Example 80

2,2,2-Trifluoroethanesulfonic acid (4-butyryl-phenyl)-[1-(2,2,2-trifluoro-ethanesulfonyl)-3-(4-trifluoromethylphenyl)-1H-pyrazol-4-ylmethyl]-amide A solution of trifluoroethylsulfonylchloride (2 eq.) in dichloromethane (5 mL) was added dropwise at 0° C. (ice bath) to a solution of 1-(4-{[3-(4-trifluoromethyl-phenyl)-1H-pyrazol-4-ylmethyl]-amino}-phenyl)-butan-1-one (50.0 mg, 0.13 mmol) and pyridine (0.15 mL). When the addition was completed, the ice bath was removed and the solution was stirred for further 12 h. The solution was washed with aqueous hydrochloric acid (2N, ca 50 mL) and then with water, and saturated aqueous sodium chloride. The organic phase was dried over sodium sulfate and thereafter chromatographed on silica gel (eluted with 10-20% ethyl acetate in heptane). Yield: 70 mg, 80%

$^1$H-NMR (400 MHz, CDCl$_3$) δ ppm 8.06 (s, 1H), 7.86 (d, 2H), 7.63 (d, 1H), 7.55 (d, 1H), 7.21 (d, 1H), 5.02 (s, 2H), 4.26 (q, 2H), 3.72 (q, 2H), 2.87 (t, 2H), 1.76 (q, 2H), 1.00 (t, 3H);
MS (ESI) 680.15 (M+H)$^+$.

Example 81

5-{[3-(4-Trifluoromethylphenyl)-1H-pyrazol-4-ylmethyl]-amino}-indan-1-one $^1$H-NMR (500 MHz, DMSO-d$_6$) δ ppm 8.02-7.73 (mbr, 5H), 7.38 (d, 1H), 7.04 (m, 1H), 6.72 (d, 1H), 6.64 (sbr, 1H), 4.39 (sbr, 2H), 2.94 (m, 2H), 2.49 (m, 2H);
MS (ESI) 372.10 (M+H)$^+$.

Example 82

6-{[3-(4-Trifluoromethylphenyl)-1H-pyrazol-4-ylmethyl]-amino}-3,4-dihydro-2H-naphthalen-1-one $^1$H-NMR (500 MHz, DMSO-d$_6$) δ ppm 13.16 (sbr, 1H), 8.00 (d, 2H), 7.93 (s, 1H), 7.84 (d, 2H), 7.73 (d, 1H), 6.92 (sbr, 1H), 6.67 (d, 1H), 6.52 (sbr, 1H), 4.42 (sbr, 2H), 2.83 (s br, 2H), 2.49 (m, 2H), 2.02 (quint., 2H);
MS (ESI) 386.15 (M+H)$^+$.

Example 83

[4-(2-Methoxy-phenoxy)-phenyl]-[3-(4-trifluoromethylphenyl)-1H-pyrazol-4-ylmethyl]-amine $^1$H-NMR (500 MHz, CDCl$_3$) δ ppm 7.77 (d, 2H), 7.61 (m, 3H), 7.08-6.78 (m, 6H), 6.60 (d, 2H), 4.25 (s br, 2H), 3.87 (s br, 3H);
MS (ESI) 440.15 (M+H)$^+$.

Example 84

N-Methoxy-N-methyl-4-{[3-(4-trifluoromethylphenyl)-1H-pyrazol-4-ylmethyl]-amino}-benzamide

MS (ESI) 405.1 (M+H)$^+$.

Example 85

4-{[3-tert-Butyl-1-(2,2,2-trifluoroethanesulfonyl)-1H-pyrazol-4-ylmethyl]-amino}-N-methoxy-N-methyl-benzamide $^1$H-NMR (500 MHz, CDCl$_3$) δ ppm 7.86 (s, 1H), 7.66 (d, 2H), 6.55 (d, 2H), 4.37-4.29 (m, 3H), 4.20 (q, 2H), 3.58 (s, 3H), 3.34 (s, 3H), 1.39 (s, 9H);
MS (ESI) 463.10 (M+H)$^+$.

Example 86

(3-tert-Butyl-1H-pyrazol-4-ylmethyl)-[3-(1-methylbutoxy)-phenyl]-amine $^1$H-NMR (500 MHz, CDCl$_3$) δ ppm 7.51 (s, 1H), 7.07 (t, 1H), 6.30-6.17 (m, 3H), 4.33 (m, 1H), 4.23 (s, 2H), 1.77-1.36 [m, 13H incl. 1.40 (s, 9H)], 1.28 (d, 3H), 0.93 (t, 3H)
MS (ESI) 316.20 (M+H)$^+$.

Example 87

(3-tert-Butyl-1H-pyrazol-4-ylmethyl)-phenylamine; compound with trifluoroacetic acid

MS (ESI) 230.0 (M+H)$^+$.

Example 88

(3-tert-Butyl-1H-pyrazol-4-ylmethyl)-o-tolylamine; compound with trifluoroacetic acid

MS (ESI) 244.1 (M+H)$^+$.

Example 89

(3-tert-Butyl-1H-pyrazol-4-ylmethyl)-m-tolylamine; compound with trifluoroacetic acid

MS (ESI) 244.1 (M+H)$^+$.

Example 90

(3-tert-Butyl-1H-pyrazol-4-ylmethyl)-p-tolylamine; compound with trifluoroacetic acid

MS (ESI) 244.1 (M+H)$^+$.

Example 91

(3-tert-Butyl-1H-pyrazol-4-ylmethyl)-(2-methoxyphenyl)-amine; compound with trifluoroacetic acid

MS (ESI) 260.1 (M+H)$^+$.

Example 92

(3-tert-Butyl-1H-pyrazol-4-ylmethyl)-(3-methoxyphenyl)-amine; compound with trifluoroacetic acid

MS (ESI) 260.1 (M+H)$^+$.

Example 93

(3-tert-Butyl-1H-pyrazol-4-ylmethyl)-(4-methoxyphenyl)-amine; compound with trifluoroacetic acid

MS (ESI) 260.1 (M+H)$^+$.

Example 94

(3-tert-Butyl-1H-pyrazol-4-ylmethyl)-(2-fluorophenyl)-amine; compound with trifluoroacetic acid

MS (ESI) 248.0 (M+H)$^+$.

Example 95

(3-tert-Butyl-1H-pyrazol-4-ylmethyl)-(3-fluorophenyl)-amine; compound with trifluoroacetic acid

MS (ESI) 248.0 (M+H)$^+$.

Example 96

(3-tert-Butyl-1H-pyrazol-4-ylmethyl)-(4-fluorophenyl)-amine; compound with trifluoroacetic acid

MS (ESI) 248.0 (M+H)$^+$.

Example 97

(3-tert-Butyl-1H-pyrazol-4-ylmethyl)-(2-chlorophenyl)-amine; compound with trifluoroacetic acid

MS (ESI) 264.0 (M+H)$^+$.

Example 98

(3-tert-Butyl-1H-pyrazol-4-ylmethyl)-(3-chlorophenyl)-amine; compound with trifluoroacetic acid

MS (ESI) 264.0 (M+H)$^+$.

Example 99

(3-tert-Butyl-1H-pyrazol-4-ylmethyl)-(4-chlorophenyl)-amine; compound with trifluoroacetic acid

MS (ESI) 264.0 (M+H)$^+$.

Example 100

(3-tert-Butyl-1H-pyrazol-4-ylmethyl)-(4-trifluoromethoxyphenyl)-amine; compound with trifluoroacetic acid

MS (ESI) 314.0 (M+H)$^+$.

Example 101

(3-tert-Butyl-1H-pyrazol-4-ylmethyl)-(3-phenoxyphenyl)-amine; compound with trifluoroacetic acid

MS (ESI) 322.3 (M+H)$^+$.

Example 102

N-(3-tert-Butyl-1H-pyrazol-4-ylmethyl)-N',N'-dimethylbenzene-1,3-diamine; compound with trifluoroacetic acid

MS (ESI) 273.1 (M+H)$^+$.

Example 103

(3-tert-Butyl-1H-pyrazol-4-ylmethyl)-(3-trifluoromethylphenyl)-amine; compound with trifluoroacetic acid

MS (ESI) 298.1 (M+H)$^+$.

Example 104

(3-tert-Butyl-1H-pyrazol-4-ylmethyl)-(4-trifluoromethylphenyl)-amine; compound with trifluoroacetic acid

MS (ESI) 298.3 (M+H)$^+$.

Example 105

(3-tert-Butyl-1H-pyrazol-4-ylmethyl)-(3-trifluoromethoxyphenyl)-amine; compound with trifluoroacetic acid

MS (ESI) 314.3 (M+H)$^+$.

Example 106

(3-tert-Butyl-1H-pyrazol-4-ylmethyl)-(4-phenoxyphenyl)-amine; compound with trifluoroacetic acid

MS (ESI) 322.1 (M+H)$^+$.

Example 107

(3-tert-Butyl-1H-pyrazol-4-ylmethyl)-(2,3-dimethylphenyl)-amine; compound with trifluoroacetic acid

MS (ESI) 258.1 (M+H)$^+$.

Example 108

(3-tert-Butyl-1H-pyrazol-4-ylmethyl)-(2,4-dimethylphenyl)-amine; compound with trifluoroacetic acid

MS (ESI) 258.1 (M+H)$^+$.

Example 109

(3-tert-Butyl-1H-pyrazol-4-ylmethyl)-(2,5-dimethylphenyl)-amine; compound with trifluoroacetic acid

MS (ESI) 258.1 (M+H)$^+$.

Example 110

(3-tert-Butyl-1H-pyrazol-4-ylmethyl)-(3,4-dimethylphenyl)-amine; compound with trifluoroacetic acid

MS (ESI) 258.1 (M+H)$^+$.

Example 111

(3-tert-Butyl-1H-pyrazol-4-ylmethyl)-(3,5-dimethylphenyl)-amine; compound with trifluoroacetic acid

MS (ESI) 258.1 (M+H)$^+$.

Example 112

(3-tert-Butyl-1H-pyrazol-4-ylmethyl)-(2,3-dimethoxyphenyl)-amine; compound with trifluoroacetic acid

MS (ESI) 290.3 (M+H)$^+$.

Example 113

(3-tert-Butyl-1H-pyrazol-4-ylmethyl)-(2,4-dimethoxyphenyl)-amine; compound with trifluoroacetic acid

MS (ESI) 290.3 (M+H)$^+$.

Example 114

(3-tert-Butyl-1H-pyrazol-4-ylmethyl)-(2,5-dimethoxyphenyl)-amine; compound with trifluoroacetic acid

MS (ESI) 290.1 (M+H)$^+$.

Example 115

(3-tert-Butyl-1H-pyrazol-4-ylmethyl)-(3,4-dimethoxyphenyl)-amine; compound with trifluoroacetic acid

MS (ESI) 290.2 (M+H)$^+$.

Example 116

(3-tert-Butyl-1H-pyrazol-4-ylmethyl)-(3,5-dimethoxyphenyl)-amine; compound with trifluoroacetic acid

MS (ESI) 290.4 (M+H)$^+$.

Example 117

Benzo[1,3]dioxol-5-yl-(3-tert-butyl-1H-pyrazol-4-ylmethyl)-amine; compound with trifluoroacetic acid

MS (ESI) 274.1 (M+H)$^+$.

Example 118

(3-tert-Butyl-1H-pyrazol-4-ylmethyl)-(3,4,5-tri-methoxyphenyl)-amine; compound with trifluoroacetic acid

MS (ESI) 320.1 (M+H)$^+$.

Example 119

(3-tert-Butyl-1H-pyrazol-4-ylmethyl)-(2,3-dichlorophenyl)-amine; compound with trifluoroacetic acid

MS (ESI) 298.0 (M+H)$^+$.

Example 120

(3-tert-Butyl-1H-pyrazol-4-ylmethyl)-(2,4-dichlorophenyl)-amine; compound with trifluoroacetic acid

MS (ESI) 298.0 (M+H)$^+$.

Example 121

(3-tert-Butyl-1H-pyrazol-4-ylmethyl)-(2,5-dichlorophenyl)-amine; compound with trifluoroacetic acid

MS (ESI) 299.8 (M+H)$^+$.

Example 122

(3-tert-Butyl-1H-pyrazol-4-ylmethyl)-(3,4-dichlorophenyl)-amine; compound with trifluoroacetic acid

MS (ESI) 298.0 (M+H)$^+$.

Example 123

(3-tert-Butyl-1H-pyrazol-4-ylmethyl)-(3,5-dichlorophenyl)-amine; compound with trifluoroacetic acid

MS (ESI) 297.9 (M+H)$^+$.

Example 124

(3-Thiophen-2-yl-1H-pyrazol-4-ylmethyl)-o-tolyl-amine; compound with trifluoroacetic acid

MS (ESI) 270.0 (M+H)$^+$.

Example 125

(3-Thiophen-2-yl-1H-pyrazol-4-ylmethyl)-p-tolyl-amine; compound with trifluoroacetic acid

MS (ESI) 270.0 (M+H)$^+$.

Example 126

(2-Methoxyphenyl)-(3-thiophen-2-yl-1H-pyrazol-4-ylmethyl)-amine; compound with trifluoroacetic acid

MS (ESI) 286.0 (M+H)$^+$.

Example 127

(3-Methoxyphenyl)-(3-thiophen-2-yl-1H-pyrazol-4-ylmethyl)-amine; compound with trifluoroacetic acid

MS (ESI) 286.0 (M+H)$^+$.

Example 128

(4-Methoxyphenyl)-(3-thiophen-2-yl-1H-pyrazol-4-ylmethyl)-amine; compound with trifluoroacetic acid

MS (ESI) 286.0 (M+H)$^+$.

Example 129

(2-Fluorophenyl)-(3-thiophen-2-yl-1H-pyrazol-4-ylmethyl)-amine; compound with trifluoroacetic acid

MS (ESI) 274.0 (M+H)$^+$.

Example 130

(3-Fluorophenyl)-(3-thiophen-2-yl-1H-pyrazol-4-ylmethyl)-amine; compound with trifluoroacetic acid

MS (ESI) 274.1 (M+H)$^+$.

Example 131

(2-Chlorophenyl)-(3-thiophen-2-yl-1H-pyrazol-4-ylmethyl)-amine; compound with trifluoroacetic acid

Example 132

(3-Chlorophenyl)-(3-thiophen-2-yl-1H-pyrazol-4-ylmethyl)-amine; compound with trifluoroacetic acid

MS (ESI) 290.2 (M+H)$^+$.

Example 133

(4-Chlorophenyl)-(3-thiophen-2-yl-1H-pyrazol-4-ylmethyl)-amine; compound with trifluoroacetic acid

MS (ESI) 290.0 (M+H)$^+$.

Example 134

(3-Thiophen-2-yl-1H-pyrazol-4-ylmethyl)-(4-trifluoromethoxyphenyl)-amine; compound with trifluoroacetic acid

MS (ESI) 339.9 (M+H)$^+$.

Example 135

(3-Phenoxy-phenyl)-(3-thiophen-2-yl-1H-pyrazol-4-ylmethyl)-amine; compound with trifluoroacetic acid

MS (ESI) 348.0 (M+H)$^+$.

Example 136

N,N-Dimethyl-N'-(3-thiophen-2-yl-1H-pyrazol-4-ylmethyl)-benzene-1,3-diamine; compound with trifluoroacetic acid

MS (ESI) 299.0 (M+H)$^+$.

Example 137

N,N-Dimethyl-N'-(3-thiophen-2-yl-1H-pyrazol-4-ylmethyl)-benzene-1,4-diamine; compound with trifluoroacetic acid

MS (ESI) 298.9 (M+H)$^+$.

Example 138

(3-Thiophen-2-yl-1H-pyrazol-4-ylmethyl)-(3-trifluoromethylphenyl)-amine; compound with trifluoroacetic acid

MS (ESI) 323.9 (M+H)$^+$.

Example 139

(3-Thiophen-2-yl-1H-pyrazol-4-ylmethyl)-(4-trifluoromethylphenyl)-amine; compound with trifluoroacetic acid

Example 140

(3-Thiophen-2-yl-1H-pyrazol-4-ylmethyl)-(3-trifluoromethoxyphenyl)-amine; compound with trifluoroacetic acid

MS (ESI) 340.0 (M+H)$^+$.

Example 141

(4-Phenoxyphenyl)-(3-thiophen-2-yl-1H-pyrazol-4-ylmethyl)-amine; compound with trifluoroacetic acid

Example 142

(2,3-Dimethylphenyl)-(3-thiophen-2-yl-1H-pyrazol-4-ylmethyl)-amine; compound with trifluoroacetic acid

MS (ESI) 284.0 (M+H)$^+$.

Example 143

(2,4-Dimethylphenyl)-(3-thiophen-2-yl-1H-pyrazol-4-ylmethyl)-amine; compound with trifluoroacetic acid

MS (ESI) 284.0 (M+H)$^+$.

Example 144

(2,5-Dimethylphenyl)-(3-thiophen-2-yl-1H-pyrazol-4-ylmethyl)-amine; compound with trifluoroacetic acid

MS (ESI) 284.0 (M+H)$^+$.

Example 145

(3,5-Dimethylphenyl)-(3-thiophen-2-yl-1H-pyrazol-4-ylmethyl)-amine; compound with trifluoroacetic acid

MS (ESI) 284.2 (M+H)$^+$.

Example 146

(2,3-Dimethoxyphenyl)-(3-thiophen-2-yl-1H-pyrazol-4-ylmethyl)-amine; compound with trifluoroacetic acid

MS (ESI) 316.0 (M+H)$^+$.

Example 147

(2,4-Dimethoxyphenyl)-(3-thiophen-2-yl-1H-pyrazol-4-ylmethyl)-amine; compound with trifluoroacetic acid

MS (ESI) 316.0 (M+H)$^+$.

Example 148

(2,5-Dimethoxyphenyl)-(3-thiophen-2-yl-1H-pyrazol-4-ylmethyl)-amine; compound with trifluoroacetic acid

MS (ESI) 316.0 (M+H)$^+$.

Example 149

(3,4-Dimethoxyphenyl)-(3-thiophen-2-yl-1H-pyrazol-4-ylmethyl)-amine; compound with trifluoroacetic acid

MS (ESI) 316.0 (M+H)$^+$.

Example 150

(3,5-Dimethoxyphenyl)-(3-thiophen-2-yl-1H-pyrazol-4-ylmethyl)-amine; compound with trifluoroacetic acid

MS (ESI) 316.0 (M+H)$^+$.

Example 151

Benzo[1,3]dioxol-5-yl-(3-thiophen-2-yl-1H-pyrazol-4-ylmethyl)-amine; compound with trifluoroacetic acid

MS (ESI) 299.9 (M+H)$^+$.

Example 152

(3-Thiophen-2-yl-1H-pyrazol-4-ylmethyl)-(3,4,5-trimethoxy-phenyl)-amine; compound with trifluoroacetic acid

MS (ESI) 346.0 (M+H)$^+$.

Example 153

(2,3-Dichlorophenyl)-(3-thiophen-2-yl-1H-pyrazol-4-ylmethyl)-amine; compound with trifluoroacetic acid

Example 154

(2,4-Dichlorophenyl)-(3-thiophen-2-yl-1H-pyrazol-4-ylmethyl)-amine; compound with trifluoroacetic acid

Example 155

(2,5-Dichlorophenyl)-(3-thiophen-2-yl-1H-pyrazol-4-ylmethyl)-amine; compound with trifluoroacetic acid

Example 156

(3,4-Dichlorophenyl)-(3-thiophen-2-yl-1H-pyrazol-4-ylmethyl)-amine; compound with trifluoroacetic acid

Example 157

(3,5-Dichlorophenyl)-(3-thiophen-2-yl-1H-pyrazol-4-ylmethyl)-amine; compound with trifluoroacetic acid

Example 158

2,2,2-Trifluoroethanesulfonic acid [3-tert-butyl-1-(2,2,2-trifluoro-ethanesulfonyl)-1H-pyrazol-4-ylmethyl]-[3-(1-methyl-butoxy)-phenyl]-amide MS (ESI) 608.10 (M+H)$^+$;
$^1$H-NMR (500 MHz, CDCl$_3$) δ ppm 7.83 (s br, 1H), 7.30-7.23 (m, 1H), 6.90-6.80 (m, 3H), 4.94 (s br, 2H), 4.31 (q, 1H), 4.13 (q, 2H), 3.80 (q, 2H), 1.74-1.61 (m br, 2H), 1.57-1.48 (m br, 1H), 1.48-1.18 [m, 14H incl. 1.29 (s, 9H)], 0.92 (t, 3H).

Example 159

2-Fluoro-4-{[3-(4-trifluoromethyl-phenyl)-1H-pyrazol-4-ylmethyl]-amino}-benzonitrile; compound with trifluoroacetic acid $^1$H-NMR (500 MHz, DMSO-d$_6$) δ ppm 13.41 and 13.10 (2×s br, NH), 7.86 (q, 3H), 7.75 (t, 2H), 7.46 (t, 1H), 7.30 (s br, NH), 6.62-6.52 (m, 2H), 4.37-4.25 (m, 2H).

Example 160

(3-tert-Butyl-1H-pyrazol-4-ylmethyl)-[4-(1,1-dioxo-1λ$^6$-thiomorpholin-4-yl)-phenyl]-amine

MS (ESI) 362.1 (M).

Example 161

(3-tert-Butyl-1H-pyrazol-4-ylmethyl)-(4-oxazol-5-yl-phenyl)-amine

MS (ESI) 297.15 (M+H)$^+$.

Example 162

(3-tert-Butyl-1H-pyrazol-4-ylmethyl)-(4-pyridin-4-yl-phenyl)-amine

MS (ESI) 307.20 (M+H)$^+$.

Example 163

(3-tert-Butyl-1H-pyrazol-4-ylmethyl)-(4-pyridin-2-yl-phenyl)-amine; compound with trifluoroacetic acid

MS (ESI) 307.20 (M+H)$^+$.

Example 164

(3-tert-Butyl-1H-pyrazol-4-ylmethyl)-(4-thiophen-3-yl-phenyl)-amine

MS (ESI) 312.10 (M+H)$^+$.

Example 165

3-Fluoro-4-{[3-(4-trifluoromethyl-phenyl)-1H-pyrazol-4-ylmethyl]-amino}-benzonitrile

MS (ESI) 597.4, 402.1, 361.1 (M+H), 288.3, 101.1.

Example 166

2-Chloro-4-{[3-(4-trifluoromethyl-phenyl)-1H-pyrazol-4-ylmethyl]-amino}-benzonitrile

MS (ESI) 418.1, 377.0 (M+H)$^+$, 101.0.

Example 167

(3-Methoxy-phenyl)-[3-(4-trifluoromethyl-phenyl)-1H-pyrazol-4-ylmethyl]-amine

MS (ESI) 348.10 (M+H)$^+$.

Example 168

(4-Ethanesulfonyl-phenyl)-[3-(4-trifluoromethyl-phenyl)-1H-pyrazol-4-ylmethyl]-amine; compound with trifluoroacetic acid

MS (ESI) 634.1, 410.1 (M+H)$^+$.

Example 169

N,N-Dimethyl-4-{[3-(4-trifluoromethyl-phenyl)-1H-pyrazol-4-ylmethyl]-amino}-benzenesulfonamide

MS (ESI) 425.10 (M+H)$^+$.

Example 170

(3-Benzyl-phenyl)-[3-(4-trifluoromethyl-phenyl)-1H-pyrazol-4-ylmethyl]-amine

MS (ESI) 408.05 (M+H)$^+$.

Example 171

(3-tert-Butyl-1H-pyrazol-4-ylmethyl)-(4-thiophen-2-yl-phenyl)-amine

MS (ESI) 312.10 (M+H)$^+$.

Example 172

(3-tert-Butyl-1H-pyrazol-4-ylmethyl)-[4-(4-methyl-piperazin-1-yl)-phenyl]-amine $^1$H-NMR (400 MHz, DMSO-d$_6$) δ ppm 12.19 (s br, NH), 7.35 (s br, 1H), 6.73 (d, 2H), 6.55 (d, 2H), 5.11 (m, 1H), 4.06 (d, 2H), 2.90 (t, 4H), 2.42 (t, 4H), 2.20 (s, 3H), 1.30 (s, 9H).

Example 173

(3-tert-Butyl-1H-pyrazol-4-ylmethyl)-[4-(4,5-dimethyl-oxazol-2-yl)-phenyl]-amine $^1$H-NMR (400 MHz, CDCl$_3$) δ ppm 7.93 (d, 2H), 7.64 (s, 1H), 6.67 (d, 2H), 2.35 (s, 3H), 2.24 (s, 3H), 1.46 (s, 9H); MS (ESI) 325.20 (M+H)$^+$.

Example 174 o-Tolyl-[3-(4-trifluoromethyl-phenyl)-1H-pyrazol-4-ylmethyl]-amine; compound with trifluoroacetic acid

MS (ESI) 332.0 (M+H)$^+$.

Example 175 m-Tolyl-[3-(4-trifluoromethyl-phenyl)-1H-pyrazol-4-ylmethyl]-amine; compound with trifluoroacetic acid

MS (ESI) 332.1 (M+H)$^+$.

Example 176 p-Tolyl-[3-(4-trifluoromethyl-phenyl)-1H-pyrazol-4-ylmethyl]-amine; compound with trifluoroacetic acid

MS (ESI) 332.2 (M+H)$^+$.

Example 177

(2-Methoxy-phenyl)-[3-(4-trifluoromethyl-phenyl)-1H-pyrazol-4-ylmethyl]-amine; compound with trifluoroacetic acid

MS (ESI) 348.0 (M+H)$^+$.

Example 178

(3-Methoxy-phenyl)-[3-(4-trifluoromethyl-phenyl)-1H-pyrazol-4-ylmethyl]-amine; compound with trifluoroacetic acid

MS (ESI) 348.0 (M+H)$^+$.

Example 179

(4-Methoxy-phenyl)-[3-(4-trifluoromethyl-phenyl)-1H-pyrazol-4-ylmethyl]-amine; compound with trifluoroacetic acid

MS (ESI) 348.1 (M+H)$^+$.

Example 180

(2-Fluoro-phenyl)-[3-(4-trifluoromethyl-phenyl)-1H-pyrazol-4-ylmethyl]-amine; compound with trifluoroacetic acid MS (ESI) 358.2 (M+Na)$^+$.

Example 181

(3-Fluoro-phenyl)-[3-(4-trifluoromethyl-phenyl)-1H-pyrazol-4-ylmethyl]-amine; compound with trifluoroacetic acid

Example 182

(4-Fluoro-phenyl)-[3-(4-trifluoromethyl-phenyl)-1H-pyrazol-4-ylmethyl]-amine; compound with trifluoroacetic acid

MS (ESI) 336.0 (M+H)$^+$.

Example 183

(2-Chloro-phenyl)-[3-(4-trifluoromethyl-phenyl)-1H-pyrazol-4-ylmethyl]-amine; compound with trifluoroacetic acid

Example 184

(3-Chloro-phenyl)-[3-(4-trifluoromethyl-phenyl)-1H-pyrazol-4-ylmethyl]-amine; compound with trifluoroacetic acid

Example 185

(4-Chloro-phenyl)-[3-(4-trifluoromethyl-phenyl)-1H-pyrazol-4-ylmethyl]-amine; compound with trifluoroacetic acid

Example 186

(4-Trifluoromethoxy-phenyl)-[3-(4-trifluoromethyl-phenyl)-1H-pyrazol-4-ylmethyl]-amine; compound with trifluoroacetic acid

Example 187

(3-Phenoxy-phenyl)-[3-(4-trifluoromethyl-phenyl)-1H-pyrazol-4-ylmethyl]-amine; compound with trifluoroacetic acid

MS (ESI) 410.1 (M+H)$^+$.

Example 188

(3-Dimethylaminomethyl-phenyl)-[5-(4-trifluoromethyl-phenyl)-1H-pyrazol-4-ylmethyl]-amine

MS (ESI) 361.1 (M+H)$^+$.

Example 189

(3-Trifluoromethyl-phenyl)-[3-(4-trifluoromethyl-phenyl)-1H-pyrazol-4-ylmethyl]-amine; compound with trifluoroacetic acid

Example 190

(4-Trifluoromethyl-phenyl)-[3-(4-trifluoromethyl-phenyl)-1H-pyrazol-4-ylmethyl]-amine; compound with trifluoroacetic acid

Example 191

(3-Trifluoromethoxy-phenyl)-[3-(4-trifluoromethyl-phenyl)-1H-pyrazol-4-ylmethyl]-amine; compound with trifluoroacetic acid

MS (ESI) 402.0 (M+H)$^+$.

Example 192

(4-Phenoxy-phenyl)-[3-(4-trifluoromethyl-phenyl)-1H-pyrazol-4-ylmethyl]-amine; compound with trifluoroacetic acid

MS (ESI) 410.1 (M+H)$^+$.

Example 193

(2,3-Dimethyl-phenyl)-[3-(4-trifluoromethyl-phenyl)-1H-pyrazol-4-ylmethyl]-amine; compound with trifluoroacetic acid

Example 194

(2,4-Dimethyl-phenyl)-[3-(4-trifluoromethyl-phenyl)-1H-pyrazol-4-ylmethyl]-amine; compound with trifluoroacetic acid

MS (ESI) 346.0 (M+H)$^+$.

Example 195

(2,5-Dimethyl-phenyl)-[3-(4-trifluoromethyl-phenyl)-1H-pyrazol-4-ylmethyl]-amine; compound with trifluoroacetic acid

MS (ESI) 346.0 (M+H)$^+$.

Example 196

(3,4-Dimethyl-phenyl)-[3-(4-trifluoromethyl-phenyl)-1H-pyrazol-4-ylmethyl]-amine; compound with trifluoroacetic acid

MS (ESI) 346.0 (M+H)$^+$.

Example 197

(3,5-Dimethyl-phenyl)-[3-(4-trifluoromethyl-phenyl)-1H-pyrazol-4-ylmethyl]-amine; compound with trifluoroacetic acid

MS (ESI) 346.1 (M+H)$^+$.

Example 198

(2,3-Dimethoxy-phenyl)-[3-(4-trifluoromethyl-phenyl)-1H-pyrazol-4-ylmethyl]-amine; compound with trifluoroacetic acid

MS (ESI) 378.1 (M+H)$^+$.

Example 199

(2,4-Dimethoxy-phenyl)-[3-(4-trifluoromethyl-phenyl)-1H-pyrazol-4-ylmethyl]-amine; compound with trifluoroacetic acid

MS (ESI) 378.1 (M+H)$^+$.

Example 200

(2,5-Dimethoxy-phenyl)-[3-(4-trifluoromethyl-phenyl)-1H-pyrazol-4-ylmethyl]-amine; compound with trifluoroacetic acid

MS (ESI) 378.1 (M+H)$^+$.

Example 201

(3,4-Dimethoxy-phenyl)-[3-(4-trifluoromethyl-phenyl)-1H-pyrazol-4-ylmethyl]-amine; compound with trifluoroacetic acid

MS (ESI) 378.1 (M+H)$^+$.

Example 202

(3,5-Dimethoxy-phenyl)-[3-(4-trifluoromethyl-phenyl)-1H-pyrazol-4-ylmethyl]-amine; compound with trifluoroacetic acid

MS (ESI) 378.1 (M+H)$^+$.

Example 203

[3-(4-Trifluoromethyl-phenyl)-1H-pyrazol-4-ylmethyl]-(3,4,5-trimethoxy-phenyl)-amine; compound with trifluoroacetic acid

MS (ESI) 408.1 (M+H)$^+$.

Example 204

(2,3-Dichloro-phenyl)-[3-(4-trifluoromethyl-phenyl)-1H-pyrazol-4-ylmethyl]-amine; compound with trifluoroacetic acid

Example 205

(2,4-Dichloro-phenyl)-[3-(4-trifluoromethyl-phenyl)-1H-pyrazol-4-ylmethyl]-amine; compound with trifluoroacetic acid

Example 206

(2,5-Dichloro-phenyl)-[3-(4-trifluoromethyl-phenyl)-1H-pyrazol-4-ylmethyl]-amine; compound with trifluoroacetic acid

Example 207

(3,4-Dichloro-phenyl)-[3-(4-trifluoromethyl-phenyl)-1H-pyrazol-4-ylmethyl]-amine; compound with trifluoroacetic acid

Example 208

(3,5-Dichloro-phenyl)-[3-(4-trifluoromethyl-phenyl)-1H-pyrazol-4-ylmethyl]-amine; compound with trifluoroacetic acid

Example 209

1-(4-{[3-(4-Methoxy-phenyl)-1H-pyrazol-4-ylmethyl]-amino}-phenyl)-butan-1-one; compound with trifluoroacetic acid

MS (ESI) 350.1 (M+H)$^+$

Example 210

1-{4-[(3-Phenyl-1H-pyrazol-4-ylmethyl)-amino]-phenyl}-butan-1-one; compound with trifluoroacetic acid

MS (ESI) 320.1 (M+H)$^+$

Example 211

1-{4-[(1,3,5-Trimethyl-1H-pyrazol-4-ylmethyl)-amino]-phenyl}-butan-1-one; compound with trifluoroacetic acid, MS (ESI) 286.3 (M+H)+

Example 212

1-{4-[(3-p-Tolyl-1H-pyrazol-4-ylmethyl)-amino]-phenyl}-butan-1-one; compound with trifluoroacetic acid

MS (ESI) 334.1 (M+H)$^+$

Example 213

1-(4-{[3-(3,5-Difluorophenyl)-1H-pyrazol-4-ylmethyl]-amino}-phenyl)-butan-1-one; compound with trifluoroacetic acid

MS (ESI) 356.1 (M+H)+

Example 214

1-{4-[(1-Phenyl-3-pyridin-4-yl-1H-pyrazol-4-ylmethyl)-amino]-phenyl}-butan-1-one; compound with trifluoroacetic acid

MS (ESI) 397.2 (M+H)+

Example 215

1-{4-[(1H-Indazol-3-ylmethyl)-amino]-phenyl}-butan-1-one; compound with trifluoroacetic acid

MS (ESI) 294.3 (M+H)+

Example 216

1-{4-[(2-Methyl-2H-pyrazol-3-ylmethyl)-amino]-phenyl}-butan-1-one; compound with trifluoroacetic acid

MS (ESI) 258.1 (M+H)+

Example 217

1-(4-{[3-(4-Chloro-phenyl)-1H-pyrazol-4-ylmethyl]-amino}-phenyl)-butan-1-one; compound with trifluoroacetic acid

MS (ESI) 354.0 (M+H)+

Example 218

1-(4-{[3-(3,4-Dimethoxy-phenyl)-1H-pyrazol-4-ylmethyl]-amino}-phenyl)-butan-1-one; compound with trifluoroacetic acid

MS (ESI) 380.1 (M+H)+

Example 219

1-{4-[(1-Methyl-1H-indazol-3-ylmethyl)-amino]-phenyl}-butan-1-one; compound with trifluoroacetic acid

MS (ESI) 308.4 (M+H)+

Example 220

1-{4-[(1-Benzyl-1H-pyrazol-4-ylmethyl)-amino]-phenyl}-butan-1-one; compound with trifluoroacetic acid

MS (ESI) 334.1 (M+H)+

Example 221

1-(4-{[3-(4-Fluorophenyl)-1-phenyl-1H-pyrazol-4-ylmethyl]-amino}-phenyl)-butan-1-one; compound with trifluoroacetic acid

MS (ESI) 414.1 (M+H)+

Example 222

1-{4-[(1-Phenyl-3-pyridin-3-yl-1H-pyrazol-4-ylmethyl)-amino]-phenyl}-butan-1-one; compound with trifluoroacetic MS (ESI) 397.1 (M+H)+

Example 223

1-{4-[(5-Methoxy-1H-indazol-3-ylmethyl)-amino]-phenyl}-butan-1-one; compound with trifluoroacetic acid

MS (ESI) 324.1 (M+H)+

Example 224

1-{4-[(3,5-Dimethyl-1H-pyrazol-4-ylmethyl)-amino]-phenyl}-butan-1-one; compound with trifluoroacetic acid

MS (ESI) 272.1 (M+H)+

Example 225

1-(4-{[4-(4-Methoxy-phenyl)-thiazol-2-ylmethyl]-amino}-phenyl)-butan-1-one; compound with trifluoroacetic acid

MS (ESI) 367.0 (M+H)+

Example 226

1-{4-[(1-Methyl-1H-benzoimidazol-2-ylmethyl)-amino]-phenyl}-butan-1-one; compound with trifluoroacetic acid

MS (ESI) 308.1 (M+H)+

Example 227

1-{4-[(3,5-Dimethyl-isoxazol-4-ylmethyl)-amino]-phenyl}-butan-1-one; compound with trifluoroacetic acid

MS (ESI) 273.3 (M+H)+

Example 228

1-{4-[(1-Methyl-1H-imidazol-4-ylmethyl)-amino]-phenyl}-butan-1-one; compound with trifluoroacetic acid

MS (ESI) 258.1 (M+H)+

Example 229

1-{4-[(5-Thiophen-2-yl-isoxazol-3-ylmethyl)-amino]-phenyl}-butan-1-one; compound with trifluoroacetic acid

MS (ESI) 327.0 (M+H)+

Example 230

1-{4-[(2,3-Dimethyl-3H-imidazol-4-ylmethyl)-amino]-phenyl}-butan-1-one; compound with trifluoroacetic acid

MS (ESI) 272.4 (M+H)+

Example 231

1-{4-[(5-Methyl-2-phenyl-oxazol-4-ylmethyl)-amino]-phenyl}-butan-1-one; compound with trifluoroacetic acid

MS (ESI) 335.1 (M+H)+

Example 232

1-{4-[(5-Furan-2-yl-isoxazol-3-ylmethyl)-amino]-phenyl}-butan-1-one; compound with trifluoroacetic acid

MS (ESI) 311.0 (M+H)+

Example 233

1-{4-[(2-Methyl-4-phenyl-thiazol-5-ylmethyl)-amino]-phenyl}-butan-1-one; compound with trifluoroacetic acid

MS (ESI) 351.1 (M+H)+

Example 232

1-(4-{[2-(4-Trifluoromethyl-phenyl)-thiazol-4-ylmethyl]-amino}-phenyl)-butan-1-one; compound with trifluoroacetic acid

MS (ESI) 405.1 (M+H)+

Example 235

1-(4-{[2-(3-Chloro-phenyl)-thiazol-4-ylmethyl]-amino}-phenyl)-butan-1-one; compound with trifluoroacetic acid

MS (ESI) 371.0 (M+H)+

Example 236

1-{4-[(5-Methyl-3H-imidazol-4-ylmethyl)-amino]-phenyl}-butan-1-one; compound with trifluoroacetic acid

MS (ESI) 258.1 (M+H)+

Example 237

1-{4-[(4-Methyl-thiazol-5-ylmethyl)-amino]-phenyl}-butan-1-one; compound with trifluoroacetic acid

MS (ESI) 275.1 (M+H)+

Example 238

1-(4-{[5-(4-Fluorophenyl)-isoxazol-3-ylmethyl]-amino}-phenyl)-butan-1-one; compound with trifluoroacetic acid

MS (ESI) 339.0 (M+H)+

Example 239

1-{4-[(5-Methyl-isoxazol-3-ylmethyl)-amino]-phenyl}-butan-1-one; compound with trifluoroacetic acid

MS (ESI) 259.1 (M+H)+

Example 240

1-{4-[(2,4-Dimethyl-thiazol-5-ylmethyl)-amino]-phenyl}-butan-1-one; compound with trifluoroacetic acid

MS (ESI) 289.3 (M+H)+

Example 241

1-{4-[(4-Methyl-thiazol-2-ylmethyl)-amino]-phenyl}-butan-1-one; compound with trifluoroacetic acid

MS (ESI) 275.3 (M+H)+

Example 242

1-(4-{[2-(2-Methoxy-phenyl)-thiazol-5-ylmethyl]-amino}-phenyl)-butan-1-one; compound with trifluoroacetic acid

MS (ESI) 367.1 (M+H)+

Example 243

1-(4-{[2-(3-Methoxy-phenyl)-thiazol-5-ylmethyl]-amino}-phenyl)-butan-1-one; compound with trifluoroacetic acid

MS (ESI) 367.1 (M+H)+

Example 244

1-(4-{[4-(4-Fluorophenyl)-thiazol-2-ylmethyl]-amino}-phenyl)-butan-1-one; compound with trifluoroacetic acid

MS (ESI) 355.0 (M+H)+

Example 245

1-{4-[(5-Methyl-2-thiophen-2-yl-oxazol-4-ylmethyl)-amino]-phenyl}-butan-1-one; compound with trifluoroacetic acid

MS (ESI) 341.0 (M+H)+

Example 246

1-{4-[(2-Phenyl-thiazol-5-ylmethyl)-amino]-phenyl}-butan-1-one; compound with trifluoroacetic acid

MS (ESI) 337.0 (M+H)+

Example 247

1-{4-[(3-Methyl-3H-imidazol-4-ylmethyl)-amino]-phenyl}-butan-1-one; compound with trifluoroacetic acid

MS (ESI) 258.1 (M+H)+

Example 248

1-{4-[(Thiazol-4-ylmethyl)-amino]-phenyl}-butan-1-one; compound with trifluoroacetic acid

MS (ESI) 261.0 (M+H)+

Example 249

1-{4-[(Thiazol-5-ylmethyl)-amino]-phenyl}-butan-1-one; compound with trifluoroacetic acid

MS (ESI) 261.0 (M+H)+

Example 250

1-{4-[(2,4-Dichloro-thiazol-5-ylmethyl)-amino]-phenyl}-butan-1-one; compound with trifluoroacetic acid

MS (ESI) 329.3 (M)+

Example 251

1-{4-[(4,5-Dimethyl-1H-imidazol-2-ylmethyl)-amino]-phenyl}-butan-1-one; compound with trifluoroacetic acid

MS (ESI) 272.1 (M+H)+

Example 252

1-{4-[(Oxazol-5-ylmethyl)-amino]-phenyl}-butan-1-one; compound with trifluoroacetic acid

MS (ESI) 245.0 (M+H)+

Example 253

1-{4-[(Oxazol-2-ylmethyl)-amino]-phenyl}-butan-1-one; compound with trifluoroacetic acid

MS (ESI) 245.0 (M+H)+

Example 254

1-(4-{[3-(3-Fluorophenyl)-isoxazol-5-ylmethyl]-amino}-phenyl)-butan-1-one; compound with trifluoroacetic acid

MS (ESI) 339.0 (M+H)+

Example 255

1-(4-{[3-(2-Fluorophenyl)-isoxazol-5-ylmethyl]-amino}-phenyl)-butan-1-one; compound with trifluoroacetic acid

MS (ESI) 339.0 (M+H)+

Example 256

1-(4-{[2-(4-Chloro-phenyl)-thiazol-4-ylmethyl]-amino}-phenyl)-butan-1-one; compound with trifluoroacetic acid

MS (ESI) 371.0 (M+H)+

Example 257

1-{4-[(2-Chloro-thiazol-5-ylmethyl)-amino]-phenyl}-butan-1-one; compound with trifluoroacetic acid

MS (ESI) 294.9 (M)+

Example 258

1-{4-[(5-Chloro-2-phenyl-3H-imidazol-4-ylmethyl)-amino]-phenyl}-butan-1-one; compound with trifluoroacetic acid

MS (ESI) 354.1 (M+H)+

Example 259

1-(4-{[2-(Toluene-4-sulfonyl)-thiazol-5-ylmethyl]-amino}-phenyl)-butan-1-one; compound with trifluoroacetic acid

MS (ESI) 415.1 (M+H)+

Example 260

1-(4-{[2-(4-Methoxy-phenoxy)-thiazol-5-ylmethyl]-amino}-phenyl)-butan-1-one; compound with trifluoroacetic acid

MS (ESI) 383.1 (M+H)+

Example 261

1-{4-[(1-Propyl-1H-imidazol-2-ylmethyl)-amino]-phenyl}-butan-1-one; compound with trifluoroacetic acid

MS (ESI) 286.1 (M+H)+

Example 262

1-{4-[(Imidazo[1,2-a]pyridin-2-ylmethyl)-amino]-phenyl}-butan-1-one; compound with trifluoroacetic acid

MS (ESI) 294.1 (M+H)+

Example 263

1-{4-[(2-Methyl-thiazol-4-ylmethyl)-amino]-phenyl}-butan-1-one; compound with trifluoroacetic acid

MS (ESI) 275.0 (M+H)+

Example 264

1-{4-[(2-Methyl-1H-imidazol-4-ylmethyl)-amino]-phenyl}-butan-1-one; compound with trifluoroacetic acid

MS (ESI) 258.0 (M+H)+

Example 265

1-(4-{[2-(4-Methoxy-phenyl)-thiazol-5-ylmethyl]-amino}-phenyl)-butan-1-one; compound with trifluoroacetic acid

MS (ESI) 367.1 (M+H)+

Example 266

1-(4-{[2-(3-Fluorophenyl)-thiazol-5-ylmethyl]-amino}-phenyl)-butan-1-one; compound with trifluoroacetic acid

MS (ESI) 355.1 (M+H)+

Example 267

1-(4-{[2-(4-Trifluoromethyl-phenyl)-thiazol-5-ylmethyl]-amino}-phenyl)-butan-1-one; compound with trifluoroacetic acid

MS (ESI) 405.1 (M+H)+

Example 268

1-{4-[(2-Isopropyl-thiazol-4-ylmethyl)-amino]-phenyl}-butan-1-one; compound with trifluoroacetic acid

MS (ESI) 303.1 (M+H)+

Example 269

2-{4-[(3-tert-Butyl-1H-pyrazol-4-ylmethyl)-amino]-phenoxy}-benzonitrile; compound with trifluoroacetic acid

MS (ESI) 347.1 (M+H)+

Example 270

(4-Butoxy-phenyl)-(3-tert-butyl-1H-pyrazol-4-ylmethyl)-amine; compound with trifluoroacetic acid

MS (ESI) 302.1 (M+H)+

Example 271

(3-tert-Butyl-1H-pyrazol-4-ylmethyl)-[3-(1,1,2,2-tetrafluoro-ethoxy)-phenyl]-amine; compound with trifluoroacetic acid

MS (ESI) 346.1 (M+H)+

Example 272

(3-tert-Butyl-1H-pyrazol-4-ylmethyl)-(4-difluoromethoxy-phenyl)-amine; compound with trifluoroacetic acid

MS (ESI) 296.1 (M+H)+

Example 273

(3-tert-Butyl-1H-pyrazol-4-ylmethyl)-(4-propoxy-phenyl)-amine; compound with trifluoroacetic acid

MS (ESI) 288.1 (M+H)+

Example 274

(3-tert-Butyl-1H-pyrazol-4-ylmethyl)-(3-difluoromethoxy-phenyl)-amine; compound with trifluoroacetic acid

MS (ESI) 296.1 (M+H)+

Example 275

(3-tert-Butyl-1H-pyrazol-4-ylmethyl)-(4-ethoxy-phenyl)-amine; compound with trifluoroacetic acid

MS (ESI) 274.1 (M+H)+

Example 276

(3-tert-Butyl-1H-pyrazol-4-ylmethyl)-[4-(2-chloro-phenoxy)-phenyl]-amine; compound with trifluoroacetic acid

MS (ESI) 356.1 (M+H)+

Example 277

(3-tert-Butyl-1H-pyrazol-4-ylmethyl)-(4-o-tolyloxy-phenyl)-amine; compound with trifluoroacetic acid

MS (ESI) 336.1 (M+H)+

Example 278

(3-tert-Butyl-1H-pyrazol-4-ylmethyl)-[4-(3,4-dichloro-phenoxy)-phenyl]-amine; compound with trifluoroacetic acid

MS (ESI) 390.1 (M)+

Example 279

(4-Benzyloxy-phenyl)-(3-tert-butyl-1H-pyrazol-4-ylmethyl)-amine; compound with trifluoroacetic acid

MS (ESI) 336.1 (M+H)+

Example 280

(3-tert-Butyl-1H-pyrazol-4-ylmethyl)-[4-(3-chloro-5-trifluoromethyl-pyridin-2-yloxy)-phenyl]-amine; compound with trifluoroacetic acid

MS (ESI) 425.1 (M+H)+

Example 281

(3-tert-Butyl-1H-pyrazol-4-ylmethyl)-[4-(chloro-difluoro-methoxy)-phenyl]-amine; compound with trifluoroacetic acid

MS (ESI) 330.1 (M+H)+

Example 282

[4-(3,5-Bis-trifluoromethyl-phenoxy)-phenyl]-(3-tert-butyl-1H-pyrazol-4-ylmethyl)-amine; compound with trifluoroacetic acid

MS (ESI) 458.2 (M+H)+

Example 283

(3-tert-Butyl-1H-pyrazol-4-ylmethyl)-[4-(2-fluoro-phenoxy)-phenyl]-amine; compound with trifluoroacetic acid

MS (ESI) 340.1 (M+H)+

Example 284

(3-tert-Butyl-1H-pyrazol-4-ylmethyl)-[4-(1-methyl-piperidin-4-yloxy)-phenyl]-amine; compound with trifluoroacetic acid

MS (ESI) 343.6 (M+H)+

Example 285

(3-tert-Butyl-1H-pyrazol-4-ylmethyl)-[4-(pyridin-2-ylmethoxy)-phenyl]-amine; compound with trifluoroacetic acid

MS (ESI) 337.1 (M+H)+

Example 286

(3-tert-Butyl-1H-pyrazol-4-ylmethyl)-(4-isobutoxy-phenyl)-amine; compound with trifluoroacetic acid

MS (ESI) 302.1 (M+H)+

Example 287

(3-tert-Butyl-1H-pyrazol-4-ylmethyl)-[4-(2,3-dimethyl-phenoxy)-phenyl]-amine; compound with trifluoroacetic acid

MS (ESI) 350.2 (M+H)+

Example 288

(3-tert-Butyl-1H-pyrazol-4-ylmethyl)-[4-(pyrimidin-2-yloxy)-phenyl]-amine; compound with trifluoroacetic acid

MS (ESI) 324.1 (M+H)+

Example 289

(3-tert-Butyl-1H-pyrazol-4-ylmethyl)-[4-(1,1,2,2-tetrafluoro-ethoxy)-phenyl]-amine; compound with trifluoroacetic acid

MS (ESI) 346.1 (M+H)+

Example 290

(3-tert-Butyl-1H-pyrazol-4-ylmethyl)-[4-(2-chloro-benzyloxy)-phenyl]-amine; compound with trifluoroacetic acid

MS (ESI) 370.1 (M+H)+

Example 291

(3-tert-Butyl-1H-pyrazol-4-ylmethyl)-[4-(pyridin-3-yloxy)-phenyl]-amine; compound with trifluoroacetic acid

MS (ESI) 323.1 (M+H)+

Example 292

(3-tert-Butyl-1H-pyrazol-4-ylmethyl)-[4-(4-fluoro-benzyloxy)-phenyl]-amine; compound with trifluoroacetic acid

MS (ESI) 354.1 (M+H)+

Example 293

(3-tert-Butyl-1H-pyrazol-4-ylmethyl)-[4-(5-trifluoromethyl-pyridin-2-yloxy)-phenyl]-amine; compound with trifluoroacetic acid

MS (ESI) 391.1 (M+H)+

Example 294

(3-tert-Butyl-1H-pyrazol-4-ylmethyl)-[4-(3-trifluoromethyl-phenoxy)-phenyl]-amine; compound with trifluoroacetic acid

MS (ESI) 390.2 (M+H)+

Example 295

(3-tert-Butyl-1H-pyrazol-4-ylmethyl)-(4-m-tolyloxy-phenyl)-amine; compound with trifluoroacetic acid

MS (ESI) 336.1 (M+H)+

Example 296

(3-tert-Butyl-1H-pyrazol-4-ylmethyl)-[4-(4-fluoro-phenoxy)-phenyl]-amine; compound with trifluoroacetic acid

MS (ESI) 340.1 (M+H)+

Example 297

(3-tert-Butyl-1H-pyrazol-4-ylmethyl)-[4-(4-chloro-phenoxy)-phenyl]-amine; compound with trifluoroacetic acid

MS (ESI) 356.1 (M+H)+

Example 298

(3-tert-Butyl-1H-pyrazol-4-ylmethyl)-[4-(3-methyl-butoxy)-phenyl]-amine; compound with trifluoroacetic acid

MS (ESI) 316.2 (M+H)+

Example 299

(3-tert-Butyl-1H-pyrazol-4-ylmethyl)-[4-(2,4-dichloro-phenoxy)-phenyl]-amine; compound with trifluoroacetic acid

MS (ESI) 390.1 (M)+

Example 300

(3-tert-Butyl-1H-pyrazol-4-ylmethyl)-(4-p-tolyloxy-phenyl)-amine; compound with trifluoroacetic acid

MS (ESI) 336.1 (M+H)+

Example 301

(3-tert-Butyl-1H-pyrazol-4-ylmethyl)-(4-isopropoxy-phenyl)-amine; compound with trifluoroacetic acid

MS (ESI) 288.3 (M+H)+

Example 302

1-{4-[(6-Dimethylamino-pyridin-3-ylmethyl)-amino]-phenyl}-butan-1-one; compound with trifluoroacetic acid

MS (ESI) 298.1 (M+H)+

Example 303

1-{4-[(6-Morpholin-4-yl-pyridin-3-ylmethyl)-amino]-phenyl}-butan-1-one; compound with trifluoroacetic acid

MS (ESI) 340.1 (M+H)+

Example 304

1-{4-[(6-Methoxy-pyridin-3-ylmethyl)-amino]-phenyl}-butan-1-one; compound with trifluoroacetic acid

MS (ESI) 285.4 (M+H)+

Example 305

1-{4-[(6-Chloro-pyridin-3-ylmethyl)-amino]-phenyl}-butan-1-one; compound with trifluoroacetic acid

MS (ESI) 289.1 (M+H)+

Example 306

1-{4-[(2-Methoxy-pyridin-3-ylmethyl)-amino]-phenyl}-butan-1-one; compound with trifluoroacetic acid

MS (ESI) 285.1 (M+H)+

Example 307

1-{4-[(2,6-Dichloro-pyridin-3-ylmethyl)-amino]-phenyl}-butan-1-one; compound with trifluoroacetic acid

MS (ESI) 322.9 (M)+

Example 308

1-{4-[(2-Fluoro-pyridin-3-ylmethyl)-amino]-phenyl}-butan-1-one; compound with trifluoroacetic acid

MS (ESI) 273.3 (M+H)+

Example 309

1-{4-[(5-Methoxy-pyridin-3-ylmethyl)-amino]-phenyl}-butan-1-one; compound with trifluoroacetic acid

MS (ESI) 285.1 (M+H)+

Example 310

1-{4-[(2-Isopropoxy-pyridin-3-ylmethyl)-amino]-phenyl}-butan-1-one; compound with trifluoroacetic acid

MS (ESI) 313.1 (M+H)+

Example 311

1-{4-[(2-Propoxy-pyridin-3-ylmethyl)-amino]-phenyl}-butan-1-one; compound with trifluoroacetic acid

MS (ESI) 313.2 (M+H)+

Example 312

1-{4-[(3,4,5,6-Tetrahydro-2H-[1,2']bipyridinyl-5'-ylmethyl)-amino]-phenyl}-butan-1-one; compound with trifluoroacetic acid

MS (ESI) 338.2 (M+H)+

Example 313

1-{4-[(6-Cyclopentyloxy-pyridin-3-ylmethyl)-amino]-phenyl}-butan-1-one; compound with trifluoroacetic acid

MS (ESI) 339.1 (M+H)+

Example 314

1-{4-[(2-Morpholin-4-yl-pyridin-3-ylmethyl)-amino]-phenyl}-butan-1-one; compound with trifluoroacetic acid

MS (ESI) 340.1 (M+H)+

Example 315

1-{4-[(5-Fluoro-2-methoxy-pyridin-3-ylmethyl)-amino]-phenyl}-butan-1-one; compound with trifluoroacetic acid

MS (ESI) 303.1 (M+H)+

Example 316

1-{4-[(5-Methyl-pyridin-3-ylmethyl)-amino]-phenyl}-butan-1-one; compound with trifluoroacetic acid

MS (ESI) 269.1 (M+H)+

Example 317

1-{4-[(2,6-Dimethoxy-pyridin-3-ylmethyl)-amino]-phenyl}-butan-1-one; compound with trifluoroacetic acid

MS (ESI) 315.1 (M+H)+

Example 318

1-{4-[(6-Fluoro-pyridin-3-ylmethyl)-amino]-phenyl}-butan-1-one; compound with trifluoroacetic acid

MS (ESI) 273.1 (M+H)+

Example 319

1-{4-[(5-Fluoro-pyridin-3-ylmethyl)-amino]-phenyl}-butan-1-one; compound with trifluoroacetic acid

MS (ESI) 273.1 (M+H)+

Example 320

1-{4-[(2,5-Dichloro-pyridin-3-ylmethyl)-amino]-phenyl}-butan-1-one; compound with trifluoroacetic acid

MS (ESI) 323.0 (M)+

Example 321

1-{4-[(2-Thiophen-3-yl-pyridin-3-ylmethyl)-amino]-phenyl}-butan-1-one; compound with trifluoroacetic acid

MS (ESI) 337.1 (M+H)+

Example 322

1-{4-[(2-Dimethylamino-pyridin-3-ylmethyl)-amino]-phenyl}-butan-1-one; compound with trifluoroacetic acid

MS (ESI) 298.1 (M+H)+

Example 323

1-{4-[(6-Trifluoromethyl-pyridin-3-ylmethyl)-amino]-phenyl}-butan-1-one; compound with trifluoroacetic acid

MS (ESI) 323.3 (M+H)+

Example 324

1-{4-[(6-Thiophen-2-yl-pyridin-3-ylmethyl)-amino]-phenyl}-butan-1-one; compound with trifluoroacetic acid

MS (ESI) 337.1 (M+H)+

Example 325

1-{4-[(6-Furan-2-yl-pyridin-3-ylmethyl)-amino]-phenyl}-butan-1-one; compound with trifluoroacetic acid

MS (ESI) 321.1 (M+H)+

Example 326

1-{4-[(4-Methyl-pyridin-3-ylmethyl)-amino]-phenyl}-butan-1-one; compound with trifluoroacetic acid

MS (ESI) 269.1 (M+H)+

Example 327

[4-(Furan-2-ylmethoxy)-phenyl]-[3-(4-trifluoromethyl-phenyl)-1H-pyrazol-4-ylmethyl]-amine; compound with trifluoroacetic acid

MS (ESI) 414.1 (M+H)+

Example 328

[4-(Thiophen-2-ylmethoxy)-phenyl]-[3-(4-trifluoromethyl-phenyl)-1H-pyrazol-4-ylmethyl]-amine; compound with trifluoroacetic acid

MS (ESI) 430.1 (M+H)+

Example 329

(3-Isopropoxy-phenyl)-[3-(4-trifluoromethyl-phenyl)-1H-pyrazol-4-ylmethyl]-amine; compound with trifluoroacetic acid

MS (ESI) 376.1 (M+H)+

Example 330

[3-(Pyridin-2-yloxy)-phenyl]-[3-(4-trifluoromethyl-phenyl)-1H-pyrazol-4-ylmethyl]-amine; compound with trifluoroacetic acid

MS (ESI) 411.1 (M+H)+

Example 331

(4-Cyclopentyloxy-phenyl)-[3-(4-trifluoromethyl-phenyl)-1H-pyrazol-4-ylmethyl]-amine; compound with trifluoroacetic acid

MS (ESI) 402.2 (M+H)+

Example 332

(2-Chloro-5-methyl-pyridin-3-yl)-[3-(4-trifluoromethyl-phenyl)-1H-pyrazol-4-ylmethyl]-amine; compound with trifluoroacetic acid

MS (ESI) 367.0 (M+H)+

Example 333

(6-Chloro-4-methyl-pyridin-3-yl)-[3-(4-trifluoromethyl-phenyl)-1H-pyrazol-4-ylmethyl]-amine; compound with trifluoroacetic acid

MS (ESI) 367.0 (M+H)+

Example 334

(4-Methyl-pyridin-2-yl)-[3-(4-trifluoromethyl-phenyl)-1H-pyrazol-4-ylmethyl]-amine; compound with trifluoroacetic acid

MS (ESI) 333.0 (M+H)+

Example 335

(6-Chloro-pyridin-3-yl)-[3-(4-trifluoromethyl-phenyl)-1H-pyrazol-4-ylmethyl]-amine; compound with trifluoroacetic acid

MS (ESI) 353.0 (M+H)+

Example 336

Phenyl-(3-{[3-(4-trifluoromethyl-phenyl)-1H-pyrazol-4-ylmethyl]-amino}-phenyl)-methanone; compound with trifluoroacetic acid

MS (ESI) 422.1 (M+H)+

Example 337

(5-Fluoro-pyridin-2-yl)-[3-(4-trifluoromethyl-phenyl)-1H-pyrazol-4-ylmethyl]-amine; compound with trifluoroacetic acid

MS (ESI) 337.0 (M+H)+

Example 338

(2-Methyl-pyridin-3-yl)-[3-(4-trifluoromethyl-phenyl)-1H-pyrazol-4-ylmethyl]-amine; compound with trifluoroacetic acid

MS (ESI) 333.0 (M+H)+

Example 339

(6-Methyl-pyridin-3-yl)-[3-(4-trifluoromethyl-phenyl)-1H-pyrazol-4-ylmethyl]-amine; compound with trifluoroacetic acid

MS (ESI) 333.0 (M+H)+

Example 340

(5-Chloro-pyridin-2-yl)-[3-(4-trifluoromethyl-phenyl)-1H-pyrazol-4-ylmethyl]-amine; compound with trifluoroacetic acid

MS (ESI) 353.0 (M+H)+

Example 341

(4,6-Dimethyl-pyridin-2-yl)-[3-(4-trifluoromethyl-phenyl)-1H-pyrazol-4-ylmethyl]-amine; compound with trifluoroacetic acid

MS (ESI) 347.0 (M+H)+

Example 342

(6-Methoxy-pyridin-3-yl)-[3-(4-trifluoromethyl-phenyl)-1H-pyrazol-4-ylmethyl]-amine; compound with trifluoroacetic acid

MS (ESI) 349.0 (M+H)+

Example 343

(5-Methyl-pyridin-2-yl)-[3-(4-trifluoromethyl-phenyl)-1H-pyrazol-4-ylmethyl]-amine; compound with trifluoroacetic acid

MS (ESI) 333.0 (M+H)+

Example 344

(6-Methyl-pyridin-2-yl)-[3-(4-trifluoromethyl-phenyl)-1H-pyrazol-4-ylmethyl]-amine; compound with trifluoroacetic acid

MS (ESI) 333.0 (M+H)+

Example 345

Pyridin-2-yl-[3-(4-trifluoromethyl-phenyl)-1H-pyrazol-4-ylmethyl]-amine; compound with trifluoroacetic acid

MS (ESI) 319.0 (M+H)+

Example 346

Pyridin-3-yl-[3-(4-trifluoromethyl-phenyl)-1H-pyrazol-4-ylmethyl]-amine; compound with trifluoroacetic acid

MS (ESI) 319.0 (M+H)+

Example 347

(3,5-Difluoro-pyridin-2-yl)-[3-(4-trifluoromethyl-phenyl)-1H-pyrazol-4-ylmethyl]-amine; compound with trifluoroacetic acid

MS (ESI) 354.9 (M+H)+

Example 348

(4-Methyl-pyridin-3-yl)-[3-(4-trifluoromethyl-phenyl)-1H-pyrazol-4-ylmethyl]-amine; compound with trifluoroacetic acid

MS (ESI) 333.0 (M+H)+

Example 349

(6-Chloro-pyridin-2-yl)-[3-(4-trifluoromethyl-phenyl)-1H-pyrazol-4-ylmethyl]-amine; compound with trifluoroacetic acid

MS (ESI) 352.9 (M)+

Example 350

(2,6-Dimethyl-pyridin-3-yl)-[3-(4-trifluoromethyl-phenyl)-1H-pyrazol-4-ylmethyl]-amine; compound with trifluoroacetic acid

MS (ESI) 347.0 (M+H)+

Example 351

(2,6-Dimethoxy-pyridin-3-yl)-[3-(4-trifluoromethyl-phenyl)-1H-pyrazol-4-ylmethyl]-amine; compound with trifluoroacetic acid

MS (ESI) 379.0 (M+H)+

Example 352

(4,6-Dimethyl-pyridin-3-yl)-[3-(4-trifluoromethyl-phenyl)-1H-pyrazol-4-ylmethyl]-amine; compound with trifluoroacetic acid

MS (ESI) 347.0 (M+H)+

Example 353

Pyridin-4-yl-(4-{[3-(4-trifluoromethyl-phenyl)-1H-pyrazol-4-ylmethyl]-amino}-phenyl)-methanone; compound with trifluoroacetic acid

MS (ESI) 423.1 (M+H)+

Example 354

(5-Chloro-pyridin-3-yl)-[3-(4-trifluoromethyl-phenyl)-1H-pyrazol-4-ylmethyl]-amine; compound with trifluoroacetic acid

MS (ESI) 352.9 (M)+

Example 355

1-(3-{[3-(4-Trifluoromethyl-phenyl)-1H-pyrazol-4-ylmethyl]-amino}-thiophen-2-yl)-ethanone; compound with trifluoroacetic acid

MS (ESI) 366.0 (M+H)+

Example 356

(6-Fluoro-pyridin-3-yl)-[3-(4-trifluoromethyl-phenyl)-1H-pyrazol-4-ylmethyl]-amine; compound with trifluoroacetic acid

MS (ESI) 337.0 (M+H)+

Example 357

(2-Methoxy-pyridin-3-yl)-[3-(4-trifluoromethyl-phenyl)-1H-pyrazol-4-ylmethyl]-amine; compound with trifluoroacetic acid

MS (ESI) 349.0 (M+H)+

Example 358

(2-Fluoro-pyridin-3-yl)-[3-(4-trifluoromethyl-phenyl)-1H-pyrazol-4-ylmethyl]-amine; compound with trifluoroacetic acid

MS (ESI) 337.0 (M+H)+

Example 359

(6-Fluoro-pyridin-2-yl)-[3-(4-trifluoromethyl-phenyl)-1H-pyrazol-4-ylmethyl]-amine; compound with trifluoroacetic acid

MS (ESI) 337.0 (M+H)+

Example 360

(5-Methoxy-pyridin-2-yl)-[3-(4-trifluoromethyl-phenyl)-1H-pyrazol-4-ylmethyl]-amine; compound with trifluoroacetic acid

MS (ESI) 349.0 (M+H)+

Example 361

(5-Fluoro-pyridin-3-yl)-[3-(4-trifluoromethyl-phenyl)-1H-pyrazol-4-ylmethyl]-amine; compound with trifluoroacetic acid

MS (ESI) 337.0 (M+H)+

Example 362

(3-Chloro-5-methyl-pyridin-2-yl)-[3-(4-trifluoromethyl-phenyl)-1H-pyrazol-4-ylmethyl]-amine; compound with trifluoroacetic acid

MS (ESI) 367.0 (M+H)+

Example 363

(5,6-Dimethyl-pyridin-2-yl)-[3-(4-trifluoromethyl-phenyl)-1H-pyrazol-4-ylmethyl]-amine; compound with trifluoroacetic acid

MS (ESI) 347.1 (M+H)+

Example 364

(2-Chloro-6-methyl-pyridin-3-yl)-[3-(4-chloro-phenyl)-1H-pyrazol-4-ylmethyl]-amine; compound with trifluoroacetic acid

MS (ESI) 333.0 (M)+

Example 365

[3-(4-Chloro-phenyl)-1H-pyrazol-4-ylmethyl]-(6-fluoro-5-methyl-pyridin-3-yl)-amine; compound with trifluoroacetic acid

MS (ESI) 317.0 (M)+

Example 366

[3-(4-Chloro-phenyl)-1H-pyrazol-4-ylmethyl]-(5-fluoro-4-methyl-pyridin-2-yl)-amine; compound with trifluoroacetic acid

MS (ESI) 316.9 (M)+

Example 367

[3-(4-Chloro-phenyl)-1H-pyrazol-4-ylmethyl]-(6-methoxy-4-methyl-pyridin-3-yl)-amine; compound with trifluoroacetic acid

MS (ESI) 329.0 (M)+

Example 368

[3-(4-Chloro-phenyl)-1H-pyrazol-4-ylmethyl]-(2-methoxy-4-methyl-pyridin-3-yl)-amine; compound with trifluoroacetic acid

MS (ESI) 329.0 (M)+

Example 369

N3-[3-(4-Chloro-phenyl)-1H-pyrazol-4-ylmethyl]-N2,N2-dimethyl-5-trifluoromethyl-pyridine-2,3-diamine; compound with trifluoroacetic acid

MS (ESI) 396.0 (M)+

Example 370

[3-(4-Chloro-phenyl)-1H-pyrazol-4-ylmethyl]-(4-methoxy-pyridin-3-yl)-amine; compound with trifluoroacetic acid

MS (ESI) 315.0 (M)+

Example 371

N5-[3-(4-Chloro-phenyl)-1H-pyrazol-4-ylmethyl]-N2,N2-dimethyl-pyridine-2,5-diamine; compound with trifluoroacetic acid

MS (ESI) 328.0 (M)+

Example 372

[3-(4-Chloro-phenyl)-1H-pyrazol-4-ylmethyl]-(4-methoxy-pyridin-2-yl)-amine; compound with trifluoroacetic acid

MS (ESI) 315.0 (M)+

Example 373

3-Methyl-4-{[3-(4-trifluoromethyl-phenyl)-1H-pyrazol-4-ylmethyl]-amino}-benzonitrile; compound with trifluoroacetic acid

MS (ESI) 357.10 (M+H)+

Example 374

1-(4-{[1-Methyl-3-(4-trifluoromethyl-phenyl)-1H-pyrazol-4-ylmethyl]-amino}-phenyl)-butan-1-one MS (ESI) 424.05 (M+Na)+

Example 375

1-(4-{[1-Methyl-5-(4-trifluoromethyl-phenyl)-1H-pyrazol-4-ylmethyl]-amino}-phenyl)-butan-1-one MS (ESI) 424.05 (M+Na)+

Example 376

[3-(2-Methyl-butoxy)-phenyl]-[3-(4-trifluoromethyl-phenyl)-1H-pyrazol-4-ylmethyl]-amine

MS (ESI) 404.20 (M+H)+

Example 377

1-(4-{[3-(4-Chloro-phenyl)-1H-pyrazol-4-ylmethyl]-amino}-phenyl)-butan-1-one; compound with methanesulfonic acid

MS (ESI) 354.15 (M+H)+

Example 378

(3-sec-Butoxy-phenyl)-[3-(4-trifluoromethyl-phenyl)-1H-pyrazol-4-ylmethyl]-amine

MS (ESI) 390.10 (M+H)+

Example 379

[3-(1-Methyl-butoxy)-phenyl]-[3-(4-trifluoromethyl-phenyl)-1H-pyrazol-4-ylmethyl]-amine

MS (ESI) 404.15 (M+H)+

Example 380

[3-(1-Ethyl-propoxy)-phenyl]-[3-(4-trifluoromethyl-phenyl)-1H-pyrazol-4-ylmethyl]-amine

MS (ESI) 404.15 (M+H)+

Example 381

(3-tert-Butyl-1H-pyrazol-4-ylmethyl)-(4-piperidin-4-yl-phenyl)-amine (hydrochloride)

MS (ESI) 313.20 (M+H)+

Example 382

(3-tert-Butyl-1H-pyrazol-4-ylmethyl)-(4-piperazin-1-yl-phenyl)-amine (hydrochloride)

Example 383

2,2,2-Trifluoro-ethanesulfonic acid (4-butyryl-phenyl)-pyridin-3-ylmethyl-amide

MS (ESI) 401.10 (M+H)+

Example 384

N,N-Dimethyl-N'-pyridin-3-ylmethyl-benzene-1,4-diamine

MS (ESI) 228.15 (M+H)+

Example 385

2,2,2-Trifluoro-ethanesulfonic acid (4-dimethylamino-phenyl)-pyridin-3-ylmethyl-amide

MS (ESI) 374.10 (M+H)+

Example 386

1-{3-[(Pyridin-3-ylmethyl)-amino]-phenyl}-butan-1-one

MS (ESI) 255.05 (M+H)+

Example 387

1-{4-[(6-Dimethylamino-pyridin-3-ylmethyl)-amino]-phenyl}-butan-1-one

MS (ESI) 298.15 (M+H)+

Example 388

N,N-Dimethyl-N'-pyridin-3-ylmethyl-benzene-1,3-diamine

MS (ESI) 228.10 (M+H)+

Example 389

2,2,2-Trifluoro-ethanesulfonic acid (3-dimethylamino-phenyl)-pyridin-3-ylmethyl-amide $^1$H-NMR (500 MHz, CDCl$_3$) δ ppm 8.51 (m, 1H), 8.38 (s, 1H), 7.69 (d, 1H), 7.23 (m sym, 1H), 7.18 (t, 1H), 6.62 (d, 1H), 6.55 (d, 1H), 6.41 (s, 1H), 4.87 (s, 2H), 3.83 (q, 2H)], 2.88 (s, 6H)

Example 390

2,2,2-Trifluoro-ethanesulfonic acid (3-butyryl-phenyl)-pyridin-3-ylmethyl-amide

MS (ESI) 401.15 (M+H)+

Example 391

2,2,2-Trifluoro-ethanesulfonic acid (4-butyryl-phenyl)-(6-dimethylamino-pyridin-3-ylmethyl)-amide

MS (ESI) 444.15 (M+H)+

Example 392

1-(3-{Methyl-[3-(4-trifluoromethyl-phenyl)-1H-pyrazol-4-ylmethyl]-amino}-phenyl)-butan-1-one

MS (ESI) 402.15 (M+H)+

Example 393

2,2,2-Trifluoro-ethanesulfonic acid (5-oxo-5,6,7,8-tetrahydro-naphthalen-2-yl)-[3-(4-trifluoromethyl-phenyl)-1H-pyrazol-4-ylmethyl]-amide (hydrochloride)

MS (ESI) 532.10 (M+H)+

Example 394

2,2,2-Trifluoro-ethanesulfonic acid [4-(2-methoxy-phenoxy)-phenyl]-[3-(4-trifluoromethyl-phenyl)-1H-pyrazol-4-ylmethyl]-amide (hydrochloride)

MS (ESI) 586.05 (M+H)+

Example 395

N,N-Dimethyl-4-{(2,2,2-trifluoro-ethanesulfonyl)-[3-(4-trifluoromethyl-phenyl)-1H-pyrazol-4-ylmethyl]-amino}-benzenesulfonamide (hydrochloride)

MS (ESI) 571.10 (M+H)+

Example 396

[3-(2-Trifluoromethyl-benzyl)-phenyl]-[3-(4-trifluoromethyl-phenyl)-1H-pyrazol-4-ylmethyl]-amine

MS (ESI) 476.15 (M+H)+

Example 397

[3-(2-Methoxy-phenoxy)-phenyl]-[3-(4-trifluoromethyl-phenyl)-1H-pyrazol-4-ylmethyl]-amine

MS (ESI) 440.15 (M+H)+

Example 398

1-(3-Chloro-4-{[3-(4-trifluoromethyl-phenyl)-1H-pyrazol-4-ylmethyl]-amino}-phenyl)-ethanone; compound with trifluoroacetic acid

MS (ESI) 394.25 (M+H)+

Example 399

(4-Methanesulfonyl-phenyl)-[3-(4-trifluoromethyl-phenyl)-1H-pyrazol-4-ylmethyl]-amine; compound with trifluoroacetic acid

MS (ESI) 396.25 (M+H)+

Example 400

2-Methyl-7-{[3-(4-trifluoromethyl-phenyl)-1H-pyrazol-4-ylmethyl]-amino}-chromen-4-one; compound with trifluoroacetic acid

MS (ESI) 400.25 (M+H)+

Example 401

1-(2-Fluoro-4-{[3-(4-trifluoromethyl-phenyl)-1H-pyrazol-4-ylmethyl]-amino}-phenyl)-ethanone; compound with trifluoroacetic acid

MS (ESI) 378.25 (M+H)+

Example 402

2,2,2-Trifluoro-ethanesulfonic acid (3-tert-butyl-1H-pyrazol-4-ylmethyl)-[4-(4,5-dimethyl-oxazol-2-yl)-phenyl]-amide (hydrochloride)

MS (ESI) 471.15 (M+H)+

Example 401

2,2,2-Trifluoro-ethanesulfonic acid (3-tert-butyl-1H-pyrazol-4-ylmethyl)-(4-oxazol-5-yl-phenyl)-amide (hydrochloride)

MS (ESI) 443.15 (M+H)+

Example 404

2,2,2-Trifluoro-ethanesulfonic acid (3-tert-butyl-1H-pyrazol-4-ylmethyl)-(4-pyridin-2-yl-phenyl)-amide (hydrochloride)

MS (ESI) 453.15 (M+H)+

Example 405

2,2,2-Trifluoro-ethanesulfonic acid (3-tert-butyl-1H-pyrazol-4-ylmethyl)-(4-pyridin-4-yl-phenyl)-amide (hydrochloride)

MS (ESI) 453.15 (M+H)+

Example 406

[3-(1-Ethyl-propoxy)-phenyl]-methyl-[3-(4-trifluoromethyl-phenyl)-1H-pyrazol-4-ylmethyl]-amine (hydrochloride)

MS (ESI) 418.35 (M+H)+

Example 407

Ethanesulfonic acid [3-(1-ethyl-propoxy)-phenyl]-[3-(4-trifluoromethyl-phenyl)-1H-pyrazol-4-ylmethyl]-amide (hydrochloride)

MS (ESI) 496.35 (M+H)+

Example 408

N-[3-(1-Ethyl-propoxy)-phenyl]-N-[3-(4-trifluoromethyl-phenyl)-1H-pyrazol-4-ylmethyl]-methanesulfonamide (hydrochloride)

MS (ESI) 482.35 (M+H)+

Example 409

1-(4-{Methyl-[3-(4-trifluoromethyl-phenyl)-1H-pyrazol-4-ylmethyl]-amino}-phenyl)-butan-1-one

MS (ESI) 402.20 (M+H)+

Example 410

1-[4-(Methyl-pyridin-3-ylmethyl-amino)-phenyl]-butan-1-one MS (ESI) 269.25 (M+H)+

Example 411

2,2,2-Trifluoro-ethanesulfonic acid (4-butyryl-phenyl)-[1-methyl-5-(4-trifluoromethyl-phenyl)-1H-pyrazol-4-ylmethyl]-amide

MS (ESI) 548.35 (M+H)+

Example 412

2,2,2-Trifluoro-ethanesulfonic acid (4-butyryl-phenyl)-[1-methyl-3-(4-trifluoromethyl-phenyl)-1H-pyrazol-4-ylmethyl]-amide

MS (ESI) 548.35 (M+H)+

Example 413

(4-Butyl-phenyl)-[3-(4-trifluoromethyl-phenyl)-1H-pyrazol-4-ylmethyl]-amine

MS (ESI) 374.15 (M+H)+

Example 414

2,2,2-Trifluoro-ethanesulfonic acid (4-butyryl-phenyl)-[3-(4-trifluoromethyl-phenyl)-1H-pyrazol-4-ylmethyl]-amide

MS (ESI) 534.10 (M+H)+

Example 415

3-{[3-(4-Chloro-phenyl)-1H-pyrazol-4-ylmethyl]-amino}-N,N-dimethyl-benzamide

MS (ESI) 355.10 (M+H)+

Example 416

1-(4-{[3-(3-Trifluoromethyl-phenyl)-1H-pyrazol-4-ylmethyl]-amino}-phenyl)-butan-1-one

MS (ESI) 388.10 (M+H)+

Example 417

N-(4-Butyryl-phenyl)-N-pyridin-3-ylmethyl-benzenesulfonamide

MS (ESI) 395.15 (M+H)+

Example 418

N-[3-(1-Ethyl-propoxy)-phenyl]-N-[3-(4-trifluoromethyl-phenyl)-1H-pyrazol-4-ylmethyl]-benzenesulfonamide (hydrochloride)

MS (ESI) 544.15 (M+H)+

Example 419

1-[3-(Methyl-pyridin-3-ylmethyl-amino)-phenyl]-butan-1-one; compound with trifluoroacetic acid

MS (ESI) 269.15 (M+H)+

Example 420

N-(3-Butyryl-phenyl)-N-pyridin-3-ylmethyl-benzenesulfonamide; compound with trifluoroacetic acid

MS (ESI) 395.10 (M+H)+

Example 421

N-(3-Butyryl-phenyl)-N-pyridin-3-ylmethyl-methanesulfonamide; compound with trifluoroacetic acid

MS (ESI) 333.05 (M+H)+

Example 422

N-(3-Butyryl-phenyl)-C-phenyl-N-pyridin-3-ylmethyl-methanesulfonamide

MS (ESI) 409.20 (M+H)+

Example 423

1-{4-[4-(Pyridin-3-yloxy)-butoxy]-phenyl}-butan-1-one

MS (ESI) 314.10 (M+H)+

Example 424

2,2,2-Trifluoro-ethanesulfonic acid (6-dimethylamino-pyridin-3-ylmethyl)-[3-(1-ethyl-propoxy)-phenyl]-amide; compound with trifluoroacetic acid

MS (ESI) 460.20 (M+H)+

Example 425

[3-(4-Chloro-phenyl)-1H-pyrazol-4-ylmethyl]-(1H-dioxo-2,3-dihydro-1H-benzo[b]thiophen-5-yl)-amine; compound with trifluoroacetic acid

MS (ESI) 374.00 (M+H)+

Example 426

7-{[3-(4-Chloro-phenyl)-1H-pyrazol-4-ylmethyl]-amino}-3,4-dihydro-2H-naphthalen-1-one

MS (ESI) 352.10 (M+H)+

Example 427

6-{[3-(4-Chloro-phenyl)-1H-pyrazol-4-ylmethyl]-amino}-indan-1-one

MS (ESI) 677.20 (2M+H)+

Example 428

4-{[3-(4-Chloro-phenyl)-1H-pyrazol-4-ylmethyl]-amino}-N-methyl-benzenesulfonamide; compound with trifluoroacetic acid

MS (ESI) 377.05 (M+H)+

Example 429

[3-(4-Chloro-phenyl)-1H-pyrazol-4-ylmethyl]-[4-(pyrrolidine-1-sulfonyl)-phenyl]-amine

MS (ESI) 417.10 (M+H)+

Example 430

3-{[3-(4-Chloro-phenyl)-1H-pyrazol-4-ylmethyl]-amino}-N,N-dimethyl-benzenesulfonamide

MS (ESI) 391.10 (M+H)+

Example 431

[3-(4-Chloro-phenyl)-1H-pyrazol-4-ylmethyl]-(1,1-dioxo-1H-benzo[b]thiophen-5-yl)-amine

MS (ESI) 372.00 (M+H)+

Example 432

4-{[3-(4-Chloro-phenyl)-1H-pyrazol-4-ylmethyl]-amino}-N,N-diethyl-benzenesulfonamide

MS (ESI) 419.10 (M+H)+

Example 433

N,N-Dimethyl-4-{[3-(3-trifluoromethyl-phenyl)-1H-pyrazol-4-ylmethyl]-amino}-benzamide

MS (ESI) 389.20 (M+H)+

Example 434

1-(2-Methoxy-4-{[3-(3-trifluoromethyl-phenyl)-1H-pyrazol-4-ylmethyl]-amino}-phenyl)-butan-1-one; compound with trifluoroacetic acid

MS (ESI) 418.10 (M+H)+

Example 435

1-(2-Hydroxy-4-{[3-(3-trifluoromethyl-phenyl)-1H-pyrazol-4-ylmethyl]-amino}-phenyl)-butan-1-one; compound with trifluoroacetic acid

MS (ESI) 404.20 (M+H)+

Example 436

1-(2-Hydroxy-3-propyl-4-{[3-(3-trifluoromethyl-phenyl)-1H-pyrazol-4-ylmethyl]-amino}-phenyl)-ethanone; compound with trifluoroacetic acid

MS (ESI) 418.20 (M+H)+

Example 437

1-[4-{[3-(4-Chloro-phenyl)-1H-pyrazol-4-ylmethyl]-amino}-2-(1-ethyl-propoxy)-phenyl]-butan-1-one

MS (ESI) 440.20 (M+H)+

Example 438

1-(4-{[3-(4-Chloro-phenyl)-1H-pyrazol-4-ylmethyl]-amino}-2-methoxy-3-methyl-phenyl)-ethanone

MS (ESI) 370.20 (M+H)+

Example 439

1-(4-{[3-(4-Chloro-phenyl)-1H-pyrazol-4-ylmethyl]-amino}-2-methoxy-3-propyl-phenyl)-ethanone; compound with trifluoroacetic acid

MS (ESI) 398.10 (M+H)+

Example 440

1-(4-{[3-(4-Chloro-phenyl)-1H-pyrazol-4-ylmethyl]-amino}-2-hydroxy-3-methyl-phenyl)-ethanone; compound with trifluoroacetic acid

MS (ESI) 356.1 (M+H)+

Example 441

2-Phenyl-1-{4-[3-(3-trifluoromethyl-phenyl)-1H-pyrazol-4-ylmethoxy]-phenyl}-ethanone; compound with trifluoroacetic acid

MS (ESI) 437.10 (M+H)+

Example 442

Cyclopentyl-{4-[3-(3-trifluoromethyl-phenyl)-1H-pyrazol-4-ylmethoxy]-phenyl}-methanone; compound with trifluoroacetic acid

MS (ESI) 415.20 (M+H)+

Example 443

4-{[3-(4-Chloro-phenyl)-1H-pyrazol-4-ylmethyl]-amino}-benzoic acid methyl ester

MS (ESI) 342.10 (M+H)+

Example 444

(4-{[3-(4-Chloro-phenyl)-1H-pyrazol-4-ylmethyl]-amino}-phenyl)-(4-methyl-piperazin-1-yl)-methanone

MS (ESI) 410.20 (M+H)+

Example 445

(4-{[3-(4-Chloro-phenyl)-1H-pyrazol-4-ylmethyl]-amino}-phenyl)-[4-(1-methyl-piperidin-4-yl)-piperazin-1-yl]-methanone; compound with trifluoroacetic acid

MS (ESI) 493.30 (M)+

Example 446

(4-{[3-(4-Chloro-phenyl)-1H-pyrazol-4-ylmethyl]-amino}-phenyl)-morpholin-4-yl-methanone; compound with trifluoroacetic acid

MS (ESI) 397.10 (M+H)+

Example 447

4-{[3-(4-Chloro-phenyl)-1H-pyrazol-4-ylmethyl]-amino}-N-methyl-N-propyl-benzamide; compound with trifluoroacetic acid

MS (ESI) 383.20 (M+H)+

Example 448

4-{[3-(4-Chloro-phenyl)-1H-pyrazol-4-ylmethyl]-amino}-N-propyl-benzamide; compound with trifluoroacetic acid

MS (ESI) 369.20 (M+H)+

Example 449

1-[3-(Benzyl-pyridin-3-ylmethyl-amino)-phenyl]-butan-1-one; compound with trifluoroacetic acid

MS (ESI) 345.20 (M+H)+

Example 450

(3-tert-Butyl-1H-pyrazol-4-ylmethyl)-[4-(1-methyl-piperidin-4-yl)-phenyl]-amine

MS (ESI) 327.20 (M+H)+

Example 451

(3-tert-Butyl-1H-pyrazol-4-ylmethyl)-[4-(4-methyl-4H-[1,2,4]triazol-3-yl)-phenyl]-amine

MS (ESI) 311.20 (M+H)+

Example 452

(3-tert-Butyl-1H-pyrazol-4-ylmethyl)-[4-(5-methyl-furan-2-yl)-phenyl]-amine

MS (ESI) 310.20 (M+H)+

Example 453

(3-tert-Butyl-1H-pyrazol-4-ylmethyl)-(3-cyclopentyloxy-phenyl)-amine

MS (ESI) 314.15 (M+H)+

Example 454

2,2,2-Trifluoro-ethanesulfonic acid [3-(1-ethyl-propoxy)-phenyl]-[3-(4-trifluoromethyl-phenyl)-1H-pyrazol-4-ylmethyl]-amide (hydrochloride)

MS (ESI) 550.10 (M+H)+

Example 455

2,2,2-Trifluoro-ethanesulfonic acid [3-(1-methyl-butoxy)-phenyl]-[3-(4-trifluoromethyl-phenyl)-1H-pyrazol-4-ylmethyl]-amide (hydrochloride)

MS (ESI) 550.10 (M+H)+

Example 456

2,2,2-Trifluoro-ethanesulfonic acid (3-sec-butoxy-phenyl)-[3-(4-trifluoromethyl-phenyl)-1H-pyrazol-4-ylmethyl]-amide (hydrochloride)

MS (ESI) 536.10 (M+H)+

Example 457

2,2,2-Trifluoro-ethanesulfonic acid [3-(2-methyl-butoxy)-phenyl]-[3-(4-trifluoromethyl-phenyl)-1H-pyrazol-4-ylmethyl]-amide (hydrochloride)

MS (ESI) 550.15 (M+H)+

Example 458

2,2,2-Trifluoro-ethanesulfonic acid (3-tert-butyl-1H-pyrazol-4-ylmethyl)-(3-cyclopentyloxy-phenyl)-amide (hydrochloride)

MS (ESI) 460.15 (M+H)+

Example 459

(3-tert-Butyl-1H-pyrazol-4-ylmethyl)-(3-thiophen-2-yl-phenyl)-amine

MS (ESI) 312.15 (M+H)+

Example 460

(3-tert-Butyl-1H-pyrazol-4-ylmethyl)-(3-furan-2-yl-phenyl)-amine

MS (ESI) 296.20 (M+H)+

Example 461

(3-tert-Butyl-1H-pyrazol-4-ylmethyl)-[3-(4-methyl-thiazol-2-yl)-phenyl]-amine

MS (ESI) 327.20 (M+H)+

Example 462

(3-tert-Butyl-1H-pyrazol-4-ylmethyl)-[3-(4,5-dimethyl-thiazol-2-yl)-phenyl]-amine

MS (ESI) 341.20 (M+H)+

Example 463

(3-tert-Butyl-1H-pyrazol-4-ylmethyl)-(3-oxazol-5-yl-phenyl)-amine

MS (ESI) 297.20 (M+H)+

Example 464

(3-tert-Butyl-1H-pyrazol-4-ylmethyl)-(3-thiophen-3-yl-phenyl)-amine

MS (ESI) 312.15 (M+H)+

Example 465

(3-tert-Butyl-1H-pyrazol-4-ylmethyl)-[3-(4,5-dimethyl-oxazol-2-yl)-phenyl]-amine

MS (ESI) 325.20 (M+H)+

Example 466

(3-tert-Butyl-1H-pyrazol-4-ylmethyl)-[3-(4-methyl-piperazin-1-yl)-phenyl]-amine

MS (ESI) 328.25 (M+H)+

Example 467

(3-tert-Butyl-1H-pyrazol-4-ylmethyl)-(3-piperazin-1-yl-phenyl)-amine (hydrochloride)

MS (ESI) 314.25 (M+H)+

Example 468

(3-tert-Butyl-1H-pyrazol-4-ylmethyl)-[3-(1,1-dioxo-1lambda%6&-isothiazolidin-2-yl)-phenyl]-amine

MS (ESI) 349.15 (M+H)+

Example 469

(3-tert-Butyl-1H-pyrazol-4-ylmethyl)-[3-(2-methyl-thiazol-4-yl)-phenyl]-amine

MS (ESI) 327.15 (M+H)+

Example 470

(3-tert-Butyl-1H-pyrazol-4-ylmethyl)-(3-pyridin-2-yl-phenyl)-amine

MS (ESI) 307.15 (M+H)+

Example 471

[4-(1-Ethyl-propoxy)-phenyl]-[3-(4-trifluoromethyl-phenyl)-1H-pyrazol-4-ylmethyl]-amine

MS (ESI) 404.35 (M+H)+

Example 472

(2-Dimethylaminomethyl-phenyl)-[3-(4-trifluoromethyl-phenyl)-1H-pyrazol-4-ylmethyl]-amine

MS (ESI) 375.20 (M+H)+

Example 473

(3-Dimethylaminomethyl-phenyl)-[3-(4-trifluoromethyl-phenyl)-1H-pyrazol-4-ylmethyl]-amine

MS (ESI) 375.20 (M+H)+

Example 474

2,2,2-Trifluoro-ethanesulfonic acid [4-(1-ethyl-propoxy)-phenyl]-[3-(4-trifluoromethyl-phenyl)-1H-pyrazol-4-ylmethyl]-amide

MS (ESI) 550.15 (M+H)+

Example 475

1-{4-[(3-Methyl-1H-pyrazol-4-ylmethyl)-amino]-phenyl}-butan-1-one

MS (ESI) 258.35 (M+H)+

Example 476

1-{4-[(3-Propyl-1H-pyrazol-4-ylmethyl)-amino]-phenyl}-butan-1-one

MS (ESI) 286.20 (M+H)+

Example 477

1-{4-[(3-Isopropyl-1H-pyrazol-4-ylmethyl)-amino]-phenyl}-butan-1-one

MS (ESI) 286.15 (M+H)+

Example 478

1-{4-[(3-Ethyl-1H-pyrazol-4-ylmethyl)-amino]-phenyl}-butan-1-one

MS (ESI) 272.25 (M+H)+

Example 479

(4-{[3-(4-Chloro-phenyl)-1H-pyrazol-4-ylmethyl]-amino}-phenyl)-morpholin-4-yl-methanone

Example 480

4-{[3-(4-Chloro-phenyl)-1H-pyrazol-4-ylmethyl]-amino}-N-methyl-N-propyl-benzamide

Example 481

4-{[3-(4-Chloro-phenyl)-1H-pyrazol-4-ylmethyl]-amino}-N-propyl-benzamide

Example 482

1-[3-(Benzyl-pyridin-3-ylmethylamino)-phenyl]-butan-1-one

The compounds of examples 483-499 were prepared by the methods depicted in the following schemes I, II and III:

Scheme I:

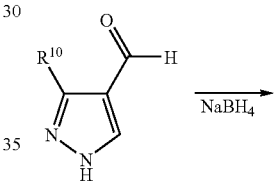

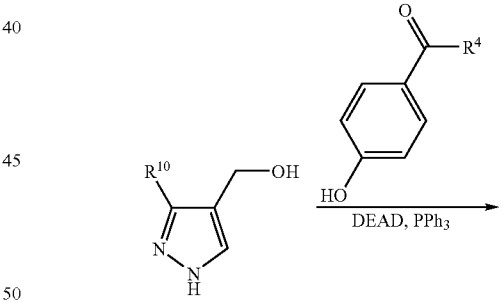

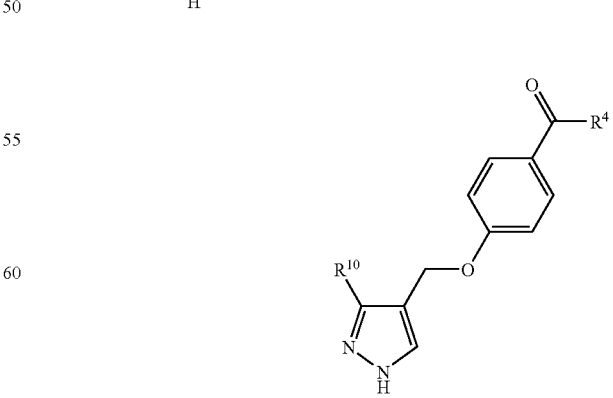

DEAD = Diethylazodicarboxylate
PPh3: Triphenylphosphine

Scheme II:
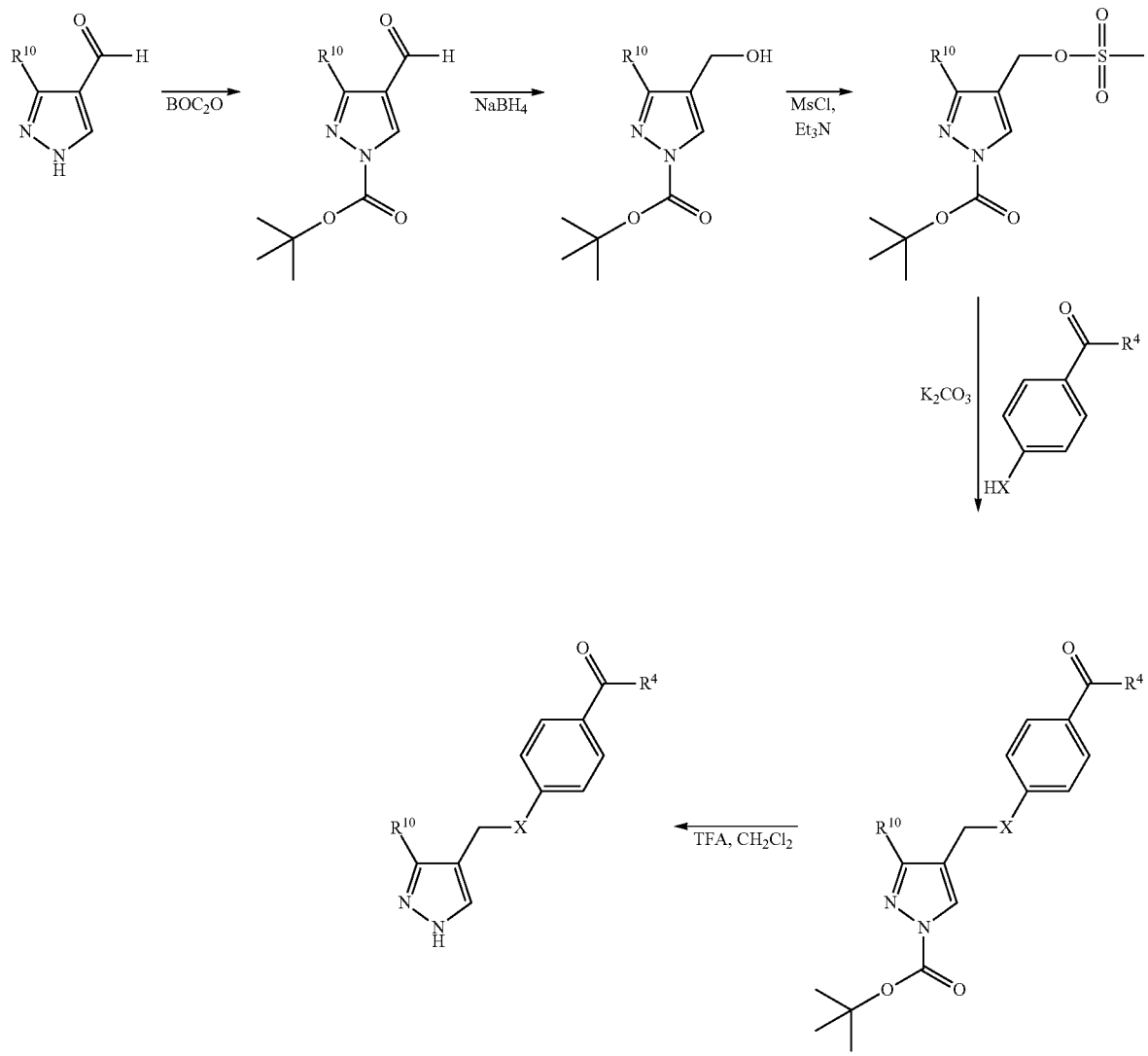
X = O or S
BOC₂O: = [(H₃C)₃C—O—C(O)]₂O
MsCl: Methylsulfonyl chloride
Et₃N: triethylamine
TFA: trifluoroacetic acid
Scheme III:
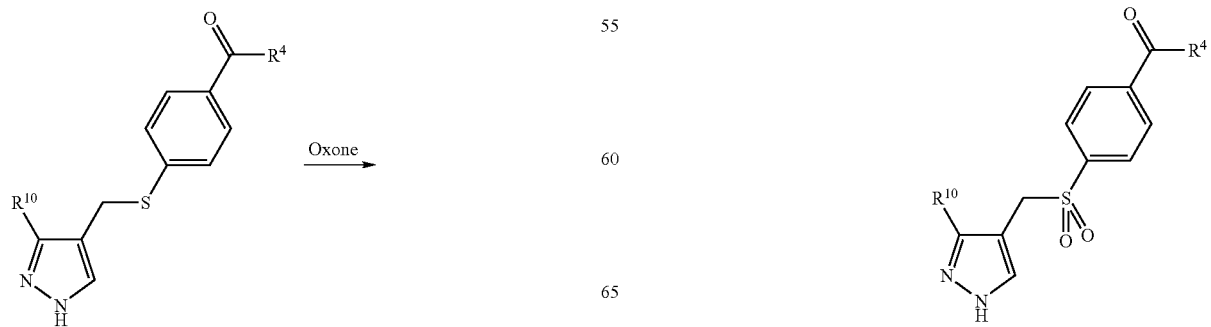

Example 483

1-{4-[3-(4-Trifluoromethyl-phenyl)-1H-pyrazol-4-ylmethoxy]-phenyl}-ethanone

ESI-MS: 361.10 [M+H]$^+$
$^1$H-NMR (500 MHz, d$^6$-DMSO): δ [ppm] 8.05 (bs, 1H); 7.95 (m, 4H); 7.75 (m, 2H); 7.15 (d, 2H); 5.20 (s, 2H); 2.50 (s, 3H).

Example 484

1-{3-Chloro-4-[3-(4-trifluoromethyl-phenyl)-1H-pyrazol-4-ylmethoxy]-phenyl}-ethanone, trifluoroacetic acid ESI-MS: 395.00 [M+H]$^+$
$^1$H-NMR (500 MHz, d$^6$-DMSO): δ [ppm] 8.00 (s, 1H); 7.95 (m, 3H); 7.90 (d, 1H); 7.75 (d, 2H); 7.45 (d, 1H); 5.30 (s, 2H); 2.50 (s, 3H).

Example 485

1-{2-Fluoro-4-[3-(4-trifluoromethyl-phenyl)-1H-pyrazol-4-ylmethoxy]-phenyl}-ethanone, acetic acid ESI-MS: 401.10 [M+Na]$^+$
$^1$H-NMR (500 MHz, d$^6$-DMSO): δ [ppm] 13.20 (bs, 1H); 8.05 (s, 1H); 7.90 (d, 2H); 7.75 (m, 4H); 7.05 (d, 1H); 6.95 (d, 1H); 5.20 (m, 2H); 2.50 (s, 3H).

Example 486

1-{3-Fluoro-4-[3-(4-trifluoromethyl-phenyl)-1H-pyrazol-4-ylmethoxy]-phenyl}-ethanone, trifluoroacetic acid ESI-MS: 379.15 [M+H]$^+$
$^1$H-NMR (500 MHz, d$^6$-DMSO): δ [ppm] 8.00 (s, 1H); 7.90 (d, 2H); 7.75 (m, 3H); 7.70 (d, 1H); 7.45 (t, 1H); 5.25 (s, 2H); 2.50 (s, 3H).

Example 487

1-{2-Methyl-4-[3-(4-trifluoromethyl-phenyl)-1H-pyrazol-4-ylmethoxy]-phenyl}-ethanone, trifluoroacetic acid ESI-MS: 375.10 [M+H]$^+$
$^1$H-NMR (500 MHz, d$^6$-DMSO): δ [ppm] 8.00 (s, 1H); 7.90 (d, 2H); 7.85 (d, 1H); 7.80 (d, 2H); 7.00 (d, 1H); 6.95 (s, 1H); 5.65 (s, 2H); 2.50 (s, 3H); 2.45 (s, 3H).

Example 488

1-{3-Methyl-4-[3-(4-trifluoromethyl-phenyl)-1H-pyrazol-4-ylmethoxy]-phenyl}-ethanone, trifluoroacetic acid ESI-MS: 375.10 [M+H]$^+$
$^1$H-NMR (500 MHz, d$^6$-DMSO): δ [ppm] 8.00 (s, 1H); 7.95 (d, 2H); 7.80 (d, 1H); 7.75 (m, 3H); 7.25 (d, 1H); 5.25 (s, 2H); 2.50 (s, 3H); 2.10 (s, 3H).

Example 489

1-{4-[3-(4-Trifluoromethyl-phenyl)-1H-pyrazol-4-ylmethoxy]-phenyl}-propan-1-one, trifluoroacetic acid $^1$H-NMR (500 MHz, d$^6$-DMSO): δ [ppm] 8.00 (s, 1H); 7.95 (m, 4H); 7.75 (d, 2H); 7.15 (d, 2H); 5.20 (s, 2H); 2.95 (m, 2H); 1.05 (t, 3H).

Example 490

1-{4-[3-(4-Trifluoromethyl-phenyl)-1H-pyrazol-4-ylmethoxy]-phenyl}-pentan-1-one, trifluoroacetic acid ESI-MS: 403.20 [M+H]$^+$
$^1$H-NMR (500 MHz, d$^6$-DMSO): δ [ppm] 13.20 (bs, 1H); 8.05 (s, 1H); 7.95 (m, 3H); 7.85 (m, 1H); 7.65 (d, 2H); 7.15 (d, 2H); 5.20 (s, 2H); 2.95 (m, 2H); 1.60 (m, 2H); 1.35 (m, 2H); 0.90 (t, 3H).

Example 491

1-{4-[3-(4-Trifluoromethyl-phenyl)-1H-pyrazol-4-ylmethoxy]-phenyl}-hexan-1-one, trifluoroacetic acid ESI-MS: 417.20 [M+H]$^+$
$^1$H-NMR (500 MHz, d$^6$-DMSO): δ [ppm] 8.00 (s, 1H); 7.95 (m, 4H); 7.80 (d, 2H); 7.15 (d, 2H); 5.20 (s, 2H); 2.90 (t, 2H); 1.60 (m, 2H); 1.30 (m, 4H); 0.85 (t, 3H).

Example 492a 4-(4-Butyryl-phenylsulfanylmethyl)-3-(4-trifluoromethyl-phenyl)-pyrazole-1-carboxylic acid tert-butyl ester ESI-MS: 405.10 [M+H-Boc]$^+$

Example 492

1-{4-[3-(4-Trifluoromethyl-phenyl)-1H-pyrazol-4-ylmethylsulfanyl]-phenyl}-butan-1-one, trifluoroacetic acid ESI-MS: 405.10 [M+H]$^+$
$^1$H-NMR (500 MHz, d$^6$-DMSO): δ [ppm] 7.95 (d, 2H); 7.85 (d, 2H); 7.80 (m, 3H); 7.40 (d, 2H); 4.40 (s, 2H); 2.95 (t, 2H); 1.60 (m, 2H); 0.90 (t, 3H).

Example 493

1-{4-[3-(4-Trifluoromethyl-phenyl)-1H-pyrazol-4-ylmethanesulfonyl]-phenyl}-butan-1-one, trifluoroacetic acid ESI-MS: 437.10 [M+H]$^+$
$^1$H-NMR (500 MHz, d$^6$-DMSO): δ [ppm] 7.90 (d, 2H); 7.65 (m, 3H); 7.60 (m, 4H); 4.75 (s, 2H); 2.95 (t, 2H); 1.65 (m, 2H); 0.95 (t, 3H).

Example 494

1-{4-[3-(4-Trifluoromethyl-phenyl)-1H-pyrazol-4-ylmethoxy]-phenyl}-butan-1-one

ESI-MS: 389.10 [M+H]$^+$
$^1$H-NMR (500 MHz, d$^6$-DMSO): δ [ppm] 13.20 (bs, 1H); 8.05 (bs, 1H); 7.95 (m, 4H); 7.75 (m, 2H); 7.15 (d, 2H); 5.20 (s, 2H); 2.90 (t, 2H); 1.60 (m, 2H); 0.90 (t, 3H).

Example 495a 4-(4-Butyryl-phenoxymethyl)-3-(4-fluorophenyl)-pyrazole-1-carboxylic acid tert-butyl ester ESI-MS: 339.10 [M+H-Boc]$^+$

Example 495

1-{4-[3-(4-Fluorophenyl)-1H-pyrazol-4-ylmethoxy]-phenyl}-butan-1-one, trifluoroacetic acid ESI-MS: 339.10 [M+H]$^+$
$^1$H-NMR (500 MHz, d$^6$-DMSO): δ [ppm] 7.95 (m, 3H); 7.75 (m, 2H); 7.25 (m, 2H); 7.15 (d, 2H); 5.15 (s, 2H); 2.95 (t, 2H); 1.65 (m, 2H); 0.90 (t, 3H).

Example 496

1-{4-[3-(4-Chloro-phenyl)-1H-pyrazol-4-ylmethoxy]-phenyl}-butan-1-one, trifluoroacetic acid salt ESI-MS: 355.10 [M+H]$^+$
$^1$H-NMR (500 MHz, d$^6$-DMSO): δ [ppm] 13.10 (bs, 1H); 8.05 (bs, 1H); 7.95 (d, 2H); 7.70 (m, 2H); 7.45 (m, 2H); 7.15 (d, 2H); 5.15 (s, 2H); 2.95 (t, 2H); 1.65 (m, 2H); 0.90 (t, 3H).

Example 497a 4-(4-Butyryl-phenoxymethyl)-3-(3-fluorophenyl)-pyrazole-1-carboxylic acid tert-butyl ester ESI-MS: 339.10 [M+H-Boc]$^+$

Example 497

1-{4-[3-(3-Fluorophenyl)-1H-pyrazol-4-ylmethoxy]-phenyl}-butan-1-one, trifluoroacetic acid salt ESI-MS: 339.10 [M+H]$^+$
$^1$H-NMR (500 MHz, d$^6$-DMSO): δ [ppm] 13.15 (bs, 1H); 8.05 (bs, 1H); 7.95 (d, 2H); 7.50 (m, 3H); 7.15 (m, 3H); 5.15 (s, 2H); 2.95 (t, 2H); 1.65 (m, 2H); 0.90 (t, 3H).

Example 498

1-{4-[3-(3-Trifluoromethyl-phenyl)-1H-pyrazol-4-ylmethoxy]-phenyl}-butan-1-one

ESI-MS: 389.20 [M+H]$^+$
$^1$H-NMR (500 MHz, d$^6$-DMSO): δ [ppm] 13.20 (bs, 1H); 8.10 (bs, 1H); 8.05 (m, 2H); 7.95 (d, 2H); 7.70 (m, 2H); 7.15 (d, 2H); 5.20 (s, 2H); 2.95 (t, 2H); 1.65 (m, 2H); 0.90 (t, 3H).

Example 499

1-[4-(3-Phenyl-1H-pyrazol-4-ylmethoxy)-phenyl]-butan-1-one, trifluoroacetic acid ESI-MS: 321.15 [M+H]$^+$
$^1$H-NMR (400 MHz, d$^6$-DMSO): δ [ppm] 7.95 (m, 3H); 7.70 (d, 2H); 7.45 (m, 2H); 7.35 (m, 1H); 7.15 (d, 2H); 5.15 (s, 2H); 2.95 (t, 2H); 1.65 (m, 2H); 0.90 (t, 3H).

The compound of example 500 was prepared by the method depicted in the following scheme IV:

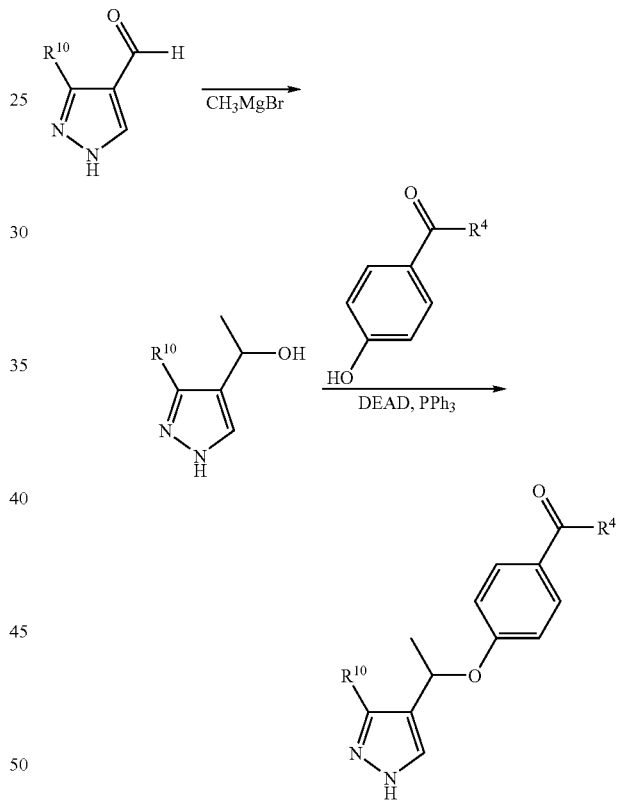

Example 500

1-{4-[1-(3-Phenyl-1H-pyrazol-4-yl)-ethoxy]-phenyl}-butan-1-one

ESI-MS: 357.20 [M+Na]$^+$
$^1$H-NMR (400 MHz, d$^6$-DMSO): δ [ppm] 13.0 (bs, 1H); 7.85 (m, 2H); 7.70-7.30 (m, 6H); 6.95 (m, 2H); 5.70 (m, 1H); 2.90 (t, 2H); 1.60 (m, 5H); 0.90 (t, 3H).

The compounds of examples 501-512 were prepared by the methods depicted in the following schemes V and VI:

Scheme V:
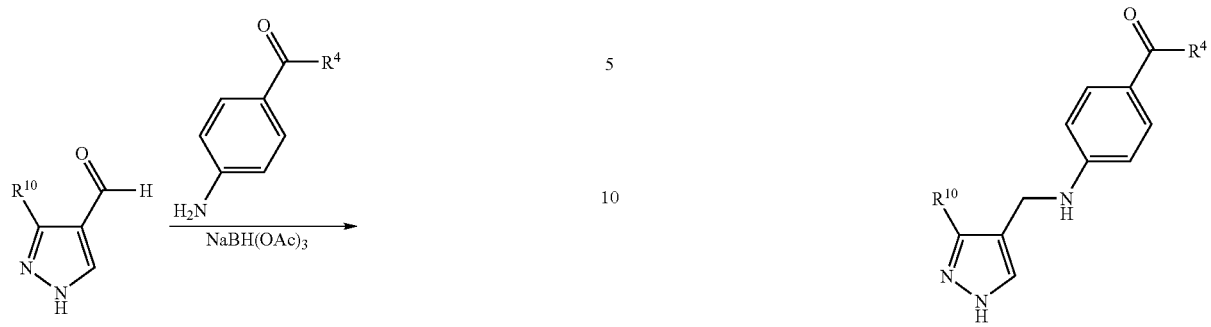
Scheme VI:
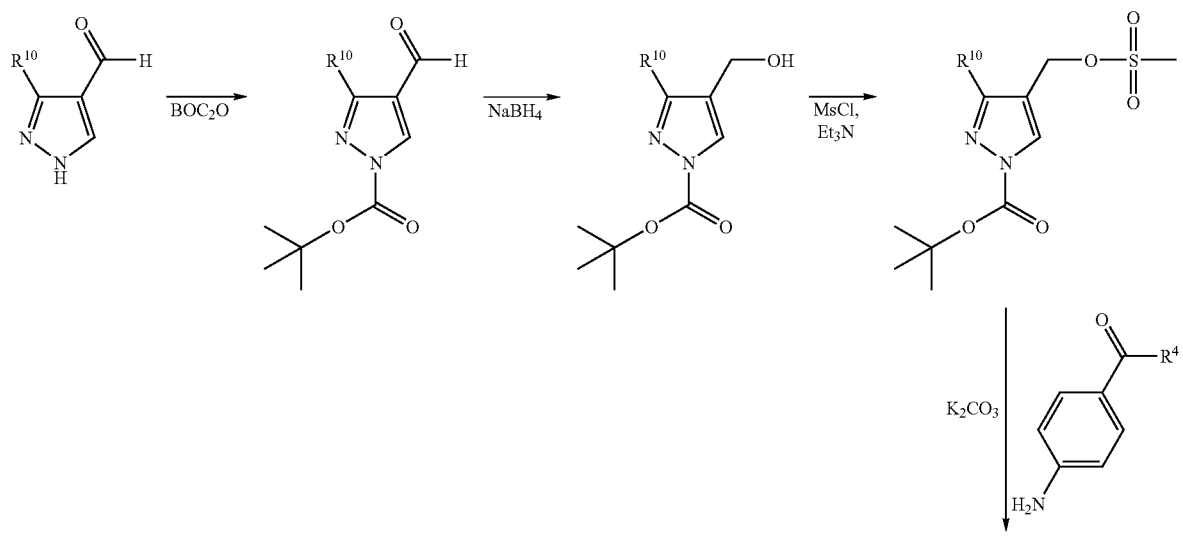
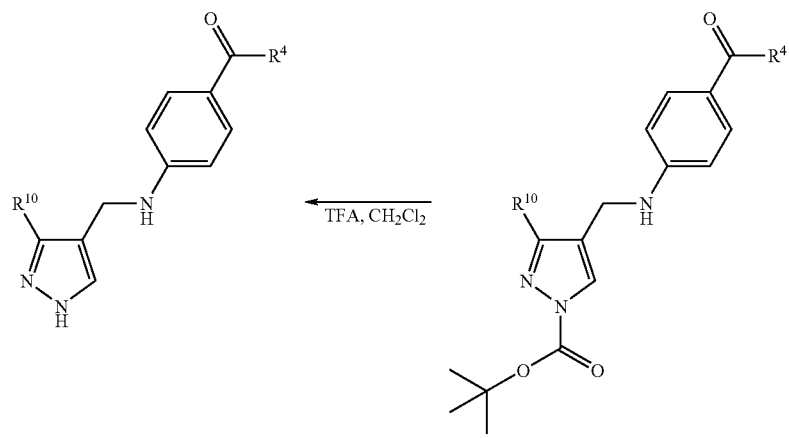

Example 501

1-(4-{[3-(4-Trifluoromethyl-phenyl)-1H-pyrazol-4-ylmethyl]-amino}-phenyl)-ethanone

Example 502

1-(3-Nitro-4-{[3-(4-trifluoromethyl-phenyl)-1H-pyrazol-4-ylmethyl]-amino}-phenyl)-ethanone, trifluoroacetic acid ESI-MS: 405.15 [M+H]$^+$
$^1$H-NMR (500 MHz, d$^6$-DMSO): δ [ppm] 8.70 (m, 1H); 8.60 (s, 1H); 7.95 (d, 1H); 7.85 (d, 2H); 7.70 (m, 3H); 7.05 (d, 1H); 4.75 (m, 2H); 2.50 (s, 3H).

Example 502

1-(3-{[3-(4-Trifluoromethyl-phenyl)-1H-pyrazol-4-ylmethyl]-amino}-phenyl)-ethanone ESI-MS: 361.00 [M+H]$^+$
$^1$H-NMR (400 MHz, d$^6$-DMSO): δ [ppm] 13.05 (bs, 1H); 7.95 (m, 2H); 7.80 (m, 3H); 7.20 (m, 3H); 6.90 (d, 1H); 6.20 (m, 1H); 4.30 (m, 2H); 2.50 (s, 3H).

Example 503

1-(3-{[3-(4-Trifluoromethyl-phenyl)-1H-pyrazol-4-ylmethyl]-amino}-phenyl)-butan-1-one, trifluoroacetic acid ESI-MS: 388.00 [M+H]$^+$
$^1$H-NMR (400 MHz, d$^6$-DMSO): δ [ppm] 7.95 (d, 2H); 7.80 (m, 3H); 7.20 (m, 3H); 6.90 (d, 1H); 5.75 (s, 1H); 4.30 (s, 2H); 2.90 (t, 2H); 1.60 (m, 2H); 0.90 (t, 3H).

Example 504

Phenyl-(4-{[3-(4-trifluoromethyl-phenyl)-1H-pyrazol-4-ylmethyl]-amino}-phenyl)-methanone ESI-MS: 422.20 [M+H]$^+$
$^1$H-NMR (500 MHz, d$^6$-DMSO): δ [ppm] 7.90 (d, 2H); 7.80 (s, 1H); 7.75 (d, 2H); 7.60 (m, 5H); 7.50 (m, 2H); 6.75 (d, 2H); 4.35 (s, 2H).

Example 505

2,2-Dimethyl-1-(4-{[3-(4-trifluoromethyl-phenyl)-1H-pyrazol-4-ylmethyl]-amino}-phenyl)-propan-1-one, trifluoroacetic acid ESI-MS: 402.20 [M+H]$^+$
$^1$H-NMR (400 MHz, CDCl$_3$): δ [ppm] 7.85 (d, 2H); 7.75 (m, 2H); 7.70 (m, 3H); 6.60 (d, 2H); 4.40 (s, 2H); 1.40 (s, 9H).

Example 506

2,2,2-Trifluoro-1-(4-{[3-(4-trifluoromethyl-phenyl)-1H-pyrazol-4-ylmethyl]-amino}-phenyl)-ethanone, trifluoroacetic acid ESI-MS: 414.10 [M+H]$^+$
$^1$H-NMR (500 MHz, d$^6$-DMSO): δ [ppm] 7.90 (d, 2H); 7.70 (m, 6H); 6.70 (d, 2H); 4.45 (s, 2H).

Example 507

1-{1-[3-(4-Trifluoromethyl-phenyl)-1H-pyrazol-4-ylmethyl]2,3-dihydro1H-indol-5-yl}-ethanone, trifluoroacetic acid

ESI-MS: 386.10 [M+H]$^+$

Example 508

1-(4-{[3-(4-Fluorophenyl)-1H-pyrazol-4-ylmethyl]-amino}-phenyl)-butan-1-one

ESI-MS: 338.20 [M+H]$^+$
$^1$H-NMR (500 MHz, d$^6$-DMSO): δ [ppm] 13.10 (bs, 1H); 7.70 (m, 5H); 7.30 (m, 2H); 6.85 (m, 1H); 6.65 (d, 2H); 4.25 (m, 2H); 2.80 (t, 2H); 1.60 (m, 2H); 0.90 (t, 3H).

Example 509

1-(4-{[3-(3-Chloro-phenyl)-1H-pyrazol-4-ylmethyl]-amino}-phenyl)-butan-1-one

ESI-MS: 354.15 [M+H]$^+$

Example 510

1-(4-{[3-(2-Chloro-phenyl)-1H-pyrazol-4-ylmethyl]-amino}-phenyl)-butan-1-one, trifluoroacetic acid ESI-MS: 354.10 [M+H]$^+$
$^1$H-NMR (500 MHz, d$^6$-DMSO): δ [ppm] 7.70 (m, 3H); 7.60 (d, 1H); 7.45 (m, 3H); 6.55 (d, 2H); 4.05 (s, 2H); 2.75 (t, 2H); 1.60 (m, 2H); 0.90 (t, 3H).

Example 511

1-(4-{[3-(3-Fluorophenyl)-1H-pyrazol-4-ylmethyl]-amino}-phenyl)-butan-1-one

ESI-MS: 338.20 [M+H]$^+$
$^1$H-NMR (500 MHz, d$^6$-DMSO): δ [ppm] 13.10 (bs, 1H); 7.75 (m, 3H); 7.50 (m, 3H); 7.15 (t, 1H); 6.85 (s, 1H); 6.65 (d, 2H); 4.30 (m, 2H); 2.80 (t, 2H); 1.60 (m, 2H); 0.90 (t, 3H).

Example 512

1-{4-[(3-Pyridin-3-yl-1H-pyrazol-4-ylmethyl)-amino]-phenyl}-butan-1-one

ESI-MS: 321.10 [M+H]$^+$
$^1$H-NMR (500 MHz, d$^6$-DMSO): δ [ppm] 8.85 (s, 1H); 8.55 (d, 1H); 8.05 (d, 1H); 7.80 (s, 1H); 7.75 (d, 2H); 7.45 (m, 1H); 6.85 (m, 1H); 6.65 (d, 2H); 4.30 (m, 2H); 2.80 (t, 2H); 1.60 (m, 2H); 0.90 (t, 3H).

The compounds of examples 513-532 were prepared by analogy to the methods depicted in the I, II, V and VI starting from a suitable heteroaromatic carbaldehyde.

Example 513

1-(4-{[4-(4-Methoxy-phenyl)-1H-pyrazol-3-ylmethyl]-amino}-phenyl)-butan-1-one

ESI-MS: 350.15 [M+H]$^+$

¹H-NMR (400 MHz, d⁶-DMSO): δ [ppm] 7.75 (m, 2H); 7.55 (m, 2H); 7.00 (m, 2H); 6.80 (s, 1H); 6.65 (m, 2H); 4.20 (m, 2H); 3.80 (s, 3H); 2.80 (m, 2H); 1.60 (m, 2H); 0.90 (m, 3H).

Example 514

1-(3-{[4-(4-Methoxy-phenyl)-1H-pyrazol-3-ylmethyl]-amino}-phenyl)-butan-1-one

ESI-MS: 350.15 [M+H]⁺

Example 515

1-(3-{[4-(4-Ethyl-phenyl)-1H-pyrazol-3-ylmethyl]-amino}-phenyl)-butan-1-one

ESI-MS: 348.15 [M+H]⁺
¹H-NMR (400 MHz, d⁶-DMSO): δ [ppm] 12.80 (m, 1H); 7.65 (s, 1H); 7.55 (d, 2H); 7.25 (d, 2H); 7.15 (m, 3H); 6.85 (d, 1H); 6.15 (m, 1H); 4.20 (m, 2H); 2.90 (t, 2H); 2.65 (m, 2H); 1.60 (m, 2H); 1.20 (t, 3H); 0.90 (t, 3H).

Example 516

1-(4-{[4-(4-Ethyl-phenyl)-1H-pyrazol-3-ylmethyl]-amino}-phenyl)-butan-1-one

ESI-MS: 348.15 [M+H]⁺
¹H-NMR (400 MHz, d⁶-DMSO): δ [ppm] 12.90 (m, 1H); 7.75 (d, 2H); 7.70 (bs, 1H); 7.55 (d, 2H); 7.25 (d, 2H); 6.80 (m, 1H); 6.65 (d, 2H); 4.25 (m, 2H); 2.80 (t, 2H); 2.65 (m, 2H); 1.60 (m, 2H); 1.20 (t, 3H); 0.90 (t, 3H).

Example 517

1-(4-{[4-(4-Trifluoromethyl-phenyl)-1H-pyrazol-3-ylmethyl]-amino}-phenyl)-butan-1-one ESI-MS: 388.20 [M+H]⁺
¹H-NMR (500 MHz, d⁶-DMSO): δ [ppm] 8.10 (s, 1H); 7.80 (m, 2H); 7.75 (d, 2H); 7.60 (m, 2H); 6.70 (d, 2H); 4.40 (s, 2H); 2.80 (t, 2H); 1.60 (m, 2H); 0.90 (m, 3H).

Example 518

1-(4-{[4-(4-Chloro-phenyl)-1H-pyrazol-3-ylmethyl]-amino}-phenyl)-butan-1-one

ESI-MS: 354.10 [M+H]⁺
¹H-NMR (500 MHz, d⁶-DMSO): δ [ppm] 7.75 (m, 3H); 7.50 (d, 2H); 7.40 (d, 2H); 6.70 (m, 2H); 4.40 (s, 2H); 2.80 (t, 2H); 1.60 (m, 2H); 0.90 (t, 3H).

Example 519

1-{4-[(5-Phenyl-2H-[1,2,3]triazol-4-ylmethyl)-amino]-phenyl}-butan-1-one

ESI-MS: 321.25 [M+H]⁺
¹H-NMR (500 MHz, d⁶-DMSO): δ [ppm] 7.75 (m, 4H); 7.50 (m, 2H); 7.40 (m, 1H); 6.70 (d, 2H); 4.50 (s, 2H); 2.70 (t, 2H); 1.60 (m, 2H); 0.90 (t, 3H).

Example 520

1-{4-[4-(4-Methoxy-phenyl)-1H-pyrazol-3-ylmethoxy]-phenyl}-butan-1-one, trifluoroacetic acid

ESI-MS: 351.20 [M+H]⁺

Example 521

1-{4-[4-(4-Ethyl-phenyl)-1H-pyrazol-3-ylmethoxy]-phenyl}-butan-1-one, trifluoroacetic acid ESI-MS: 371.20 [M+Na]⁺
¹H-NMR (400 MHz, d⁶-DMSO): δ [ppm] 7.95 (d, 2H); 7.90 (s, 1H); 7.60 (d, 2H); 7.25 (d, 2H); 7.15 (d, 2H); 5.15 (s, 2H); 2.90 (m, 2H); 2.65 (m, 2H); 1.65 (m, 2H); 1.20 (t, 3H); 0.90 (t, 3H).

Example 522

1-[4-(4-Bromo-1H-pyrazol-3-ylmethoxy)-phenyl]-butan-1-one

ESI-MS: 322.00/324.00 [M+H]⁺
¹H-NMR (400 MHz, d⁶-DMSO): δ [ppm] 13.10 (bs, 1H); 7.75 (d, 2H); 6.90 (s, 1H); 6.70 (d, 2H); 4.25 (bs, 2H); 2.80 (m, 2H); 1.60 (m, 2H); 0.90 (t, 3H).

Example 523

1-{4-[(4-Phenyl-1H-pyrrol-3-ylmethyl)-amino]-phenyl}-butan-1-one

ESI-MS: 319.20 [M+H]⁺
¹H-NMR (500 MHz, d⁶-DMSO): δ [ppm] 10.90 (s, 1H); 7.75 (d, 2H); 7.45 (d, 2H); 7.30 (m, 2H); 7.15 (t, 1H); 7.05 (s, 1H); 6.85 (s, 1H); 6.70 (s, 1H); 6.65 (d, 2H); 4.20 (d, 2H); 2.80 (t, 2H); 1.60 (m, 2H); 0.90 (t, 3H).

Example 524

1-{4-[(3-Phenyl-pyridin-4-ylmethyl)-amino]-phenyl}-butan-1-one, trifluoroacetic acid ESI-MS: 331.20 [M+H]⁺
¹H-NMR (400 MHz, d⁶-DMSO): δ [ppm] 8.65 (s, 1H); 7.70 (d, 2H); 7.60 (d, 1H); 7.55 (m, 5H); 7.25 (bs, 1H); 6.45 (d, 2H); 4.40 (s, 2H); 2.75 (t, 2H); 1.55 (m, 2H); 0.90 (t, 3H).

Example 525

1-{4-[(4-Phenyl-pyridin-3-ylmethyl)-amino]-phenyl}-butan-1-one, trifluoroacetic acid ESI-MS: 331.10 [M+H]⁺
¹H-NMR (400 MHz, d⁶-DMSO): δ [ppm] 8.70 (s, 1H); 8.65 (d, 1H); 7.70 (d, 2H); 7.55 (bs, 6H); 7.10 (m, 1H); 6.50 (d, 2H); 4.35 (s, 2H); 2.75 (t, 2H); 1.55 (m, 2H); 0.90 (t, 3H).

Example 526

1-{4-[(2-Phenyl-pyridin-3-ylmethyl)-amino]-phenyl}-butan-1-one

ESI-MS: 331.20 [M+H]⁺

$^1$H-NMR (400 MHz, d$^6$-DMSO): δ [ppm] 8.55 (d, 1H); 7.80 (d, 1H); 7.65 (d, 2H); 7.60 (d, 2H); 7.45 (m, 3H); 7.40 (m, 1H); 7.15 (m, 1H); 6.45 (d, 2H); 4.35 (d, 2H); 2.75 (t, 2H); 1.55 (m, 2H); 0.85 (t, 3H).

Example 527

1-{4-[(6-Phenyl-pyridin-3-ylmethyl)-amino]-phenyl}-butan-1-one

ESI-MS: 331.20 [M+H]$^+$
$^1$H-NMR (400 MHz, d$^6$-DMSO): δ [ppm] 8.65 (s, 1H); 8.05 (d, 2H); 7.95 (d, 1H); 7.80 (d, 1H); 7.75 (d, 2H); 7.45 (m, 3H); 7.20 (m, 1H); 6.65 (d, 2H); 4.45 (d, 2H); 2.80 (t, 2H); 1.55 (m, 2H); 0.90 (t, 3H).

Example 528

1-(4-{[6-(4-Fluorophenyl)-pyridin-2-ylmethyl]-amino}-phenyl)-butan-1-one

ESI-MS: 349.20 [M+H]$^+$
$^1$H-NMR (400 MHz, d$^6$-DMSO): δ [ppm] 8.15 (m, 2H); 7.85 (d, 2H); 7.75 (d, 2H); 7.30 (m, 4H); 6.65 (d, 2H); 4.55 (d, 2H); 2.75 (t, 2H); 1.55 (m, 2H); 0.90 (t, 3H).

Example 529

1-{4-[(Pyrazolo[1,5-a]pyridin-3-ylmethyl)-amino]-phenyl}-butan-1-one $^1$H-NMR (500 MHz, d$^6$-DMSO): δ [ppm] 8.65 (d, 1H); 8.05 (s, 1H); 7.75 (d, 1H); 7.70 (d, 2H); 7.20 (t, 1H); 6.95 (m, 1H); 6.85 (t, 1H); 6.70 (d, 2H); 4.45 (s, 2H); 2.75 (t, 2H); 1.55 (m, 2H); 0.90 (t, 3H).

Example 530

1-{4-[(3-Methyl-5-phenyl-isoxazol-4-ylmethyl)-amino]-phenyl}-butan-1-one, trifluoroacetic acid

ESI-MS: 335.10 [M+H]$^+$

The compounds of examples 531-590 were prepared by analogy to the methods depicted in the I, II, V and VI starting from a suitable heteroaromatic carbaldehyde and the compound of the following formulae, wherein X is NH or O and R$^{4c}$ and Q are as defined herein:

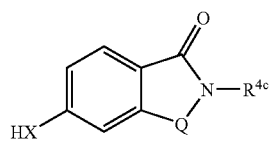

Example 531a 4-(1-Oxo-2-propyl-2,3-dihydro-1H-isoindol-5-yloxymethyl)-3-(4-trifluoromethyl-phenyl)-pyrazole-1-carboxylic acid tert-butyl ester

ESI-MS: 516.20 [M+H]$^+$

Example 531

2-Propyl-5-[3-(4-trifluoromethyl-phenyl)-1H-pyrazol-4-ylmethoxy]-2,3-dihydro-isoindol-1-one ESI-MS: 416.35 [M+H]$^+$
$^1$H-NMR (400 MHz, d$^6$-DMSO): δ [ppm] 8.00 (s, 1H); 7.95 (d, 2H); 7.75 (d, 2H); 7.60 (d, 1H); 7.25 (s, 1H); 7.10 (d, 1H); 5.20 (s, 2H); 4.40 (s, 2H); 3.45 (t, 2H); 1.60 (m, 2H); 0.85 (t, 3H).

Example 532

2-Propyl-5-[3-(3-trifluoromethyl-phenyl)-1H-pyrazol-4-ylmethoxy]-2,3-dihydro-isoindol-1-one ESI-MS: 416.20 [M+H]$^+$
$^1$H-NMR (400 MHz, d$^6$-DMSO): δ [ppm] 13.20 (bs, 1H); 8.10 (s, 1H); 8.05 (m, 2H); 7.70 (m, 2H); 7.60 (d, 1H); 7.25 (s, 1H); 7.10 (d, 1H); 5.15 (s, 2H); 4.40 (s, 2H); 3.45 (t, 2H); 1.60 (m, 2H); 0.85 (t, 3H).

Example 533

5-[3-(4-Fluorophenyl)-1H-pyrazol-4-ylmethoxy]-2-propyl-2,3-dihydro-isoindol-1-one, trifluoroacetic acid ESI-MS: 366.20 [M+H]$^+$
$^1$H-NMR (400 MHz, d$^6$-DMSO): δ [ppm] 7.95 (s, 1H); 7.70 (m, 2H); 7.55 (d, 1H); 7.25 (m, 3H); 7.10 (d, 1H); 5.10 (s, 2H); 4.40 (s, 2H); 3.45 (t, 2H); 1.60 (m, 2H); 0.85 (t, 3H).

Example 534

5-[3-(4-Chloro-phenyl)-1H-pyrazol-4-ylmethoxy]-2-propyl-2,3-dihydro-isoindol-1-one, trifluoroacetic acid ESI-MS: 382.10 [M+H]$^+$
$^1$H-NMR (400 MHz, d$^6$-DMSO): δ [ppm] 7.95 (s, 1H); 7.70 (d, 2H); 7.60 (d, 1H); 7.50 (d, 2H); 7.25 (s, 1H); 7.10 (d, 1H); 5.10 (s, 2H); 4.40 (s, 2H); 3.45 (t, 2H); 1.60 (m, 2H); 0.85 (t, 3H).

Example 535

5-[3-(3-Chloro-phenyl)-1H-pyrazol-4-ylmethoxy]-2-propyl-2,3-dihydro-isoindol-1-one, trifluoroacetic acid ESI-MS: 382.20 [M+H]$^+$
$^1$H-NMR (400 MHz, d$^6$-DMSO): δ [ppm] 8.00 (s, 1H); 7.75 (s, 1H); 7.65 (d, 1H); 7.60 (d, 1H); 7.45 (t, 1H); 7.40 (d, 1H); 7.25 (s, 1H); 7.10 (d, 1H); 5.15 (s, 2H); 4.40 (s, 2H); 3.45 (t, 2H); 1.60 (m, 2H); 0.85 (t, 3H).

Example 536a 3-(3-Fluorophenyl)-4-(1-oxo-2-propyl-2,3-dihydro-1H-isoindol-5-yloxymethyl)-pyrazole-1-carboxylic acid tert-butyl ester

ESI-MS: 466.20 [M+H]$^+$

Example 536

5-[3-(3-Fluorophenyl)-1H-pyrazol-4-ylmethoxy]-2-propyl-2,3-dihydro-isoindol-1-one ESI-MS: 366.10 [M+H]$^+$
$^1$H-NMR (400 MHz, d$^6$-DMSO): δ [ppm] 13.15 (bs, 1H); 8.00 (s, 1H); 7.60 (m, 2H); 7.50 (m, 2H); 7.25 (s, 1H); 7.20 (t, 1H); 7.15 (d, 1H); 5.15 (s, 2H); 4.40 (s, 2H); 3.45 (m, 2H); 1.60 (m, 2H); 0.85 (t, 3H).

Example 537

5-(3-Phenyl-1H-pyrazol-4-ylmethoxy)-2-propyl-2,3-dihydro-isoindol-1-one, trifluoroacetic acid ESI-MS: 348.20 [M+H]$^+$
$^1$H-NMR (400 MHz, d$^6$-DMSO): δ [ppm] 7.90 (s, 1H); 7.70 (d, 2H); 7.60 (d, 1H); 7.45 (m, 2H); 7.35 (m, 1H); 7.25 (s, 1H); 7.10 (d, 1H); 5.10 (s, 2H); 4.40 (s, 2H); 3.45 (m, 2H); 1.60 (m, 2H); 0.85 (t, 3H).

Example 538

5-[3-(3-Trifluoromethyl-phenyl)-1H-pyrazol-4-ylmethoxy]-2-(3,3,3-trifluoro-propyl)-2,3-dihydro-isoindol-1-one, trifluoroacetic acid ESI-MS: 470.10 [M+H]$^+$
$^1$H-NMR (500 MHz, MeOD): δ [ppm] 8.05 (s, 1H); 7.95 (d, 1H); 7.90 (s, 1H); 7.70 (d, 1H); 7.65 (d, 1H); 7.60 (t, 1H); 7.20 (s, 1H); 7.10 (d, 1H); 5.15 (s, 2H); 4.50 (s, 2H); 3.85 (t, 2H); 2.60 (m, 2H).

Example 539

5-[3-(4-Chloro-phenyl)-1H-pyrazol-4-ylmethoxy]-2-(3,3,3-trifluoro-propyl)-2,3-dihydro-isoindol-1-one, trifluoroacetic acid ESI-MS: 436.10 [M+H]$^+$
$^1$H-NMR (500 MHz, MeOD): δ [ppm] 7.85 (s, 1H); 7.65 (m, 3H); 7.40 (d, 2H); 7.15 (s, 1H); 7.10 (d, 1H); 5.10 (s, 2H); 4.45 (s, 2H); 3.85 (t, 2H); 2.60 (m, 2H).

Example 540

5-[3-(4-Fluorophenyl)-1H-pyrazol-4-ylmethoxy]-2-(3,3,3-trifluoro-propyl)-2,3-dihydro-isoindol-1-one, trifluoroacetic acid ESI-MS: 420.10 [M+H]$^+$
$^1$H-NMR (500 MHz, MeOD): δ [ppm] 7.85 (s, 1H); 7.70 (m, 3H); 7.15 (m, 3H); 7.10 (d, 1H); 5.10 (s, 2H); 4.45 (s, 2H); 3.85 (t, 2H); 2.60 (m, 2H).

Example 541

5-[3-(3-Fluorophenyl)-1H-pyrazol-4-ylmethoxy]-2-(3,3,3-trifluoro-propyl)-2,3-dihydro-isoindol-1-one, trifluoroacetic acid ESI-MS: 420.10 [M+H]$^+$
$^1$H-NMR (500 MHz, MeOD): δ [ppm] 7.85 (s, 1H); 7.70 (d, 1H); 7.50 (d, 1H); 7.45 (m, 2H); 7.20 (s, 1H); 7.10 (m, 2H); 5.15 (s, 2H); 4.45 (s, 2H); 3.85 (t, 2H); 2.60 (m, 2H).

Example 542

5-[3-(4-Trifluoromethyl-phenyl)-1H-pyrazol-4-ylmethoxy]-2-(3,3,3-trifluoro-propyl)-2,3-dihydro-isoindol-1-one, trifluoroacetic acid ESI-MS: 470.10 [M+H]$^+$
$^1$H-NMR (400 MHz, d$^6$-DMSO): δ [ppm] 8.05 (s, 1H); 7.95 (d, 2H); 7.80 (d, 2H); 7.60 (d, 1H); 7.30 (s, 1H); 7.15 (d, 1H); 5.20 (s, 2H); 4.45 (s, 2H); 3.75 (m, 2H); 2.65 (m, 2H).

Example 543

5-(3-Phenyl-1H-pyrazol-4-ylmethoxy)-2-(3,3,3-trifluoro-propyl)-2,3-dihydro-isoindol-1-one, trifluoroacetic acid ESI-MS: 402.10 [M+H]$^+$
$^1$H-NMR (500 MHz, d$^6$-DMSO): δ [ppm] 7.95 (bs, 1H); 7.70 (d, 2H); 7.60 (d, 1H); 7.45 (m, 2H); 7.35 (m, 1H); 7.25 (d, 1H); 7.15 (m, 2H); 5.10 (s, 2H); 4.45 (s, 2H); 3.75 (m, 2H); 2.65 (m, 2H).

Example 544

2-Butyl-5-[3-(4-trifluoromethyl-phenyl)-1H-pyrazol-4-ylmethoxy]-2,3-dihydro-isoindol-1-one ESI-MS: 430.20 [M+H]$^+$
$^1$H-NMR (500 MHz, d$^6$-DMSO): δ [ppm] 8.05 (s, 1H); 7.95 (d, 2H); 7.80 (d, 2H); 7.60 (d, 1H); 7.25 (s, 1H); 7.15 (d, 1H); 5.20 (s, 2H); 4.40 (s, 2H); 3.45 (t, 2H); 1.55 (m, 2H); 1.25 (m, 2H); 0.9 (t, 3H).

Example 545a 4-(2-Butyl-1-oxo-2,3-dihydro-1H-isoindol-5-yloxymethyl)-3-(3-trifluoromethyl-phenyl)-pyrazole-1-carboxylic acid tert-butyl ester

ESI-MS: 530.30 [M+H]$^+$

Example 545

2-Butyl-5-[3-(3-trifluoromethyl-phenyl)-1H-pyrazol-4-ylmethoxy]-2,3-dihydro-isoindol-1-one ESI-MS: 430.20 [M+H]$^+$
$^1$H-NMR (500 MHz, d$^6$-DMSO): δ [ppm] 8.05 (m, 3H); 7.70 (m, 2H); 7.60 (d, 1H); 7.25 (s, 1H); 7.10 (d, 1H); 5.15 (s, 2H); 4.40 (s, 2H); 3.50 (m, 2H); 1.55 (m, 2H); 1.30 (m, 2H); 0.9 (t, 3H).

Example 546a 4-(2-Butyl-1-oxo-2,3-dihydro-1H-isoindol-5-yloxymethyl)-3-(4-chloro-phenyl)-pyrazole-1-carboxylic acid tert-butyl ester

ESI-MS: 496.20 [M+H]$^+$

Example 546

2-Butyl-5-[3-(4-chloro-phenyl)-1H-pyrazol-4-ylmethoxy]-2,3-dihydro-isoindol-1-one

ESI-MS: 396.20 [M+H]$^+$

Example 547

2-Butyl-5-[3-(3,4-dichloro-phenyl)-1H-pyrazol-4-ylmethoxy]-2,3-dihydro-isoindol-1-one, trifluoroacetic acid ESI-MS: 430.10/432.10 [M+H]$^+$
$^1$H-NMR (400 MHz, d$^6$-DMSO): δ [ppm] 8.00 (s, 1H); 7.95 (s, 1H); 7.70 (m, 2H); 7.60 (d, 1H); 7.25 (s, 1H); 7.10 (d, 1H); 5.15 (s, 2H); 4.40 (s, 2H); 3.50 (m, 2H); 1.55 (m, 2H); 1.30 (m, 2H); 0.90 (t, 3H).

Example 548

2-Butyl-5-[3-(4-fluorophenyl)-1H-pyrazol-4-ylmethoxy]-2,3-dihydro-isoindol-1-one, trifluoroacetic acid ESI-MS: 380.20 [M+H]$^+$
$^1$H-NMR (500 MHz, d$^6$-DMSO): δ [ppm] 7.90 (s, 1H); 7.70 (m, 2H); 7.60 (d, 1H); 7.25 (m, 3H); 7.10 (d, 1H); 5.10 (s, 2H); 4.40 (s, 2H); 3.45 (t, 2H); 1.55 (m, 2H); 1.25 (m, 2H); 0.85 (t, 3H).

Example 549

2-Butyl-5-[3-(3-chloro-phenyl)-1H-pyrazol-4-ylmethoxy]-2,3-dihydro-isoindol-1-one, trifluoroacetic acid ESI-MS: 396.20 [M+H]$^+$
$^1$H-NMR (500 MHz, d$^6$-DMSO): δ [ppm] 8.00 (bs, 1H); 7.75 (s, 1H); 7.65 (d, 1H); 7.60 (d, 1H); 7.45 (t, 1H); 7.40 (d, 1H); 7.25 (s, 1H); 7.10 (d, 1H); 5.15 (s, 2H); 4.40 (s, 2H); 3.45 (t, 2H); 1.55 (m, 2H); 1.25 (m, 2H); 0.9 (t, 3H).

Example 550

2-Butyl-5-[3-(3-fluorophenyl)-1H-pyrazol-4-ylmethoxy]-2,3-dihydro-isoindol-1-one, trifluoroacetic acid ESI-MS: 380.20 [M+H]$^+$
$^1$H-NMR (500 MHz, d$^6$-DMSO): δ [ppm] 8.00 (s, 1H); 7.55 (m, 2H); 7.45 (m, 2H); 7.25 (s, 1H); 7.15 (t, 1H); 7.10 (d, 1H); 5.15 (s, 2H); 4.35 (s, 2H); 3.45 (t, 2H); 1.55 (m, 2H); 1.25 (m, 2H); 0.9 (t, 3H).

Example 551

2-Butyl-5-(3-phenyl-1H-pyrazol-4-ylmethoxy)-2,3-dihydro-isoindol-1-one, trifluoroacetic acid ESI-MS: 362.20 [M+H]$^+$
$^1$H-NMR (500 MHz, d$^6$-DMSO): δ [ppm] 9.50 (bs, 2H); 7.90 (s, 1H); 7.65 (d, 2H); 7.55 (d, 1H); 7.45 (m, 2H); 7.35 (t, 1H); 7.25 (s, 1H); 7.10 (d, 1H); 5.10 (s, 2H); 4.40 (s, 2H); 3.45 (t, 2H); 1.55 (m, 2H); 1.30 (m, 2H); 0.9 (t, 3H).

Example 552

2-(4,4,4-Trifluoro-butyl)-5-[3-(4-trifluoromethyl-phenyl)-1H-pyrazol-4-ylmethoxy]-2,3-dihydro-isoindol-1-one, trifluoroacetic acid ESI-MS: 484.20 [M+H]$^+$
$^1$H-NMR (500 MHz, d$^6$-DMSO): δ [ppm] 8.00 (s, 1H); 7.90 (d, 2H); 7.80 (d, 2H); 7.60 (d, 1H); 7.25 (s, 1H); 7.10 (d, 1H); 5.15 (s, 2H); 4.45 (s, 2H); 3.55 (t, 2H); 2.30 (m, 2H); 1.80 (m, 2H).

Example 553

5-(3-Phenyl-1H-pyrazol-4-ylmethoxy)-2-(4,4,4-trifluoro-butyl)-2,3-dihydro-isoindol-1-one, trifluoroacetic acid ESI-MS: 416.20 [M+H]$^+$
$^1$H-NMR (500 MHz, d$^6$-DMSO): δ [ppm] 7.90 (s, 1H); 7.70 (d, 2H); 7.60 (d, 1H); 7.45 (m, 2H); 7.35 (m, 1H); 7.25 (s, 1H); 7.10 (d, 1H); 5.10 (s, 2H); 4.45 (s, 2H); 3.55 (t, 2H); 2.30 (m, 2H); 1.80 (m, 2H).

Example 554

5-[3-(3,4-dichloro-phenyl)-1H-pyrazol-4-ylmethoxy]-2-(4,4,4-trifluoro-butyl)-2,3-dihydro-isoindol-1-one, trifluoroacetic acid ESI-MS: 484.10/486.10 [M+H]$^+$
$^1$H-NMR (500 MHz, d$^6$-DMSO): δ [ppm] 8.00 (s, 1H); 7.90 (s, 1H); 7.70 (m, 2H); 7.60 (d, 1H); 7.25 (s, 1H); 7.10 (d, 1H); 5.15 (s, 2H); 4.45 (s, 2H); 3.55 (t, 2H); 2.30 (m, 2H); 1.80 (m, 2H).

Example 555

2-(3-Methyl-butyl)-5-[3-(4-trifluoromethyl-phenyl)-1H-pyrazol-4-ylmethoxy]-2,3-dihydro-isoindol-1-one, trifluoroacetic acid ESI-MS: 444.20 [M+H]$^+$
$^1$H-NMR (500 MHz, d$^6$-DMSO): δ [ppm] 8.05 (s, 1H); 7.95 (d, 2H); 7.80 (d, 2H); 7.60 (d, 1H); 7.25 (s, 1H); 7.10 (d, 1H); 5.15 (s, 2H); 4.40 (s, 2H); 3.50 (m, 2H); 1.50 (m, 2H); 0.9 (d, 6H).

Example 556

2-(3-Methyl-butyl)-5-(3-phenyl-1H-pyrazol-4-ylmethoxy)-2,3-dihydro-isoindol-1-one, trifluoroacetic acid ESI-MS: 376.20 [M+H]$^+$
$^1$H-NMR (500 MHz, d$^6$-DMSO): δ [ppm] 7.90 (bs, 1H); 7.70 (d, 2H); 7.55 (d, 1H); 7.45 (t, 1H); 7.35 (t, 1H); 7.25 (s, 1H); 7.10 (d, 1H); 5.10 (s, 2H); 4.40 (s, 2H); 3.50 (m, 2H); 1.45 (m, 2H); 0.9 (d, 6H).

Example 557

5-(3-Phenyl-1H-pyrazol-4-ylmethoxy)-2-(2-trifluoromethoxy-ethyl)-2,3-dihydro-isoindol-1-one, trifluoroacetic acid

ESI-MS: 418.15 [M+H]$^+$

¹H-NMR (500 MHz, d⁶-DMSO): δ [ppm] 7.90 (s, 1H); 7.70 (d, 2H); 7.60 (d, 1H); 7.45 (m, 2H); 7.35 (t, 1H); 7.30 (s, 1H); 7.10 (d, 1H); 5.10 (s, 2H); 4.45 (s, 2H); 4.30 (m, 2H); 3.80 (m, 2H).

Example 558a 4-(2-Ethyl-1-oxo-2,3-dihydro-1H-isoindol-5-yloxymethyl)-3-(3-trifluoromethyl-phenyl)-pyrazole-1-carboxylic acid tert-butyl ester

ESI-MS: 502.20 [M+H]⁺

Example 558

2-Ethyl-5-[3-(3-trifluoromethyl-phenyl)-1H-pyrazol-4-ylmethoxy]-2,3-dihydro-isoindol-1-one

ESI-MS: 402.10 [M+H]⁺

Example 559

2-Ethyl-5-[3-(4-fluorophenyl)-1H-pyrazol-4-yl-methoxy]-2,3-dihydro-isoindol-1-one ESI-MS: 352.20 [M+H]⁺
¹H-NMR (500 MHz, d⁶-DMSO): δ [ppm] 7.90 (s, 1H); 7.70 (m, 2H); 7.55 (d, 1H); 7.25 (m, 3H); 7.10 (d, 1H); 5.10 (s, 2H); 4.40 (s, 2H); 3.45 (m, 2H); 1.15 (t, 3H).

Example 560

2-Ethyl-5-[3-(3-fluorophenyl)-1H-pyrazol-4-yl-methoxy]-2,3-dihydro-isoindol-1-one ESI-MS: 352.20 [M+H]⁺
¹H-NMR (500 MHz, d⁶-DMSO): δ [ppm] 7.95 (s, 1H); 7.60 (d, 1H); 7.55 (d, 1H); 7.45 (m, 2H); 7.25 (s, 1H); 7.15 (t, 1H); 7.10 (d, 1H); 5.05 (s, 2H); 4.40 (s, 2H); 3.45 (m, 2H); 1.15 (t, 3H).

Example 561

5-[3-(3-Chloro-phenyl)-1H-pyrazol-4-ylmethoxy]-2-ethyl-2,3-dihydro-isoindol-1-one, trifluoroacetic acid ESI-MS: 368.10 [M+H]⁺
¹H-NMR (500 MHz, d⁶-DMSO): δ [ppm] 8.00 (s, 1H); 7.75 (s, 1H); 7.65 (d, 1H); 7.60 (d, 1H); 7.45 (t, 1H); 7.40 (d, 1H); 7.25 (s, 1H); 7.10 (d, 1H); 5.15 (s, 2H); 4.40 (s, 2H); 3.50 (m, 2H); 1.15 (t, 3H).

Example 562

5-[3-(4-Chloro-phenyl)-1H-pyrazol-4-ylmethoxy]-2-ethyl-2,3-dihydro-isoindol-1-one ESI-MS: 368.10 [M+H]⁺
¹H-NMR (500 MHz, d⁶-DMSO): δ [ppm] 13.15 (bs, 1H); 8.00 (bs, 1H); 7.70 (m, 2H); 7.60 (d, 1H); 7.45 (m, 2H); 7.25 (s, 1H); 7.10 (d, 1H); 5.10 (s, 2H); 4.40 (s, 2H); 3.50 (m, 2H); 1.15 (t, 3H).

Example 563

2-Ethyl-5-(3-phenyl-1H-pyrazol-4-ylmethoxy)-2,3-dihydro-isoindol-1-one, trifluoroacetic acid

ESI-MS: 334.10 [M+H]⁺

Example 564

2-(2-Bromo-ethyl)-5-[3-(4-trifluoromethyl-phenyl)-1H-pyrazol-4-ylmethoxy]-2,3-dihydro-isoindol-1-one, trifluoroacetic acid ESI-MS: 480.10/482.10 [M+H]⁺
¹H-NMR (500 MHz, d⁶-DMSO): δ [ppm] 7.90 (m, 3H); 7.70 (m, 3H); 7.20 (s, 1H); 7.10 (d, 1H); 5.15 (s, 2H); 4.55 (s, 2H); 4.00 (t, 2H); 3.70 (t, 3H).

Example 565

2-(2-Bromo-ethyl)-5-[3-(3-trifluoromethyl-phenyl)-1H-pyrazol-4-ylmethoxy]-2,3-dihydro-isoindol-1-one, trifluoroacetic acid ESI-MS: 480.10/482.10 [M+H]⁺
¹H-NMR (500 MHz, d⁶-DMSO): δ [ppm] 8.05 (s, 1H); 7.95 (d, 1H); 7.90 (s, 1H); 7.70 (d, 1H); 7.65 (d, 1H); 7.60 (t, 1H); 7.20 (s, 1H); 7.10 (d, 1H); 5.15 (s, 2H); 4.55 (s, 2H); 4.00 (t, 2H); 3.70 (t, 3H).

Example 566

2-(2,2-Difluoro-ethyl)-5-[3-(4-trifluoromethyl-phenyl)-1H-pyrazol-4-ylmethoxy]-2,3-dihydro-isoindol-1-one, trifluoroacetic acid ESI-MS: 438.10 [M+H]⁺
¹H-NMR (500 MHz, MeOD): δ [ppm] 7.90 (s, 1H); 7.85 (d, 2H); 7.70 (m, 3H); 7.20 (s, 1H); 7.15 (d, 1H), 6.10 (t, J=70 Hz, 1H); 5.15 (s, 2H); 4.55 (s, 2H); 3.95 (t, 2H).

Example 567

2-(2,2-Difluoro-ethyl)-5-(3-phenyl-1H-pyrazol-4-ylmethoxy)-2,3-dihydro-isoindol-1-one, trifluoroacetic acid ESI-MS: 370.10 [M+H]⁺
¹H-NMR (500 MHz, d⁶-DMSO): δ [ppm] 7.80 (s, 1H); 7.70 (d, 1H); 7.65 (d, 2H); 7.40 (m, 2H); 7.35 (d, 1H); 7.10 (s, 1H); 7.05 (d, 1H); 6.10 (t, J=70 Hz, 1H); 5.10 (s, 2H); 4.50 (s, 2H); 3.95 (t, 2H).

Example 568

2-(2,2,2-Trifluoro-ethyl)-5-[3-(4-trifluoromethyl-phenyl)-1H-pyrazol-4-ylmethoxy]-2,3-dihydro-isoindol-1-one, trifluoroacetic acid

ESI-MS: 456.10 [M+H]⁺

Example 569

2-(2,2,2-Trifluoro-ethyl)-5-[3-(3-trifluoromethyl-phenyl)-1H-pyrazol-4-ylmethoxy]-2,3-dihydro-isoindol-1-one, trifluoroacetic acid ESI-MS: 456.10 [M+H]$^+$
$^1$H-NMR (500 MHz, d$^6$-DMSO): δ [ppm] 8.05 (m, 3H); 7.65 (m, 3H); 7.35 (s, 1H); 7.15 (d, 1H); 5.15 (s, 2H); 4.55 (s, 2H); 4.35 (m, 2H).

Example 570

5-[3-(4-Fluorophenyl)-1H-pyrazol-4-ylmethoxy]-2-(2,2,2-trifluoro-ethyl)-2,3-dihydro-isoindol-1-one, trifluoroacetic acid

ESI-MS: 406.10 [M+H]$^+$

Example 571

5-[3-(3-Fluorophenyl)-1H-pyrazol-4-ylmethoxy]-2-(2,2,2-trifluoro-ethyl)-2,3-dihydro-isoindol-1-one, trifluoroacetic acid ESI-MS: 406.10 [M+H]$^+$
$^1$H-NMR (500 MHz, d$^6$-DMSO): δ [ppm] 8.00 (s, 1H); 7.70 (d, 1H); 7.55 (d, 1H); 7.45 (m, 2H); 7.35 (s, 1H); 7.20 (m, 2H); 5.15 (s, 2H); 4.55 (s, 2H); 4.35 (m, 2H).

Example 572

5-[3-(4-Trifluoromethyl-phenyl)-1H-pyrazol-4-ylmethoxy]-2,3-dihydro-isoindol-1-one, trifluoroacetic acid ESI-MS: 374.10 [M+H]$^+$
$^1$H-NMR (500 MHz, d$^6$-DMSO): δ [ppm] 7.90 (m, 3H); 7.70 (m, 3H); 7.20 (s, 1H); 7.10 (d, 1H); 5.15 (s, 2H); 4.40 (s, 2H).

Example 573

2-Methyl-5-[3-(4-trifluoromethyl-phenyl)-1H-pyrazol-4-ylmethoxy]-2,3-dihydro-isoindol-1-one, trifluoroacetic acid ESI-MS: 388.10 [M+H]$^+$
$^1$H-NMR (500 MHz, d$^6$-DMSO): δ [ppm] 7.80 (m, 4H); 7.70 (d, 2H); 7.05 (d, 1H); 7.00 (s, 1H); 5.10 (s, 2H); 4.35 (s, 2H); 3.20 (s, 3H).

Example 574a 4-(1-Oxo-2-propyl-1,2,3,4-tetrahydro-isoquinolin-6-yloxymethyl)-3-(4-trifluoromethyl-phenyl)-pyrazole-1-carboxylic acid tert-butyl ester

Example 574

2-Propyl-6-[3-(4-trifluoromethyl-phenyl)-1H-pyrazol-4-ylmethoxy]-3,4-dihydro-2H-isoquinolin-1-one, trifluoroacetic acid ESI-MS: 430.10 [M+H]$^+$
$^1$H-NMR (400 MHz, d$^6$-DMSO): δ [ppm] 8.00 (s, 1H); 7.95 (d, 2H); 7.80 (m, 3H); 7.00 (d, 1H); 6.95 (s, 1H); 5.15 (s, 2H); 3.50 (t, 2H); 3.40 (t, 2H); 2.90 (m, 2H); 1.55 (m, 2H); 0.85 (t, 3H).

Example 575a

4-[(1-Oxo-2-propyl-2,3-dihydro-1H-isoindol-5-ylamino)-methyl]-3-(4-trifluoromethyl-phenyl)-pyrazole-1-carboxylic acid tert-butyl ester

ESI-MS: 515.20 [M+H]$^+$

Example 575

2-Propyl-5-{[3-(4-trifluoromethyl-phenyl)-1H-pyrazol-4-ylmethyl]-amino}-2,3-dihydro-isoindol-1-one, trifluoroacetic acid ESI-MS: 415.20 [M+H]$^+$
$^1$H-NMR (500 MHz, d$^6$-DMSO): δ [ppm] 7.90 (m, 2H); 7.80 (m, 3H); 7.35 (d, 1H); 6.75 (m, 2H); 4.30 (m, 4H); 3.40 (m, 2H); 1.55 (m, 2H); 0.85 (t, 3H).

Example 576

5-{[3-(4-Chloro-phenyl)-1H-pyrazol-4-ylmethyl]-amino}-2-propyl-2,3-dihydro-isoindol-1-one, trifluoroacetic acid ESI-MS: 381.20 [M+H]$^+$
$^1$H-NMR (500 MHz, d$^6$-DMSO): δ [ppm] 7.75 (s, 1H); 7.70 (d, 2H); 7.50 (d, 2H); 7.35 (d, 1H); 6.70 (m, 2H); 4.30 (s, 2H); 4.25 (s, 2H); 3.35 (t, 2H); 1.55 (m, 2H); 0.85 (t, 3H).

Example 577

5-{[3-(3-Chloro-phenyl)-1H-pyrazol-4-ylmethyl]-amino}-2-propyl-2,3-dihydro-isoindol-1-one, trifluoroacetic acid ESI-MS: 381.20 [M+H]$^+$
$^1$H-NMR (500 MHz, d$^6$-DMSO): δ [ppm] 7.75 (s, 1H); 7.70 (s, 1H); 7.65 (d, 1H); 7.45 (t, 1H); 7.40 (d, 1H); 7.35 (d, 1H); 6.75 (m, 2H); 4.25 (m, 4H); 3.40 (t, 2H); 1.55 (m, 2H); 0.85 (t, 3H).

Example 578

2-Propyl-5-{[3-3-trifluoromethyl-phenyl)-1H-pyrazol-4-ylmethyl]-amino}-2,3-dihydro-isoindol-1-one, trifluoroacetic acid ESI-MS: 415.20 [M+H]$^+$
$^1$H-NMR (500 MHz, d$^6$-DMSO): δ [ppm] 8.00 (s, 1H); 7.95 (d, 1H); 7.80 (s, 1H); 7.70 (m, 2H); 7.35 (d, 1H); 6.75 (m, 2H); 4.30 (s, 4H); 3.40 (t, 2H); 1.55 (m, 2H); 0.85 (t, 3H).

Example 579

5-{[3-(4-Fluorophenyl)-1H-pyrazol-4-ylmethyl]-amino}-2-propyl-2,3-dihydro-isoindol-1-one, trifluoroacetic acid

ESI-MS: 365.20 [M+H]$^+$

¹H-NMR (500 MHz, d⁶-DMSO): δ [ppm] 7.75 (s, 1H); 7.70 (m, 2H); 7.35 (d, 1H); 7.25 (m, 2H); 6.70 (m, 2H); 4.25 (s, 2H); 4.20 (s, 2H); 3.40 (t, 2H); 1.55 (m, 2H); 0.85 (t, 3H).

Example 580

5-{[3-(3-Fluorophenyl)-1H-pyrazol-4-ylmethyl]-amino}-2-propyl-2,3-dihydro-isoindol-1-one, trifluoroacetic acid ESI-MS: 365.20 [M+H]⁺
¹H-NMR (500 MHz, d⁶-DMSO): δ [ppm] 7.75 (s, 1H); 7.55 (d, 1H); 7.45 (d, 1H); 7.35 (d, 1H); 7.15 (t, 1H); 6.75 (m, 2H); 4.30 (m, 4H); 3.40 (t, 2H); 1.55 (m, 2H); 0.85 (t, 3H).

Example 581

5-[(3-Phenyl-1H-pyrazol-4-ylmethyl)-amino]-2-propyl-2,3-dihydro-isoindol-1-one, trifluoroacetic acid ESI-MS: 347.20 [M+H]⁺
¹H-NMR (400 MHz, d⁶-DMSO): δ [ppm] 7.70 (s, 1H); 7.65 (d, 2H); 7.45 (m, 2H); 7.35 (m, 2H); 6.75 (m, 2H); 4.30 (s, 2H); 4.25 (s, 2H); 3.40 (t, 2H); 1.55 (m, 2H); 0.85 (t, 3H).

Example 582

2-Propyl-5-{[4-3-trifluoromethyl-phenyl)-1H-pyrazol-3-ylmethyl]-amino}-2,3-dihydro-isoindol-1-one, trifluoroacetic acid

ESI-MS: 415.20 [M+H]⁺

Example 583

2-Propyl-5-{[3-(4-trifluoromethyl-phenyl)-1H-pyrazol-4-ylmethyl]-amino}-isoindole-1,3-dione, trifluoroacetic acid ESI-MS: 429.10 [M+H]⁺
¹H-NMR (500 MHz, d⁶-DMSO): δ [ppm] 7.90 (d, 2H); 7.80 (s, 1H); 7.75 (d, 2H); 7.55 (d, 1H); 7.30 (bs, 1H); 7.00 (s, 1H); 6.90 (d, 1H); 4.40 (s, 2H); 3.45 (t, 2H); 1.55 (m, 2H); 0.85 (t, 3H).

Example 584

2-Propyl-6-{[3-(4-trifluoromethyl-phenyl)-1H-pyrazol-4-ylmethyl]-amino}-2,3-dihydro-isoquinolin-1-one, trifluoroacetic acid ESI-MS: 427.15 [M+H]⁺
¹H-NMR (500 MHz, d⁶-DMSO): δ [ppm] 7.90 (m, 3H); 7.85 (s, 1H); 7.80 (d, 2H); 7.25 (d, 1H); 6.85 (d, 1H); 6.55 (s, 1H); 6.30 (d, 1H); 4.35 (s, 2H); 3.80 (m, 2H); 1.65 (m, 2H); 0.85 (t, 3H).

Example 585a

4-[1-Oxo-2-(4-trifluoromethoxy-benzyl)-2,3-dihydro-1H-isoindol-5-yloxymethyl]-3-(4-trifluoromethyl-phenyl)-pyrazole-1-carboxylic acid tert-butyl ester

ESI-MS: 648.20 [M+H]⁺

Example 585

2-(4-Trifluoromethoxy-benzyl)-5-[3-(4-trifluoromethyl-phenyl)-1H-pyrazol-4-ylmethoxy]-2,3-dihydro-isoindol-1-one, trifluoroacetic acid ESI-MS: 548.10 [M+H]⁺
¹H-NMR (500 MHz, d⁶-DMSO): δ [ppm] 8.00 (s, 1H); 7.90 (d, 2H); 7.80 (d, 2H); 7.65 (d, 1H); 7.40 (d, 2H); 7.35 (d, 2H); 7.25 (s, 1H); 7.15 (d, 1H); 5.15 (s, 2H); 4.75 (s, 2H); 4.35 (s, 2H).

Example 586

2-Cyclohexylmethyl-5-[3-(4-trifluoromethyl-phenyl)-1H-pyrazol-4-ylmethoxy]-2,3-dihydro-isoindol-1-one, trifluoroacetic acid ESI-MS: 470.20 [M+H]⁺
¹H-NMR (500 MHz, d⁶-DMSO): δ [ppm] 8.05 (s, 1H); 7.95 (d, 2H); 7.80 (d, 2H); 7.60 (d, 1H); 7.25 (s, 1H); 7.15 (d, 1H); 5.20 (s, 2H); 4.40 (m, 1H); 3.30 (d, 2H); 1.65 (m, 3H); 1.60 (m, 3H); 1.15 (m, 3H), 0.90 (m, 2H).

Example 587

2-Isobutyl-5-[3-(4-trifluoromethyl-phenyl)-1H-pyrazol-4-ylmethoxy]-2,3-dihydro-isoindol-1-one, trifluoroacetic acid ESI-MS: 430.20 [M+H]⁺
¹H-NMR (500 MHz, d⁶-DMSO): δ [ppm] 8.05 (s, 1H); 7.95 (d, 2H); 7.80 (d, 2H); 7.60 (d, 1H); 7.25 (s, 1H); 7.15 (d, 1H); 5.20 (s, 2H); 4.40 (m, 1H); 3.30 (d, 2H); 2.00 (m, 1H); 0.85 (d, 6H).

Example 588

2-Cyclopentyl-5-[3-(4-trifluoromethyl-phenyl)-1H-pyrazol-4-ylmethoxy]-2,3-dihydro-isoindol-1-one ESI-MS: 442.10 [M+H]⁺
¹H-NMR (500 MHz, d⁶-DMSO): δ [ppm] 13.25 (bs, 1H); 8.10 (bs, 1H); 7.95 (m, 2H); 7.80 (m, 2H); 7.55 (d, 1H); 7.25 (s, 1H); 7.15 (d, 1H); 5.20 (s, 2H); 4.55 (m, 1H); 4.40 (s, 2H); 1.85 (m, 2H); 1.75 (m, 2H); 1.65 (m, 4H).

Example 589a 4-(1-Oxo-2-phenzyl-2,3-dihydro-1H-isoindol-5-yloxymethyl)-3-(4-trifluoromethyl-phenyl)-pyrazole-1-carboxylic acid tert-butyl ester

ESI-MS: 550.20 [M+H]⁺

Example 589

2-Phenyl-5-[3-(4-trifluoromethyl-phenyl)-1H-pyrazol-4-ylmethoxy]-2,3-dihydro-isoindol-1-one ESI-MS: 550.10 [M+H]⁺
¹H-NMR (500 MHz, d⁶-DMSO): δ [ppm] 13.30 (bs, 1H); 8.05 (bs, 1H); 7.95 (m, 2H); 7.90 (d, 2H); 7.80 (m, 2H); 7.70 (d, 1H); 7.45 (m, 2H); 7.35 (s, 1H); 7.15 (m, 2H); 5.20 (s, 2H); 4.95 (s, 2H).

Example 590

5-[(3-Methyl-5-phenyl-isoxazol-4-ylmethyl)-amino]-2-propyl-2,3-dihydro-isoindol-1-one, trifluoroacetic acid ESI-MS: 362.20 [M+H]$^+$
$^1$H-NMR (500 MHz, d$^6$-DMSO): δ [ppm] 7.70 (d, 2H); 7.55 (m, 3H); 7.35 (d, 1H); 6.70 (d, 1H); 6.65 (s, 1H); 4.25 (s, 2H); 4.20 (s, 2H); 3.35 (t, 2H); 2.30 (s, 3H); 1.55 (m, 2H); 0.85 (m, 3H).

Examples of Galenic Administration Forms
A) Tablets

Tablets of the following composition are pressed on a tablet press in the customary manner:
- 40 mg of substance from Example 4
- 120 mg of corn starch
- 13.5 mg of gelatin
- 45 mg of lactose
- 2.25 mg of Aerosil® (chemically pure silicic acid in submicroscopically fine dispersion)
- 6.75 mg of potato starch (as a 6% paste)

B) Sugar-Coated Tablets
- 20 mg of substance from Example 4
- 60 mg of core composition
- 70 mg of saccharification composition The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

Biological Tests:

I Generation of a HEK293 cell clones permanently expressing mGlu receptors and functional evaluation of the cells a) mGlu2 Receptor For the purpose of the present study, a cell line permanently expressing the human mGlu2 receptor, the rat glutamate transporter rGLAST and the alpha subunit of G16 was generated by transfection. Briefly, HEK293 cells were seeded in petri dishes (diameter 15 cm) at a density of 2×10$^6$ cells in DMEM with glutamax (Invitrogen, GIBCO #21885-025), 10% dialyzed Fetal Calf Serum (Invitrogen, Gibco #26400-044), and incubated at 37° C. over night. The following day cells were transfected with Lipofectamine (Invitrogen, Gibco #18324-012) as recommended by the manufacturer, using linearized pcDNA3.1 (V5/His)-hmGlu2 receptor (ScaI) and pcDNA3.1 Zeo-Ga16 IRES rGLAST (SspI). After transfection the cells were selected in DMEM Glutamax Medium (Invitrogen, GIBCO #21885-025), containing 10% dialyzed fetal calf serum (FCS; (Invitrogen, Gibco #26400-044), antibiotic/antimycotic, 800 µg/ml Geneticin (G418) and 250 µg/ml Zeozin. Single clones were isolated manually and further subcloned by serial dilution.

The function of the mGlu2 receptor was determined by evaluating intracellular Ca$^{2+}$ concentrations under standard conditions in a fluorometric imaging plate reader (FLIPR, Molecular Devices, Union City, Calif. 94587, USA) by measuring the response of the cells to a test compound. The FLIPR assay is a common functional assay to monitor native or recombinant Galphaq-coupled receptors, and native or recombinant receptors normally linked to other G-protein signalling cascades, which are coupled to calcium through co-expression of an alpha subunit of a promiscuous or chimeric G-protein. In the assay the increase of intracellular calcium is measured through a calcium-dependent fluorescent dye (e.g. Fluo-4 AM) in the FLIPR instrument.

For selection of a suitable cell clone and also the subsequent measurements of the selected clone, 4×10$^4$ cells/well were plated on poly-D-lysine coated Biocoat-plates multiwell 96 in DMEM Glutamax (GIBCO #21885-025)/10% dialyzed FCS over night. The following day, the medium was aspirated and exchanged for glutamate-free DMEM (Gibco #21969-035), without FCS or glutamine, containing 50 µg/ml gentamycin (Gibco #15750). Cells were again incubated over night. Before the measurement, cells were loaded with 2 µM Fluo-4 AM (Molecular Probes, F14201; stock solution 1 mM in DMSO) and 0.02% Pluronic F127 (Molecular Probes, P3000; stock solution 10% in DMSO) in DMEM medium (Gibco #21969-035) for 45 minutes at 37° C. in a final volume of 100 µl per well. Finally, the plates were washed in a BioTec cell washer with HBSS, containing 20 mM HEPES. The end-volume in each well was 100 µl. The plates were subsequently measured in a fluorometric imaging plate reader (FLIPR, Molecular Devices, Union City, Calif. 94587, USA).

The compounds of the present invention were tested in the above-described FLIPR assay using the selected cell clone. Increased intracellular calcium levels were quantified following addition of test compound (agonism), as well as following addition of a submaximal concentration of 1 micromolar (1 µM) glutamate (potentiation).

For the determination of the effect of the test compound by itself (agonism) or by increasing the response to a submaximal concentration (e.g. 1 µM) of glutamate (potentiation), the resulting signal is determined by subtraction of the background fluorescence from the maximal fluorescent peak height of the respective response. In the FLIPR instrument the compound is given to the cell and its flourescence response quantified by the FLIPR instrument (agonism). The concentration at which the compound exerts half its maximal effect is named the 'effective concentration 50' or 'EC$_{50}$'. The maximal effect induced by the test substance is normalized to the maximal effect exerted by 100 µM glutamate (set at 100%).

Ten minutes after addition of the test compound to the plate, 1 µM glutamate is added. A potentiator enhances the response of the receptor to glutamate. The response to glutamate in the presence of test compound is quantified. The concentration at which the test compound is able to exert half its maximal potentiation effect to glutamate is named the 'EC$_{50}$'. The maximal response to 1 micromolar glutamate in the presence of test compound is normalized to the maximal effect exerted by 100 µM glutamate (set at 100%). Least squares curve fitting with a four-parameter equation is then applied to the resulting dose-response curve to determine the resulting EC$_{50}$ values (Graph Pad Prism). A control cell line, HEK293 cells expressing permanently rGLAST and Galpha16 was also plated at 4×10$^4$ cells/well for parallel testing to verify specificity of the test compound for mGlu2 receptor agonism or potentiation. The EC$_{50}$ values are given in table 1.

Highly potent or key compounds were further characterized by measurement of their efficacy and potency to inhibit forskolin-induced cAMP levels in these cells on their own (agonism) or to potentiate the effect of glutamate (potentiation). Cyclic AMP levels were quantified using Alphascreen technology (PerkinElmer Life and Analytical Sciences, 710 Bridgeport Avenue, Shelton, Conn. USA) as described by the manufacturer for determining the effects of Galphai coupled receptors. The concentration at which a compound exerts half its maximal effect is named the 'effective concentration 50' or 'EC$_{50}$'. The maximal effect induced by the test substance is normalized to the maximal effect exerted by 100 PM glutamate (100%). Least squares curve fitting with a four-parameter equation is then applied to the resulting dose-response curve to determine the resulting $EC_{50}$ values (Graph Pad Prism).

The compounds of the following examples had activity in potentiating the mGlu2 receptor in the aforementioned assays, generally with an $EC_{50}$ of not more than about 10 μM. Preferred compounds within the present invention had activity in potentiating the mGlu2 receptor in the aforementioned assays with an $EC_{50}$ of less than about 1 μM. Such a result is indicative of the intrinsic activity of the compounds in use as potentiators of mGlu2 receptor activity.

TABLE 1

$EC_{50}$ values of potentiation effect to glutamate

| Compound Ex.# | $EC_{50}$[1] |
|---|---|
| 9 | ++ |
| 13 | ++ |
| 16 | ++ |
| 23 | ++ |
| 25 | ++ |
| 35 | ++ |
| 37 | ++ |
| 40 | +++ |
| 42 | +++ |
| 43 | ++ |
| 46 | ++ |
| 45 | ++ |
| 49 | ++ |
| 50 | ++ |
| 52 | ++ |
| 53 | ++ |
| 55 | ++ |
| 56 | ++ |
| 57 | ++ |
| 58 | ++ |
| 60 | ++ |
| 68 | ++ |
| 71 | ++ |
| 73 | +++ |
| 75 | ++ |
| 76 | +++ |
| 77 | +++ |
| 81 | ++ |
| 82 | +++ |
| 83 | +++ |
| 82 | ++ |
| 116 | ++ |
| 117 | ++ |
| 169 | ++ |
| 209 | +++ |
| 210 | +++ |
| 211 | ++ |
| 212 | +++ |
| 213 | +++ |
| 214 | ++ |
| 215 | ++ |
| 216 | ++ |
| 217 | +++ |
| 218 | +++ |
| 219 | ++ |
| 220 | ++ |
| 221 | ++ |
| 222 | ++ |
| 223 | ++ |
| 224 | ++ |
| 226 | ++ |
| 227 | ++ |
| 228 | ++ |
| 232 | ++ |
| 233 | ++ |
| 242 | ++ |
| 243 | ++ |
| 245 | ++ |
| 246 | ++ |
| 250 | ++ |

TABLE 1-continued $EC_{50}$ values of potentiation effect to glutamate

| Compound Ex.# | $EC_{50}$[1] |
|---|---|
| 255 | ++ |
| 260 | ++ |
| 268 | ++ |
| 273 | ++ |
| 281 | ++ |
| 284 | ++ |
| 285 | ++ |
| 286 | ++ |
| 298 | ++ |
| 307 | ++ |
| 310 | ++ |
| 311 | ++ |
| 312 | ++ |
| 313 | ++ |
| 317 | ++ |
| 321 | ++ |
| 340 | ++ |
| 341 | ++ |
| 349 | ++ |
| 351 | ++ |
| 355 | ++ |
| 363 | ++ |
| 374 | +++ |
| 375 | +++ |
| 378 | ++ |
| 379 | ++ |
| 380 | ++ |
| 383 | ++ |
| 385 | ++ |
| 386 | ++ |
| 387 | ++ |
| 389 | ++ |
| 390 | +++ |
| 391 | ++ |
| 392 | ++ |
| 399 | ++ |
| 400 | ++ |
| 401 | ++ |
| 416 | ++ |
| 423 | ++ |
| 430 | ++ |
| 433 | ++ |
| 434 | +++ |
| 436 | ++ |
| 437 | ++ |
| 440 | +++ |
| 442 | +++ |
| 443 | ++ |
| 454 | ++ |
| 455 | ++ |
| 456 | ++ |
| 457 | ++ |
| 458 | ++ |
| 475 | ++ |
| 476 | ++ |
| 477 | ++ |
| 478 | ++ |
| 483 | ++ |
| 485 | ++ |
| 487 | ++ |
| 488 | ++ |
| 489 | +++ |
| 490 | +++ |
| 491 | +++ |
| 492 | ++ |
| 494 | +++ |
| 495 | +++ |
| 496 | +++ |
| 497 | +++ |
| 498 | +++ |
| 499 | +++ |
| 501 | ++ |
| 502 | ++ |
| 503 | ++ |
| 504 | ++ |
| 506 | ++ |

TABLE 1-continued

EC$_{50}$ values of potentiation effect to glutamate

| Compound Ex.# | EC$_{50}$[1] |
|---|---|
| 507 | ++ |
| 508 | +++ |
| 509 | +++ |
| 510 | +++ |
| 511 | +++ |
| 513 | +++ |
| 514 | ++ |
| 515 | ++ |
| 516 | +++ |
| 517 | +++ |
| 518 | ++ |
| 519 | ++ |
| 520 | +++ |
| 521 | +++ |
| 522 | ++ |
| 523 | ++ |
| 524 | ++ |
| 525 | +++ |
| 526 | ++ |
| 529 | ++ |
| 531 | +++ |
| 532 | +++ |
| 533 | +++ |
| 534 | +++ |
| 535 | +++ |
| 536 | +++ |
| 537 | +++ |
| 538 | +++ |
| 539 | +++ |
| 540 | +++ |
| 541 | +++ |
| 542 | +++ |
| 543 | +++ |
| 544 | +++ |
| 545 | +++ |
| 546 | +++ |
| 547 | +++ |
| 548 | +++ |
| 549 | +++ |
| 550 | +++ |
| 551 | +++ |
| 552 | +++ |
| 553 | +++ |
| 554 | +++ |
| 558 | +++ |
| 559 | +++ |
| 560 | +++ |
| 562 | +++ |
| 563 | +++ |
| 564 | +++ |
| 565 | +++ |
| 566 | +++ |
| 567 | +++ |
| 568 | +++ |
| 569 | +++ |
| 570 | +++ |
| 571 | +++ |
| 573 | +++ |
| 574 | +++ |
| 576 | +++ |
| 577 | +++ |
| 578 | +++ |
| 579 | +++ |
| 580 | +++ |
| 581 | +++ |
| 582 | ++ |
| 584 | +++ |
| 585 | +++ |
| 586 | +++ |
| 587 | +++ |
| 588 | +++ |
| 589 | ++ |
| 590 | +++ |

[1] +++: EC$_{50}$ < 1 µM ++: 1 µM ≤ EC$_{50}$ ≤ 10 µM b) mGlu3 Receptor

For the purpose of the present study, we generated by transfection a cell line permanently expressing the human mGlu3 receptor, the rat glutamate transporter rGLAST and the alpha subunit of G16. Briefly, HEK293 cells were seeded in petri dishes (diameter 15 cm) at a density of 2×10$^6$ cells in DMEM with glutamax (Invitrogen, GIBCO #21885-025), 10% dialyzed Fetal Calf Serum (Invitrogen, Gibco #26400-044), and incubated at 37° C. over night. The following day cells were transfected with Lipofectamine (Invitrogen, Gibco #18324-012) as recommended by the manufacturer, using linearized pcDNA3.1 (V5/His)-hmGlu3 receptor (ScaI) and pcDNA3.1 Zeo-Ga16 IRES rGLAST (SspI). After transfection the cells were selected in DMEM Glutamax Medium (Invitrogen, GIBCO #21885-025), containing 10% dialyzed fetal calf serum (FCS; (Invitrogen, Gibco #26400-044), antibiotic/antimycotic, 800 µg/ml Geneticin (G418) and 250 µg/ml Zeozin. Single clones were isolated manually and further subcloned by serial dilution. Function was tested with FLIPR as described above.

c) mGlu4 Receptor

For the purpose of the present study, we generated by transfection a cell line permanently expressing human mGlu4 receptor, the rat glutamate transporter rGLAST and the alpha subunit of G15. Briefly, HEK293 cells were seeded in petri dishes (diameter 15 cm) at a density of 2×10$^6$ cells in DMEM glutamax, 10% dialyzed FCS, and incubated at 37° C. over night. The following day cells were transfected with Lipofectamine (Invitrogen, Karlsruhe, Germany) as recommended by the manufacturer, using linearised pcDNA3-hmGlu4 (SspI) and pcDNA3.1(+) Hygro-rGLAST IRES Ga15 (SspI). After transfection the cells were cultured in DMEM Glutamax Medium (Invitrogen), containing 10% dialyzed fetal calf serum (FCS; Invitrogen), antibiotic/antimycotic, 800 µg/ml Geneticin (G418) and 150 µg/ml Hygromycin, and single clones were isolated manually and subcloned by serial dilution. Function was tested with FLIPR as described above.

d) mGlu7 Receptor

For the purpose of the present study, we generated by transfection a cell line permanently expressing human mGlu7a receptor, the rat glutamate transporter rGLAST and the alpha subunit of G15. Briefly, HEK293 cells were seeded in petri dishes (diameter 15 cm) at a density of 2×10$^6$ cells in DMEM glutamax, 10% dialyzed FCS, and incubated at 37° C. over night. The following day cells were transfected with Lipofectamine (Invitrogen, Karlsruhe, Germany) as recommended by the manufacturer, using linearised pcDNA3(−)-hmGlu7a (SspI). After transfection cells were cultured in DMEM Glutamax Medium (Invitrogen), containing 10% dialyzed fetal calf serum (FCS; Invitrogen), antibiotic/antimycotic (Invitrogen) and 800 µg/ml Geneticin (G418). Single clones were isolated manually, tested for reduction of cellular cAMP (alpha screen) and subcloned by FACS. Single cell clones were retested for cAMP reduction, and transfected with pcDNA3.1 (+) Hygro rGLAST IRES Ga15 (SspI). The transfection was done identical as described above. Cells were selected in DMEM Glutamax, 10% dialyzed FCS, antibiotic/antimycotic, 800 µg/ml G418 and 150 µg/ml Hygromycin. Single clones were isolated by serial dilution and tested by FLIPR as described above.

e) mGlu1 and 5 Receptors

For the purpose of the present study, we generated by transfection a cell line permanently expressing human mGlu5a and the rat glutamate transporter rGLAST. Briefly, cells were transfected with Lipofectamine (Invitrogen, Karlsruhe, Germany), using linearised pcDNA3-hmGlu5a (ScaI) and pIRES-rGlast (SspI). After transfection the cells were cultured in DMEM Glutamax Medium (Invitrogen), containing 10% dialyzed fetal calf serum (FCS; Invitrogen), antibiotic/antimycotic, 800 μg/ml Geneticin (G418) and 150 μg/ml Hygromycin, and single clones were isolated manually. Identically, a cell line expressing mGlu1a was generated. Functional clones were selected using intracellular $Ca^{2+}$ measurements with a fluorescence imaging plate reader (FLIPR) under standard conditions as described above.

f) 5HT2A-Receptor Binding Studies f.1 Radioligand Binding to Cloned Human $5\text{-}HT_{2A}$ CHO-K1 cells stably expressing the human $5\text{-}HT_{2A}$ receptor (Euroscreen-ES-313-C, protein ID NP 036679) were cultured in UltraCHO™ medium with glutamine (Cambrex Bio Science, Walkersville, Inc., USA) supplemented with 1% fetal calf serum. Cell ghosts were prepared. For inhibition studies, 0.4 nM [$^3$H]-ketanserin and cell ghosts (6.5-8.5 μg protein/assay) were incubated in the presence of various concentrations of test compounds in a total volume of 200 μL. Non-specific binding was determined using 1 μM mianserine. The binding reaction was carried out for 1 h at room temperature and terminated by filtration on Packard Unifilter GF/C (0.3% PEI) plates with a Tomtec MachIII U 96-well-plate harvester. After the plates had been dried for 2 h at 55° C. in a drying chamber, a scintillation cocktail (BetaPlate Scint; PerkinElmer) was added. Radioactivity was measured in a Microbeta Trilux two hours after the addition of the scintillation mixture.

f.2 Determining Antagonistic Activity by Intracellular $Ca^{2+}$ Mobilization

Intracellular $Ca^{2+}$ increase was measured with a FLIPR384 instrument (Molecular Devices). Cells were seeded on black 96-well cell culture plates and cultivated in 100 μl growth medium over night at 37° C., 5% CO2. The next day cell were incubated over night in serum free medium. On the day of experiment, cells were loading with 100 μl Ca3 Assay Kit Reagent (as described by the manufacturer Molecular Divices, Ismaning/München, Germany), incubated for 1-2 h at 37° C. and 5% CO2 in the dark, followed by 30-60 min incubation at room temperature before plates were transferred into the instrument.

Concentration response curves after addition of substances were used to calculate $EC_{50}$ values using GraphPadPrism. For antagonists, $IC_{50}$ values were calculated using concentration response curves after addition of 50 nM 5-HT. $IC_{50}$ values were converted to an apparent Kb using the functional equivalent of the Cheng-Prusoff equation.

The compounds of the working examples frequently have $Ki(5HT_{2A})$ binding constants below 1 μM, in particular of at most 0.5 μM, more preferably at most 250 nM or especially at most 100 nM. The compounds show an antagonistic behaviour.

We claim:
1. A compound of formula I

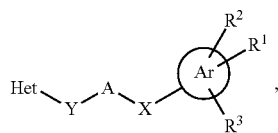

(I)

wherein
X is selected from the group consisting of O, S, S(O), $S(O)_2$, NH, NHC(O), and $NR^x$;

$R^x$ is $C_1\text{-}C_6$-alkyl, which is unsubstituted or carries one radical selected from the group consisting of OH, $C_1\text{-}C_4$-alkoxy, $C_3\text{-}C_8$-cycloalkyl, and phenyl, wherein the phenyl ring itself is unsubstituted or carries 1, 2, 3, 4 or 5 identical or different radicals $R^{xa}$, $C_1\text{-}C_6$-haloalkyl, $C_3\text{-}C_8$-cycloalkyl, $C_1\text{-}C_6$-alkoxy, $C_1\text{-}C_6$-haloalkoxy, phenyl, 5- or 6-membered hetaryl having 1, 2 or 3 heteroatoms as ring members, the heteroatoms being selected from the group consisting of O, S, and N, wherein hetaryl and phenyl are unsubstituted or carry 1, 2, 3, 4 or 5 identical or different radicals $R^{xb}$, $C(=O)\text{—}R^{x1}$, $C(=O)\text{—}OR^{x2}$, $C(=O)NR^{x3}R^{x4}$, $S(O)_2R^{x5}$ or $S(O)_2NR^{x3}R^{x4}$; wherein $R^{x1}$ is selected from the group consisting of hydrogen, $C_1\text{-}C_8$-alkyl, which is unsubstituted or carries one radical selected from the group consisting of OH, $C_1\text{-}C_4$-alkoxy, $C_3\text{-}C_8$-cycloalkyl, and phenyl wherein the phenyl ring itself is unsubstituted or carries 1, 2, 3, 4 or 5 identical or different radicals $R^{xa}$, $C_1\text{-}C_6$-haloalkyl, $C_3\text{-}C_8$-cycloalkyl, which is unsubstituted or carries 1, 2, 3 or 4 radicals selected from the group consisting of halogen, $C_1\text{-}C_4$-alkyl, and $C_1\text{-}C_4$-alkoxy, phenyl, and 5- or 6-membered hetaryl having 1, 2 or 3 heteroatoms as ring members, the heteroatoms being selected from the group consisting of O, S, and N, wherein phenyl and hetaryl are unsubstituted or may carry a fused benzene ring and/or 1, 2, 3, 4 or 5 identical or different radicals $R^{xb}$;

$R^{xa}$ is selected from the group consisting of halogen, CN, OH, $C_1\text{-}C_4$-alkyl, $C_3\text{-}C_6$-cycloalkyl, $C_1\text{-}C_4$-haloalkyl, $C_1\text{-}C_4$-alkoxy, and $C_1\text{-}C_4$-haloalkoxy;

$R^{xb}$ is selected from the group consisting of halogen, CN, OH, $C_1\text{-}C_4$-alkyl, $C_3\text{-}C_6$-cycloalkyl, $C_1\text{-}C_4$-haloalkyl, $C_1\text{-}C_4$-alkoxy, and $C_1\text{-}C_4$-haloalkoxy;

$R^{x2}$ is selected from the group consisting of $C_1\text{-}C_3$-alkyl, which is unsubstituted or carries one radical selected from the group consisting of OH, $C_1\text{-}C_4$-alkoxy, $C_3\text{-}C_8$-cycloalkyl, and phenyl, wherein the phenyl ring itself is unsubstituted or carries 1, 2, 3, 4 or 5 identical or different radicals $R^{xa}$, $C_1\text{-}C_8$-haloalkyl, and $C_3\text{-}C_8$-cycloalkyl, which is unsubstituted or carries 1, 2, 3 or 4 radicals selected from the group consisting of halogen, $C_1\text{-}C_4$-alkyl, and $C_1\text{-}C_4$-alkoxy;

$R^{x3}$ is selected from the group consisting of hydrogen, $C_1\text{-}C_8$ alkyl, which is unsubstituted or carries one radical selected from the group consisting of OH, $C_1\text{-}C_4$-alkoxy, $C_3\text{-}C_8$-cycloalkyl, and phenyl, wherein the phenyl ring itself is unsubstituted or carries 1, 2, 3, 4 or 5 identical or different radicals $R^{xa}$, $C_1\text{-}C_6$-haloalkyl, $C_1\text{-}C_8$alkoxy, $C_1\text{-}C_8$haloalkoxy, and $C_3\text{-}C_8$-cycloalkyl, which is unsubstituted or carries 1, 2, 3 or 4 radicals selected from the group consisting of halogen, $C_1\text{-}C_4$-alkyl, and $C_1\text{-}C_4$-alkoxy;

$R^{x4}$ is selected from the group consisting of hydrogen and $C_1\text{-}C_3$-alkyl, or $R^{x3}$ and $R^{x4}$ together with the nitrogen atom, to which they are bound, form a heterocyclic radical, selected from the group consisting of pyrrolidinyl, piperidinyl, piperazinyl, N-alkylpiperazinyl, N-phenylpiperazinyl, and morpholinyl; and $R^{x5}$ has one of the meanings given for $R^{x1}$;

Y is a chemical bond;

A is $CR^aR^b$, wherein $R^a$ and $R^b$ are, independently of each other, selected from the group consisting of hydrogen, halogen, $C_1\text{-}C_4$-alkyl, $C_1\text{-}C_4$-haloalkyl, $C_1\text{-}C_4$-alkoxy, and $C_1$-$C_4$-haloalkoxy; $R^b$ may also be OH, if $R^a$ is hydrogen, $C_1$-$C_4$-alkyl, or $C_1$-$C_4$-haloalkyl;

Ar is phenyl;

$R^1$ is $C(=O)$—$R^4$;

$R^2$ is selected from the group consisting of hydrogen, CN, OH, halogen, $C_1$-$C_8$-alkyl, which is unsubstituted or carries one radical selected from the group consisting of OH, $C_3$-$C_6$-cycloalkyl, and $C_1$-$C_4$-alkoxy, $C_3$-$C_6$-cycloalkyl, $C_1$-$C_8$-haloalkyl, $C_1$-$C_8$-alkoxy, and $C_1$-$C_8$-haloalkoxy;

$R^3$ is selected from the group consisting of hydrogen, halogen, $C_1$-$C_4$-alkyl, which is unsubstituted or carries one radical selected from the group consisting of OH and $C_1$-$C_4$-alkoxy, $C_1$-$C_4$-haloalkyl, $C_1$-$C_4$-alkoxy, $C_1$-$C_4$-haloalkoxy, and $C_3$-$C_8$-cycloalkyl, which is unsubstituted or carries 1, 2, 3 or 4 radicals selected from the group consisting of halogen, $C_1$-$C_4$-alkyl, and $C_1$-$C_4$-alkoxy;

$R^4$ is selected from the group consisting of $C_3$-$C_8$-alkyl, which is unsubstituted or carries one radical selected from the group consisting of OH, $C_1$-$C_4$-alkoxy, $C_3$-$C_8$-cycloalkyl, and phenyl, wherein the phenyl ring itself is unsubstituted or carries 1, 2, 3, 4 or 5 identical or different radicals $R^{4a}$, $C_1$-$C_8$-haloalkyl, $C_2$-$C_8$-alkenyl, $C_2$-$C_8$-alkynyl, $C_3$-$C_8$-cycloalkyl, which is unsubstituted or carries 1, 2, 3 or 4 radicals selected from the group consisting of halogen, $C_1$-$C_4$-alkyl, and $C_1$-$C_4$-alkoxy, phenyl, which is unsubstituted or carries 1, 2, 3, 4 or 5 identical or different radicals $R^{4b}$, and 5- or 6-membered hetaryl having 1, 2 or 3 heteroatoms as ring members, the heteroatoms being selected from the group consisting of O, S, and N, wherein hetaryl is unsubstituted or carries 1, 2, 3 or 4 identical or different radicals $R^{4b}$, or $R^4$ together with $R^2$ forms a $C_1$-$C_5$-alkylene or $C_2$-$C_5$-alkenylene moiety, wherein one $CH_2$-moiety may be replaced by oxygen, sulphur or a N—$R^{4c}$-moiety and wherein $C_1$-$C_5$-alkylene and $C_2$-$C_5$-alkenylene may be unsubstituted or carry 1, 2, 3, or 4 radicals selected from the group consisting of halogen, CN, OH, $NH_2$, $C_1$-$C_4$-alkyl, $C_3$-$C_6$-cycloalkyl, $C_1$-$C_4$-haloalkyl, $C_1$-$C_4$-alkylamino, di-($C_1$-$C_4$-alkyl)amino, $C_1$-$C_4$-alkoxy, and $C_1$-$C_4$-haloalkoxy;

$R^{4a}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy, and $C_1$-$C_4$-haloalkoxy;

$R^{4b}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy, and $C_1$-$C_4$-haloalkoxy;

$R^{4c}$ is selected from the group consisting of hydrogen, CN, OH, $C_1$-$C_8$-alkyl, which is unsubstituted or carries a radical selected from the group consisting of $C_1$-$C_4$-alkoxy, $C_1$-$C_4$-alkylthio, $C_1$-$C_4$-haloalkoxy, $C_1$-$C_4$-haloalkylthio, $C_3$-$C_6$-cycloalkyl, which is unsubstituted or carries 1, 2, 3, 4 or 5 identical or different radicals selected from the group consisting of halogen and $C_1$-$C_4$-alkyl, and phenyl or benzyl, wherein the phenyl ring in the last two radicals itself is unsubstituted or carries 1, 2, 3, 4 or 5 identical or different radicals selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy, and $C_1$-$C_4$-haloalkoxy, $C_3$-$C_6$-cycloalkyl, $C_1$-$C_4$-haloalkyl, $C_1$-$C_4$-alkoxy, and $C_1$-$C_4$-haloalkoxy;

Het is pyrazolyl, wherein Het is unsubstituted or may carry a first substituent $R^{10}$ and additionally may carry 1 or 2 further substituents selected from the group consisting of $R^{11}$, and $R^{12}$;

$R^{10}$ is selected from the group consisting of halogen, cyano, $C_1$-$C_8$-alkyl, which is unsubstituted or carries one radical selected from the group consisting of OH, $C_1$-$C_4$-alkoxy, and phenyl, wherein the phenyl ring itself is unsubstituted or carries 1, 2, 3, 4 or 5 identical or different radicals $R^{4a}$, $C_1$-$C_8$-alkoxy, which is unsubstituted or carries one radical selected from the group consisting of OH, $C_1$-$C_4$-alkoxy, and phenyl, wherein the phenyl ring itself is unsubstituted or carries 1, 2, 3, 4 or 5 identical or different radicals $R^{4a}$, $C_1$-$C_8$-haloalkyl, $C_1$-$C_8$-haloalkoxy, $C_2$-$C_8$-alkenyl, $C_2$-$C_8$-alkynyl, $C_3$-$C_8$-cycloalkyl, which is unsubstituted or carries 1, 2, 3 or 4 radicals selected from the group consisting of halogen, $C_1$-$C_4$-alkyl, and $C_1$-$C_4$-alkoxy, $C_3$-$C_8$-cycloalkoxy, which is unsubstituted or carries 1, 2, 3 or 4 radicals selected from the group consisting of halogen, $C_1$-$C_4$-alkyl, and $C_1$-$C_4$-alkoxy, $C(=O)$—$R^{13}$, $C(=O)$—$OR^{14}$, $NR^{15}R^{16}$, $C(=O)NR^{15}R^{16}$, $SO_2R^{17}$, phenyl, O-phenyl, $CH_2$-phenyl, $CH(CH_3)$-phenyl, CH(OH)phenyl, S-phenyl, O—$CH_2$-phenyl, wherein the phenyl ring in the last seven mentioned radicals may be unsubstituted or may carry 1, 2, 3, 4 or 5 substituents selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy, and $C_1$-$C_4$-haloalkoxy, and 5- or 6-membered heteroaryl, having 1, 2, or 3 heteroatoms as ring members, the heteroatoms being selected from the group consisting of O, S, and N, which is unsubstituted or may carry 1, 2, 3, 4 or 5 substituents selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy, and $C_1$-$C_4$-haloalkoxy;

$R^{11}$ is selected from the group consisting of CN, OH, halogen, $C_1$-$C_8$ alkyl, which is unsubstituted or carries one radical selected from the group consisting of OH and $C_1$-$C_4$-alkoxy, $C_1$-$C_8$-haloalkyl, $C_1$-$C_8$-alkoxy, $C_1$-$C_8$-haloalkoxy, and phenyl, which may be unsubstituted or may carry 1, 2, 3, 4, or 5 substituents selected from the group consisting of halogen, CN, $C_1$-$C_4$-alkyl, $C_1$-$C_4$-haloalkyl, $C_1$-$C_4$-alkoxy, and $C_1$-$C_4$-haloalkoxy;

$R^{12}$ is selected from the group consisting of CN, OH, halogen, $C_1$-$C_8$-alkyl, which is unsubstituted or carries one radical selected from OH and $C_1$-$C_4$-alkoxy, $C_1$-$C_8$-haloalkyl, $C_1$-$C_8$-alkoxy, and $C_1$-$C_8$-haloalkoxy, or $R^{11}$ and $R^{12}$ together with the carbon atom, to which they are bound, form a carbonyl group;

$R^{13}$ is selected from the group consisting of hydrogen, $C_1$-$C_8$-alkyl, which is unsubstituted or carries one radical selected from the group consisting of OH, $C_1$-$C_4$-alkoxy, and phenyl, wherein the phenyl ring itself is unsubstituted or carries 1, 2, 3, 4 or 5 identical or different radicals $R^{13a}$, $C_1$-$C_8$-haloalkyl, $C_3$-$C_8$-cycloalkyl, which is unsubstituted or carries 1, 2, 3 or 4 radicals selected from the group consisting of halogen, $C_1$-$C_4$-alkyl, and $C_1$-$C_4$-alkoxy, phenyl, and 5- or 6-membered hetaryl having 1, 2 or 3 heteroatoms as ring members, the heteroatoms being selected from the group consisting of O, S, and N, wherein phenyl and hetaryl are unsubstituted or carry 1, 2, 3, 4 or 5 identical or different radicals $R^{13b}$;

$R^{13a}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy, and $C_1$-$C_4$-haloalkoxy;

$R^{13b}$ is selected from the group consisting of halogen, CN, OH, $C_1$-$C_4$-alkyl, $C_3$-$C_6$-cycloalkyl, $C_1$-$C_4$-haloalkyl, $C_1$-$C_4$-alkoxy, and $C_1$-$C_4$-haloalkoxy;

$R^{14}$ is selected from the group consisting of $C_1$-$C_3$-alkyl, which is unsubstituted or carries one radical selected from the group consisting of OH, $C_1$-$C_4$-alkoxy, and phenyl, wherein the phenyl ring itself is unsubstituted or carries 1, 2, 3, 4 or 5 identical or different radicals $R^{13a}$, $C_1$-$C_8$-haloalkyl, and $C_3$-$C_8$-cycloalkyl, which is unsubstituted or carries 1, 2, 3 or 4 radicals selected from the group consisting of halogen, $C_1$-$C_4$-alkyl, and $C_1$-$C_4$-alkoxy;

$R^{15}$ is selected from the group consisting of hydrogen, $C_1$-$C_8$-alkyl, which is unsubstituted or carries one radical selected from the group consisting of OH, $C_1$-$C_4$-alkoxy, and phenyl, wherein the phenyl ring itself is unsubstituted or carries 1, 2, 3, 4 or 5 identical or different radicals $R^{13a}$, and $C_3$-$C_8$-cycloalkyl, which is unsubstituted or carries 1, 2, 3 or 4 radicals selected from the group consisting of halogen, $C_1$-$C_4$-alkyl, and $C_1$-$C_4$-alkoxy;

$R^{16}$ is selected from the group consisting of hydrogen and $C_1$-$C_8$-alkyl, or $R^{15}$ and $R^{16}$ together with the nitrogen atom, to which they are bound, form a heterocyclic radical, selected from the group consisting of pyrrolidinyl, piperidinyl, piperazinyl, N-alkylpiperazinyl, N-phenylpiperazinyl, and morpholinyl;

$R^{17}$ is selected from the group consisting of $C_1$-$C_8$-alkyl, which is unsubstituted or carries one radical selected from the group consisting of OH, $C_1$-$C_4$-alkoxy, and phenyl, wherein the phenyl ring itself is unsubstituted or carries 1, 2, 3, 4 or 5 identical or different radicals $R^{17}$, $C_1$-$C_8$-haloalkyl, $C_3$-$C_8$-cycloalkyl, which is unsubstituted or carries 1, 2, 3 or 4 radicals selected from the group consisting of halogen, $C_1$-$C_4$-alkyl, and $C_1$-$C_4$-alkoxy, phenyl, and 5- or 6-membered hetaryl having 1, 2 or 3 heteroatoms as ring members, the heteroatoms being selected from the group consisting of O, S, and N, wherein phenyl and hetaryl are unsubstituted or carry 1, 2, 3, 4, or 5 identical or different radicals $R^{17b}$, wherein $R^{17a}$ is as defined for $R^{13a}$ and $R^{17b}$ is as defined for $R^{13b}$; or a pharmaceutically acceptable salt or tautomer thereof.

2. A compound according to claim 1, wherein X is O, NH or $NR^X$.

3. A compound according to claim 1, wherein A is $CH_2$.

4. A compound according to claim 1 of the formula Ia

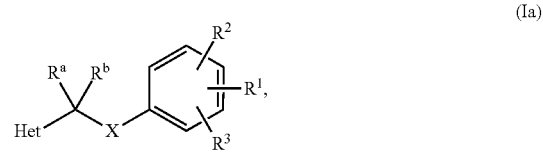

(Ia)

wherein $R^a$ and $R^b$ are, independently of each other, selected from the group consisting of hydrogen, halogen, $C_1$-$C_4$alkyl, $C_1$-$C_4$-haloalkyl, $C_1$-$C_4$alkoxy, and $C_1$-$C_4$haloalkoxy; $R^b$ may also be OH, if $R^a$ is hydrogen, $C_1$-$C_4$ alkyl, or $C_1$-$C_4$haloalkyl; and X is O, NH, or N—$R^x$, wherein Het, $R^x$, $R^1$, $R^2$ and $R^3$ are as defined in claim 1, or a pharmaceutically acceptable salt or tautomer thereof.

5. A compound according to claim 4, wherein $R^a$ and $R^b$ are hydrogen.

6. A compound according to claim 1, wherein Het is a radical of the formulae

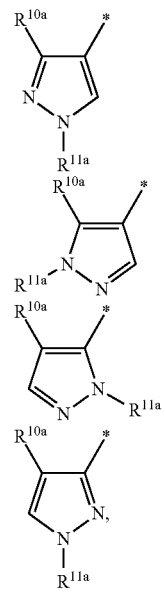

wherein $R^{10a}$ is hydrogen or has one of the meanings given for $R^{10}$, $R^{11a}$ is hydrogen or has one of the meanings given for $R^{11}$ and wherein * denotes the point of attachment to the moiety Y.

7. A compound according to claim 1, wherein $R^1$ is located in the 3- or 4-position of the phenyl ring.

8. A compound according to claim 7, wherein $R^4$ is selected from the group consisting of $C_3$-$C_8$-alkyl, which is unsubstituted or carries one radical selected from the group consisting of OH, $C_1$-$C_4$-alkoxy, $C_3$-$C_8$-cycloalkyl, and phenyl, wherein the phenyl ring itself is unsubstituted or carries 1, 2, 3, 4 or 5 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy, and trifluoromethoxy, $C_1$-$C_8$-haloalkyl, $C_3$-$C_8$-cycloalkyl, which is unsubstituted or carries 1, 2, 3, or 4 radicals selected from the group consisting of halogen, $C_1$-$C_4$-alkyl, and $C_1$-$C_4$-alkoxy, phenyl, which is unsubstituted or carries 1, 2, 3, 4 or 5 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy, and trifluoromethoxy, and 5- or 6-membered hetaryl having 1, 2 or 3 heteroatoms as ring members, the heteroatoms being selected from the group consisting of O, S, and N, wherein hetaryl is unsubstituted or carries 1, 2, 3, or 4 identical or different radicals selected from the group consisting of fluorine, chlorine, CN, $C_1$-$C_2$-alkyl, $C_1$-$C_2$-alkoxy, difluoromethyl, trifluoromethyl, difluoromethoxy, and trifluoromethoxy.

9. A compound according to claim 7, wherein $R^2$ is bound to the 3-position of the benzene ring, and $R^4$ together with $R^2$ forms a $C_1$-$C_5$-alkylene or $C_2$-$C_5$alkenylene moiety, wherein one $CH_2$-moiety may be replaced by oxygen, sulphur or a N—$R^{4c}$-moiety, and wherein $C_1$-$C_5$-alkylene and $C_2$-$C_5$-alkenylene may be unsubstituted or carry 1, 2, 3, or 4 radicals selected from the group consisting of halogen, CN, OH, $NH_2$, $C_1$-$C_4$-alkyl, $C_3$-$C_6$-cycloalkyl, $C_1$-$C_4$-haloalkyl, $C_1$-$C_4$-alkylamino, di-($C_1$-$C_4$-alkyl)amino, $C_1$-$C_4$-alkoxy, and $C_1$-$C_4$-haloalkoxy.

10. A pharmaceutical composition comprising at least one compound as claimed in claim 1, together with at least one physiologically acceptable carrier or auxiliary substance.

11. The compound according to claim 1 of the formulae Ia.1.a, Ia.2.a, Ia.3.a, or Ia.4.a

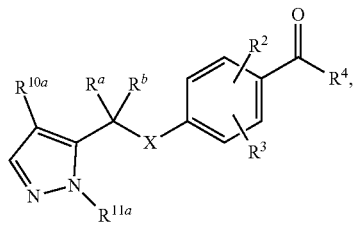
(Ia.1.a)

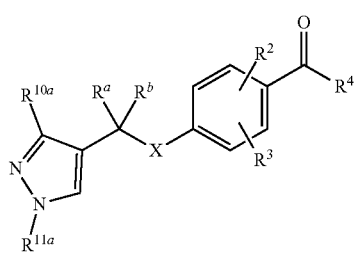
(Ia.2.a)

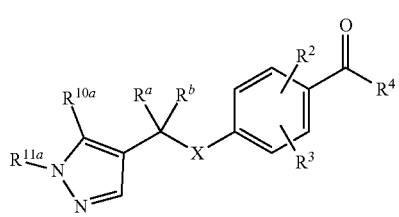
(Ia.3.a)

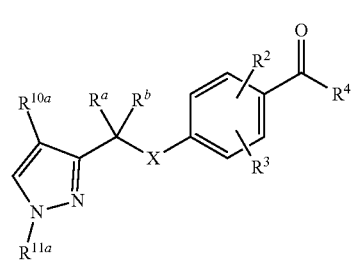
(Ia.4.a)

wherein $R^a$ and $R^b$ are, independently of each other, selected from the group consisting of hydrogen, halogen, $C_1$-$C_4$-alkyl, $C_1$-$C_4$-haloalkyl, $C_1$-$C_4$-alkoxy, and $C_1$-$C_4$-haloalkoxy; $R^b$ may also be OH, if $R^a$ is hydrogen, $C_1$-$C_4$-alkyl, or $C_1$-$C_4$-haloalkyl;

X is O, NH, or N—$R^x$, wherein $R^x$, $R^4$, $R^2$ and $R^3$ are as defined in claim 1, $R^{10a}$ is hydrogen or has one of the meanings given for $R^{10}$, $R^{11a}$ is hydrogen or has one of the meanings given for $R^{11}$, or a pharmaceutically acceptable salt thereof.

12. The compound according to claim 11, wherein $R^a$ and $R^b$ are hydrogen.

13. The compound according to claim 1, which is of the formulae Ia.1.a', Ia.2.a'. Ia.3.a', or Ia.4.a'

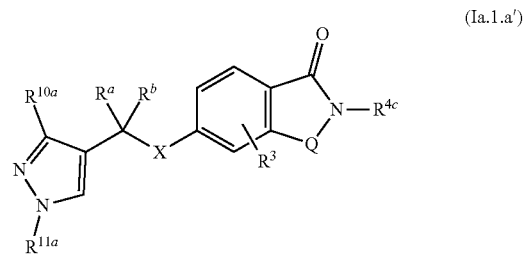
(Ia.1.a')

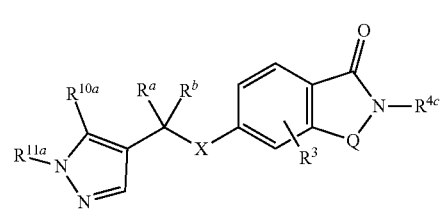
(Ia.2.a')

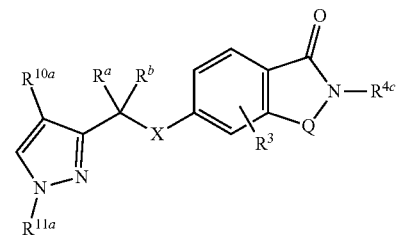
(Ia.3.a')

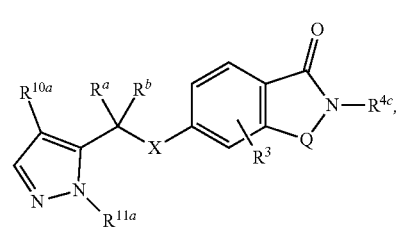
(Ia.4.a')

wherein -Q- is —C($R^{Q1}R^{Q2}$)—, —C($R^{Q1}R^{Q2}$)—C($R^{Q3}R^{Q4}$)—, or —C($R^{Q1}$)═C($R^{Q2}$)—, wherein $R^{Q1}$, $R^{Q2}$, $R^{Q3}$, $R^{Q4}$ are each independently of each other selected from the group consisting of hydrogen, halogen, CN, OH, $NH_2$, $C_1$-$C_4$-alkyl, $C_3$-$C_6$-cycloalkyl, $C_1$-$C_4$-haloalkyl, $C_1$-$C_4$-alkylamino, di-($C_1$-$C_4$-alkyl)amino, $C_1$-$C_4$-alkoxy, and $C_1$-$C_4$-haloalkoxy; $R^a$ and $R^b$ are, independently of each other, selected from the group consisting of hydrogen, halogen, $C_1$-$C_4$-alkyl, $C_1$-$C_4$-haloalkyl, $C_1$-$C_4$-alkoxy, and $C_1$-$C_4$-haloalkoxy; $R^b$ may also be OH, if $R^a$ is hydrogen, $C_1$-$C_4$-alkyl, or $C_1$-$C_4$-haloalkyl;

X is O, NH or N—$R^x$, wherein $R^x$, $R^4$ and $R^3$ are as defined in claim 1, $R^{10a}$ is hydrogen or has one of the meanings given for $R^{10}$, $R^{11a}$ is hydrogen or has one of the meanings given for $R^{11}$, or a pharmaceutically acceptable salt thereof.

14. The compound according to claim 13, wherein $R^a$ and $R^b$ are hydrogen.

15. The compound according to claim 13, wherein Q is $CH_2$.

16. The compound according to claim 1, which is selected from the group consisting of
1-{4-[(1-Methyl-1H-pyrazol-4-ylmethyl)amino]phenyl}butan-1-one;
1-{4-[(5-Methyl-2H-pyrazol-3-ylmethyl)amino]phenyl}butan-1-one;
1-(4-{[4-Bromo-2-(4-chlorobenzyl)-2H-pyrazol-3-ylmethyl]amino}phenyl)butan-1-one;
1-(4-{[3-(Thiophen-2-yl)-1H-pyrazol-4-ylmethyl]amino}phenyl)butan-1-one;
1-(4-{[3-(4-(Trifluoromethylphenyl)-1H-pyrazol-4-ylmethyl]amino}phenyl)butan-1-one;
1-{4-[(2,5-Dimethyl-2H-pyrazol-3-ylmethyl)amino]phenyl}butan-1-one;
1-{4-[(5-Methyl-1-phenyl-1H-pyrazol-4-ylmethyl)amino]phenyl}butan-1-one;
1-(4-{[5-(4-Chlorophenoxy)-1,3-dimethyl-1H-pyrazol-4-ylmethyl]amino}phenyl)butan-1-one;
1-(4-{[5-(3-Chlorophenoxy)-1,3-dimethyl-1H-pyrazol-4-ylmethyl]amino}phenyl)butan-1-one;
1-{4-[(5-Chloro-3-methyl-1-phenyl-1-pyrazol-4-ylmethyl)amino]phenyl}butan-1-one;
1-(4-{[5-Chloro-1-methyl-3-(phenylthiomethyl)-1H-pyrazol-4-yl]methylamino}phenyl)butan-1-one;
1-(4-{[5-Chloro-1-methyl-3-(trifluoromethyl)-1H-pyrazol-4-yl]methylamino}phenyl)butan-1-one;
1-{4-[(1-Ethyl-5-methyl-1H-pyrazol-4-ylmethyl)amino]phenyl}butan-1-one;
1-{4-[(3,5-Dimethyl-1-phenyl-1H-pyrazol-4-ylmethyl)amino]phenyl}butan-1-one;
1-{4-[(2-Phenyl-2H-pyrazol-3-ylmethyl)amino]phenyl}butan-1-one;
1-{4-[(1-tert-Butyl-3,5-dimethyl-1H-pyrazol-4-ylmethyl)amino]phenyl}butan-1-one;
1-{4-[(5-Methyl-2H-pyrazol-3-ylmethyl)amino]phenyl}butan-1-one;
1-{4-[(1,5-Dimethyl-1H-pyrazol-4-ylmethyl)amino]phenyl}butan-1-one;
1-{4-[(1,3-Dimethyl-1H-pyrazol-4-ylmethyl)amino]phenyl}butan-1-one;
1-{4-[(1-Methyl-1H-pyrazol-4-ylmethyl)amino]phenyl}butan-1-one;
1-(4-{[3-(5-Methylfuran-2-yl)-1-phenyl-1H-pyrazol-4-ylmethyl]amino}phenyl)butan-1-one;
1-(4-{[1-Phenyl-3-(thiophen-2-yl)-1H-pyrazol-4-ylmethyl]amino}phenyl)butan-1-one;
1-{4-[(1-Ethyl-5-methyl-1H-pyrazol-4-ylmethyl)amino]phenyl}butan-1-one;
1-{4-[(1-Ethyl-3-methyl-1H-pyrazol-4-ylmethyl)amino]phenyl}butan-1-one;
1-{4-[(1-Ethyl-1H-pyrazol-4-ylmethyl)amino]phenyl}butan-1-one;
1-{4-[(1H-Pyrazol-4-ylmethyl)amino]phenyl}butan-1-one;
1-{4-[(2,5-Dimethyl-1H-pyrazol-3-ylmethyl)amino]phenyl}butan-1-one;
1-{4-[(3-Methyl-1-propyl-1H-pyrazol-4-ylmethyl)amino]phenyl}butan-1-one;
1-{4-[(5-Methyl-1-propyl-1H-pyrazol-4-ylmethyl)amino])phenyl}butan-1-one;
1-{4-[(1-Methyl-1H-pyrazol-3-ylmethyl)amino]phenyl}butan-1-one;
1-{4-[(1-Methyl-5-phenyl-1H-pyrazol-4-ylmethyl)amino]phenyl}) butan-1-one;
1-{4-[(1,5-Dimethyl-1H-pyrazol-3-ylmethyl)amino]phenyl}butan-1-one;
1-{4-[(1-Isopropyl-1H-pyrazol-4-ylmethyl)amino]phenyl}butan-1-one;
1-(4-{[3-(4-Hydroxyphenyl)-1H-pyrazol-4-ylmethyl]amino}phenyl)butan-1-one;
1-{4-[(3-tert-Butyl-1H-pyrazol-4-ylmethyl)amino]phenyl}butan-1-one;
2,2,2-Trifluoroethanesulfonic acid (4-butyryl-phenyl)-[1-(2,2,2-trifluoro-ethanesulfonyl)-3-(4-trifluoromethylphenyl)-1H-pyrazol-4-ylmethyl]-amide;
5-{[3-(4-Trifluoromethylphenyl)-1H-pyrazol-4-ylmethyl]-amino}-indan-1-one;
6-{[3-(4-Trifluoromethylphenyl)-1H-pyrazol-4-ylmethyl]-amino}-3,4-dihydro-2H-naphthalen-1-one;
Ethanesulfonic acid (4-butyryl-phenyl)-[3-(4-trifluoromethyl-phenyl)-1H-pyrazol-4-ylmethyl]-amide;
2,2,2-Trifluoro-ethanesulfonic acid (4-butyryl-phenyl)-[3-(4-trifluoromethyl-phenyl)-1H-pyrazol-4-ylmethyl]-amide;
2,2,2-Trifluoro-ethanesulfonic acid (3-butyryl-phenyl)-[3-(4-trifluoromethyl-phenyl)-1H-pyrazol-4-ylmethyl]-amide;
Ethanesulfonic acid (3-butyryl-phenyl)-[3-(4-trifluoromethyl-phenyl)-1H-pyrazol-4-ylmethyl]-amide;
Ethanesulfonic acid (3-butyryl-phenyl)-(3-thiophen-2-yl-1H-pyrazol-4-ylmethyl)-amide;
2,2,2-Trifluoro-ethanesulfonic acid (3-butyryl-phenyl)-(3-thiophen-2-yl-1H-pyrazol-4-ylmethyl)-amide;
2,2,2-Trifluoro-ethanesulfonic acid (4-butyryl-phenyl)-(3-thiophen-2-yl-1H-pyrazol-4-ylmethyl)-amide;
Ethanesulfonic acid (4-butyryl-phenyl)-(3-thiophen-2-yl-1H-pyrazol-4-ylmethyl)-amide;
Ethanesulfonic acid (3-tert-butyl-1H-pyrazol-4-ylmethyl)-(4-butyryl-phenyl)-amide;
2,2,2-Trifluoro-ethanesulfonic acid (3-tert-butyl-1H-pyrazol-4-ylmethyl)-(4-butyryl-phenyl)-amide;
2,2,2-Trifluoro-ethanesulfonic acid (3-tert-butyl-1H-pyrazol-4-ylmethyl)-(3-butyryl-phenyl)-amide;
Ethanesulfonic acid (3-tert-butyl-1H-pyrazol-4-ylmethyl)-(3-butyryl-phenyl)-amide;
1-(4-{[3-(4-Methoxy-phenyl)-1H-pyrazol-4-ylmethyl]-amino}-phenyl)-butan-1-one;
1-{4-[(3-Phenyl-1H-pyrazol-4-ylmethyl)-amino]-phenyl}-butan-1-one;
1-{4-[(1,3,5-Trimethyl-1H-pyrazol-4-ylmethyl)-amino]-phenyl}-butan-1-one;
1-{4-[(3-p-Tolyl-1H-pyrazol-4-ylmethyl)-amino]-phenyl}-butan-1-one;
1-(4-{[3-(3,5-Difluoro-phenyl)-1H-pyrazol-4-ylmethyl]-amino}-phenyl)-butan-1-one;

1-{4-[(1-Phenyl-3-pyridin-4-yl-1H-pyrazol-4-ylmethyl)-amino]-phenyl}-butan-1-one;
1-{4-[(2-Methyl-2H-pyrazol-3-ylmethyl)-amino]-phenyl}-butan-1-one;
1-(4-{[3-(4-Chloro-phenyl)-1H-pyrazol-4-ylmethyl]-amino}-phenyl)-butan-1-one;
1-(4-{[3-(3,4-Dimethoxy-phenyl)-1H-pyrazol-4-ylmethyl]-amino}-phenyl)-butan-1-one;
1-{4-[(1-Benzyl-1H-pyrazol-4-ylmethyl)-amino]-phenyl}-butan-1-one;
1-(4-{[3-(4-Fluoro-phenyl)-1-phenyl-1H-pyrazol-4-ylmethyl]-amino}-phenyl)-butan-1-1-one;
1-{4-[(1-Phenyl-3-pyridin-3-yl-1H-pyrazol-4-ylmethyl)-amino]-phenyl}-butan-1-one;
1-{4-[(3,5-Dimethyl-1H-pyrazol-4-ylmethyl)-amino]-phenyl}-butan-1-one;
1-(4-{[1-Methyl-3-(4-trifluoromethyl-phenyl)-1H-pyrazol-4-ylmethyl]-amino}-phenyl)-butan-1-one;
1-(4-{[1-Methyl-5-(4-trifluoromethyl-phenyl)-1H-pyrazol-4-ylmethyl]-amino}-phenyl)-butan-1-one;
1-(4-{[3-(4-Chloro-phenyl)-1H-pyrazol-4-ylmethyl]-amino}-phenyl)-butan-1-one;
1-(3-{Methyl-[3-(4-trifluoromethyl-phenyl)-1H-pyrazol-4-ylmethyl]-amino}-phenyl)-butan-1-one;
2,2,2-Trifluoro-ethanesulfonic acid (5-oxo-5,6,7,8-tetrahydro-naphthalen-2-yl)-[3-(4-trifluoromethyl-phenyl)-1H-pyrazol-4-ylmethyl]-amide;
2-Methyl-7-{[3-(4-trifluoromethyl-phenyl)-1H-pyrazol-4-ylmethyl]-amino}-chromen-4-one;
1-(4-{Methyl-[3-(4-trifluoromethyl-phenyl)-1H-pyrazol-4-ylmethyl]-amino}-phenyl)-butan-1-one;
2,2,2-Trifluoro-ethanesulfonic acid (4-butyryl-phenyl)-[1-methyl-5-(4-trifluoromethyl-phenyl)-1H-pyrazol-4-ylmethyl]-amide;
2,2,2-Trifluoro-ethanesulfonic acid (4-butyryl-phenyl)-[1-methyl-3-(4-trifluoromethyl-phenyl)-1H-pyrazol-4-ylmethyl]-amide;
2,2,2-Trifluoro-ethanesulfonic acid (4-butyryl-phenyl)-[3-(4-trifluoromethyl-phenyl)-1H-pyrazol-4-ylmethyl]-amide;
1-(4-{[3-(3-Trifluoromethyl-phenyl)-1H-pyrazol-4-ylmethyl]-amino}-phenyl)-butan-1-one;
7-{[3-(4-Chloro-phenyl)-1H-pyrazol-4-ylmethyl]-amino}-3,4-dihydro-2H-naphthalen-1-one;
6-{[3-(4-Chloro-phenyl)-1H-pyrazol-4-ylmethyl]-amino}-indan-1-one;
1-(2-Methoxy-4-{[3-(3-trifluoromethyl-phenyl)-1H-pyrazol-4-ylmethyl]-amino}-phenyl)-butan-1-one;
1-(2-Hydroxy-4-{[3-(3-trifluoromethyl-phenyl)-1H-pyrazol-4-ylmethyl]-amino}-phenyl)-butan-1-one;
1-[4-{[3-(4-Chloro-phenyl)-1H-pyrazol-4-ylmethyl]-amino}-2-(1-ethyl-propoxy)-phenyl]-butan-1-one;
1-{4-[(3-Methyl-1H-pyrazol-4-ylmethyl)-amino]-phenyl}-butan-1-one;
1-{4-[(3-Propyl-1H-pyrazol-4-ylmethyl)-amino]-phenyl}-butan-1-one;
1-{4-[(3-Isopropyl-1H-pyrazol-4-ylmethyl)-amino]-phenyl}-butan-1-one;
1-{4-[(3-Ethyl-1H-pyrazol-4-ylmethyl)-amino]-phenyl}-butan-1-one;
1-{4-[3-(4-Trifluoromethyl-phenyl)-1H-pyrazol-4-ylmethoxy]-phenyl}-pentan-1-one;
1-{4-[3-(4-Trifluoromethyl-phenyl)-1H-pyrazol-4-ylmethoxy]-phenyl}-hexan-1-one;
1-{4-[3-(4-Trifluoromethyl-phenyl)-1H-pyrazol-4-ylmethylsulfanyl]-phenyl}-butan-1-one;
1-{4-[3-(4-Trifluoromethyl-phenyl)-1H-pyrazol-4-ylmethanesulfonyl]-phenyl}-butan-1-one;
1-{4-[3-(4-Trifluoromethyl-phenyl)-1H-pyrazol-4-ylmethoxy]-phenyl}-butan-1-one;
1-{4-[3-(4-Fluoro-phenyl)-1H-pyrazol-4-ylmethoxy]-phenyl}-butan-1-one;
1-{4-[3-(4-Chloro-phenyl)-1H-pyrazol-4-ylmethoxy]-phenyl}-butan-1-one;
1-{4-[3-(3-Fluoro-phenyl)-1H-pyrazol-4-ylmethoxy]-phenyl}-butan-1-one;
1-{4-[3-(3-Trifluoromethyl-phenyl)-1H-pyrazol-4-ylmethoxy]-phenyl}-butan-1-one;
1-[4-(3-Phenyl-1H-pyrazol-4-ylmethoxy)-phenyl]-butan-1-one, trifluoroacetic acid;
1-{4-[1-(3-Phenyl-1H-pyrazol-4-yl)-ethoxy]-phenyl}-butan-1-one;
1-(4-{[3-(4-Trifluoromethyl-phenyl)-1H-pyrazol-4-ylmethyl]-amino}-phenyl)-ethanone;
1-(3-Nitro-4-{[3-(4-trifluoromethyl-phenyl)-1H-pyrazol-4-ylmethyl]-amino}-phenyl)-ethanone;
1-(3-{[3-(4-Trifluoromethyl-phenyl)-1H-pyrazol-4-ylmethyl]-amino}-phenyl)-butan-1-one;
1-(4-{[3-(4-Fluoro-phenyl)-1H-pyrazol-4-ylmethyl]-amino}-phenyl)-butan-1-one;
1-(4-{[3-(3-Chloro-phenyl)-1H-pyrazol-4-ylmethyl]-amino}-phenyl)-butan-1-one;
1-(4-{[3-(2-Chloro-phenyl)-1H-pyrazol-4-ylmethyl]-amino}-phenyl)-butan-1-one;
1-(4-{[3-(3-Fluoro-phenyl)-1H-pyrazol-4-ylmethyl]-amino}-phenyl)-butan-1-one;
1-{4-[(3-Pyridin-3-yl-1H-pyrazol-4-ylmethyl)-amino]-phenyl}-butan-1-one;
1-(4-{[4-(4-Methoxy-phenyl)-1H-pyrazol-3-ylmethyl]-amino}-phenyl)-butan-1-one;
1-(3-{[4-(4-Methoxy-phenyl)-1H-pyrazol-3-ylmethyl]-amino}-phenyl)-butan-1-one;
1-(3-{[4-(4-Ethyl-phenyl)-1H-pyrazol-3-ylmethyl]-amino}-phenyl)-butan-1-one;
1-(4-{[4-(4-Ethyl-phenyl)-1H-pyrazol-3-ylmethyl]-amino}-phenyl)-butan-1-one;
1-(4-{[4-(4-Trifluoromethyl-phenyl)-1H-pyrazol-3-ylmethyl]-amino}-phenyl)-butan-1-one;
1-(4-{[4-(4-Chloro-phenyl)-1H-pyrazol-3-ylmethyl]-amino}-phenyl)-butan-1-one;
1-{4-[4-(4-Methoxy-phenyl)-1H-pyrazol-3-ylmethoxy]-phenyl}-butan-1-one;
1-{4-[4-(4-Ethyl-phenyl)-1H-pyrazol-3-ylmethoxy]-phenyl}-butan-1-one;
1-[4-(4-Bromo-1H-pyrazol-3-ylmethoxy)-phenyl]-butan-1-one;
1-{4-[(4-Phenyl-1H-pyrrol-3-ylmethyl)-amino]-phenyl}-butan-1-one;
2-Propyl-5-[3-(4-trifluoromethyl-phenyl)-1H-pyrazol-4-ylmethoxy]-2,3-dihydro-isoindol-1-one;
2-Propyl-5-[3-(3-trifluoromethyl-phenyl)-1H-pyrazol-4-ylmethoxy]-2,3-dihydro-isoindol-1-one;
5-[3-(4-Fluoro-phenyl)-1H-pyrazol-4-ylmethoxy]-2-propyl-2,3-dihydro-isoindol-1-one;
5-[3-(4-Chloro-phenyl)-1H-pyrazol-4-ylmethoxy]-2-propyl-2,3-dihydro-isoindol-1-one;
5-[3-(3-Chloro-phenyl)-1H-pyrazol-4-ylmethoxy]-2-propyl-2,3-dihydro-isoindol-1-one;
5-[3-(3-Fluoro-phenyl)-1H-pyrazol-4-ylmethoxy]-2-propyl-2,3-dihydro-isoindol-1-one;
5-(3-Phenyl-1H-pyrazol-4-ylmethoxy)-2-propyl-2,3-dihydro-isoindol-1-one;

5-[3-(3-Trifluoromethyl-phenyl)-1H-pyrazol-4-yl-methoxy]-2-(3,3,3-trifluoro-propyl)-2,3-dihydro-isoindol-1-one;
5-[3-(4-Chloro-phenyl)-1H-pyrazol-4-ylmethoxy]-2-(3,3,3-trifluoro-propyl)-2,3-dihydro-isoindol-1-one;
5-[3-(4-Fluoro-phenyl)-1H-pyrazol-4-ylmethoxy]-2-(3,3,3-trifluoro-propyl)-2,3-dihydro-isoindol-1-one;
5-[3-(3-Fluoro-phenyl)-1H-pyrazol-4-ylmethoxy]-2-(3,3,3-trifluoro-propyl)-2,3-dihydro-isoindol-1-one;
5-[3-(4-Trifluoromethyl-phenyl)-1H-pyrazol-4-yl-methoxy]-2-(3,3,3-trifluoro-propyl)-2,3-dihydro-isoindol-1-one;
5(3-Phenyl-1H-pyrazol-4-ylmethoxy)-243,3,3-trifluoro-propyl)-2,3-dihydro-isoindol-1-one;
2-Butyl-5-[3-(4-trifluoromethyl-phenyl)-1H-pyrazol-4-ylmethoxy]-2,3-dihydro-isoindol-1-one;
2-Butyl-5-[3-(3-trifluoromethyl-phenyl)-1H-pyrazol-4-ylmethoxy]-2,3-dihydro-isoindol-1-one;
2-Butyl-5-[3-(4-chloro-phenyl)-1H-pyrazol-4-yl-methoxy]-2,3-dihydro-isoindol-1-one;
2-Butyl-5-[3-(3,4-dichloro-phenyl)-1H-pyrazol-4-yl-methoxy]-2,3-dihydro-isoindol-1-one;
2-Butyl-5-[3-(4-fluoro-phenyl)-1H-pyrazol-4-yl-methoxy]-2,3-dihydro-isoindol-1-one;
2-Butyl-5-[3-(3-chloro-phenyl)-1H-pyrazol-4-yl-methoxy]-2,3-dihydro-isoindol-1-one;
2-Butyl-5-[3-(3-fluoro-phenyl)-1H-pyrazol-4-yl-methoxy]-2,3-dihydro-isoindol-1-one;
2-Butyl-5-(3-phenyl-1H-pyrazol-4-ylmethoxy)-2,3-dihydro-isoindol-1-one, trifluoroacetic acid;
2-(4,4,4-Trifluoro-butyl)-5-[3-(4-trifluoromethyl-phenyl)-1H-pyrazol-4-ylmethoxy]-2,3-dihydro-isoindol-1-one;
5-(3-Phenyl-1H-pyrazol-4-ylmethoxy)-2-(4,4,4-trifluoro-butyl)-2,3-dihydro-isoindol-1-one;
5-[3-(3,4-dichloro-phenyl)-1H-pyrazol-4-ylmethoxy]-2-(4,4,4-trifluoro-butyl)-2,3-dihydro-isoindol-1-one;
2-(3-Methyl-butyl)-5-[3-(4-trifluoromethyl-phenyl)-1H-pyrazol-4-ylmethoxy]-2,3-dihydro-isoindol-1-one;
2-(3-Methyl-butyl)-5-(3-phenyl-1H-pyrazol-4-yl-methoxy)-2,3-dihydro-isoindol-1-one;
5-(3-Phenyl-1H-pyrazol-4-ylmethoxy)-2-(2-trifluoromethoxy-ethyl)-2,3-dihydro-isoindol-1-one;
2-Ethyl-5-[3-(3-trifluoromethyl-phenyl)-1H-pyrazol-4-ylmethoxy]-2,3-dihydro-isoindol-1-one;
2-Ethyl-5-[3-(4-fluoro-phenyl)-1H-pyrazol-4-yl-methoxy]-2,3-dihydro-isoindol-1-one;
2-Ethyl-5-[3-(3-fluoro-phenyl)-1H-pyrazol-4-yl-methoxy]-2,3-dihydro-isoindol-1-one;
5-[3-(3-Chloro-phenyl)-1H-pyrazol-4-ylmethoxy]-2-ethyl-2,3-dihydro-isoindol-1-one;
5-[3-(4-Chloro-phenyl)-1H-pyrazol-4-ylmethoxy]-2-ethyl-2,3-dihydro-isoindol-1-one;
2-Ethyl-5-(3-phenyl-1H-pyrazol-4-ylmethoxy)-2,3-dihydro-isoindol-1-one;
2-(2-Bromo-ethyl)-5-[3-(4-trifluoromethyl-phenyl)-1H-pyrazol-4-ylmethoxy]-2,3-dihydro-isoindol-1-one;
2-(2-Bromo-ethyl)-5-[3-(3-trifluoromethyl-phenyl)-1H-pyrazol-4-ylmethoxy]-2,3-dihydro-isoindol-1-one;
2-(2,2-Difluoro-ethyl)-5-[3-(4-trifluoromethyl-phenyl)-1H-pyrazol-4-ylmethoxy]-2,3-dihydro-isoindol-1-one;
2-(2,2-Difluoroethyl)-5-(3-phenyl-1H-pyrazol-4-yl-methoxy)-2,3-dihydro-isoindol-1-one;
2-(2,2,2-Trifluoroethyl)-5-[3-(4-trifluoromethyl-phenyl)-1H-pyrazol-4-ylmethoxy]-2,3-dihydro-isoindol-1-one;
2-(2,2,2-Trifluoroethyl)-5-[3-(3-trifluoromethyl-phenyl)-1H-pyrazol-4-ylmethoxy]-2,3-dihydro-isoindol-1-one;
5-[3-(4-Fluorophenyl)-1H-pyrazol-4-ylmethoxy]-2-(2,2,2-trifluoro-ethyl)-2,3-dihydro-isoindol-1-one;
5-[3-(3-Fluorophenyl)-1H-pyrazol-4-ylmethoxy]-2-(2,2,2-trifluoro-ethyl)-2,3-dihydro-isoindol-1-one;
5-[3-(4-Trifluoromethylphenyl)-1H-pyrazol-4-yl-methoxy]-2,3-dihydro-isoindol-1-one;
2-Methyl-5-[3-(4-trifluoromethylphenyl)-1H-pyrazol-4-ylmethoxy]-2,3-dihydro-isoindol-1-one;
2-Propyl-6-[3-(4-trifluoromethylphenyl)-1H-pyrazol-4-ylmethoxy]-3,4-dihydro-2H-isoquinolin-1-one;
2-Propyl-5-{[3-(4-trifluoromethylphenyl)-1H-pyrazol-4-ylmethyl]-amino}-2,3-dihydro-isoindol-1-one;
5-{[3-(4-Chlorophenyl)-1H-pyrazol-4-ylmethyl]-amino}-2-propyl-2,3-dihydro-isoindol-1-one;
5-{[3-(3-Chlorophenyl)-1H-pyrazol-4-ylmethyl]-amino}-2-propyl-2,3-dihydro-isoindol-1-one;
2-Propyl-5-{[3-3-trifluoromethyl-phenyl)-1H-pyrazol-4-ylmethyl]-amino}-2,3-dihydro-isoindol-1-one;
5-{[3-(4-Fluorophenyl)-1H-pyrazol-4-ylmethyl]-amino}-2-propyl-2,3-dihydro-isoindol-1-one;
5-{[3-(3-Fluorophenyl)-1H-pyrazol-4-ylmethyl]-amino}-2-propyl-2,3-dihydro-isoindol-1-one;
5-[(3-Phenyl-1H-pyrazol-4-ylmethyl)-amino]-2-propyl-2,3-dihydro-isoindol-1-one;
2-Propyl-5-{[4-3-trifluoromethyl-phenyl)-1H-pyrazol-3-ylmethyl]-amino}-2,3-dihydro-isoindol-1-one;
2-Propyl-5-{[3-(4-trifluoromethyl-phenyl)-1H-pyrazol-4-ylmethyl]-amino}-isoindole-1,3-dione;
2-Propyl-6 {[3-(4-trifluoromethyl-phenyl)-1H-pyrazol-4-ylmethyl]-amino}-2,3-dihydro-isoquinolin-1-one;
2-(4-Trifluoromethoxy-benzyl)-5-[3-(4-trifluoromethyl-phenyl)-1H-pyrazol-4-ylmethoxy]-2,3-dihydro-isoindol-1-one;
2-Cyclohexylmethyl-5-[3-(4-trifluoromethyl-phenyl)-1H-pyrazol-4-ylmethoxy]-2,3-dihydro-isoindol-1-one;
2-Isobutyl-5-[3-(4-trifluoromethyl-phenyl)-1H-pyrazol-4-ylmethoxy]-2,3-dihydro-isoindol-1-one;
2-Cyclopentyl-5-[3-(4-trifluoromethyl-phenyl)-1H-pyrazol-4-ylmethoxy]-2,3-dihydro-isoindol-1-one; and
2-Phenyl-5-[3-(4-trifluoromethyl-phenyl)-1H-pyrazol-4-ylmethoxy]-2,3-dihydro-isoindol-1-one;
or a pharmaceutically acceptable salt thereof.

17. The compound according to formula Ia.1.a' of claim 13, which is selected from the group consisting of
2-Propyl-5-[3-(4-trifluoromethyl-phenyl)-1H-pyrazol-4-ylmethoxy]-2,3-dihydro-isoindol-1-one;
2-Butyl-5-[3-(3-trifluoromethyl-phenyl)-1H-pyrazol-4-ylmethoxy]-2,3-dihydro-isoindol-1-one;
2-Butyl-5-[3-(4-fluorophenyl)-1H-pyrazol-4-yl-methoxy]-2,3-dihydro-isoindol-1-one, trifluoroacetic acid; and
2-Butyl-5-(3-phenyl-1H-pyrazol-4-ylmethoxy)-2,3-dihydro-isoindol-1-one, trifluoroacetic acid;
or a pharmaceutically acceptable salt thereof.

18. A compound, which is selected from the group consisting of
3-[(3-tert-Butyl-1H-pyrazol-4-ylmethyl)-amino]-phenol;
1-{4-[(5-Phenyl-2H-[1,2,3]triazol-4-ylmethyl)-amino]-phenyl}-butan-1-one;
1-{4-[(3-Phenyl-pyridin-4-ylmethyl)-amino]-phenyl}-butan-1-one;
1-{4-[(4-Phenyl-pyridin-3-ylmethyl)-amino]-phenyl}-butan-1-one;
1-{4-[(2-Phenyl-pyridin-3-ylmethyl)-amino]-phenyl}-butan-1-one;
1-{4-[(6-Phenyl-pyridin-3-ylmethyl)-amino]-phenyl}-butan-1-one;

1-(4-{[6-(4-Fluoro-phenyl)-pyridin-2-ylmethyl]-amino}-phenyl)-butan-1-one;
1-{4-[(Pyrazolo[1,5-a]pyridin-3-ylmethyl)-amino]-phenyl}-butan-1-one;
1-{4-[(3-Methyl-5-phenyl-isoxazol-4-ylmethyl)-amino]-phenyl}-butan-1-one;
5-[(3-Methyl-5-phenyl-isoxazol-4-ylmethyl)-amino]-2-propyl-2,3-dihydro-isoindol-1-one; and
1-[3-(Benzyl-pyridin-3-ylmethylamino)-phenyl]-butan-1-one;
or a pharmaceutically acceptable salt thereof.

* * * * *